US011525129B2

(12) United States Patent
Raj et al.

(10) Patent No.: US 11,525,129 B2
(45) Date of Patent: Dec. 13, 2022

(54) LACTASE ENZYMES WITH IMPROVED PROPERTIES

(71) Applicant: Chr. Hansen A/S, Hoersholm (DK)

(72) Inventors: Hans Raj, Hoersholm (DK); Pernille Smith, Broenshoej (DK); Thomas Eckhardt, Birkeroed (DK); Vojislav Vojinovic, Graested (DK); Charlotte Elisabeth Grüner Schöller, Virum (DK); Johannes Maarten Van Den Brink, Herlev (DK)

(73) Assignee: Chr. Hansen A/S, Hoersholm (DK)

( * ) Notice: Subject to any disclaimer, the term of this patent is extended or adjusted under 35 U.S.C. 154(b) by 358 days.

(21) Appl. No.: 16/604,129

(22) PCT Filed: Apr. 11, 2018

(86) PCT No.: PCT/EP2018/059250
§ 371 (c)(1),
(2) Date: Oct. 9, 2019

(87) PCT Pub. No.: WO2018/189224
PCT Pub. Date: Oct. 18, 2018

(65) Prior Publication Data
US 2021/0355471 A1  Nov. 18, 2021

(30) Foreign Application Priority Data
Apr. 11, 2017 (EP) .................................. 17166021

(51) Int. Cl.
*C12N 9/38* (2006.01)
*A23L 29/00* (2016.01)

(52) U.S. Cl.
CPC ............ *C12N 9/2471* (2013.01); *A23L 29/06* (2016.08)

(58) Field of Classification Search
CPC .......... C12Y 302/01023; C12N 9/2471; C07K 14/195; A23L 29/06
See application file for complete search history.

(56) References Cited

U.S. PATENT DOCUMENTS

| | | |
|---|---|---|
| 10,058,107 B2 | 8/2018 | Hendriksen et al. |
| 10,306,902 B2 | 6/2019 | Hendriksen et al. |
| 10,555,541 B2 | 2/2020 | Hendriksen et al. |
| 2009/0297660 A1 | 12/2009 | Silver et al. |
| 2010/0285175 A1 | 11/2010 | Hendriksen et al. |
| 2012/0058223 A1 | 3/2012 | Stougaard et al. |
| 2019/0343138 A1 | 11/2019 | Ba et al. |
| 2020/0120946 A1 | 4/2020 | Hendriksen et al. |
| 2020/0123519 A1 | 4/2020 | Bongiorni et al. |
| 2021/0032615 A1 | 2/2021 | Raj et al. |
| 2021/0037844 A1 | 2/2021 | Hendriksen et al. |
| 2021/0348147 A1 | 2/2021 | Raj et al. |

FOREIGN PATENT DOCUMENTS

| | | |
|---|---|---|
| EP | 1 227 152 A1 | 7/2002 |
| EP | 2 530 148 A1 | 12/2012 |
| RU | 2278160 C2 | 9/2005 |
| RU | 2009120742 | 12/2010 |
| WO | WO-2005/084411 A2 | 9/2005 |
| WO | WO-2005/086794 A2 | 9/2005 |
| WO | WO-2007/088324 A1 | 8/2007 |
| WO | WO-2007/110619 A1 | 10/2007 |
| WO | WO-2008/033520 A2 | 3/2008 |
| WO | WO-2009/009142 A2 | 1/2009 |
| WO | WO-2009/071539 A1 | 6/2009 |
| WO | WO-2010/092057 A1 | 8/2010 |
| WO | WO-2015/107050 A1 | 7/2015 |
| WO | WO-2018/130630 A1 | 7/2018 |
| WO | WO-2018/187524 A1 | 10/2018 |

OTHER PUBLICATIONS

Broun et al., Catalytic plasticity of fatty acid modification enzymes underlying chemical diversity of plant lipids. Science, 1998, vol. 282: 1315-1317. (Year: 1998).*
Devos et al., Practical limits of function prediction. Proteins: Structure, Function, and Genetics. 2000, vol. 41: 98-107. (Year: 2000).*
Seffernick et al., Melamine deaminase and Atrazine chlorohydrolase: 98 percent identical but functionally different. J. Bacteriol., 2001, vol. 183 (8): 2405-2410. (Year: 2001).*
Whisstock et al., Prediction of protein function from protein sequence. Q. Rev. Biophysics., 2003, vol. 36 (3): 307-340. (Year: 2003).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*
Office Action dated Jan. 22, 2021, in U.S. Appl. No. 16/998,706 (US 2021-0032615).
U.S. Appl. No. 17/285,288, filed Apr. 14, 2021, Hans Raj et al.
U.S. Appl. No. 16/604,133, filed Oct. 9, 2019, Raj et al.
U.S. Appl. No. 16/604,134, filed Oct. 9, 2019, Raj et al.
"Uniprot: A0A0B5J47" (Apr. 1, 2015), Retrieved from the Internet, URL:http://ibis/exam/dbfetch.jsp?id=UNIPROT:A0A0B5J47 (Retrieved on May 11, 2017).
"Uniprot: A0AS2MCC8—beta galactosidase," (Feb. 17, 2016) Retrieved from the Internet, URL: https://ibis/exam/dbfetch.jsp?id=UNIPROT:A0A0S2MCC8 [retrieved on Mar. 9, 2018).
Horner et al., "β-Galactosidase activity of commercial lactase samples in raw and pasteurized milk at refrigerated temperatures," J. Dairy Sci. 94: 3242-3249 (Jul. 2011).

(Continued)

*Primary Examiner* — Ganapathirama Raghu
(74) *Attorney, Agent, or Firm* — Foley & Lardner LLP

(57) ABSTRACT

Disclosed are peptides and dimeric peptides exhibiting beta-galactosidase enzyme activity, as well as methods for producing a dairy product using them, and dairy products made by such methods. In some embodiments, the peptides exhibit beta-galactosidase enzyme activity at low and/or high temperatures.

14 Claims, 16 Drawing Sheets

Figure 1:
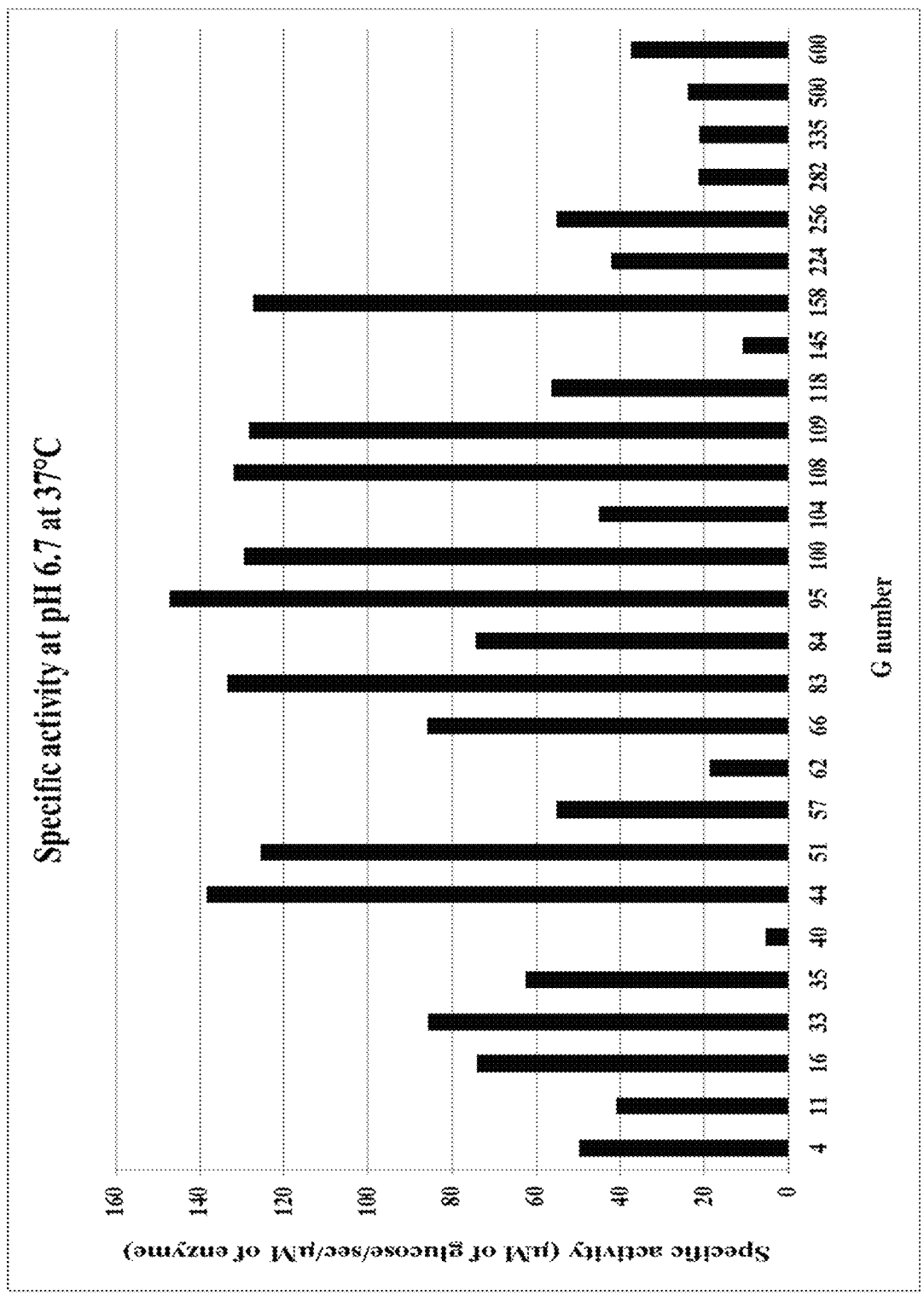

Specification includes a Sequence Listing.

(56) References Cited

OTHER PUBLICATIONS

Nakagawa et al., "Overexpression and functional analysis of cold-active β-galactosidase from Arthrobacter psychrolocatohilus strain F2," Protein Expression and Purification 54(2) (May 2007) 295-299 (Available on line Mar. 2007).
Palak-Szukalska et al., "A novel cold-active β-D-galactosidase with transglycosylation activity from the *Arthrobacter* sp. 32cB—Gene cloning, purification and characterization," Process Biochemistry 49 (214) 2122-2133 (Available online Sep. 28, 2014).
Schmidt et al., "Identification, cloning and expression of a cold-active β-galactosidase from a novel Arctic bacterium, Alkalilactibacillus ikkense," (2010) Environmental Technology, 31:10, 1107-1114 (Published online Jun. 2010).
Wang et al., "A novel cold-adapted β-galactosidase isolated from *Halomonas* sp. S62: gene cloning, purification and enzymatic characterization," World J. Microbiol Biotechnol (Mar. 2013) 29:1473-1480 (Published on line Mar. 2013).
Wierzbicka-Wos et al., "A novel cold-active β-D-galactosidase from the *Paracoccus* sp. 32d—gene cloning, purification and characterization," Microbial Cell Factories 2011, 10, No. 1, pp. 1-12.
DATABASE GenBank: ACE06986.1, (Jun. 8, 2012).
DATABASE GenBank: CDR82630.1, (Jun. 11, 2014).
"Chapter 3 Lactose content of milk and milk products," The American Journal of Clinical Nutrition, vol. 48, No. 4 pp. 1099-1044 (Oct. 1988) Available online, URL: https://academic.oup.com/ajcn/article-abstract/48/4/1099/4791817?redirectedFrom=fulltext.
Kreft et al., "Lactose hydrolysing ability of sonicated cultures of *Lactobacillus delbrueckii* ssp. bulgaricus 11842," le Lait, INRA Editions 81(3) pp. 355-364 (2001).
Office Action dated Jun. 9, 2021, in Application No. U.S. Appl. No. 16/998,706 (US 2021-0032615).
Rhimi et al., "Exploring the acidotolerance of β-galactosidase from *Lactobacillus delbrueckii* subsp. bulgaricus: an attractive enzyme for lactose bioconversion," Research in Microbiology, vol. 160 pp. 775-784 (2009) (Available online Sep. 2009).
Uniprot:G6F860 (Oct. 2020).
Van De Guchte, et. al., Beta-galactosidase [*Lactobacillus delbrueckii* subsp. bulgaaricus ATCC 11842 = JCM 1002] GenBank: CAI98003 [Feb. 2015].
Guo et al., "Protein tolerance to random amino acid change," PNAS, vol. 101, No. 25, pp. 9205-9210 (Jun. 2004).
Keskin et al., "A new, structurally nonredundant, diverse data set of protein-protein interfaces and its implications," Protein Science, vol. 13, pp. 1043-1055 (2004).
Klimova E.V. Advantages of using beta-galactosidase for hydrolysis of lactose and obtaining galactooligosaccharides; prospects for the use of the obtained products in industrial food technologies, Food and processing industry, Abstract journal, No. 4, 2008, p. 1269.
Ogurtsov A.N., Methods of bioinformatic analysis, Textbook, Kharkov, 2011, NTU "KhPI", pp. 4-5, 25.
Singer et al., "Genes & Genomes, A changing Perspective," University Science Books Mill Valley, CA (1998).
UniProt Accession Nos. TrEMBL, A7A6G3_BIFAD, Aug. 11, 2007, Q38UW6_LACSS, Nov. 11, 2005, Q38UW7_LACSS, Nov. 22, 2005, R5YYA0_9LACO, Jul. 24, 2013, F0TG79_LACAM, May 3, 2011, K2MWD3_BIFBI, Nov. 28, 2012, D4QFE8_BIFBI, Jul. 15, 2012, A0A133L394_BIFBR, Jul. 8, 2016, A0A1VSPPN6_9BIFI, Jul. 7, 2017, A0A1Q6ESN3_9BIFI, Apr. 12, 2016, A0A045FVZ6_LACDE, Mar. 16, 2017, 0A1L3JVR5_LACDL, Mar. 15, 2017, F0K2P6_LACD2, May 3, 2011 A0A0D5MI45_LACHE, May 27, 2015, A0A0D5MHU_LACHE, May 27, 2015, A0A1V8RDS6_BIFIN, Jun. 7, 2017, B3XQL8_LACRI, Nov. 23, 2008, B3XQL9_LACRI, Sep. 23, 2008, U6F4Q6_LACHE, Jan. 22, 2014, A8YWA0_LACH4, Jan. 15, 2008, LOCMGO_9LACO, Mar. 6, 2016, A0A0M410A2_STRR, Dec. 9, 2015, A0A0C0RIHO_9LACO, Nov. 11, 2015, 0A174B8K1_BIFAD, Apr. 7, 2016.
Office Action and Search Report dated May 14, 2021 in Russian Application No. 2019134223/10.
Office Action dated Apr. 12, 2022 in U.S. Appl. No. 16/998,706 (US 2021-0032615).
GenBank Accession No. CAI98003.1 Feb. 27, 2015.
Kreft et al., "Lactose hydrolysing ability of sonicated cultures of *Lactobacillus delbrueckii* ssp. bulgaricus 11842," Le Lait, vol. 81, No. 3, pp. 355-364 (Jan. 2001).
Rhimi et al., "Exploring the acidotolerance of B-galactosidase from *Lactobacillus delbrueckii* subsp. bulgaricus: an attractive enzyme for lactose bioconversion," Research in Microbiology, vol. 160, pp. 775-784 (Sep. 2009).
UniProt Accession No. F0K2P6, May 3, 2011.
UniProt Accession No. G6F860, Jan. 25, 2012.

\* cited by examiner

| G no | pH 6.7 at 4°C | pH 6,7 at 37°C | pH 6,7 at 43°C | % gal inhibition |
|---|---|---|---|---|
| 4 | 9,4 | 118,1 | 84,7 | 34 |
| 11 | 8,4 | 69,2 | 111,3 | 9 |
| 16 | 1,6 | 23,4 | 17,0 | 45 |
| 33 | 12,5 | 130,1 | 173,3 | 3 |
| 35 | 12,5 | 121,0 | 100,9 | 27 |
| 40 | 1,2 | 15,8 | 12,4 | 53 |
| 44 | 24,2 | 331,5 | 295,9 | 35 |
| 51 | 20,7 | 250,6 | 214,3 | 35 |
| 57 | 7,4 | 104,6 | 97,2 | 47 |
| 62 | 5,2 | 48,5 | 37,6 | 83 |
| 66 | 15,2 | 187,2 | 136,8 | 23 |
| 83 | 26,9 | 272,9 | 195,1 | 37 |
| 84 | 15,9 | 161,9 | 118,0 | 31 |
| 95 | 28,8 | 288,1 | 250,7 | 37 |
| 100 | 27,9 | 339,9 | 238,1 | 39 |
| 104 | 12,9 | 90,5 | 112,9 | 1 |
| 108 | 27,2 | 277,9 | 213,1 | 34 |
| 109 | 25,3 | 300,1 | 218,3 | 30 |
| 118 | 16,9 | 113,8 | 122,3 | 14 |
| 145 | 2,4 | 24,1 | 22,6 | 64 |
| 158 | 34,2 | 254,7 | 334,8 | 27 |
| 224 | 11,2 | 389,9 | 131,4 | 48 |
| 256 | 15,5 | 111,3 | 112,8 | 14 |
| 282 | 8,4 | 58,5 | 48,6 | 62 |
| 335 | 4,4 | 42,4 | 30,9 | 50 |
| 500 | 3,9 | 46,9 | 13,1 | 35 |
| 600 | 7,4 | 61,9 | 45,6 | 44 |

Figure 14

| G no | pH 5.5 at 4°C | pH 5.5 at 37°C | pH 5.5 at 43°C |
|---|---|---|---|
| 4 | 1,4 | 44,1 | 29,6 |
| 11 | 7,6 | 57,9 | 75,5 |
| 16 | 0,2 | 0,7 | 0,4 |
| 33 | 10,4 | 88,2 | 89,9 |
| 35 | 1,7 | 51,3 | 40,9 |
| 40 | 3,3 | 21,8 | 15,7 |
| 44 | 4,9 | 111,2 | 80,7 |
| 51 | 4,0 | 84,6 | 58,8 |
| 57 | 0,6 | 17,8 | 13,1 |
| 62 | 6,0 | 60,5 | 49,7 |
| 66 | 0,8 | 63,3 | 42,7 |
| 83 | 6,7 | 108,4 | 57,2 |
| 84 | 8,4 | 99,4 | 62,4 |
| 95 | 7,0 | 121,3 | 64,7 |
| 100 | 5,9 | 128,2 | 55,2 |
| 104 | 10,6 | 60,4 | 60,5 |
| 108 | 7,0 | 116,5 | 69,5 |
| 109 | 5,7 | 116,5 | 62,6 |
| 118 | 14,8 | 76,0 | 65,0 |
| 145 | 4,9 | 28,8 | 15,8 |
| 158 | 18,4 | 129,4 | 126,8 |
| 224 | 4,4 | 21,0 | 7,4 |
| 256 | 14,0 | 62,7 | 57,0 |
| 282 | 6,4 | 50,8 | 24,9 |
| 335 | 0,3 | 9,4 | 3,1 |
| 500 | 0,1 | 0,4 | 0,5 |
| 600 | 4,0 | 32,7 | 26,9 |

Figure 15

| G no | pH 4.5 at 4°C | pH 4.5 at 37°C | pH 4.5 at 43°C |
|---|---|---|---|
| 4 | 1,2 | 2,9 | 2,0 |
| 11 | 1,7 | 18,9 | 3,3 |
| 16 | 0,1 | 0 | 0 |
| 33 | 1,6 | 24,7 | 0,7 |
| 35 | 1,6 | 3,7 | 2,5 |
| 40 | 3,4 | 12,9 | 10,6 |
| 44 | 4,3 | 12,5 | 11,8 |
| 51 | 3,9 | 12,8 | 11,0 |
| 57 | 0,4 | 0,1 | -0,5 |
| 62 | 4,2 | 19,9 | 16,6 |
| 66 | 0,8 | 1,6 | 1,2 |
| 83 | 5,6 | 11,2 | 12,4 |
| 84 | 7,9 | 22,7 | 17,1 |
| 95 | 7,0 | 12,8 | 10,4 |
| 100 | 5,6 | 12,5 | 11,4 |
| 104 | 4,5 | 29,7 | 24,1 |
| 108 | 6,7 | 14,3 | 12,8 |
| 109 | 5,5 | 10,4 | 19,8 |
| 118 | 5,8 | 37,5 | 25,6 |
| 145 | 5,0 | 8,9 | 7,2 |
| 158 | 4,2 | 12,7 | 25,1 |
| 224 | 4,1 | 0,0 | 0,0 |
| 256 | 7,9 | 23,2 | 17,2 |
| 282 | 6,3 | 7,5 | 7,2 |
| 335 | 0,3 | 0 | 0,0 |
| 500 | 0,0 | 0 | 0 |
| 600 | 1,6 | 12,2 | 5,0 |

Figure 16

LACTASE ENZYMES WITH IMPROVED PROPERTIES

CROSS-REFERENCE TO RELATED APPLICATIONS

The present application is the U.S. National Stage of International Application No. PCT/EP2018/059250 filed Apr. 11, 2018, and claims priority to European Patent Application No. 17166021.0 filed Apr. 11, 2017.

SEQUENCE LISTING

The instant application contains a Sequence Listing which has been filed electronically in ASCII format and is hereby incorporated by reference in its entirety. Said ASCII copy, created on Jan. 21, 2020, is named 030427-0308 SL.txt and is 253,388 bytes in size.

FIELD OF THE INVENTION

The present invention relates to new improved peptide or dimeric peptides exhibiting beta-galactosidase enzyme activity as well as improved methods for reducing the lactose content in compositions, such as dairy products.

BACKGROUND OF THE INVENTION

In order to grow on milk, lactose hydrolysis is a good way for lactic acid bacteria to obtain glucose and galactose as carbon source. Lactase (beta-galactosidase; EC 3.2.1.23) is the enzyme that performs the hydrolysis step of the milk sugar lactose into monosaccharides. The commercial use of lactase is to break down lactose in dairy products. Lactose intolerant people have difficulties to digest dairy products with high lactose levels. It is estimated that about 70% of the world's population has a limited ability to digest lactose. Accordingly, there is a growing demand for dairy food products that contain no or only low levels of lactose.

Lactases have been isolated from a large variety of organisms, including microorganisms like *Kluyveromyces* and *Bacillus*. *Kluyveromyces*, especially *K. fragilis* and *K. lactis*, and other fungi such as those of the genera *Candida*, *Torula* and *Torulopsis*, are a common source of fungal lactases, whereas *B. coagulans* and *B. circulans* are well known sources for bacterial lactases. Several commercial lactase preparations derived from these organisms are available such as Lactozym® (available from Novozymes, Denmark), HA-Lactase (available from Chr. Hansen, Denmark) and Maxilact® (available from DSM, the Netherlands), all from *K. lactis*. All these lactases are so-called neutral lactases having a pH optimum between pH 6 and pH 8, as well as a temperature optimum around 37° C. When such lactases are used in the production of, e.g. low-lactose yoghurt, the enzyme treatment will either have to be done in a separate step before fermentation or rather high enzyme dosages have to be used because their activity will drop as the pH decreases during fermentation. Also, these lactases are not suitable for hydrolysis of lactose in milk performed at high temperature, which would in some cases be beneficial in order to keep the microbial count low and thus ensure high milk quality. Furthermore, the known lactases would not be suitable for use in a desired process for the production of ultra-heat treated (UHT) milk, wherein enzymes were added prior to the UHT treatment.

WO2010092057 and WO0104276 relates to cold-active beta-galactosidases. WO07110619 relates to beta-galactosidase with high transgalactosylating activity, whereas WO2009071539 relates to beta-galactosidase with lower transgalactosylating activity.

OBJECT OF THE INVENTION

It is an object of embodiments of the invention to provide beta-galactosidases with properties that enable the production of improved lactose-free or low-lactose products.

It is a further object of embodiments of the invention to provide beta-galactosidases with properties that enable the improved, such as easier, faster, more reliable or less expensive production methods for the lowering of lactose in a product, such as lactose-free or low-lactose products.

SUMMARY OF THE INVENTION

The present inventor(s) have identified beta-galactosidases with properties not previously described that enable the production of improved lactose-free or low-lactose products as well as enabling improved production methods for such lactose-free or low-lactose products. In particular these beta-galactosidases have been shown to be very stable with relatively high activity at a very broad range of both temperatures as well as pH values. They are also useable at specific temperatures, such as at high temperatures and pH values not normally seen with these enzymes. First of all, this enables to the use of beta-galactosidases at specific pH values and temperatures that were not known to be possible. It also enables the use of the same specific enzyme in several different applications, which is highly requested in the industry.

So, in a first aspect the present invention relates to a peptide exhibiting beta-galactosidase enzyme activity, which has an amino acid sequence represented by SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, or an amino acid sequence thereof having not more than 1, 2, 3, 4, 5, 6, 7, 8, 9, 10, 11, 12, 13, 14, 15, 16, 17, 18, 19, 20, 21, or 22 amino acid substitutions, additions or deletions.

In a second aspect the present invention relates to a dimeric peptide exhibiting beta-galactosidase enzyme activity, which dimeric peptide consist of two peptides having an amino acid sequence represented by SEQ ID NO: 2 and 3; 5 and 6; 20 and 21; 23 and 24; 26 and 27; or 28 and 29, or enzymatically active fragments thereof, or an amino acid sequence of any one thereof having not more than 1, 2, 3, 4, 5, 6, 7, 8, 9, 10, 11, 12, 13, 14, 15, 16, 17, 18, 19, 20, 21, or 22 amino acid substitutions, additions or deletions.

In a third aspect the present invention relates to a nucleotide sequence which encodes a peptide or dimeric peptide exhibiting beta-galactosidase enzyme activity according to the invention.

In a further aspect the present invention relates to a host cell comprising a nucleotide sequence which encodes a peptide or dimeric peptide exhibiting beta-galactosidase enzyme activity according to the invention.

In a further aspect the present invention relates to a method for producing a peptide or dimeric peptide exhibiting beta-galactosidase enzyme activity according to the invention, which method comprises the expression of a vector containing a nucleotide sequence according to the invention in a suitable host cell; and purifying said peptide or dimeric peptide from the expression products of said host cell.

In a further aspect the present invention relates to a method for reducing the lactose content in a composition containing lactose, such as in a dairy products, comprising the step of contacting said composition with a peptide or dimeric peptide exhibiting beta-galactosidase enzyme activity, which peptide has an amino acid sequence represented by SEQ ID NO:1-33; or which dimeric peptide consist of two peptides having an amino acid sequence represented by SEQ ID NO: 2 and 3, 5 and 6, 20 and 21, 23 and 24, 26 and 27, or 28 and 29; or a sequence with at least 80% sequence identity to any one of said sequences; or a host cell expressing any one of said peptides, at a pH ranging from 3-10 and at a temperature ranging from 0° C.-140° C.

In a further aspect the present invention relates to the use of a peptide or dimeric peptide exhibiting beta-galactosidase enzyme activity, which peptide has an amino acid sequence represented by SEQ ID NO:1-33, or which dimeric peptide consist of two peptides having an amino acid sequence represented by SEQ ID NO: 2 and 3, 5 and 6, 20 and 21, 23 and 24, 26 and 27, or 28 and 29; or a sequence with at least 80% sequence identity to any one of said sequences; or a host cell expressing any one of said peptides for producing a dairy product with a reduced lactose content.

In some embodiments this composition containing lactose or this dairy product is selected from the group consisting of lactose-free milk, low-lactose milk, yoghurt, including unpasteurized as well as pre and post-pasteurized yoghurt, cheese, fermented milk products, dietary supplement and probiotic dietary products. In some other embodiments this host cell is any one selected from a bacteria of the genus *Bifidobacterium*, such as *Bifidobacterium adolescentis, Bifidobacterium bifidum, Bifidobacterium breve, Bifidobacterium catenulatum, Bifidobacterium longum* or from the genus *Lactobacillus*, such as *L. sakei, L. amylovorus, L. delbrueckii* subsp. *bulgaricus, L. delbrueckii* subsp. *lactis, L. delbrueckii* subsp. *Indicus, L. crispatus, L. reuteri, L. helveticus* or from *Streptococcus thermophilus*. In some other embodiments the lactose concentration is reduced to less than about 1%, such as to less than about 0.1% or lower, such as to less than about 0.01%.

In a further aspect the present invention relates to a method for producing a dairy product the method comprising the steps of:
a) providing a milk-based substrate comprising lactose;
b) adding a peptide or dimeric peptide exhibiting beta-galactosidase activity, which peptide has an amino acid sequence represented by SEQ ID NO:1-33; or which dimeric peptide consist of two peptides having an amino acid sequence represented by SEQ ID NO: 2 and 3, 5 and 6, 20 and 21, 23 and 24, 26 and 27, or 28 and 29; or a sequence with at least 80% sequence identity to any one of said sequences to said milk-based substrate comprising lactose; and
c) treating said milk-based substrate with said peptide or dimeric peptide exhibiting beta-galactosidase activity.

In a further aspect the present invention relates to a dairy product prepared by a method according to the invention.

In a further aspect the present invention relates to a food product, such as a dairy product comprising a peptide or dimeric peptide exhibiting beta-galactosidase enzyme activity, which peptide has an amino acid sequence represented by SEQ ID NO:1-33, or which dimeric peptide consist of two peptides having an amino acid sequence represented by SEQ ID NO: 2 and 3, 5 and 6, 20 and 21, 23 and 24, 26 and 27, or 28 and 29; or a sequence with at least 80% sequence identity to any one of said sequences.

In a further aspect the present invention relates to a food product, such as a dairy product comprising a host cell expressing a peptide or dimeric peptide exhibiting beta-galactosidase enzyme activity, which peptide has an amino acid sequence represented by SEQ ID NO:1-33, or which dimeric peptide consist of two peptides having an amino acid sequence represented by SEQ ID NO: 2 and 3, 5 and 6, 20 and 21, 23 and 24, 26 and 27, or 28 and 29; or a sequence with at least 80% sequence identity to any one of said sequences. In some specific embodiments such a food product is selected from beverages, infant foods, cereals, bread, biscuits, confectionary, cakes, food supplements, dietary supplements, probiotic comestible products, prebiotic comestible products, animal feeds, poultry feeds and medicaments, or a dairy product selected from the group consisting of lactose-free milk, low-lactose milk, dried milk powder, baby milks, yoghurt, ice cream, cheese, fermented milk products, dietary supplement and probiotic dietary products.

LEGENDS TO THE FIGURE

FIG. 1. The specific activity of the purified enzymes determined at pH 6.7 at 37° C. with lactose as substrate, described SUAL-1, discussed in example 6. The measured standard deviation at the given condition was less than 6%.

Figure 2:
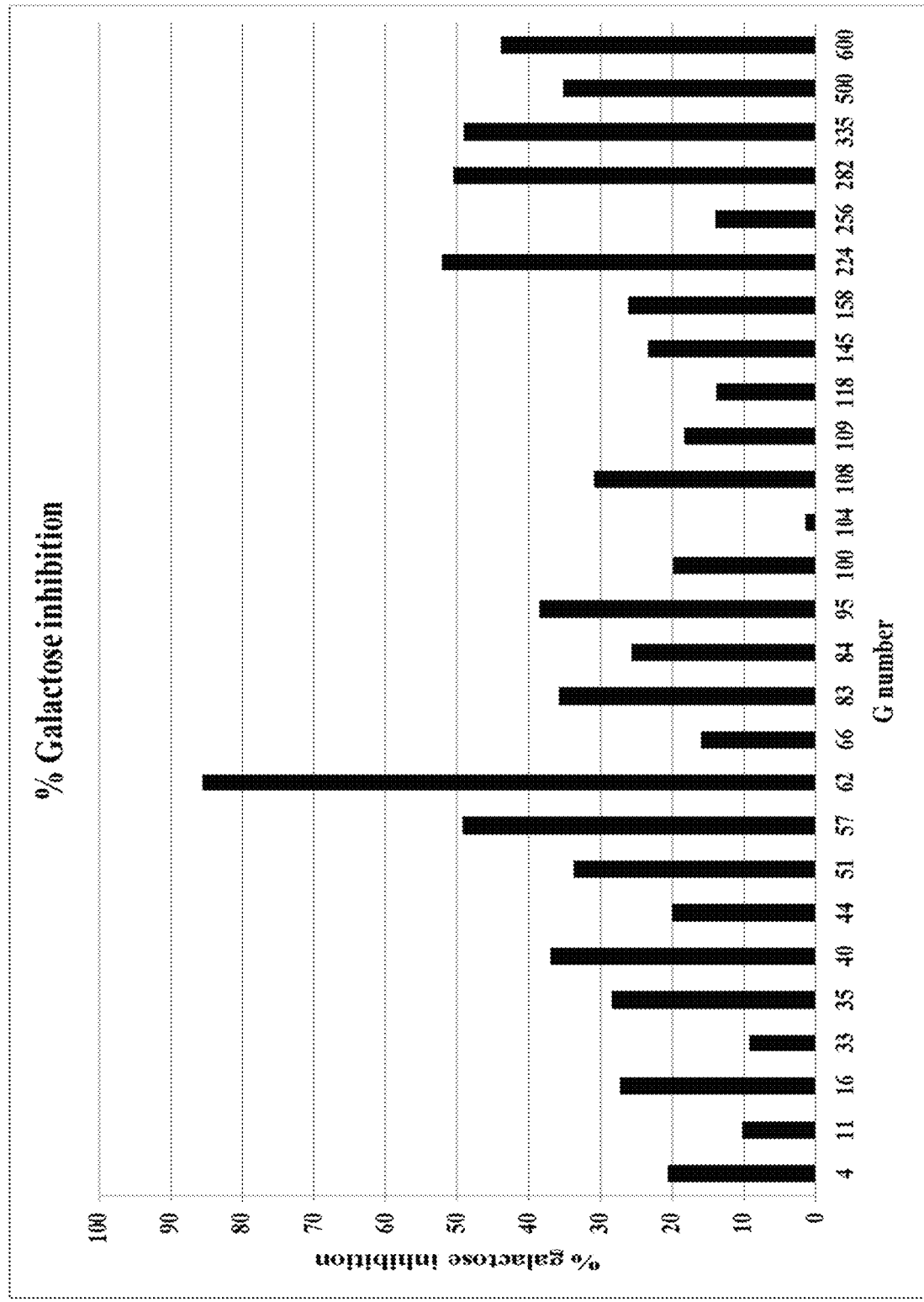

FIG. 2. The specific activity of the purified enzymes determined at pH 6.7 at 37° C. in presence of galactose, described as SUAG, discussed in example 7. The measured standard deviation at the given condition was less than 15%.

Figure 3:
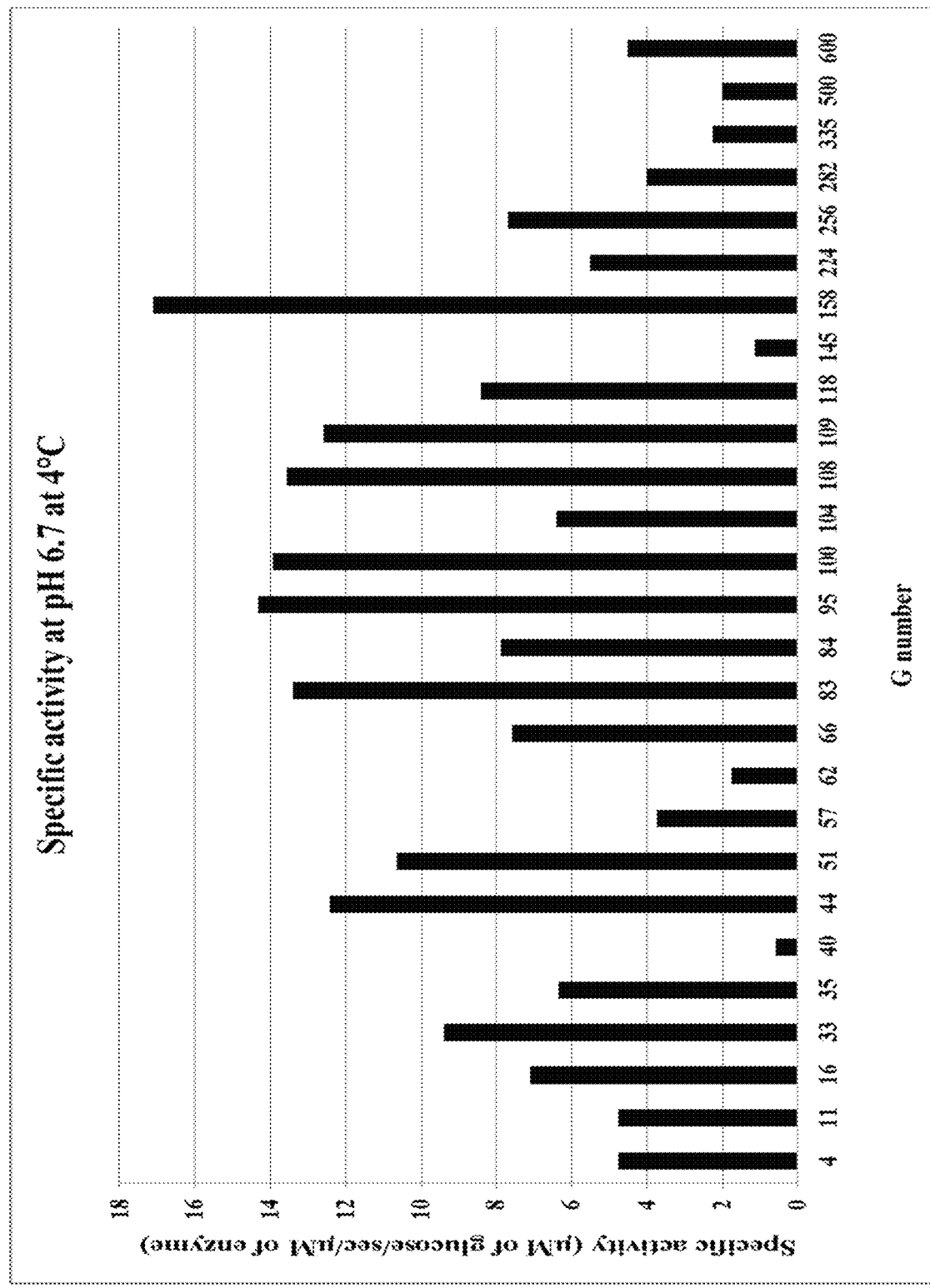

FIG. 3. The specific activity of the purified enzymes determined at pH 6.7 at 4° C. with lactose as substrate, described as SUAL-2, discussed in example 8. The measured standard deviation at the given condition was less than 5%.

Figure 4:
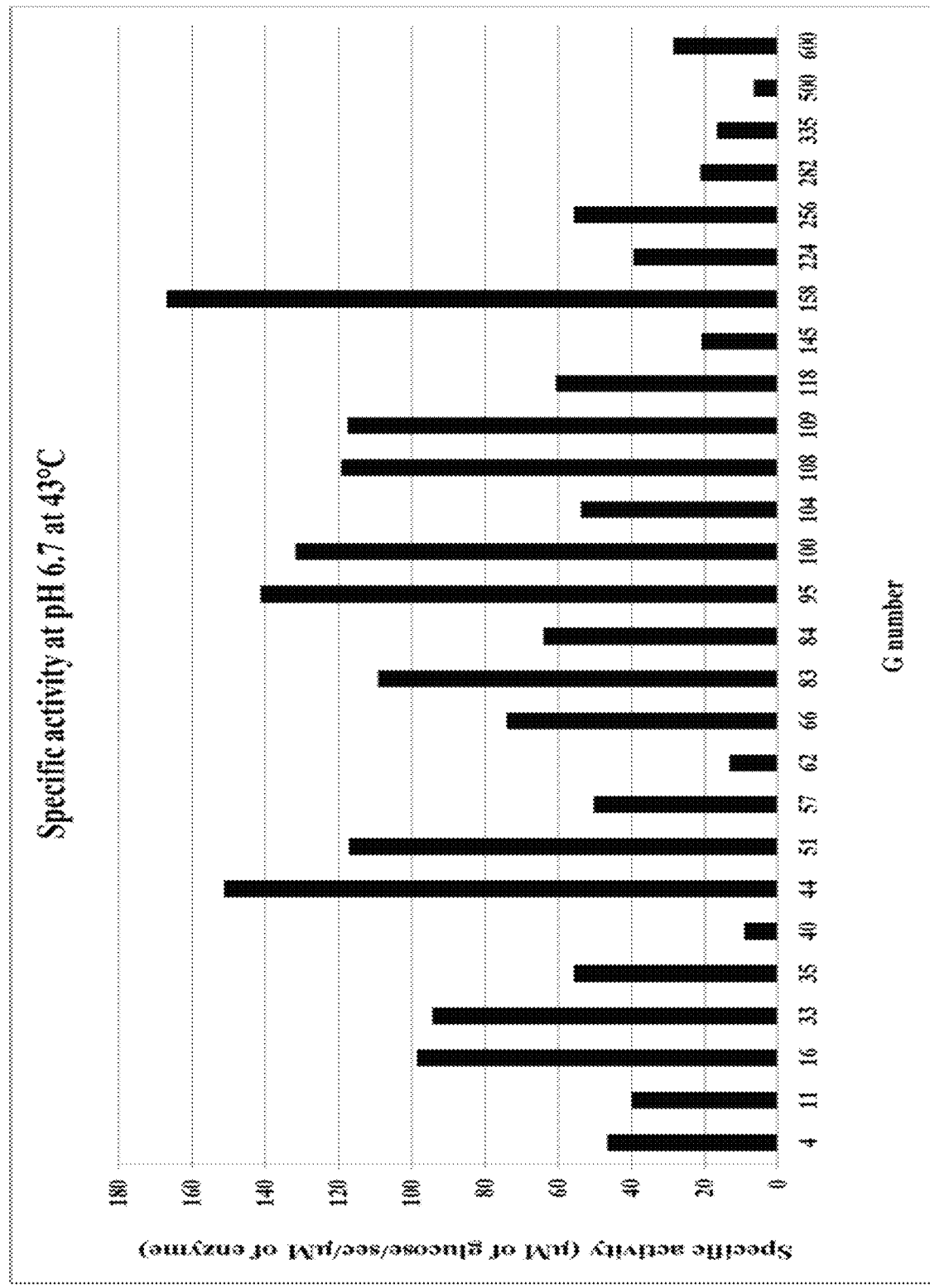

FIG. 4. The specific activity of the purified enzymes determined at pH 6.7 at 43° C. with lactose as substrate, described as SUAL-3, discussed in example 9. The measured standard deviation at the given condition was less than 5%.

Figure 5:
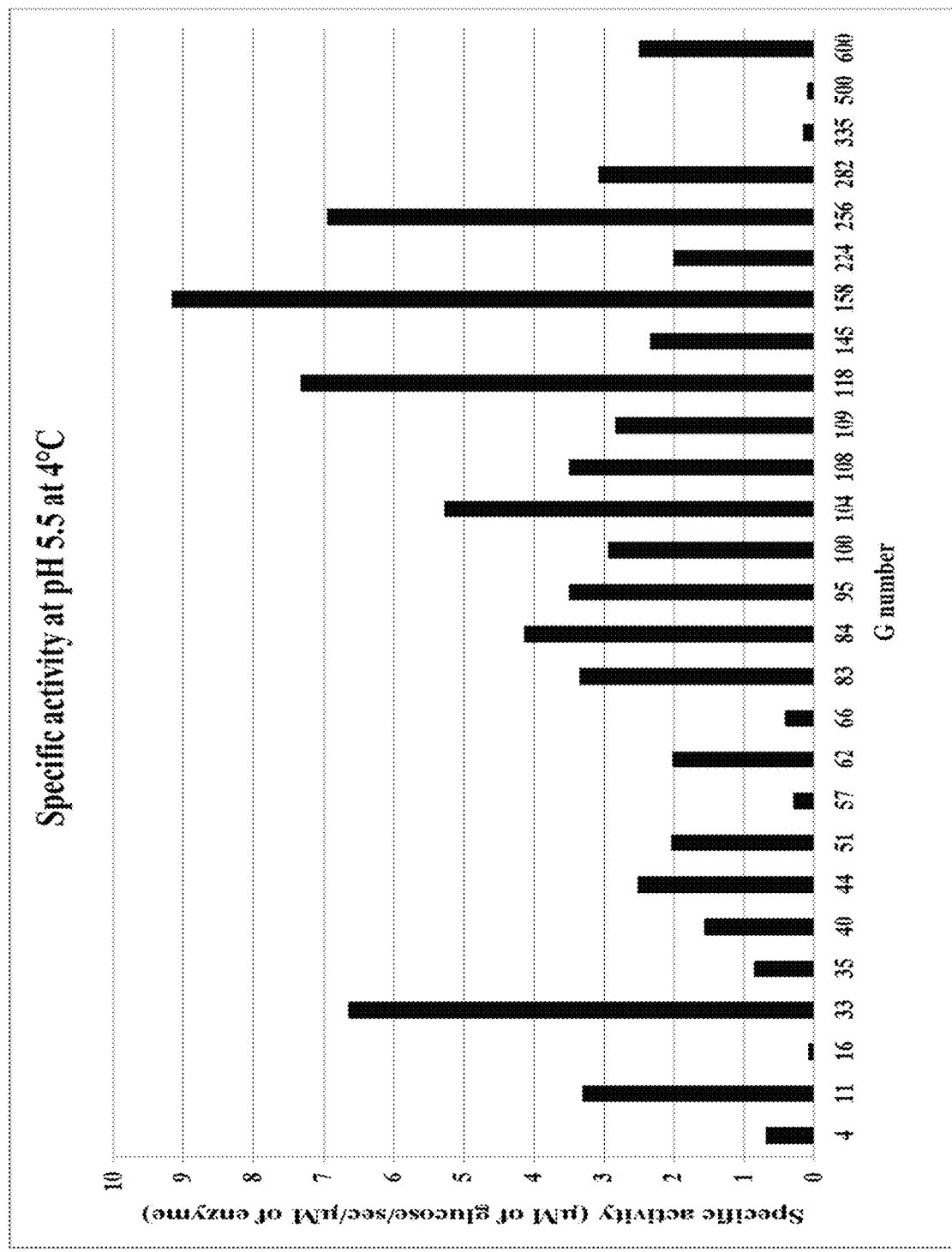

FIG. 5. The specific activity of the purified enzymes determined at pH 5.5 at 4° C. with lactose as substrate, described as SUAL-4, discussed in example 10. The measured standard deviation at the given condition was less than 5%.

Figure 6:
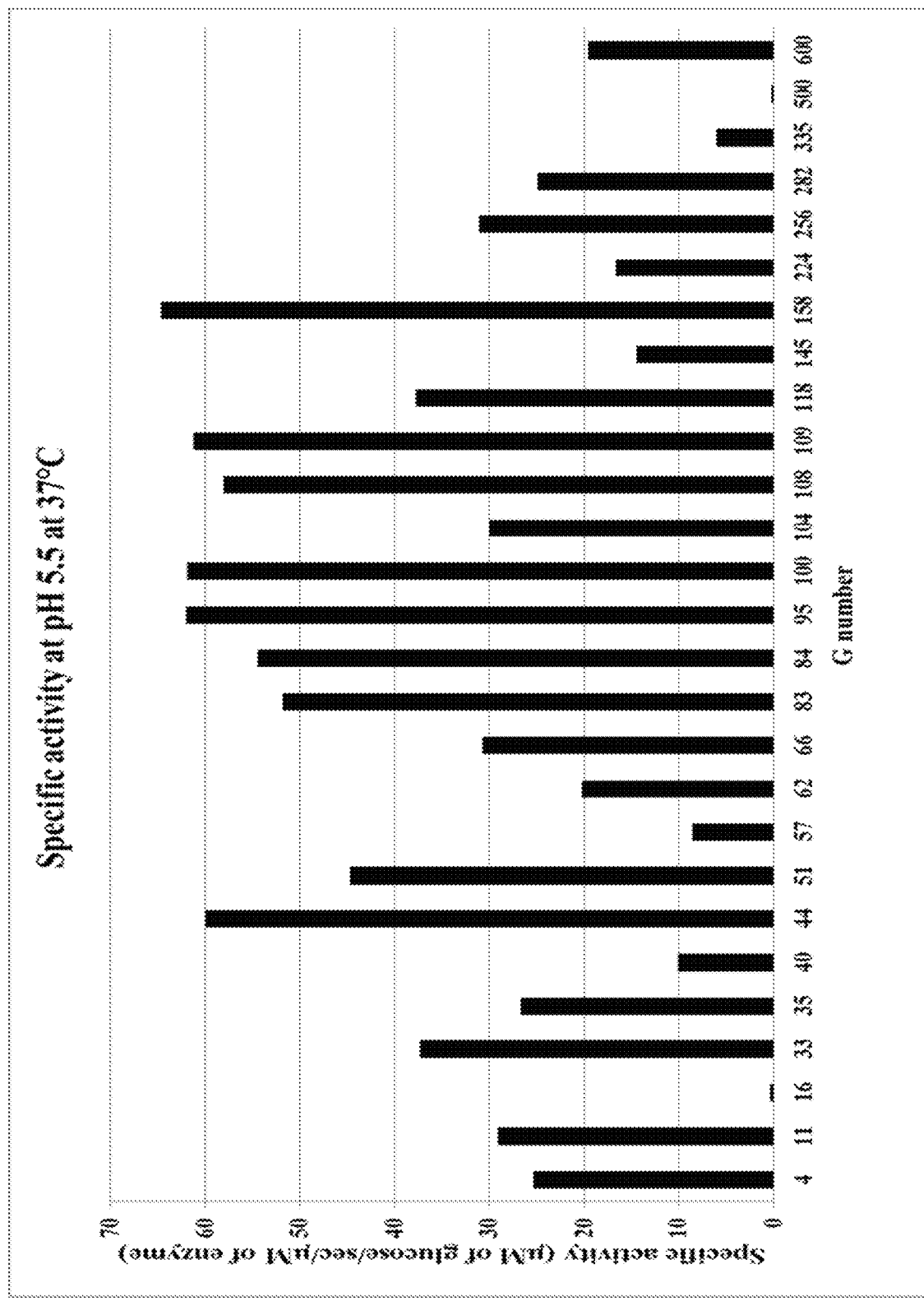

FIG. 6. The specific activity of the purified enzymes determined at pH 5.5 at 37° C. with lactose as substrate, described as SUAL-5, discussed in example 11. The measured standard deviation at the given condition was less than 5%.

Figure 7:
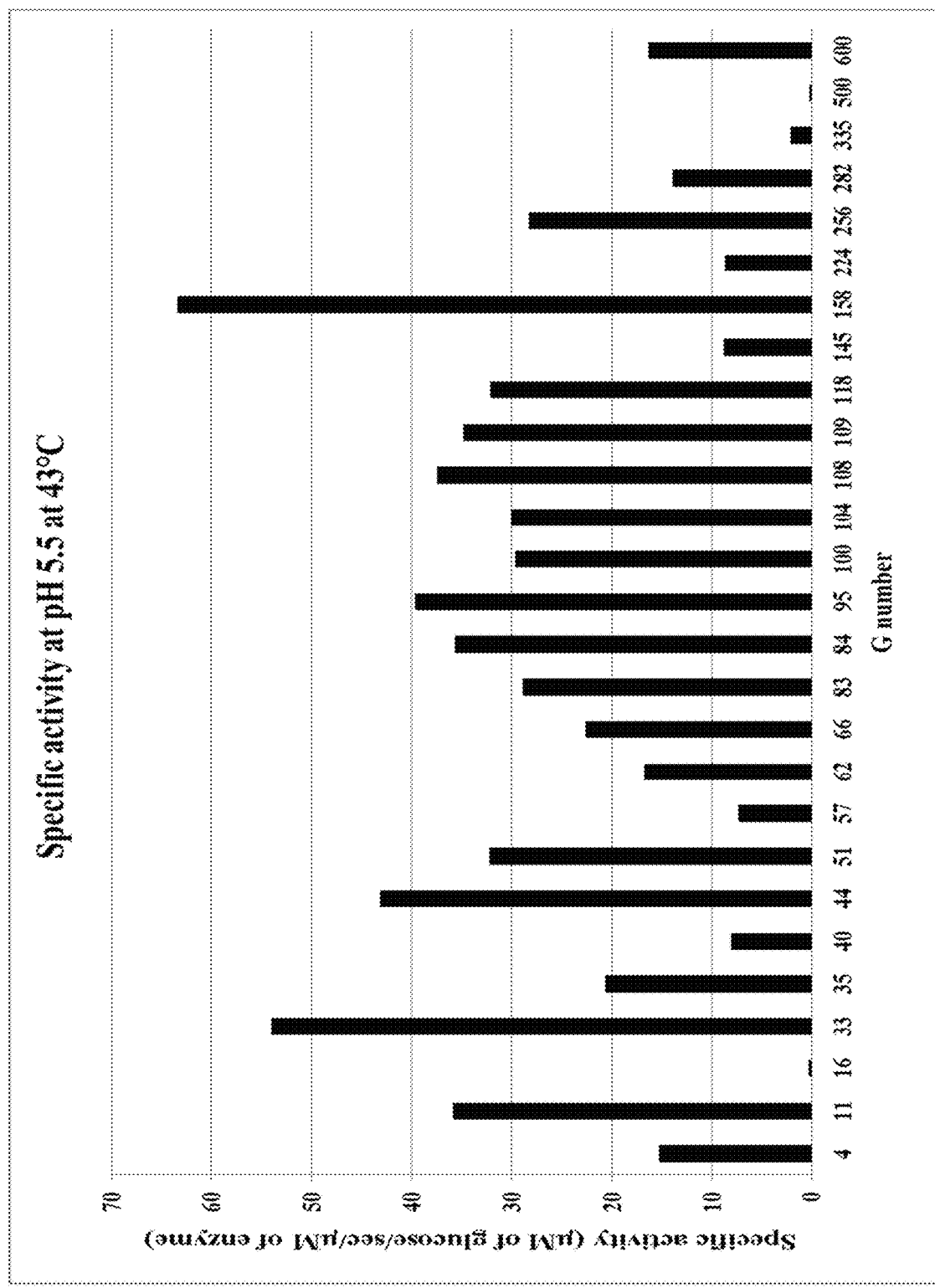

FIG. 7. The specific activity of the purified enzymes determined at pH 5.5 at 43° C. with lactose as substrate, described as SUAL-6, discussed in example 12. The measured standard deviation at the given condition was less than 5%.

Figure 8:
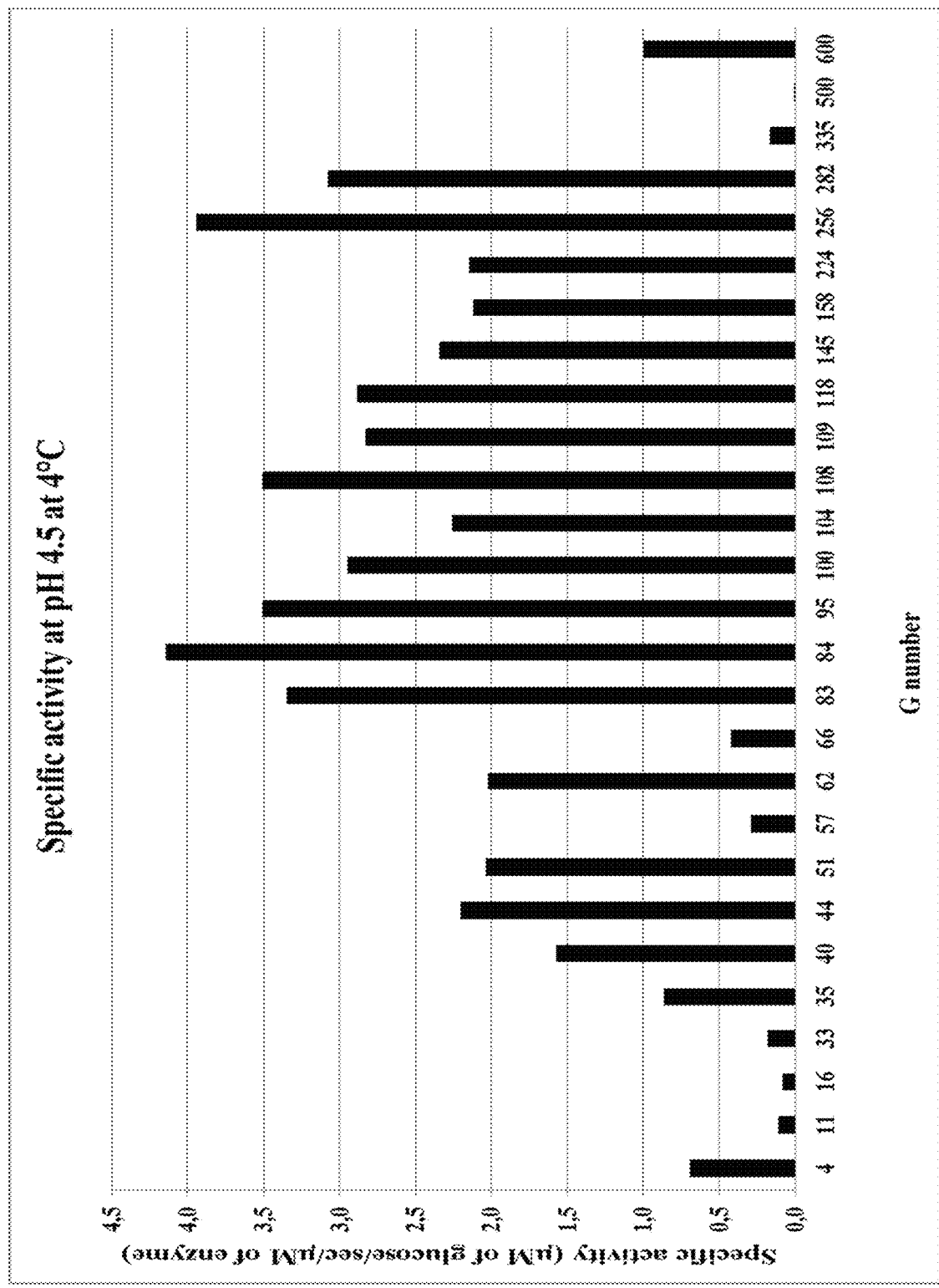

FIG. 8. The specific activity of the purified enzymes determined at pH 4.5 at 4° C. with lactose as substrate, described as SUAL-7, discussed in example 13. The measured standard deviation at the given condition was less than 5%.

Figure 9:
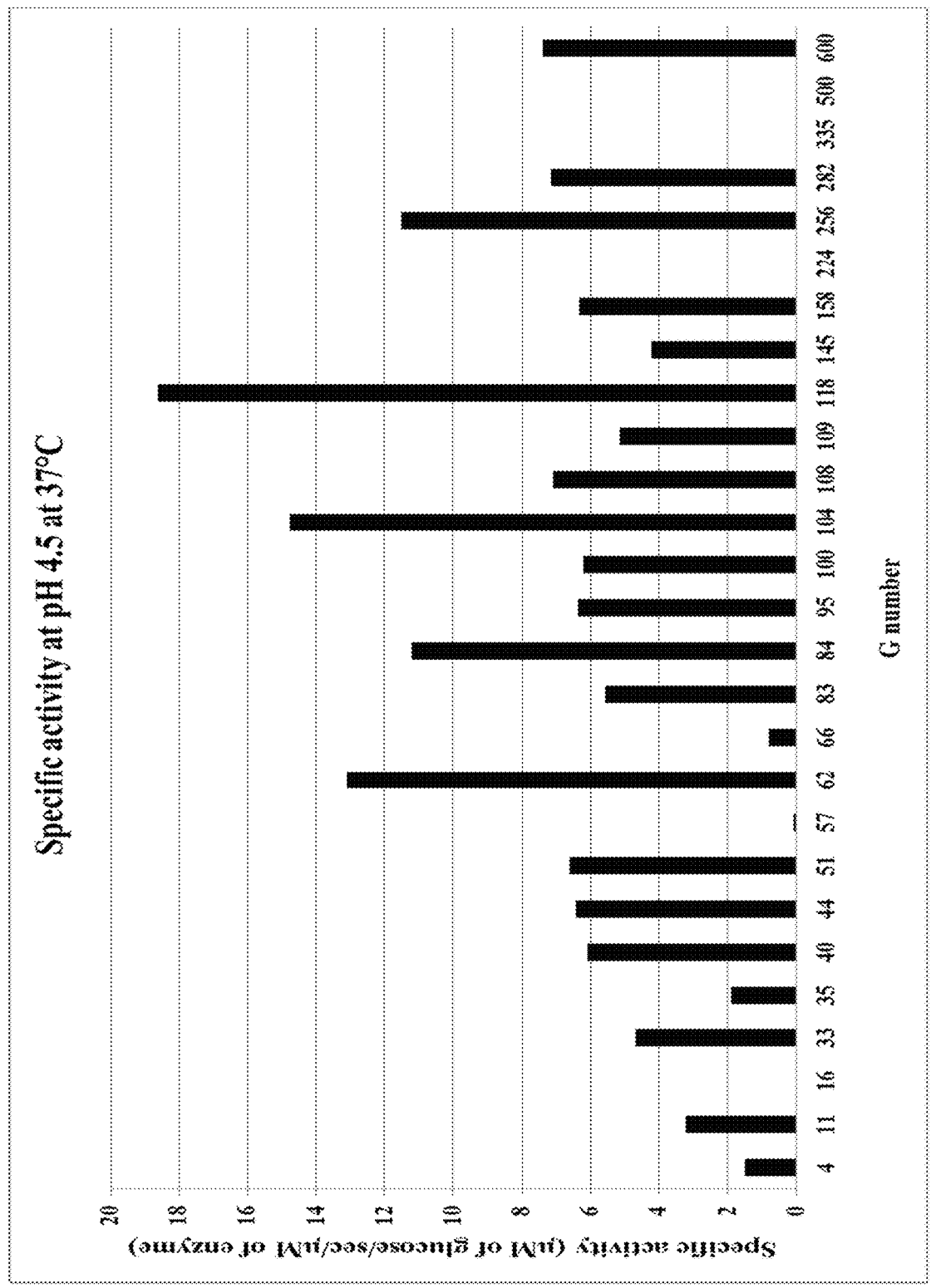

FIG. 9. The specific activity of the purified enzymes determined at pH 4.5 at 37° C. with lactose as substrate, described as SUAL-8, discussed in example 14. The measured standard deviation at the given condition was less than 5%.

Figure 10:
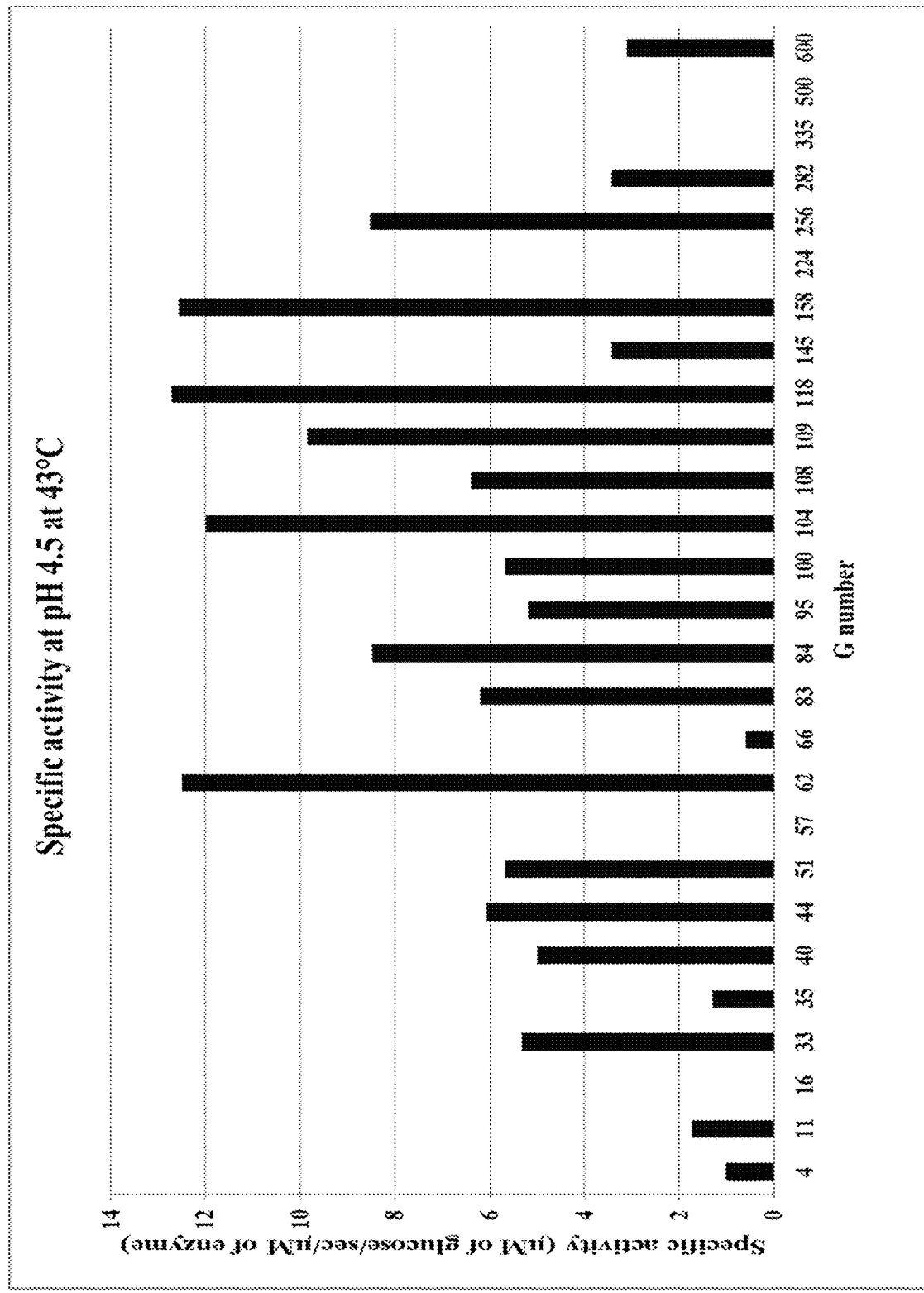

FIG. 10. The specific activity of the purified enzymes determined at pH 4.5 at 43° C. with lactose as substrate, described as SUAL-9, discussed in example 15. The measured standard deviation at the given condition was less than 5%.

Figure 11:
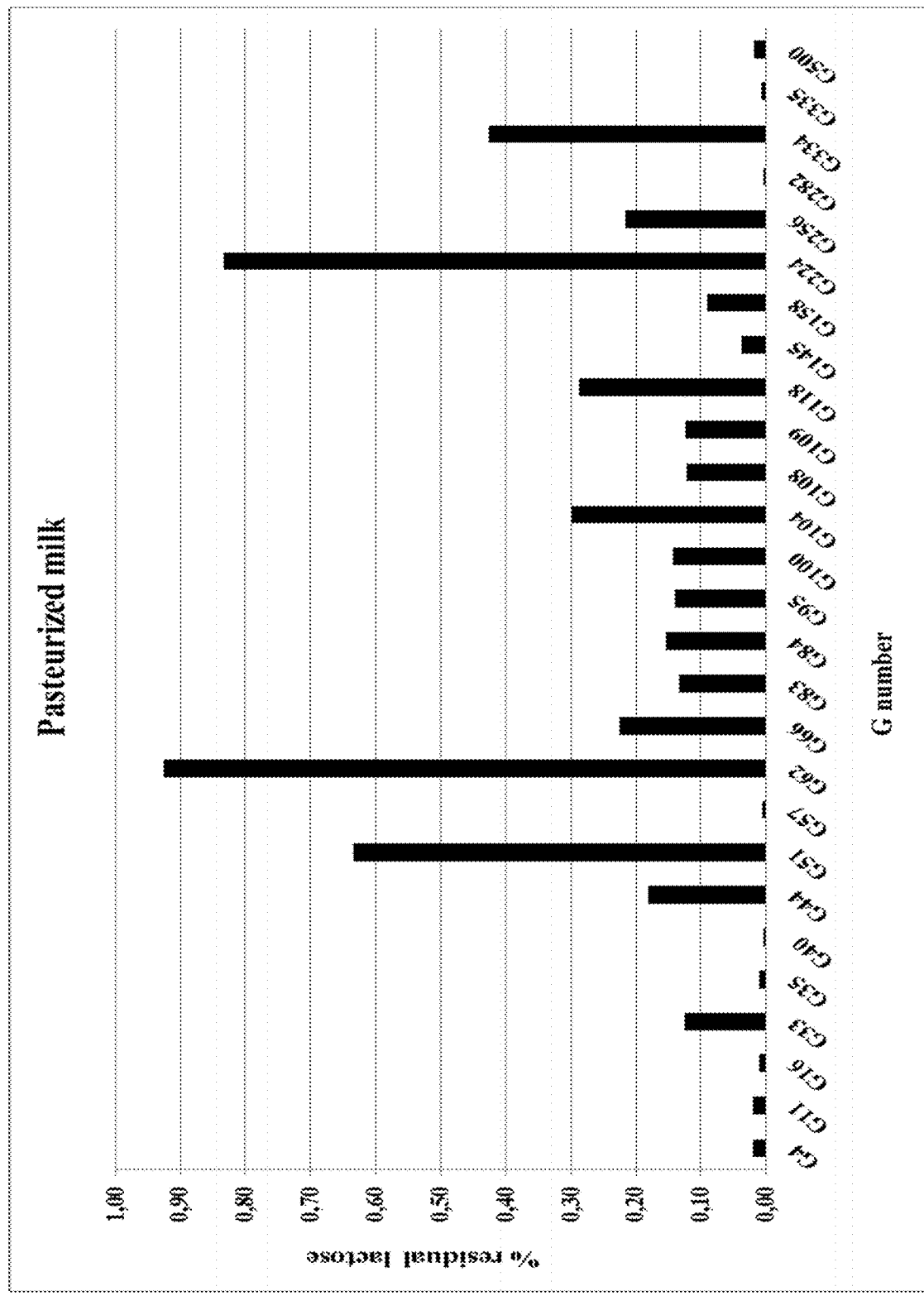

FIG. 11. The percentage residual lactose in the pasteurized milk, after the treatment with a fixed amount of the enzyme, after 24 hr at 5° C. determined using HPLC.

Figure 12:
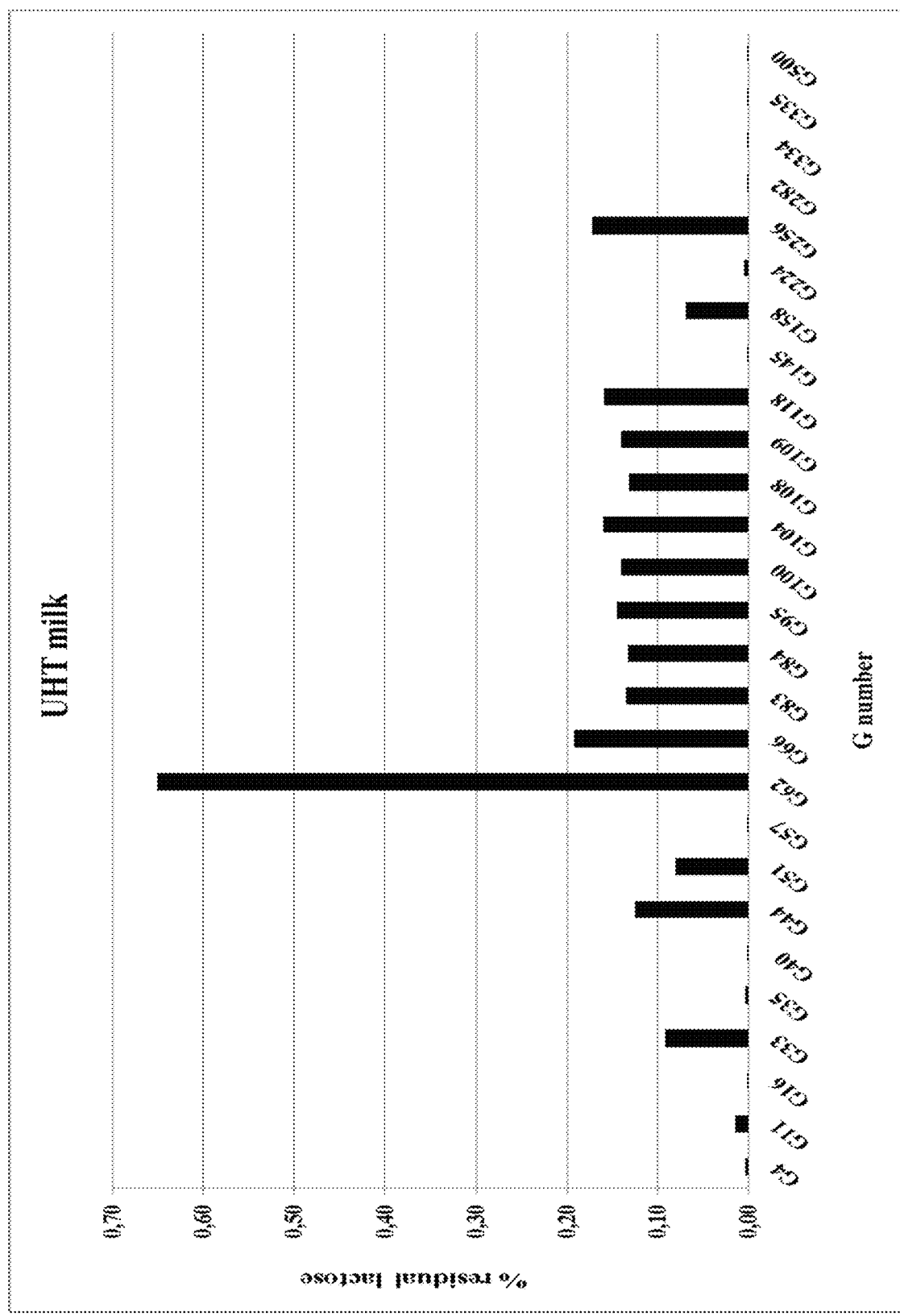

FIG. 12. The percentage residual lactose in the UHT milk, after the treatment with a fixed amount of the enzyme, after 24 hr at 25° C. determined using HPLC.

Figure 13:
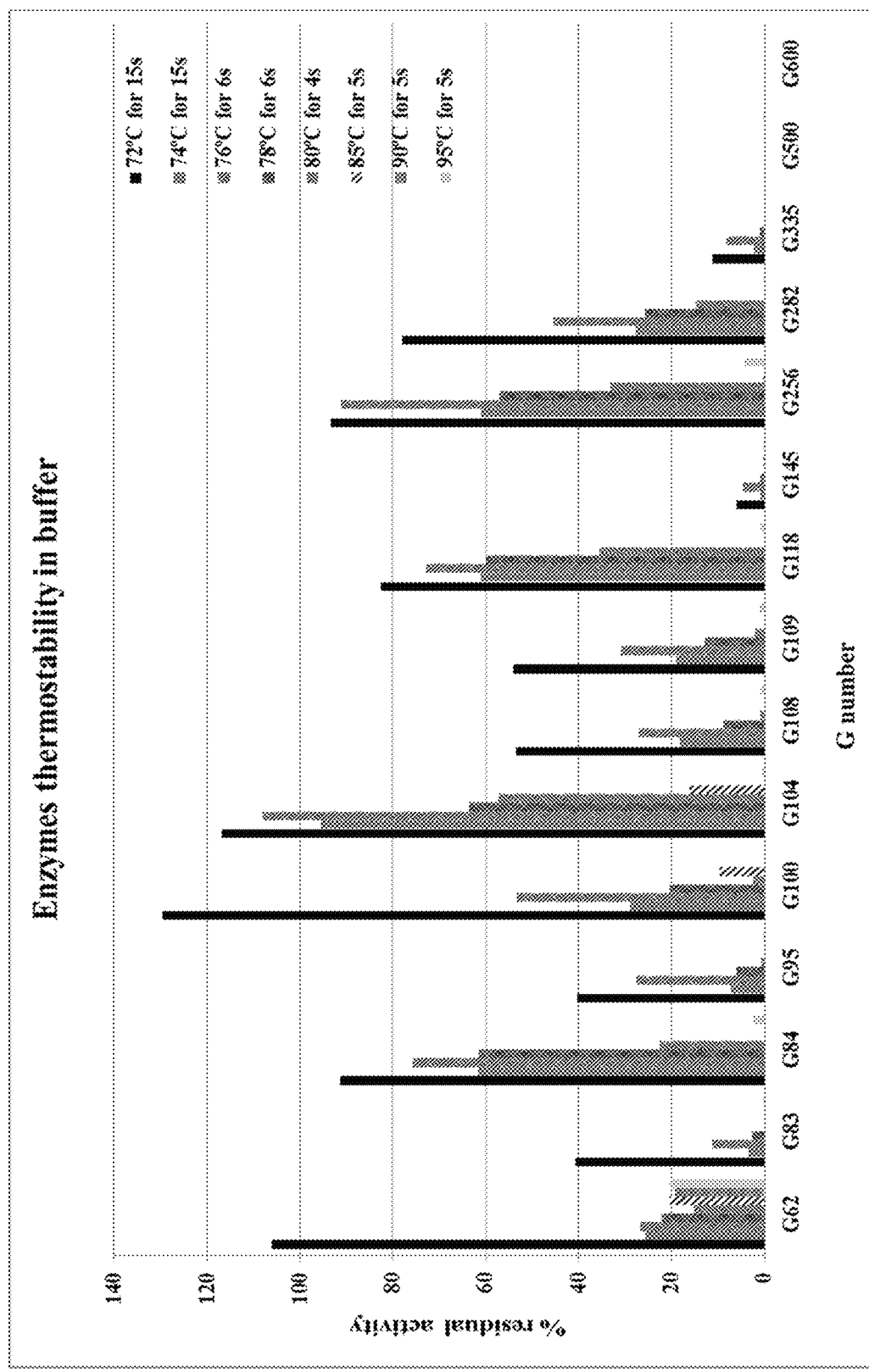

FIG. 13. The percentage residual activity of the purified enzymes at elevated temperatures, determined using lactose as substrate. The activity at pH 6.7 at 37° C. was considered as 100%.

FIG. 14. The specific activity of the purified enzymes determined at pH 6.7 at 4° C., 37° C. and 43° C. The measured specific activity is described as μmol glucose formed per minute per mg of enzyme. The galactose inhibition method is described in example 7 and calculated based on the μmol glucose formed per minute per mg of enzyme.

FIG. 15. The specific activity of the purified enzymes determined at pH 5.5 at 4° C., 37° C. and 43° C. The measured specific activity is described as μmol glucose formed per minute per mg of enzyme.

FIG. 16. The specific activity of the purified enzymes determined at pH 4.5 at 4° C., 37° C. and 43° C. The measured specific activity is described as μmol glucose formed per minute per mg of enzyme.

DETAILED DISCLOSURE OF THE INVENTION

The present inventors have found that certain peptides and dimeric peptides exhibiting beta-galactosidase enzyme activity are surprisingly stabile at many different physical conditions giving a relatively high activity outside of the ranges normally seen to be optimal for this class of enzymes.

Accordingly, these by the present inventors identified enzymes have a relatively high activity around 4° C. or 5° C. and may thus be used for lactose hydrolysis in the production of e.g. fresh milk. Moreover, the enzymes have also a relatively high activity in the range of 10° C.-25° C. and the exact same enzymes may thus be used for lactose hydrolysis in UHT milk. This feasibility of the enzymes even at broad ranges of temperatures is highly relevant since milk may be stored at room/ambient temperature which may be different in different parts of the world, also depending on the seasons. For the UHT treatment, the temperature is typically either around 135° C. or around 140° C. It is highly wanted that the enzymes may have activity in the range of a temperature up to 140° C. so that the enzyme may be added to raw milk before the UHT step. In the current practices the enzyme is added after the UHT step because the enzymes known in the art has a significant decrease in functional activity, such as to a value below measurable activity following the high heat treatment step. Also the milk is stored at room temperature which may vary significantly in different parts of the world.

Also these novel improved peptides exhibiting beta-galactosidase enzyme activity have been found to have activity in the temperature range normally used for pasteurization. Accordingly, these enzymes may be added to raw milk prior to pasteurization. It is to be understood that the enzymes known in the art has a significant decrease in functional activity, such as to a value below measurable activity following a pasteurization step.

A further advantage of these novel improved peptides exhibiting beta-galactosidase enzyme activity is that they have a relatively low degree of galactose inhibition. The lower galactose inhibition of these novel enzymes is highly relevant for applications wherein very low lactose concentrations are desired.

In terms of applicability for fermented products it is highly advantageous that the enzymes as described herein have a high beta-galactosidase enzymatic activity at a relatively broad temperature range of between 4° C.-43° C., such as around 37° C., where fermentation would normally be optimal, but also that this activity of the beta-galactosidase enzyme is present at low pH, such as down to 4.5, or down to 4.0, or down to 3.5, or even down to pH 3.

In summary, it has been found by the present inventors that some peptides exhibiting beta-galactosidase enzyme activity is active over wide range of temperature, active over wide range of pH, has a general high hydrolytic activity without side activities, that these peptides have no or little galactose inhibition, such as less than 60%, and that they are stable over long-term storage.

The beta-galactosidase activity may be determined by measuring the amount of released glucose after incubation with lactose at set conditions. Released glucose can be detected by a coloring reaction.

Definitions

The term "milk", as used herein and in the context of the present invention, is to be understood as the lacteal secretion obtained by milking any mammal, such as cow, sheep, goats, buffalo or camel.

The term "composition containing lactose" as used herein refers to any composition, such as any liquid that contain lactose in significant measurable degree, such as a lactose content higher than 0.002% (0.002 g/100 ml). Encompassed within this term are milk and milk-based substrates.

The term "milk-based substrate", in the context of the present invention, may be any raw and/or processed milk material. Useful milk-based substrates include, but are not limited to solutions/suspensions of any milk or milk like products comprising lactose, such as whole or low fat milk, skim milk, buttermilk, low-lactose milk, reconstituted milk powder, condensed milk, solutions of dried milk, UHT milk, whey, whey permeate, acid whey, cream, fermented milk products, such as yoghurt, cheese, dietary supplement and probiotic dietary products. Typically the term milk-based substrate refers to a raw or processed milk material that is processed further in order to produce a dairy product.

The term "pasteurization" as used herein refers to the process of reducing or eliminating the presence of live organisms, such as microorganisms in a milk-based substrate. Preferably, pasteurization is attained by maintaining a specified temperature for a specified period of time. The specified temperature is usually attained by heating. The temperature and duration may be selected in order to kill or inactivate certain bacteria, such as harmful bacteria, and/or to inactivate enzymes in the milk. A rapid cooling step may follow.

The term "dairy product" as used herein may be any food product wherein one of the major constituents is milk-based. Usually the major constituent is milk-based and in some embodiments, the major constituent is a milk-based substrate which has been treated with an enzyme having beta-galactosidase activity according to a method of the present invention.

A dairy product according to the invention may be, e.g., skim milk, low fat milk, whole milk, cream, UHT milk, milk having an extended shelf life, a fermented milk product, cheese, yoghurt, butter, dairy spread, butter milk, acidified milk drink, sour cream, whey based drink, ice cream, condensed milk, dulce de leche or a flavored milk drink.

A dairy product may additionally comprise non-milk components, e.g. vegetable components such as, e.g., vegetable oil, vegetable protein, and/or vegetable carbohydrates. Dairy products may also comprise further additives such as, e.g., enzymes, flavoring agents, microbial cultures such as probiotic cultures, salts, sweeteners, sugars, acids, fruit, fruit prep, fruit juices, or any other component known in the art as a component of, or additive to, a dairy product.

The terms "fermented dairy product" or "fermented milk product" as used herein is to be understood as any dairy product wherein any type of fermentation forms part of the production process. Examples of fermented dairy products are products like yoghurt, buttermilk, creme fraiche, quark and fromage frais. A fermented dairy product may be produced by or include steps of any method known in the art.

The term "fermentation" as used herein refers to the conversion of carbohydrates into alcohols or acids through the action of a microorganism. In some embodiments fermentation according to the present invention comprises the conversion of lactose to lactic acid. In the context of the present invention, "microorganism" may include any bacterium or fungus being able to ferment the milk substrate.

The term "increased beta-galactosidase enzyme activity" as used herein refers to a relatively higher specific activity of a beta-galactosidase enzyme in comparison to a reference sequence.

The term "peptide exhibiting beta-galactosidase enzyme activity" as used herein refers to any peptide, which has enzymatic activity to catalyze the hydrolysis of the disaccharide lactose into its component monosaccharides glucose and galactose. This peptide may also be referred to as a lactase or simply a beta-galactosidase (EC: 3.2.1.23).

The terms "peptide" and "oligopeptide" as used in the context of this present application are considered synonymous (as is commonly recognized) and each term can be used interchangeably as the context requires to indicate a chain of at least two amino acids coupled by peptidyl linkages. The word "polypeptide" is used herein for chains containing more than ten amino acid residues. All peptide and polypeptide formulas or sequences herein are written from left to right and in the direction from amino terminus to carboxy terminus. "Proteins" as used herein refers to peptide sequences as they are produced by some host organism and may include posttranslational modification, such as added glycans.

The terms "amino acid" or "amino acid sequence," as used herein, refer to an oligopeptide, peptide, polypeptide, or protein sequence, or a fragment of any of these, and to naturally occurring or synthetic molecules. In this context, "fragment" refer to fragments of a peptide exhibiting beta-galactosidase enzyme activity, which retain some enzymatic activity. Where "amino acid sequence" is recited herein to refer to an amino acid sequence of a naturally occurring protein molecule, "amino acid sequence" and like terms are not meant to limit the amino acid sequence to the complete native amino acid sequence associated with the recited peptide molecule.

Exemplary peptides of the invention also include fragments of at least about 50, 100, 150, 200, 250, 300, 350, 400, 450, 500, 550, 600, 650, 700, 750, 800 or more residues in length, or over the full length of an enzyme. Accordingly a "peptide fragment" or "enzymatically active fragment" of the invention are fragments that retain at least some functional enzymatic activity. Typically a peptide fragment of the invention will still contain the functional catalytic domain or other essential active sites of the peptide exhibiting beta-galactosidase enzyme activity. Other domains may be deleted.

Typically, the specific beta-galactosidase enzyme activity will be measured and indicated as μmol of glucose formed/min/mg of enzyme used. This specific value however will vary depending on conditions applied, such as temperature, and pH. Accordingly, values for beta-galactosidase enzyme activity may also be referred to as relative to a reference known enzyme, such as the beta-galactosidase enzyme defined by SEQ ID NO:34 OR SEQ ID NO:35.

Alternatively the specific beta-galactosidase enzyme activity may be measured and indicated as μM of glucose formed per second per μM of enzyme used. This specific value however will vary depending on conditions applied, such as temperature, and pH. ½

Unless otherwise stated the term "Sequence identity" for amino acids as used herein refers to the sequence identity calculated as $(n_{ref}-n_{dif}) \cdot 100/n_{ref}$, wherein $n_{dif}$ is the total number of non-identical residues in the two sequences when aligned and wherein $n_{ref}$ is the number of residues in one of the sequences.

In some embodiments the sequence identity is determined by conventional methods, e.g., Smith and Waterman, 1981, Adv. Appl. Math. 2:482, by the search for similarity method of Pearson & Lipman, 1988, Proc. Natl. Acad. Sci. USA 85:2444, using the CLUSTAL W algorithm of Thompson et al., 1994, Nucleic Acids Res 22:467380, by computerized implementations of these algorithms (GAP, BESTFIT, FASTA, and TFASTA in the Wisconsin Genetics Software Package, Genetics Computer Group). The BLAST algorithm (Altschul et al., 1990, Mol. Biol. 215:403-10) for which software may be obtained through the National Center for Biotechnology Information www.ncbi.nlm.nih.gov/) may also be used. When using any of the aforementioned algorithms, the default parameters for "Window" length, gap penalty, etc., are used.

A peptide with a specific amino acid sequence as described herein may vary from a reference peptide sequence by any of amino acid substitutions, additions/insertions, or deletions.

Some embodiments according to the present invention refers to the use of a peptide with an amino acid sequence represented by SEQ ID NO:1-33 or a sequence with at least 80% sequence identity to any one of said sequences. In some embodiments this sequence identity may be at least about 81%, 82%, 83%, 84%, 85%, 86%, 87%, 88%, 89%, 90%, 91%, 92%, 93%, 94%, 95%, 96%, 97%, 98%, or 99%, such as a peptide with not more than 1, 2, 3, 4, 5, 6, 7, 8, 9, 10, 11, 12, 13, 14, 15, 16, 17, 18, 19, 20, 21, or 22 amino acid substitutions, additions or deletions as compared to any one reference amino acid sequence represented by SEQ ID NO:1-33. The invention also features biologically active fragments of the peptides according to the invention. Biologically active fragments of a peptide of the invention include peptides comprising amino acid sequences sufficiently identical to or derived from the amino acid sequence of peptide of the invention which include fewer amino acids than the full length protein but which exhibit a substantial part of the biological activity of the corresponding full-length peptide. Typically, biologically active fragments comprise a domain or motif with at least one activity of a variant protein of the invention. A biologically active fragment of a peptide of the invention can be a peptide which is, for example, 100, 200, 300, 400, 500, 600, 700, 800, 900, 1000 or more amino acids in length.

The term "host cell", as used herein, includes any cell type which is susceptible to transformation, transfection, transduction, and the like with a nucleic acid construct or expression vector comprising a polynucleotide encoding the peptides of the present invention. A host cell may be the cell type, where a specific enzyme is derived from or it may be an alternative cell type susceptible to the production of a specific enzyme. The term includes both wild type and attenuated strains.

Suitable host cell may be any bacteria including lactic acid within the order "Lactobacillales" which includes *Lactococcus* spp., *Streptococcus* spp., *Lactobacillus* spp., *Leuconostoc* spp., *Pseudoleuconostoc* spp., *Pediococcus* spp., *Brevibacterium* spp., *Enterococcus* spp. and *Propionibacterium* spp. Also included are lactic acid producing bacteria belonging to the group of anaerobic bacteria, bifidobacteria, i.e. *Bifidobacterium* spp., which are frequently used as food cultures alone or in combination with lactic acid bacteria. Also included within this definition are *Lactococcus lactis, Lactococcus lactis* subsp. *cremoris, Leuconostoc mesenteroides* subsp. *cremoris, Pseudoleuconostoc mesenteroides* subsp. *cremoris, Pediococcus pentosaceus, Lactococcus lactis* subsp. *lactis* biovar. *diacetylactis, Lactobacillus casei* subsp. *casei* and *Lactobacillus paracasei* subsp. *Paracasei* and thermophilic lactic acid bacterial species include as examples *Streptococcus thermophilus, Enterococcus faecium, Lactobacillus delbrueckii* subsp. *lactis, Lactobacillus helveticus, Lactobacillus delbrueckii* subsp. *bulgaricus* and *Lactobacillus acidophilus*. Other specific bacteria within this definition includes bacteria of the family Bifidobacteriaceae, such as from the genus *Bifidobacterium*, such as from a strain of *Bifidobacterium animalis* or *Bifidobacterium longum, Bifidobacterium adolescentis, Bifidobacterium bifodum, Bifidobacterium breve, Bifidobacterium catenulatum, Bifidobacterium infantus* or from the genus *Lactobacillus*, such as *L. sakei, L. amylovorus, L. delbrueckii* subsp. *Lactis*, and *L. helveticus*.

Also included within this definition of host cells include strain of *Agaricus*, e.g. *A. bisporus*; *Ascovaginospora*; *Aspergillus*, e.g. *A. niger, A. awamori, A. foetidus, A. japonicus, A. oryzae*; *Candida*; *Chaetomium*; *Chaetotomastia*; *Dictyostelium*, e.g. *D. discoideum*; *Kluveromyces*, e.g. *K. fragilis, K. lactis*; *Mucor*, e.g. *M. javanicus, M. mucedo, M. subtilissimus*; *Neurospora*, e.g. *N. crassa*; *Rhizomucor*, e.g. *R. pusillus*; *Rhizopus*, e.g. *R. arrhizus, R. japonicus, R. stolonifer*; *Sclerotinia*, e.g. *S. libertiana*; *Torula*; *Torulopsis*; *Trichophyton*, e.g. *T. rubrum*; *Whetzelinia*, e.g. *W. sclerotiorum*; *Bacillus*, e.g. *B. coagulans, B. circulans, B. megaterium, B. novalis, B. subtilis, B. pumilus, B. stearothermophilus, B. thuringiensis*; *Bifidobacterium*, e.g. *B. longum, B. bifidum, B. animalis*; *Chryseobacterium*; *Citrobacter*, e.g. *C. freundii*; *Clostridium*, e.g. *C. perfringens*; *Diplodia*, e.g. *D. gossypina*; *Enterobacter*, e.g. *E. aerogenes, E. cloacae Edwardsiella, E. tarda*; *Erwinia*, e.g. *E. herbicola*; *Escherichia*, e.g. *E. coli*; *Klebsiella*, e.g. *K. pneumoniae*; *Miriococcum*; *Myrothesium*; *Mucor*; *Neurospora*, e.g. *N. crassa*; *Proteus*, e.g. *P. vulgaris*; *Providencia*, e.g. *P. stuartii*; *Pycnoporus*, e.g. *Pycnoporus cinnabarinus, Pycnoporus sanguineus*; *Ruminococcus*, e.g. *R. torques*; *Salmonella*, e.g. *S. typhimurium*; *Serratia*, e.g. *S. liquefasciens, S. marcescens*; *Shigella*, e.g. *S. flexneri*; *Streptomyces*, e.g. *S. antibioticus, S. castaneoglobisporus, S. violeceoruber*; *Trametes*; *Trichoderma*, e.g. *T. reesei, T. viride*; *Yersinia*, e.g. *Y. enterocolitica*.

Specific Embodiments of the Invention

As described above the present invention relates to a peptide exhibiting beta-galactosidase enzyme activity, which has an amino acid sequence represented by SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, or an amino acid sequence thereof having not more than 1, 2, 3, 4, 5, 6, 7, 8, 9, 10, 11, 12, 13, 14, 15, 16, 17, 18, 19, 20, 21, or 22 amino acid substitutions, additions or deletions.

Accordingly, in one embodiment the present invention relates to a peptide exhibiting beta-galactosidase enzyme activity, which has an amino acid sequence represented by SEQ ID NO: 1, or an amino acid sequence thereof having not more than 1, 2, 3, 4, 5, 6, 7, 8, 9, 10, 11, 12, 13, 14, 15, 16, 17, 18, 19, 20, 21, or 22 amino acid substitutions, additions or deletions. In one embodiment the present invention relates to a peptide exhibiting beta-galactosidase enzyme activity, which has an amino acid sequence represented by SEQ ID NO: 2, or an amino acid sequence thereof having not more than 1, 2, 3, 4, 5, 6, 7, 8, 9, 10, 11, 12, 13, 14, 15, 16, 17, 18, 19, 20, 21, or 22 amino acid substitutions, additions or deletions. In one embodiment the present invention relates to a peptide exhibiting beta-galactosidase enzyme activity, which has an amino acid sequence represented by SEQ ID NO: 3, or an amino acid sequence thereof having not more than 1, 2, 3, 4, 5, 6, 7, 8, 9, 10, 11, 12, 13, 14, 15, 16, 17, 18, 19, 20, 21, or 22 amino acid substitutions, additions or deletions. In one embodiment the present invention relates to a peptide exhibiting beta-galactosidase enzyme activity, which has an amino acid sequence represented by SEQ ID NO: 4, or an amino acid sequence thereof having not more than 1, 2, 3, 4, 5, 6, 7, 8, 9, 10, 11, 12, 13, 14, 15, 16, 17, 18, 19, 20, 21, or 22 amino acid substitutions, additions or deletions. In one embodiment the present invention relates to a peptide exhibiting beta-galactosidase enzyme activity, which has an amino acid sequence represented by SEQ ID NO: 5, or an amino acid sequence thereof having not more than 1, 2, 3, 4, 5, 6, 7, 8, 9, 10, 11, 12, 13, 14, 15, 16, 17, 18, 19, 20, 21, or 22 amino acid substitutions, additions or deletions. In one embodiment the present invention relates to a peptide exhibiting beta-galactosidase enzyme activity, which has an amino acid sequence represented by SEQ ID NO: 6, or an amino acid sequence thereof having not more than 1, 2, 3, 4, 5, 6, 7, 8, 9, 10, 11, 12, 13, 14, 15, 16, 17, 18, 19, 20, 21, or 22 amino acid substitutions, additions or deletions. In one embodiment the present invention relates to a peptide exhibiting beta-galactosidase enzyme activity, which has an amino acid sequence represented by SEQ ID NO: 7, or an amino acid sequence thereof having not more than 1, 2, 3, 4, 5, 6, 7, 8, 9, 10, 11, 12, 13, 14, 15, 16, 17, 18, 19, 20, 21, or 22 amino acid substitutions, additions or deletions. In one embodiment the present invention relates to a peptide exhibiting beta-galactosidase enzyme activity, which has an amino acid sequence represented by SEQ ID NO: 8, or an amino acid sequence thereof having not more than 1, 2, 3, 4, 5, 6, 7, 8, 9, 10, 11, 12, 13, 14, 15, 16, 17, 18, 19, 20, 21, or 22 amino acid substitutions, additions or deletions. In one embodiment the present invention relates to a peptide exhibiting beta-galactosidase enzyme activity, which has an amino acid sequence represented by SEQ ID NO: 9, or an amino acid sequence thereof having not more than 1, 2, 3, 4, 5, 6, 7, 8, 9, 10, 11, 12, 13, 14, 15, 16, 17, 18, 19, 20, 21, or 22 amino acid substitutions, additions or deletions. In one embodiment the present invention relates to a peptide exhibiting beta-galactosidase enzyme activity, which has an amino acid sequence represented by SEQ ID NO: 10, or an amino acid sequence thereof having not more than 1, 2, 3, 4, 5, 6, 7, 8, 9, 10, 11, 12, 13, 14, 15, 16, 17, 18, 19, 20, 21, or 22 amino acid substitutions, additions or deletions. In one embodiment the present invention relates to a peptide exhibiting beta-galactosidase enzyme activity, which has an amino acid sequence represented by SEQ ID NO: 11, or an amino acid sequence thereof having not more than 1, 2, 3, 4, 5, 6, 7, 8, 9, 10, 11, 12, 13, 14, 15, 16, 17, 18, 19, 20, 21, or 22 amino acid substitutions, additions or deletions. In one embodiment the present invention relates to a peptide exhibiting beta-galactosidase enzyme activity, which has an amino acid sequence represented by SEQ ID NO: 12, or an amino acid sequence thereof having not more than 1, 2, 3, 4, 5, 6, 7, 8, 9, 10, 11, 12, 13, 14, 15, 16, 17, 18, 19, 20, 21, or 22 amino acid substitutions, additions or deletions. In one embodiment the present invention relates to a peptide exhibiting beta-galactosidase enzyme activity, which has an amino acid sequence represented by SEQ ID NO: 13, or an amino acid sequence thereof having not more than 1, 2, 3, 4, 5, 6, 7, 8, 9, 10, 11, 12, 13, 14, 15, 16, 17, 18, 19, 20, 21, or 22 amino acid substitutions, additions or deletions. In one embodiment the present invention relates to a peptide exhibiting beta-galactosidase enzyme activity, which has an amino acid sequence represented by SEQ ID NO: 14, or an amino acid sequence thereof having not more than 1, 2, 3, 4, 5, 6, 7, 8, 9, 10, 11, 12, 13, 14, 15, 16, 17, 18, 19, 20, 21, or 22 amino acid substitutions, additions or deletions. In one embodiment the present invention relates to a peptide exhibiting beta-galactosidase enzyme activity, which has an amino acid sequence represented by SEQ ID NO: 15, or an amino acid sequence thereof having not more than 1, 2, 3, 4, 5, 6, 7, 8, 9, 10, 11, 12, 13, 14, 15, 16, 17, 18, 19, 20, 21, or 22 amino acid substitutions, additions or deletions. In one embodiment the present invention relates to a peptide exhibiting beta-galactosidase enzyme activity, which has an amino acid sequence represented by SEQ ID NO: 16, or an amino acid sequence thereof having not more than 1, 2, 3, 4, 5, 6, 7, 8, 9, 10, 11, 12, 13, 14, 15, 16, 17, 18, 19, 20, 21, or 22 amino acid substitutions, additions or deletions. In one embodiment the present invention relates to a peptide exhibiting beta-galactosidase enzyme activity, which has an amino acid sequence represented by SEQ ID NO: 17, or an amino acid sequence thereof having not more than 1, 2, 3, 4, 5, 6, 7, 8, 9, 10, 11, 12, 13, 14, 15, 16, 17, 18, 19, 20, 21, or 22 amino acid substitutions, additions or deletions. In one embodiment the present invention relates to a peptide exhibiting beta-galactosidase enzyme activity, which has an amino acid sequence represented by SEQ ID NO: 18, or an amino acid sequence thereof having not more than 1, 2, 3, 4, 5, 6, 7, 8, 9, 10, 11, 12, 13, 14, 15, 16, 17, 18, 19, 20, 21, or 22 amino acid substitutions, additions or deletions. In one embodiment the present invention relates to a peptide exhibiting beta-galactosidase enzyme activity, which has an amino acid sequence represented by SEQ ID NO: 19, or an amino acid sequence thereof having not more than 1, 2, 3, 4, 5, 6, 7, 8, 9, 10, 11, 12, 13, 14, 15, 16, 17, 18, 19, 20, 21, or 22 amino acid substitutions, additions or deletions. In one embodiment the present invention relates to a peptide exhibiting beta-galactosidase enzyme activity, which has an amino acid sequence represented by SEQ ID NO: 20, or an amino acid sequence thereof having not more than 1, 2, 3, 4, 5, 6, 7, 8, 9, 10, 11, 12, 13, 14, 15, 16, 17, 18, 19, 20, 21, or 22 amino acid substitutions, additions or deletions. In one embodiment the present invention relates to a peptide exhibiting beta-galactosidase enzyme activity, which has an amino acid sequence represented by SEQ ID NO: 21, or an amino acid sequence thereof having not more than 1, 2, 3, 4, 5, 6, 7, 8, 9, 10, 11, 12, 13, 14, 15, 16, 17, 18, 19, 20, 21, or 22 amino acid substitutions, additions or deletions. In one embodiment the present invention relates to a peptide exhibiting beta-galactosidase enzyme activity, which has an amino acid sequence represented by SEQ ID NO: 22, or an amino acid sequence thereof having not more than 1, 2, 3, 4, 5, 6, 7, 8, 9, 10, 11, 12, 13, 14, 15, 16, 17, 18, 19, 20, 21, or 22 amino acid substitutions, additions or deletions. In one embodiment the present invention relates to a peptide exhibiting beta-galactosidase enzyme activity, which has an amino acid sequence represented by SEQ ID NO: 23, or an amino acid sequence thereof having not more than 1, 2, 3, 4, 5, 6, 7, 8, 9, 10, 11, 12, 13, 14, 15, 16, 17, 18, 19, 20, 21, or 22 amino acid substitutions, additions or deletions. In one embodiment the present invention relates to a peptide exhibiting beta-galactosidase enzyme activity, which has an amino acid sequence represented by SEQ ID NO: 24, or an amino acid sequence thereof having not more than 1, 2, 3, 4, 5, 6, 7, 8, 9, 10, 11, 12, 13, 14, 15, 16, 17, 18, 19, 20, 21, or 22 amino acid substitutions, additions or deletions. In one embodiment the present invention relates to a peptide exhibiting beta-galactosidase enzyme activity, which has an amino acid sequence represented by SEQ ID NO: 25, or an amino acid sequence thereof having not more than 1, 2, 3, 4, 5, 6, 7, 8, 9, 10, 11, 12, 13, 14, 15, 16, 17, 18, 19, 20, 21, or 22 amino acid substitutions, additions or deletions. In one embodiment the present invention relates to a peptide exhibiting beta-galactosidase enzyme activity, which has an amino acid sequence represented by SEQ ID NO: 26, or an amino acid sequence thereof having not more than 1, 2, 3, 4, 5, 6, 7, 8, 9, 10, 11, 12, 13, 14, 15, 16, 17, 18, 19, 20, 21, or 22 amino acid substitutions, additions or deletions. In one embodiment the present invention relates to a peptide exhibiting beta-galactosidase enzyme activity, which has an amino acid sequence represented by SEQ ID NO: 27, or an amino acid sequence thereof having not more than 1, 2, 3, 4, 5, 6, 7, 8, 9, 10, 11, 12, 13, 14, 15, 16, 17, 18, 19, 20, 21, or 22 amino acid substitutions, additions or deletions. In one embodiment the present invention relates to a peptide exhibiting beta-galactosidase enzyme activity, which has an amino acid sequence represented by SEQ ID NO: 28, or an amino acid sequence thereof having not more than 1, 2, 3, 4, 5, 6, 7, 8, 9, 10, 11, 12, 13, 14, 15, 16, 17, 18, 19, 20, 21, or 22 amino acid substitutions, additions or deletions. In one embodiment the present invention relates to a peptide exhibiting beta-galactosidase enzyme activity, which has an amino acid sequence represented by SEQ ID NO: 29, or an amino acid sequence thereof having not more than 1, 2, 3, 4, 5, 6, 7, 8, 9, 10, 11, 12, 13, 14, 15, 16, 17, 18, 19, 20, 21, or 22 amino acid substitutions, additions or deletions. In one embodiment the present invention relates to a peptide exhibiting beta-galactosidase enzyme activity, which has an amino acid sequence represented by SEQ ID NO: 30, or an amino acid sequence thereof having not more than 1, 2, 3, 4, 5, 6, 7, 8, 9, 10, 11, 12, 13, 14, 15, 16, 17, 18, 19, 20, 21, or 22 amino acid substitutions, additions or deletions. In one embodiment the present invention relates to a peptide exhibiting beta-galactosidase enzyme activity, which has an amino acid sequence represented by SEQ ID NO: 31, or an amino acid sequence thereof having not more than 1, 2, 3, 4, 5, 6, 7, 8, 9, 10, 11, 12, 13, 14, 15, 16, 17, 18, 19, 20, 21, or 22 amino acid substitutions, additions or deletions. In one embodiment the present invention relates to a peptide exhibiting beta-galactosidase enzyme activity, which has an amino acid sequence represented by SEQ ID NO: 32, or an amino acid sequence thereof having not more than 1, 2, 3, 4, 5, 6, 7, 8, 9, 10, 11, 12, 13, 14, 15, 16, 17, 18, 19, 20, 21, or 22 amino acid substitutions, additions or deletions. In one embodiment the present invention relates to a peptide exhibiting beta-galactosidase enzyme activity, which has an amino acid sequence represented by SEQ ID NO: 33, or an amino acid sequence thereof having not more than 1, 2, 3, 4, 5, 6, 7, 8, 9, 10, 11, 12, 13, 14, 15, 16, 17, 18, 19, 20, 21, or 22 amino acid substitutions, additions or deletions.

In some embodiments the peptide according to the invention has a beta-galactosidase activity measured as µM of glucose formed per second per µM of enzyme under conditions as given in example 8 described herein at a temperature of about 4° C. and a pH of 6.7, which activity is exceeding the activity of a beta-galactosidase enzyme defined by SEQ ID NO:34 OR SEQ ID NO:35 by at least about 20%, such as at least about 30%, such as at least about 40%, such as at least about 50%, such as at least about 60%, such as at least about 70%, such as at least about 80%, such as at least about 90%, such as at least about 100%, such as at least about 200%, such as at least about 300%, such as at least about 400%, such as at least about 500%.

In some embodiments the peptide according to the invention has a beta-galactosidase activity measured as µM of glucose formed per second per µM of enzyme at a temperature of about 4° C. and a pH of 6.7, which activity is exceeding the activity of a beta-galactosidase enzyme defined by SEQ ID NO:34 OR SEQ ID NO:35 by at least about 20%, such as at least about 30%, such as at least about 40%, such as at least about 50%, such as at least about 60%, such as at least about 70%, such as at least about 80%, such as at least about 90%, such as at least about 100%, such as at least about 200%, such as at least about 300%, such as at least about 400%, such as at least about 500%. In some embodiments the peptide according to the invention has a beta-galactosidase activity measured as µM of glucose formed per second per µM of enzyme at a temperature of about 4° C. and a pH of 6.7, which activity is higher than about 2, such as higher than about 4, such as higher than about 6, such as higher than about 8, such as higher than about 10, such as higher than about 12, such as higher than about 14, such as higher than about 16 µM of glucose formed per second per µM of enzyme.

In some embodiments the peptide according to the invention has a beta-galactosidase activity measured as µM of glucose formed per second per µM of enzyme under conditions as given in example 10 described herein at a temperature of about 4° C. and a pH of 5.5, which activity is exceeding the activity of a beta-galactosidase enzyme defined by SEQ ID NO:34 OR SEQ ID NO:35 by at least about 20%, such as at least about 30%, such as at least about 40%, such as at least about 50%, such as at least about 60%, such as at least about 70%, such as at least about 80%, such as at least about 90%, such as at least about 100%, such as at least about 200%, such as at least about 300%, such as at least about 400%, such as at least about 500%.

In some embodiments the peptide according to the invention has a beta-galactosidase activity measured as µM of glucose formed per second per µM of enzyme at a temperature of about 4° C. and a pH of 5.5, which activity is exceeding the activity of a beta-galactosidase enzyme defined by SEQ ID NO:34 OR SEQ ID NO:35 by at least about 20%, such as at least about 30%, such as at least about 40%, such as at least about 50%, such as at least about 60%, such as at least about 70%, such as at least about 80%, such as at least about 90%, such as at least about 100%, such as at least about 200%, such as at least about 300%, such as at least about 400%, such as at least about 500%. In some embodiments the peptide according to the invention has a beta-galactosidase activity measured as µM of glucose formed per second per µM of enzyme at a temperature of about 4° C. and a pH of 5.5, which activity is higher than about 1, such as higher than about 2, such as higher than about 3, such as higher than about 4, such as higher than about 5, such as higher than about 6, such as higher than about 7, such as higher than about 8 µM of glucose formed per second per µM of enzyme.

In some embodiments the peptide according to the invention has a beta-galactosidase activity measured as µM of glucose formed per second per µM of enzyme under conditions as given in example 13 described herein at a temperature of about 4° C. and a pH of 4.5, which activity is exceeding the activity of a beta-galactosidase enzyme defined by SEQ ID NO:34 OR SEQ ID NO:35 by at least about 20%, such as at least about 30%, such as at least about 40%, such as at least about 50%, such as at least about 60%, such as at least about 70%, such as at least about 80%, such as at least about 90%, such as at least about 100%, such as at least about 200%, such as at least about 300%, such as at least about 400%, such as at least about 500%.

In some embodiments the peptide according to the invention has a beta-galactosidase activity measured as µM of glucose formed per second per µM of enzyme at a temperature of about 4° C. and a pH of 4.5, which activity is exceeding the activity of a beta-galactosidase enzyme defined by SEQ ID NO:34 OR SEQ ID NO:35 by at least about 20%, such as at least about 30%, such as at least about 40%, such as at least about 50%, such as at least about 60%, such as at least about 70%, such as at least about 80%, such as at least about 90%, such as at least about 100%, such as at least about 200%, such as at least about 300%, such as at least about 400%, such as at least about 500%. In some embodiments the peptide according to the invention has a beta-galactosidase activity measured as µM of glucose formed per second per µM of enzyme at a temperature of about 4° C. and a pH of 4.5, which activity is higher than about 0.5, such as higher than about 1.0, such as higher than about 1.5, such as higher than about 2.0, such as higher than about 2.5, such as higher than about 3.0, such as higher than about 3.5, such as higher than about 4.0 µM of glucose formed per second per µM of enzyme.

In some embodiments the peptide according to the invention has a beta-galactosidase activity measured as µM of glucose formed per second per µM of enzyme under conditions as given in example 9 described herein at a temperature of about 43° C. and a pH of 6.7, which activity is exceeding the activity of a beta-galactosidase enzyme defined by SEQ ID NO:34 OR SEQ ID NO:35 by at least about 20%, such as at least about 30%, such as at least about 40%, such as at least about 50%, such as at least about 60%, such as at least about 70%, such as at least about 80%, such as at least about 90%, such as at least about 100%, such as at least about 200%, such as at least about 300%, such as at least about 400%, such as at least about 500%.

In some embodiments the peptide according to the invention has a beta-galactosidase activity measured as µM of glucose formed per second per µM of enzyme at a temperature of about 43° C. and a pH of 6.7, which activity is exceeding the activity of a beta-galactosidase enzyme defined by SEQ ID NO:34 OR SEQ ID NO:35 by at least about 20%, such as at least about 30%, such as at least about 40%, such as at least about 50%, such as at least about 60%, such as at least about 70%, such as at least about 80%, such as at least about 90%, such as at least about 100%, such as at least about 200%, such as at least about 300%, such as at least about 400%, such as at least about 500%. In some embodiments the peptide according to the invention has a beta-galactosidase activity measured as µM of glucose formed per second per µM of enzyme at a temperature of about 43° C. and a pH of 6.7, which activity is higher than about 10, such as higher than about 20, such as higher than about 40, such as higher than about 60, such as higher than about 80, such as higher than about 100, such as higher than about 120, such as higher than about 140, such as higher than about 160 µM of glucose formed per second per µM of enzyme.

In some embodiments the peptide according to the invention has a beta-galactosidase activity measured as µM of glucose formed per second per µM of enzyme under conditions as given in example 12 described herein at a temperature of about 43° C. and a pH of 5.5, which activity is exceeding the activity of a beta-galactosidase enzyme defined by SEQ ID NO:34 OR SEQ ID NO:35 by at least about 20%, such as at least about 30%, such as at least about 40%, such as at least about 50%, such as at least about 60%, such as at least about 70%, such as at least about 80%, such as at least about 90%, such as at least about 100%, such as at least about 200%, such as at least about 300%, such as at least about 400%, such as at least about 500%.

In some embodiments the peptide according to the invention has a beta-galactosidase activity measured as µM of glucose formed per second per µM of enzyme at a temperature of about 43° C. and a pH of 5.5, which activity is exceeding the activity of a beta-galactosidase enzyme defined by SEQ ID NO:34 OR SEQ ID NO:35 by at least about 20%, such as at least about 30%, such as at least about 40%, such as at least about 50%, such as at least about 60%, such as at least about 70%, such as at least about 80%, such as at least about 90%, such as at least about 100%, such as at least about 200%, such as at least about 300%, such as at least about 400%, such as at least about 500%. In some embodiments the peptide according to the invention has a beta-galactosidase activity measured as µM of glucose formed per second per µM of enzyme at a temperature of about 43° C. and a pH of 5.5, which activity is higher than about 5, such as higher than about 10, such as higher than about 15, such as higher than about 20, such as higher than about 25, such as higher than about 30, such as higher than about 35, such as higher than about 40, such as higher than about 45, such as higher than about 50, such as higher than about 55, such as higher than about 60 µM of glucose formed per second per µM of enzyme.

In some embodiments the peptide according to the invention has a beta-galactosidase activity measured as µM of glucose formed per second per µM of enzyme under conditions as given in example 15 described herein at a temperature of about 43° C. and a pH of 4.5, which activity is exceeding the activity of a beta-galactosidase enzyme defined by SEQ ID NO:34 OR SEQ ID NO:35 by at least about 20%, such as at least about 30%, such as at least about 40%, such as at least about 50%, such as at least about 60%, such as at least about 70%, such as at least about 80%, such as at least about 90%, such as at least about 100%, such as at least about 200%, such as at least about 300%, such as at least about 400%, such as at least about 500%.

In some embodiments the peptide according to the invention has a beta-galactosidase activity measured as µM of glucose formed per second per µM of enzyme at a temperature of about 43° C. and a pH of 4.5, which activity is exceeding the activity of a beta-galactosidase enzyme defined by SEQ ID NO:34 OR SEQ ID NO:35 by at least about 20%, such as at least about 30%, such as at least about 40%, such as at least about 50%, such as at least about 60%, such as at least about 70%, such as at least about 80%, such as at least about 90%, such as at least about 100%, such as at least about 200%, such as at least about 300%, such as at least about 400%, such as at least about 500%. In some embodiments the peptide according to the invention has a beta-galactosidase activity measured as µM of glucose formed per second per µM of enzyme at a temperature of about 43° C. and a pH of 4.5, which activity is higher than about 1, such as higher than about 2, such as higher than about 3, such as higher than about 4, such as higher than about 5, such as higher than about 6, such as higher than about 7, such as higher than about 8, such as higher than about 9, such as higher than about 10, such as higher than about 11, such as higher than about 12 µM of glucose formed per second per µM of enzyme.

In some embodiments the peptide according to the invention has a beta-galactosidase activity measured as µM of glucose formed per second per µM of enzyme under conditions as given in example 6 described herein at a temperature of about 37° C. and a pH of 6.7, which activity is exceeding the activity of a beta-galactosidase enzyme defined by SEQ ID NO:34 OR SEQ ID NO:35 by at least about 20%, such as at least about 30%, such as at least about 40%, such as at least about 50%, such as at least about 60%, such as at least about 70%, such as at least about 80%, such as at least about 90%, such as at least about 100%, such as at least about 200%, such as at least about 300%, such as at least about 400%, such as at least about 500%.

In some embodiments the peptide according to the invention has a beta-galactosidase activity measured as µM of glucose formed per second per µM of enzyme at a temperature of about 37° C. and a pH of 6.7, which activity is exceeding the activity of a beta-galactosidase enzyme defined by SEQ ID NO:34 OR SEQ ID NO:35 by at least about 20%, such as at least about 30%, such as at least about 40%, such as at least about 50%, such as at least about 60%, such as at least about 70%, such as at least about 80%, such as at least about 90%, such as at least about 100%, such as at least about 200%, such as at least about 300%, such as at least about 400%, such as at least about 500%. In some embodiments the peptide according to the invention has a beta-galactosidase activity measured as µM of glucose formed per second per µM of enzyme at a temperature of about 37° C. and a pH of 6.7, which activity is higher than about 10, such as higher than about 20, such as higher than about 30, such as higher than about 40, such as higher than about 50, such as higher than about 60, such as higher than about 70, such as higher than about 80, such as higher than about 90, such as higher than about 100, such as higher than about 110, such as higher than about 120, such as higher than about 130 µM of glucose formed per second per µM of enzyme.

In some embodiments the peptide according to the invention has a beta-galactosidase activity measured as µM of glucose formed per second per µM of enzyme under conditions as given in example 11 described herein at a temperature of about 37° C. and a pH of 5.5, which activity is exceeding the activity of a beta-galactosidase enzyme defined by SEQ ID NO:34 OR SEQ ID NO:35 by at least about 20%, such as at least about 30%, such as at least about 40%, such as at least about 50%, such as at least about 60%, such as at least about 70%, such as at least about 80%, such as at least about 90%, such as at least about 100%, such as at least about 200%, such as at least about 300%, such as at least about 400%, such as at least about 500%.

In some embodiments the peptide according to the invention has a beta-galactosidase activity measured as µM of glucose formed per second per µM of enzyme at a temperature of about 37° C. and a pH of 5.5, which activity is exceeding the activity of a beta-galactosidase enzyme defined by SEQ ID NO:34 OR SEQ ID NO:35 by at least about 20%, such as at least about 30%, such as at least about 40%, such as at least about 50%, such as at least about 60%, such as at least about 70%, such as at least about 80%, such as at least about 90%, such as at least about 100%, such as at least about 200%, such as at least about 300%, such as at least about 400%, such as at least about 500%. In some embodiments the peptide according to the invention has a beta-galactosidase activity measured as μM of glucose formed per second per μM of enzyme at a temperature of about 37° C. and a pH of 5.5, which activity is higher than about 5, such as higher than about 10, such as higher than about 15, such as higher than about 20, such as higher than about 25, such as higher than about 30, such as higher than about 35, such as higher than about 40, such as higher than about 45, such as higher than about 50, such as higher than about 55, such as higher than about 60 μM of glucose formed per second per μM of enzyme.

In some embodiments the peptide according to the invention has a beta-galactosidase activity measured as μM of glucose formed per second per μM of enzyme under conditions as given in example 14 described herein at a temperature of about 37° C. and a pH of 4.5, which activity is exceeding the activity of a beta-galactosidase enzyme defined by SEQ ID NO:34 OR SEQ ID NO:35 by at least about 20%, such as at least about 30%, such as at least about 40%, such as at least about 50%, such as at least about 60%, such as at least about 70%, such as at least about 80%, such as at least about 90%, such as at least about 100%, such as at least about 200%, such as at least about 300%, such as at least about 400%, such as at least about 500%.

In some embodiments the peptide according to the invention has a beta-galactosidase activity measured as μM of glucose formed per second per μM of enzyme at a temperature of about 37° C. and a pH of 4.5, which activity is exceeding the activity of a beta-galactosidase enzyme defined by SEQ ID NO:34 OR SEQ ID NO:35 by at least about 20%, such as at least about 30%, such as at least about 40%, such as at least about 50%, such as at least about 60%, such as at least about 70%, such as at least about 80%, such as at least about 90%, such as at least about 100%, such as at least about 200%, such as at least about 300%, such as at least about 400%, such as at least about 500%. In some embodiments the peptide according to the invention has a beta-galactosidase activity measured as μM of glucose formed per second per μM of enzyme at a temperature of about 37° C. and a pH of 4.5, which activity is higher than about 1, such as higher than about 2, such as higher than about 3, such as higher than about 4, such as higher than about 5, such as higher than about 6, such as higher than about 7, such as higher than about 8, such as higher than about 9, such as higher than about 10, such as higher than about 11, such as higher than about 12, such as higher than about 13, such as higher than about 14, such as higher than about 15, such as higher than about 16, such as higher than about 17, such as higher than about 18 μM of glucose formed per second per μM of enzyme.

In some embodiments the peptide according to the invention is derived from a bacteria of the genus *Bifidobacterium*, such as *Bifidobacterium adolescentis*, *Bifidobacterium bifidum*, *Bifidobacterium breve*, *Bifidobacterium catenulatum*, *Bifidobacterium longum* or from the genus *Lactobacillus*, such as *L. sakei*, *L. amylovorus*, *L. delbrueckii* subsp. *bulgaricus*, *L. delbrueckii* subsp. *lactis*, *L. delbrueckii* subsp. *Indicus*, *L. crispatus*, *L. reuteri*, *L. helveticus* or from *Streptococcus thermophilus*.

In some embodiments the peptide according to the invention exhibit a galactose inhibition less than 60%, such as less than 55%, such as less than 50%, such as less than about 45%, such as less than about 40%.

As described above at part of the present invention relates to a method for producing a dairy product the method comprising the steps of
a) providing a milk-based substrate comprising lactose;
b) adding an peptide exhibiting beta-galactosidase activity and having an amino acid sequence represented by SEQ ID NO:1-33 or a sequence with at least 80% sequence identity to any one of said sequences to said milk-based substrate comprising lactose; and
c) treating said milk-based substrate with said peptide exhibiting beta-galactosidase activity.

In some embodiments according to the present invention this peptide is derived from any one bacteria of the genus *Bifidobacterium*, such as *Bifidobacterium adolescentis*, *Bifidobacterium bifidum*, *Bifidobacterium breve*, *Bifidobacterium catenulatum*, *Bifidobacterium longum* or from the genus *Lactobacillus*, such as *L. sakei*, *L. amylovorus*, *L. delbrueckii* subsp. *bulgaricus*, *L. delbrueckii* subsp. *lactis*, *L. delbrueckii* subsp. *Indicus*, *L. crispatus*, *L. reuteri*, *L. helveticus* or from *Streptococcus thermophilus*.

In some embodiments according to the present invention step c) takes place at a pH within a range of 3-10, such as within a range of 3-9, such as within a range of 3-8, such as within a range of 3-7, such as within a range of 3-6, such as within a range of 3-5, such as within a range of 3-4, such as within a range of 4-10, such as within a range of 4-9, such as within a range of 4-8, such as within a range of 4-7, such as within a range of 4-6, such as within a range of 4-5, such as within a range of 5-10, such as within a range of 5-9, such as within a range of 5-8, such as within a range of 5-7, such as within a range of 5-6, such as within a range of 6-10, such as within a range of 6-9, such as within a range of 6-8, such as within a range of 6-7.

In some embodiments according to the present invention step c) or a part of step c) takes place at a temperature of not more than about 25° C., such as not more than about 20° C., such as not more than about 18° C., such as not more than about 16° C., such as not more than about 14° C., such as not more than about 12° C., such as not more than about 10° C., such as not more than about 8° C., such as not more than about 7° C., such as not more than about 6° C., such as not more than about 5° C., such as not more than about 4° C., such as not more than about 3° C., such as not more than about 2° C.

In some embodiments according to the present invention step c) or a part of step c) takes place at a temperature of at least about 25° C., such as at least about 30° C., such as at least about 35° C., such as at least about 40° C., such as at least about 45° C., such as at least about 50° C., such as at least about 55° C., such as at least about 60° C., such as at least about 65° C., such as at least about 70° C., such as at least about 75° C., such as at least about 80° C., such as at least about 85° C., such as at least about 90° C., such as at least about 95° C., such as at least about 100° C., such as at least about 110° C., such as at least about 120° C., such as at least about 130° C., such as at least about 120° C., such as at least about 130° C., such as at least about 135° C., such as at least about 140° C.

In some embodiments according to the present invention the dairy product is selected from the group consisting of lactose-free milk, low-lactose milk, yoghurt, cheese, fermented milk products, dietary supplement and probiotic dietary products.

In some embodiments according to the present invention the milk-based substrate is selected from fresh milk or raw milk obtained directly from a step of pasteurization, milk obtained directly after a step of ultra-heat treatment (UHT), or milk obtained directly after a step of fermentation.

In some embodiments according to the present invention the galactose inhibition of the peptide used is less than 60%, such as less than 55%, such as less than 50%, such as less than about 45%, such as less than about 40%.

In some embodiments according to the present invention the dairy product is fermented milk product and said step b) is performed during or prior to fermentation.

In some embodiments according to the present invention the method does not require the addition of further enzyme after fermentation.

In some embodiments according to the present invention the dairy product is fermented milk product and said step b) is performed immediately following fermentation.

In some embodiments according to the present invention the dairy product is fresh milk and said step b) is performed prior to, in conjunction with, or immediately following a step of pasteurization.

In some embodiments according to the present invention the dairy product is ultra-heat treatment (UHT) milk and said step b) is performed prior to, in conjunction with, or immediately following a step of ultra-heat treatment.

In some embodiments according to the present invention step c) is started at a temperature of between 40° C. and 100° C., such as at a temperature of between 50° C. and 100° C. such as at a temperature of between 60° C. and 100° C., such as at a temperature of between 70° C. and 100° C., such as at a temperature of between 80° C. and 100° C., such as at a temperature of between 40° C. and 90° C., such as at a temperature of between 40° C. and 80° C., such as at a temperature of between 40° C. and 70° C., such as at a temperature of between 40° C. and 60° C., such as at a temperature of between 40° C. and 50° C.

In some embodiments according to the present invention the peptide when hydrolyzing the lactose in the milk-based substrate has a ratio of lactase to transgalactosylase activity of more than 1:1.

In some embodiments according to the present invention less than 80% of the lactose has been hydrolyzed when step c) is completed, and wherein more than 90% of the lactose has been hydrolyzed after one week.

Numbered Embodiments

1. A peptide exhibiting beta-galactosidase enzyme activity, which has an amino acid sequence represented by SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, or enzymatically active fragments thereof, or an amino acid sequence of any one thereof having not more than 1, 2, 3, 4, 5, 6, 7, 8, 9, 10, 11, 12, 13, 14, 15, 16, 17, 18, 19, 20, 21, or 22 amino acid substitutions, additions or deletions.

2. A dimeric peptide exhibiting beta-galactosidase enzyme activity, which dimeric peptide consist of two peptides having an amino acid sequence represented by SEQ ID NO: 2 and 3, 5 and 6, 20 and 21, 23 and 24, 26 and 27, or 28 and 29; or enzymatically active fragments thereof, or an amino acid sequence of any one thereof having not more than 1, 2, 3, 4, 5, 6, 7, 8, 9, 10, 11, 12, 13, 14, 15, 16, 17, 18, 19, 20, 21, or 22 amino acid substitutions, additions or deletions.

3. The peptide or dimeric peptide according to embodiments 1 or 2, which has a beta-galactosidase activity measured as µM of glucose formed per second per µM of enzyme under conditions as given in example 8 described herein at a temperature of about 4° C. and a pH of 6.7, which activity is exceeding the activity of a beta-galactosidase enzyme defined by SEQ ID NO:34 OR SEQ ID NO:35 by at least about 20%, such as at least about 30%, such as at least about 40%, such as at least about 50%, such as at least about 60%, such as at least about 70%, such as at least about 80%, such as at least about 90%, such as at least about 100%, such as at least about 200%, such as at least about 300%, such as at least about 400%, such as at least about 500%.

4. The peptide or dimeric peptide according to any one of embodiments 1-3, which has a beta-galactosidase activity measured as µM of glucose formed per second per µM of enzyme under conditions as given in example 10 described herein at a temperature of about 4° C. and a pH of 5.5, which activity is exceeding the activity of a beta-galactosidase enzyme defined by SEQ ID NO:34 OR SEQ ID NO:35 by at least about 20%, such as at least about 30%, such as at least about 40%, such as at least about 50%, such as at least about 60%, such as at least about 70%, such as at least about 80%, such as at least about 90%, such as at least about 100%, such as at least about 200%, such as at least about 300%, such as at least about 400%, such as at least about 500%.

5. The peptide or dimeric peptide according to any one of embodiments 1-4, which has a beta-galactosidase activity measured as µM of glucose formed per second per µM of enzyme under conditions as given in example 13 described herein at a temperature of about 4° C. and a pH of 4.5, which activity is exceeding the activity of a beta-galactosidase enzyme defined by SEQ ID NO:34 OR SEQ ID NO:35 by at least about 20%, such as at least about 30%, such as at least about 40%, such as at least about 50%, such as at least about 60%, such as at least about 70%, such as at least about 80%, such as at least about 90%, such as at least about 100%, such as at least about 200%, such as at least about 300%, such as at least about 400%, such as at least about 500%.

6. The peptide or dimeric peptide according to any one of embodiments 1-5, which has a beta-galactosidase activity measured as µM of glucose formed per second per µM of enzyme under conditions as given in example 9 described herein at a temperature of about 43° C. and a pH of 6.7, which activity is exceeding the activity of a beta-galactosidase enzyme defined by SEQ ID NO:34 OR SEQ ID NO:35 by at least about 20%, such as at least about 30%, such as at least about 40%, such as at least about 50%, such as at least about 60%, such as at least about 70%, such as at least about 80%, such as at least about 90%, such as at least about 100%, such as at least about 200%, such as at least about 300%, such as at least about 400%, such as at least about 500%.

7. The peptide or dimeric peptide according to any one of embodiments 1-6, which has a beta-galactosidase activity measured as µM of glucose formed per second per µM of enzyme under conditions as given in example 12 described herein at a temperature of about 43° C. and a pH of 5.5, which activity is exceeding the activity of a beta-galactosidase enzyme defined by SEQ ID NO:34 OR SEQ ID NO:35 by at least about 20%, such as at least about 30%, such as at least about 40%, such as at least about 50%, such as at least about 60%, such as at least about 70%, such as at least about 80%, such as at least about 90%, such as at least about 100%, such as at least about 200%, such as at least about 300%, such as at least about 400%, such as at least about 500%.

8. The peptide or dimeric peptide according to any one of embodiments 1-7, which has a beta-galactosidase activity measured as µM of glucose formed per second per µM of enzyme under conditions as given in example 15 described herein at a temperature of about 43° C. and a pH of 4.5, which activity is exceeding the activity of a beta-galactosidase enzyme defined by SEQ ID NO:34 OR SEQ ID NO:35 by at least about 20%, such as at least about 30%, such as at least about 40%, such as at least about 50%, such as at least about 60%, such as at least about 70%, such as at least about 80%, such as at least about 90%, such as at least about 100%, such as at least about 200%, such as at least about 300%, such as at least about 400%, such as at least about 500%.

9. The peptide or dimeric peptide according to any one of embodiments 1-8, which has a beta-galactosidase activity measured as µM of glucose formed per second per µM of enzyme under conditions as given in example 6 described herein at a temperature of about 37° C. and a pH of 6.7, which activity is exceeding the activity of a beta-galactosidase enzyme defined by SEQ ID NO:34 OR SEQ ID NO:35 by at least about 20%, such as at least about 30%, such as at least about 40%, such as at least about 50%, such as at least about 60%, such as at least about 70%, such as at least about 80%, such as at least about 90%, such as at least about 100%, such as at least about 200%, such as at least about 300%, such as at least about 400%, such as at least about 500%.

10. The peptide or dimeric peptide according to any one of embodiments 1-9, which has a beta-galactosidase activity measured as µM of glucose formed per second per µM of enzyme under conditions as given in example 11 described herein at a temperature of about 37° C. and a pH of 5.5, which activity is exceeding the activity of a beta-galactosidase enzyme defined by SEQ ID NO:34 OR SEQ ID NO:35 by at least about 20%, such as at least about 30%, such as at least about 40%, such as at least about 50%, such as at least about 60%, such as at least about 70%, such as at least about 80%, such as at least about 90%, such as at least about 100%, such as at least about 200%, such as at least about 300%, such as at least about 400%, such as at least about 500%.

11. The peptide or dimeric peptide according to any one of embodiments 1-10, which has a beta-galactosidase activity measured as µM of glucose formed per second per µM of enzyme under conditions as given in example 14 described herein at a temperature of about 37° C. and a pH of 4.5, which activity is exceeding the activity of a beta-galactosidase enzyme defined by SEQ ID NO:34 OR SEQ ID NO:35 by at least about 20%, such as at least about 30%, such as at least about 40%, such as at least about 50%, such as at least about 60%, such as at least about 70%, such as at least about 80%, such as at least about 90%, such as at least about 100%, such as at least about 200%, such as at least about 300%, such as at least about 400%, such as at least about 500%.

12. The peptide or dimeric peptide according to any one of embodiments 1-11, derived from a bacteria of the genus *Bifidobacterium*, such as *Bifidobacterium adolescentis*, *Bifidobacterium bifidum*, *Bifidobacterium breve*, *Bifidobacterium catenulatum*, *Bifidobacterium longum* or from the genus *Lactobacillus*, such as *L. sakei*, *L. amylovorus*, *L. delbrueckii* subsp. *bulgaricus*, *L. delbrueckii* subsp. *lactis*, *L. delbrueckii* subsp. *lndicus*, *L. crispatus*, *L. reuteri*, *L. helveticus* or from *Streptococcus thermophilus*.

13. The peptide or dimeric peptide according to any one of embodiments 1-12, wherein said peptide or dimeric peptide exhibit a galactose inhibition less than 60%, such as less than 55%, such as less than 50%, such as less than about 45%, such as less than about 40%.

14. A nucleotide sequence which encodes a peptide or dimeric peptide as defined in any one of embodiments 1-13.

15. A host cell comprising a nucleotide sequence as defined in embodiment 14.

16. A method for producing a peptide or dimeric peptide as defined in any one of the embodiments 1-13, which method comprises the expression of a vector containing a nucleotide sequence as defined in embodiment 14 in a suitable host cell; and purifying said peptide or dimeric peptide from the expression products of said host cell.

17. A method for reducing the lactose content in a composition containing lactose, such as in a dairy products, comprising the step of contacting said composition with a peptide or dimeric peptide exhibiting beta-galactosidase enzyme activity, which peptide has an amino acid sequence represented by SEQ ID NO:1-33, or which dimeric peptide consist of two peptides having an amino acid sequence represented by SEQ ID NO: 2 and 3, 5 and 6, 20 and 21, 23 and 24, 26 and 27, or 28 and 29; or enzymatically active fragments thereof, or any sequence with at least 80% sequence identity to any one of said sequences or enzymatically active fragments; or a host cell expressing any one of said peptide or dimeric peptide, at a pH ranging from 3-10 and at a temperature ranging from 0° C.-140° C.

18. The method according to embodiment 17, wherein said composition is a dairy product selected from the group consisting of lactose-free milk, low-lactose milk, yoghurt, cheese, fermented milk products, dietary supplement and probiotic dietary products.

19. The method according to any one of embodiments 17-18, wherein said host cell is any one selected from a bacteria of the genus *Bifidobacterium*, such as *Bifidobacterium adolescentis*, *Bifidobacterium bifidum*, *Bifidobacterium breve*, *Bifidobacterium catenulatum*, *Bifidobacterium longum* or from the genus *Lactobacillus*, such as *L. sakei*, *L. amylovorus*, *L. delbrueckii* subsp. *bulgaricus*, *L. delbrueckii* subsp. *lactis*, *L. delbrueckii* subsp. *lndicus*, *L. crispatus*, *L. reuteri*, *L. helveticus* or from *Streptococcus thermophilus*.

20. The method according to any one of embodiments 17-19, wherein the lactose concentration is reduced to less than about 1%, such as to less than about 0.1% or lower, such as to less than about 0.01%.

21. Use of a peptide or dimeric peptide exhibiting beta-galactosidase enzyme activity, which peptide has an amino acid sequence represented by SEQ ID NO:1-33, or which dimeric peptide consist of two peptides having an amino acid sequence represented by SEQ ID NO: 2 and 3, 5 and 6, 20 and 21, 23 and 24, 26 and 27, or 28 and 29; or a sequence with at least 80% sequence identity to any one of said sequences; or a host cell expressing any one of said peptide or dimeric peptide for producing a dairy product with a reduced lactose content.

22. The use according to embodiment 21, wherein said dairy product is selected from the group consisting of lactose-free milk, low-lactose milk, yoghurt, cheese, fermented milk products, dietary supplement and probiotic dietary products.

23. The use according to any one of embodiments 21-22, wherein said host cell is any one selected from a bacteria of the genus *Bifidobacterium*, such as *Bifidobacterium adoles-*

*centis, Bifidobacterium bifidum, Bifidobacterium breve, Bifidobacterium catenulatum, Bifidobacterium longum* or from the genus *Lactobacillus*, such as *L. sakei, L. amylovorus, L. delbrueckii* subsp. *bulgaricus, L. delbrueckii* subsp. *lactis, L. delbrueckii* subsp. *lndicus, L. crispatus, L. reuteri, L. helveticus* or from *Streptococcus thermophilus.*

24. A method for producing a dairy product the method comprising the steps of
a) providing a milk-based substrate comprising lactose;
b) adding an peptide or dimeric peptide exhibiting beta-galactosidase activity, which peptide has an amino acid sequence represented by SEQ ID NO:1-33; or which dimeric peptide consist of two peptides having an amino acid sequence represented by SEQ ID NO: 2 and 3, 5 and 6, 20 and 21, 23 and 24, 26 and 27, or 28 and 29; or a sequence with at least 80% sequence identity to any one of said sequences to said milk-based substrate comprising lactose; and
c) treating said milk-based substrate with said peptide or dimeric peptide exhibiting beta-galactosidase activity.

25. The method according to embodiment 24, wherein said peptide or dimeric peptide is derived from any one bacteria of the genus *Bifidobacterium*, such as *Bifidobacterium adolescentis, Bifidobacterium bifidum, Bifidobacterium breve, Bifidobacterium catenulatum, Bifidobacterium longum* or from the genus *Lactobacillus*, such as *L. sakei, L. amylovorus, L. delbrueckii* subsp. *bulgaricus, L. delbrueckii* subsp. *lactis, L. delbrueckii* subsp. *lndicus, L. crispatus, L. reuteri, L. helveticus* or from *Streptococcus thermophilus.*

26. The method according to any one of embodiments 24-25, wherein step c) takes place at a pH within a range of 3-10, such as within a range of 3-9, such as within a range of 3-8, such as within a range of 3-7, such as within a range of 3-6, such as within a range of 3-5, such as within a range of 3-4, such as within a range of 4-10, such as within a range of 4-9, such as within a range of 4-8, such as within a range of 4-7, such as within a range of 4-6, such as within a range of 4-5, such as within a range of 5-10, such as within a range of 5-9, such as within a range of 5-8, such as within a range of 5-7, such as within a range of 5-6, such as within a range of 6-10, such as within a range of 6-9, such as within a range of 6-8, such as within a range of 6-7.

27. The method according to any one of embodiments 24-26, wherein step c) or a part of step c) takes place at a temperature of not more than about 25° C., such as not more than about 20° C., such as not more than about 18° C., such as not more than about 16° C., such as not more than about 14° C., such as not more than about 12° C., such as not more than about 10° C., such as not more than about 8° C., such as not more than about 7° C., such as not more than about 6° C., such as not more than about 5° C., such as not more than about 4° C., such as not more than about 3° C., such as not more than about 2° C.

28. The method according to any one of embodiments 24-27, wherein step c) or a part of step c) takes place at a temperature of at least about 25° C., such as at least about 30° C., such as at least about 35° C., such as at least about 40° C., such as at least about 45° C., such as at least about 50° C., such as at least about 55° C., such as at least about 60° C., such as at least about 65° C., such as at least about 70° C., such as at least about 75° C., such as at least about 80° C., such as at least about 85° C., such as at least about 90° C., such as at least about 95° C., such as at least about 100° C., such as at least about 110° C., such as at least about 120° C., such as at least about 130° C., such as at least about 120° C., such as at least about 130° C., such as at least about 135° C., such as at least about 140° C.

29. The method according to any one of embodiments 24-28, wherein said dairy product is selected from the group consisting of lactose-free milk, low-lactose milk, yoghurt, cheese, fermented milk products, dietary supplement and probiotic dietary products.

30. The method according to any one of embodiments 24-29, wherein said milk-based substrate is selected from fresh milk or raw milk obtained directly from a step of pasteurization, milk obtained directly after a step of ultra-heat treatment (UHT), or milk obtained directly after a step of fermentation.

31. The method according to any one of embodiments 24-30, wherein the galactose inhibition of said peptide or dimeric peptide is less than 60%, such as less than 55%, such as less than 50%, such as less than about 45%, such as less than about 40%.

32. The method according to any one of embodiments 24-31, wherein said dairy product is fermented milk product and said step b) is performed during or prior to fermentation.

33. The method according to embodiment 32, which method does not require the addition of further enzyme after fermentation.

34. The method according to any one of embodiments 24-31, wherein said dairy product is fermented milk product and said step b) is performed immediately following fermentation.

35. The method according to any one of embodiments 24-31, wherein said dairy product is fresh milk and said step b) is performed prior to, in conjunction with, or immediately following a step of pasteurization.

36. The method according to any one of embodiments 24-31, wherein said dairy product is ultra-heat treatment (UHT) milk and said step b) is performed prior to, in conjunction with, or immediately following a step of ultra-heat treatment.

37. The method according to any one of embodiments 24-36, wherein step c) is started at a temperature of between 40° C. and 100° C., such as at a temperature of between 50° C. and 100° C. such as at a temperature of between 60° C. and 100° C., such as at a temperature of between 70° C. and 100° C., such as at a temperature of between 80° C. and 100° C., such as at a temperature of between 40° C. and 90° C., such as at a temperature of between 40° C. and 80° C., such as at a temperature of between 40° C. and 70° C., such as at a temperature of between 40° C. and 60° C., such as at a temperature of between 40° C. and 50° C.

38. The method according to any one of embodiments 24-37, wherein the peptide or dimeric peptide when hydrolysing the lactose in the milk-based substrate has a ratio of lactase to transgalactosylase activity of more than 1:1.

39. The method according to any one of embodiments 24-38, wherein less than 80% of the lactose has been hydrolyzed when step c) is completed, and wherein more than 90% of the lactose has been hydrolyzed after one week.

40. A dairy product prepared by a method as defined in any one of embodiments 24-39.

41. A food product, such as a dairy product comprising a peptide or dimeric peptide exhibiting beta-galactosidase enzyme activity, which peptide has an amino acid sequence represented by SEQ ID NO:1-33, or which dimeric peptide consist of two peptides having an amino acid sequence represented by SEQ ID NO: 2 and 3, 5 and 6, 20 and 21, 23 and 24, 26 and 27, or 28 and 29; or a sequence with at least 80% sequence identity to any one of said sequences.

42. A food product, such as a dairy product comprising a host cell expressing a peptide or dimeric peptide exhibiting beta-galactosidase enzyme activity, which peptide has an amino acid sequence represented by SEQ ID NO:1-33, or which dimeric peptide consist of two peptides having an amino acid sequence represented by SEQ ID NO: 2 and 3, 5 and 6, 20 and 21, 23 and 24, 26 and 27, or 28 and 29; or a sequence with at least 80% sequence identity to any one of said sequences.

43. The food product according to embodiment 42, which is selected from beverages, infant foods, cereals, bread, biscuits, confectionary, cakes, food supplements, dietary supplements, probiotic comestible products, prebiotic comestible products, animal feeds, poultry feeds and medicaments, or a dairy product selected from the group consisting of lactose-free milk, low-lactose milk, dried milk powder, baby milks, yoghurt, ice cream, cheese, fermented milk products, dietary supplement and probiotic dietary products.

Sequences

TABLE 1

The gene numbers with corresponding sequence identification number.

| Gene number | Sequence Identity number | Species name |
|---|---|---|
| G4 | SEQ ID No 1 | *Bifidobacterium adolescentis* |
| G16 | SEQ ID No 2 (domain a) SEQ ID No 3 (domain b) | *Lactobacillus sakei* |
| G35 | SEQ ID No 4 | *Bifidobacterium adolescentis* |
| G40 | SEQ ID No 5 (domain a) SEQ ID No 6 (domain b) | *Lactobacillus amylovorus* |
| G44 | SEQ ID No 7 | *Bifidobacterium bifidum* |
| G51 | SEQ ID No 8 | *Bifidobacterium bifidum* |
| G57 | SEQ ID No 9 | *Bifidobacterium breve* |
| G62 | SEQ ID No 10 | *Bifidobacterium catenulatum* |
| G66 | SEQ ID No 11 | *Bifidobacterium catenulatum* |

TABLE 1-continued

The gene numbers with corresponding sequence identification number.

| Gene number | Sequence Identity number | Species name |
|---|---|---|
| G83 | SEQ ID No 12 | *Lactobacillus delbrueckii* subsp. *bulgaricus* |
| G84 | SEQ ID No 13 | *Lactobacillus delbrueckii* subsp. *lactis* |
| G95 | SEQ ID No 14 | *Lactobacillus delbrueckii* subsp. *bulgaricus* |
| G100 | SEQ ID No 15 | *Lactobacillus delbrueckii* subsp. *bulgaricus* |
| G104 | SEQ ID No 16 | *Lactobacillus delbrueckii* subsp. *lactis* |
| G108 | SEQ ID No 17 | *Lactobacillus delbrueckii* subsp. *bulgaricus* |
| G109 | SEQ ID No 18 | *Lactobacillus delbrueckii* subsp. *bulgaricus* |
| G118 | SEQ ID No 19 | *Lactobacillus delbrueckii* subsp. *lactis* |
| G145 | SEQ ID No 20 (domain a) SEQ ID No 21 (domain b) | *Lactobacillus helvaticus* |
| G158 | SEQ ID No 22 | *Bifidobacterium longum* |
| G224 | SEQ ID No 23 (domain a) SEQ ID No 24 (domain b) | *Lactobacillus reuteri* |
| G256 | SEQ ID No 25 | *Lactobacillus delbrueckii* subsp. *lactis* |
| G282 | SEQ ID No 26 (domain a) SEQ ID No 27 (domain b) | *Lactobacillus helvaticus* |
| G334 | SEQ ID No 28 (domain a) SEQ ID No 29 (domain b) | *Lactobacillus crispatus* |
| G335 | SEQ ID No 30 | *Streptococcus thermophilus* |
| G336 | SEQ ID No 31 | *Lactobacillus delbrueckii* subsp. *indicus* |
| G11 | SEQ ID No 32 | *Bifidobacterium adolescentis* |
| G33 | SEQ ID No 33 | *Bifidobacterium adolescentis* |
| G600 | SEQ ID No 34 | *Bifidobacterium bifidum* |
| G500 | SEQ ID No 35 | *Kluyveromyces lactis* |

SEQ ID No. 1

MADTAELAIVHATTASASWLTDPTVFAANRKPAHSSHRYVIGETSEPKQSLDGEWKVRIEQARNVDVESAPFAAVDFEDGDFG

AIEVPGHLQMAGYLKNKYVNIQYPWDGHEDPQAPNIPENNHVAIYRRRFALDAQLARTLENDGTVSLTFHGAATAIYVWLDGT

FVGYGEDGFTPSEFDVTEALRNGNGNAADSPEAEHTLTVACYEYSSASWLEDQDFWRLHGLFRTVELAAQPHTHVETVQLEAD

YTAADTAGTADTAELNAALTLRNSADAMTIESTLRDGDGNVVWESTQACNGEIALNSGKMTNIAPWSAESPTLYTLTVRVVGH

DGAIIETVTQKIGFRTFRIENGIMTLNGKRIVFKGADRHEFDAKRGRAITREDMLSDVVFCKRHNINAIRTSHYPNQEYWYDL

CDEYGLYLIDETNMETHGTWVANNVERPEDGIPGSRPEWEGACVDRINSMMRRDYNHPSVLIWSLGNESSAGEVFRAMYRHAH

TIDPNRPVHYEGSVHMREFEDVTDIESRMYAHADEIERYLNDGSPAHTDGPKKPYISCEYMHAMGNSCGNMDEYTALERYPMY

QGGFIWDFIDQAIETKLPDGTTRMCYGGDFGDRPSDYEFSGDGLLFADRTPSPKAQEVKQLYANVKIVVSVDEARITNDNLFV

STGDYRFVLRILADGKPVWSTTRRFDVAAGESASFEVDWPVDDYRSNAEELVLEVSQQLGNACDWAPAGYELAFGQCVVAGAK

TTADAVDAAGAPADGTVTLGRWNAGVRGQGREALFSRTQGGMVSYTFGEREFVLRRPSITTFRPLTDNDRGAGHAFERAAWAV

AGKYARCVDCAIANRGENAVEATYTYELAIPQRTKVTVRYVADTAGLVSLDVEYPGEKNGDLPTIPAFGIEWALPVEYANLRF

YGAGPEETYADRRHAKLGVWSTTAGDDCAPYLLPQETGNHEDVRWAEITDDSGHGVRVKRGAGAKPFAMSLLPYSSTMLEEAL

HQDELPKPRHMFLRLLAAQMGVGGDDSWMSPVHEQYQLPADQPLSLNVQLKLF (G16 Domain a)

SEQ ID No. 2

MQPNIQWLDTPAVFRVGQLPAHSDHRYYATLAEMAQQQSSFEQSLNGTWQFHYSVNAASRPKSFYELAPFDAQDFEPITVPQHI

ELAGYEQLHYINTMYPWEGHYYRRPAFSTSDDKQHLGMFSEADYNPVGSYLHHFDLTPALRNQRVIIRFEGVEQAMYVWLNGQ

FIGYAEDSFTPSEFDLTPYLKETDNCLAVEVHKRSSAAFIEDQDFFRFFGIFRDVKLLAKPRTHLEDLWVIPEYDVVQQTGQV

KLRLQFSGDENRVHLRIRDQHQIILTADLTSAAQVNGLYKMPELVQAWSNQTPNLYTLELEVVDQAGETIEISQQPFGFRKIE

-continued

```
IKDKVMLLNGKRLVINGVNRHEWHPETGRTITAEDEAWDIACMQRNHINAVRTSHYPDRLSFYNGCDQAGIYMMAETNLESHG
SWQKMGAVEPSWNVPGSYDEWEAATLDRARTNFETFKNHVSILFWSLGNESYAGSVLEKMNAYYKQQDPTRLVHYEGVFRAPE
YKATISDVESRMYATPAEIKAYLDNAPQKPFILCEYMHDGNSLGGMQSYIDLLSQYDMYQGGFIWDFIDQALLVTDPVTGQR
ELRYGGDFDDRPSDYEFSGDGLVFATRDEKPAMQEVRYYYGEHK
```

(G16 Domain b)

SEQ ID No. 3

```
MKNQQCRRLDTIMANTNKRLAVIFGDVTLGLKGPDFHYLFSYQTGGPESLRIQGKEWLYRSPKPTFWRATTDNDRGNQFPLKS
GMWLAADQFIACQSITVAIDGQTIPLPIAPENNRYSGQETAQEVTVTYTYQTITTPQTTVEVSYTIQASGKIRVAVTYHGQAG
LPSLPVFGLRFVMPTPAIRFIYQGLSGETYPDRMAGGMAGEYEVTGLPVTPYLVPQDCGVHMATDWVTIYRQAVLDNRLREPV
ETGLKFKMVDQPFAFSCLPYTAEELENATHHSELPAPHRTVLSLLGAVRGVGGIDSWGSDVEAAYQIDATQDHHLEFEISF
```

SEQ ID No. 4

```
MADTAELAIVHATTASASWLTDPTVFAANRKPAHSSHRYVIGETSEPKQSLDGEWKVRIEQARNVDVESAPFAAVDFEDGDFG
AIEVPGHLQMAGYLKNKYVNIQYPWDGHEDPQAPNIPENNHVAIYRRRFALDAQLARTLENDGTVSLTFHGAATAIYVWLDGT
FVGYGEDGFTPSEFDVTEALRNGNGNAADSPEAEHTLTVACYEYSSASWLEDQDFWRLHGLFRTVELAAQPHTHVETVQLEAD
YTAADTAGTADTAELNAALTLRNPADAMTIESTLRDGDGNVVWESTQACNGEIALNSGKMTNIAPWSAESPTLYTLTVRVVGH
DGAIIETVTQKIGFRTFRIENGIMTLNGKRIVFKGADRHEFDAKRGRAITREDMLSDVVFCKRHNINAIRTSHYPNQEYWYDL
CDEYGLYLIDETNMETHGTWVANNVERPEDGIPGSRPEWEGACVDRINSMMRRDYNHPSVLIWSLGNESSAGEVFRAMYRHAH
TIDPNRPVHYEGSVHMREFEDVTDIESRMYAHADEIERYLNDGSPAHTDGPKKPYISCEYMHAMGNSCGNMDEYTALERYPMY
QGGFIWDFIDQAIETKLPDGTTRMCYGGDFGDRPSDYEFSGDGLLFADRTPSPKAQEVKQLYANVKIAVSVDEARITNDNLFV
STGDYRFVLRILADGKPVWSTTRRFDVAAGESASFEVDWPVDDYRSNAEELVLEVSQQLGNACDWAPAGYELAFGQCVVAGAK
TTADAVDAAGAPADGTVTLGRWNAGVRGQGREALFSRTQGGMVSYTFGEREFVLRRPSITTFRPLTDNDRGAGHAFERAAWAV
AGKYARCVDCAIANRGENAVEATYTYELAIPQRTKVTVRYVADTAGLVSLDVEYPGEKNGDLPTIPAFGIEWALPVEYANLRF
YGAGPEETYADRRHAKLGVWSTTAGDDCAPYLLPQETGNHEDVRWAEITDDSGHGVRVKRGAGAKPFAMSLLPYSSTMLEEAL
HQDELPKPRHMFLRLLAAQMGVGGDDSWMSPVHEQYQLPADQPLSLNVQKLF
```

(G40 Domain a)

SEQ ID No. 5

```
MKANIKWLDDPEVFRINQLPAHSDHPFYKDYREWQNHSSSFKQSLNGAWQFHFSKDPQSRPIDFYKRSFDSSSFDTIPVPSEI
ELNGYAQNQYTNILYPWESKIYRKPAYTLGRGIKDGDFSQGKDNTVGSYLKHFDLNPALAGHDIHIQFEGVERAMYVYLNGHF
IGYAEDSFTPSEFDLTPYIQAKDNILAVEVFKHSTASWLEDQDMFRFSGIFRSVELLALPRTHLMDLDIKPTVVNDYHDGVFN
AKLHFMGKTSGNVHVLIEDIDGKTLLNKKLPLKSTVEIENETFANVHLWDNHDPYLYQLIIEVHDQDGKLVELIPYQFGFRKI
EITKDHVVLLNGKRLIINGVNRHEWDAKRGRSITLADMKQDIATFKHNNINAVRTCHYPNQIPWYYLCDQNGIYMMAENNLES
HGTWQKLGQVEATSNVPGSIPEWREVVVDRARSNYETFKNHTAILFWSLGNESYAGSNIAAMNKLYKDHDSSRLTHYEGVFHA
PEFKKEISDLESCMYLPPKEAEEYLQNPKKPLVECEYMHDMGTPDGGMGSYIKLIDKYPQYMGGFIWDFIDQALLVHDPVSGQ
DVLRYGGDFDDRHSDYEFSGDGLMFADRTPKPAMQEVRYYYGLHK
```

(G40 Domain b)

SEQ ID No. 6

```
MAYTNNLHVVYGEASLGVNGQDFAYLFSYERGGLESLKIKDKEWLYRTPTPTFWRATTDNDRGSGFNQKAAQWLGADMFTKCV
GIHVQVDDHRFDELPVAPINNQFSNQEFAHEVKVAFDYETLTTPATKVKIIYNINDFGHMTITMHYFGKKGLPPLPVIGMRFI
MPTKAKSFDYTGLSGETYPDRMAGAERGTFHIDGLPVTKYLVPQENGMHMQTNELVITRNSTQNNADKDGDFSLKITQTKQPF
NFSLLPYTAEELENATHIEELPLARRSVLVIAGAVRGVGGIDSWGSDVEEQYHIDPEQDHEFSFTLN
```

SEQ ID No. 7

```
MNTTDDQRKNGDPIVSPSIPTTAWLADPRVYAVHRLDAHSDHACWSRSPVDGESTDLRQSLDGEWRVRVETAPTGRFPDGTSD
GPDWISDVSPLFAAPGFDDSSFSRVQVPSHLETAGLLAPQYVNVQYPWDGHEDPKAPAIPEHGHVAVYRREFDADGEVAQAVR
```

-continued

EGRPVTLTFQGAATAIYVWLNGSFIGYAEDSFTPSEFDVTDAIKVDGNVLAVACYEYSSASWLEDQDFWRLHGLFRSVELNAR
PAAHVADLHADADWDLATSRGSLSLDVLIDGAANAATADFALRDKNGTIVWRTATKADGTLHAEAEIDDAAPWSAERPDLYEL
SVTLLDADGKVLETARTRIGFRHVAIEDGILKLNGKRLVFRGVNRHEFDCRRGRAITEEDMLWDIRFMKRHNINAVRTSHYPN
QSRWYELCDEYGIYLIDETNLETHGSWNSPGDIPVGTSVPGDDEAWLGACIDRLDSMILRDRNHPSVLVWSLGNESYAGEVLK
AMSAHAHQLDPGRPVHYEGVNWNHAYDGISDFESRMYAKPAEIQDWLEHGDERGEASKPFVSCEYMHAMGNSCGGLSEFIDLE
RYERYSGGFIWDYIDQGLVQRLPDGSERLSVGGEWGDRPTDYEFVGNGIVFADRTPSPKAQEVKQLYSPVKLAPDGHGVTIEN
RNLFAGTDGYVFAARLLEDGHEIWHADYRFDVAAGDTQHHDIAFPDIDADGDTREVTYEVDLLLAEATAWAPAGYELAFGQLT
GTLNPEQDITETSHDDDGRATRTLSRWNAGIRRDDEEILLSRTQGGIVSWKRDDREMVIRRPELVTFRPLTDNDRGNHSGFDR
AAWFAAGRYAIVTETKIHESDDGLVAEYQYELADPNHTPVSVTYHVNSDMRMQLTVEYPGNATDMASLPAFGIEWELPGEYDR
LRYYGPGPEETYRDRKQGGKLGIWDATAKASMAPYLMVQETGSHEDVRWLEATDIQGHGLRVTQRGDRHFTASLLPWNTYTIE
AARRHEDLPKPRHNYLRLLAAQMGVGGDDSWGAPVHTAYQLPAGRPLTLDVNLELI

SEQ ID No. 8

MNTTDDQRKNGDPIVSPSIPTTAWLADPRVYAVHRLDAHSDHACWSRSPVDGESTDLRQSLDGEWRVRVETAPTGRFPDGTSD
GPDWISDVSPLFAAPGFDDSSFSRVQVPSHLETAGLLAPQYVNVQYPWDGHEDPKAPAIPEHGHVAVYRREFDADGEVAQAVR
EGRPVTLTFQGAATAIYVWLNGSFIGYAEDSFTPSEFDVTDAIKVDGNVLAVACYEYSSASWLEDQDFWRLHGLFRSVELNAR
PAAHVADLHADADWDLATSRGSLSLDVLIDGAANAATADFALWDKNGTIVWHIVTKADGTLHAEAEIDDAAPWSAERPDLYEL
SVTLLDADGKVLETARTRIGFRHVAIEDGILKLNGKRLVFRGVNRHEFDCRRGRAITEEDMLWDIRFMKRHNINAVRTSHYPN
QSRWYELCDEYGIYLIDETNLETHGSWNSPGDIPVGTSVPGDDEAWLGACIDRLDSMILRDRNHPSVLVWSLGNESYAGEVLK
AMSAHAHRLDPGRPVHYEGVNWNHAYDGISDFESRMYAKPAEIQDWLEHGDERGEASKPFVSCEYMHAMGNSCGGLSEFIDLE
RYERYSGGFIWDYIDQGLVQRLPDGSERLSVGGEWGDRPTDYEFVGNGIVFADRTPSPKAQEVKQLYSPVKLAPDGHGVTIEN
RNLFAGTDGYVFAARLLEDGHEIWHADYRFDVAAGDTQHHDIAFPDIDADGDTREVTYEVDLLLAEATAWAPAGYELAFGQLT
GTLNPEQDITETSHDDDGRATRTLSRWNAGIRRDDKEILLSRTQGGIVSWKRDDREMVIRRPELVTFRPLTDNDRGNHSGFDR
AAWFAAGRYAIVTETKIHESDDGLVAEYQYELADPNHTPVSVTYHVNSDMRMQLTVEYPGNATDMASLPAFGIEWELPGEYDR
LRYYGPGPEETYRDRKQGGKLGIWDATAKASMAPYLMVQETGSHEDVRWLEATDIQGHGLRVTQRGDRHFTASLLPWNTYMIE
AARRHEDLPEPRHNYLRLLAAQMGVGGDDSWGAPVHTAYQLPAGRPLTLDVNLELI

SEQ ID No. 9

MTNSMQGKAKTIMTNLQSAQQFSQAWLTDPRVFAVNRLAAHSSHKFYDHSPQCGEAMDLKQSLDGQWRVQMLDLADLADNELA
EAAFAQPGYDAAGFSPIEVPSALETKGFLNHQYVNQQYPWSGHESPVAPDVPKHNHVALYRHEFSLEPKAAAVLEANKTAADD
AAKRRVTLTFQGAATAIVVWLNGAFIGYAEDSFTPSEFDVTDVLRDGVNTLAVACFEFSSASWLEDQDFWRLHGIFRSVELEA
QPLVHVNDLRVLADYDHTTGEGSLDVVALLRNAGTAAAVAATVLDAAGNTVWHSKLTAGADAETLTVKANVGKVNPWSAEEPT
LYTLQVVATDAAGQVIEAALQRIGFRHFAIEDGLMKLNGKRIVFKGVDRHEFDARTGRTIAEADMIEDIHSFKRLNINAVRTS
HYPNETRWYELCDEYGIYVLDETNLETHGSWTDPGDVFQPARAIPGSKDEWRAACVDRTASMVRRDYNHPSVVIWSLGNEAFG
GDVFYSMRDFVHENDPFRPVHYEGTFNDPEFSAATDIMSRMYAKPDEIVKLYLGEDGKKPYISCEYSHSMGNSTGGLHLYTEL
ERYPLYQGGFIWDYVDQALWQDCGNGTERLAYGGDFEDRPNDYEFSGDGVMFADRTPSPKAQEVKQLYANVKLVPDESGVTIT
NDNLFISTASSLFTARVLVDGAERWHANYRFDVPAGETVREPIAFPKVTDLVALSGSAEVTYEVDQRLAEATDWAPAGYELTF
GQYVAAVSFDDGAADAVVAGDAEVAADGFNAGIHTDFGEVLLSKTQGGMVSFKRDGREMVIRRPNLTTFRALTDNDRGNGSGF
ERAQWMAAGRYARVTGTSVEETADGKGLKATYSYELADAKHTPVTVHYEVDAALRVHLTVEYPGEADAATLPAFGLEWILPKQ
YDRLRFYGLGPEETYADRLHGAKLGVFSRTAAEDCAPYLLPQETGNHEQVRWAEITDEYGHGMRVTAAGGTRFATSLLPYSSL
MFEDALHQNELPKPRHTFLRLLAAQMGVGGDDTWGAPVHDEFQVPADQPLKLDVTLELI

SEQ ID No. 10

MTQRRSYRWPQPLAGQQARIWYGGDYNPDQWPEEVWDDDVRLMKKAGVNLVSVGIFSWAKIETSEGVYDFDWLDRIIDKLGEA
GIAVDLASATASPPMWLTQAHPEVLWKDYRGDVCQPGARQHWRPTSPVFREYALKLCRAMAEHYKGNPYVVAWHVSNEYGCHN

-continued

RFDYSEDAERAFRKWCEERYGTIDAVNDAWGTAFWAQRMNDFTEIVPPRFIGDGNFMNPGKLLDFKRFSSDALKAFYVAERDA

LAEITPDLPLTTNFMVSAAGSVLDYDDWGREVDFVSNDHYFIPGEAHLDELAFSASLVDGIARKDPWFLMEHSISAVNWRPVN

YRKEPGQLVRDSLAHVAMGADAVCYFQWRQSKAGAEKFHSAMVPHTGEDSAVFRDVCELGADLNTLADNGLLGTKLAKSKVAV

VFDYESEWATEHTATPTQKVHHVDEPLQWFRALADHGVTADVVPVSSNWDEYEVVVLPSVYILSEETTRRVRDYVVNGGRLIV

TYYTGLSDEKDHVWLGGYPGSIRDVVGVRVEEFMPMGDDFPGVPDCLGLSNGAVAHDIADVIGSVDGTATVLETFRDDPWTGM

DGAPAIVANTFGEGRSVYVGARLGRDGIAKSLPEIFESLGMAETGENDSRVLRVEREGSDGSRFVFSFNRTHEAVQIPFEGKI

VVSSFAEVSGENVSIKPNGVIVTKQ

SEQ ID No. 11

MANSNRVEHASETWLTDATVFEVNRTPAHSNHKCFTHDPQSGEHSDLTQSLDGEWRVEIVQASDIDFNEEPFVAENFDDSSFC

RAQVPGHLQMAGLLKNKYVNIQYPWDGHENPLEPNVPENNHVALYRRKFVVSKRLADTKESEGSVSIVFHGMATAIYVWVNGL

FAGYGEDGFTPNEFDITDLLHDGENVVAVACYEYSSASWLEDQDFWRLHGLFRSVELTAQPHVHVENMQLEADWDAESGTASL

DAALSVRNASDAATISATLKDSEGNVVWEASTNADANTTFASGSLQGLEPWSAESPSLYELEVNVIDQAGNIVEAAVQKVGFR

RFRIENGIMTLNGKRIVFKGADRHEFDAKRGRSITEQDMIDDVIFCKRHNINAIRTSHYPNQERWYDLCDEYGIYLIDETNLE

THGSWCLPGDVVTAETAVPGSKAHWEGACVDRVNSMVRRDYNHPSVVIWSLGNESYTGDVFRAMYKHVHDIDPNRPVHYEGVT

KNRDYDDVTDIETRMYEHADVVEEYLKNDPQKPYISCEYMHAMGNSVGNLDEYTALERYPHYQGGFIWDFIDQAIYATQPDGS

TRLCYGGDFGDRPSDYEFSGNGLVFADRTPTPKAQEVKQLYSNVHIDVTDRSVSIKNDNLFISTGGYQFVLRILADGEPVWQS

ERRFDVPADSACTFDVEWPVDLYRANADELVLEVSQRLAEATDWAPAGYELAFGQTIVAGTKAAEDAALPADGIVTVGRWNAG

VQGSGREILLSRTQGGLVSYTFDGHEFVLRRPAITTFRALTDNDRGAGHGFERAQWMVAGRYARCVDNVIEQVDEDTLKAVYT

YELATPQCTKVTVGYTADTTGRLNLHVEYPGESGELPTIPAFGIEWTLPVQYSNLRFFGAGPEETYQDRKHAKLGVWSTDAFK

DHAPYLMPQETGNHEEVRWAEITDENGHGLRVSRANGAAPFAVSLQPYSSFMIEEAQHQDELPAPKHMFLRVLAAQMGVGGDD

SWMSPVHSQYHITADQPISLDVNLELI

SEQ ID No. 12

MSNKLVKEKRVDQADLAWLTDPEVYEVNTIPPHSDHESFQSQEELEEGKSSLVQSLDGDWLIDYAENGQGPVNFYAEDFDDSN

FKSVKVPGNLELQGFGQPQYVNVQYPWDGSEEIFPPQIPSKNPLASYVRYFDLDEAFWDKEVSLKFDGAATAIYVWLNGHFVG

YGEDSFTPSEFMVTKFLKKENNRLAVALYKYSSASWLEDQDFWRMSGLFRSVTLQAKPRLHLEDLKLTASLTDNYQKGKLEVE

ANIAYRLPNASFKLEVRDSEGDLVAEKLGPIRSEQLEFTLADLPVAAWSAEKPNLYQVRLYLYQAGSLLEVSRQEVGFRNFEL

KDGIMYLNGQRIVFKGANRHEFDSKLGRAITEEDMIWDIKTMKRSNINAVRCSHYPNQSLFYRLCDKYGLYVIDEANLESHGT

WEKVGGHEDPSFNVPGDDQHWLGASLSRVKNMMARDKNHASILIWSLGNESYAGTVFAQMADYVRKADPTRVQHYEGVTHNRK

FDDATQIESRMYAPAKVIEEYLTNKPAKPFISVEYAHAMGNSVGDLAAYTALEKYPHYQGGFIWDWIDQGLEKDGHLLYGGDF

DDRPTDYEFCGNGLVFADRTESPKLANVKALYANLKLEVKDGQLFLKNDNLFTNSSSYYFLTSLLVDGKLTYQSRPLTFGLEP

GESGTFALPWPEVADEKGEVVYRVTAHLKEDLPWADEGFTVAEAEEVAQKLPEFKPEGRPDLVDSDYNLGLKGNNFQILFSKV

KGWPVSLKYAGREYLKRLPEFTFWRALTDNDRGAGYGYDLARWENAGKYARLKDISCEVKEDSVLVKTAFTLPVALKGDLTVT

YEVDGRGKIAVTADFPGAEEAGLLPAFGLNLALPKELTDYRYYGLGPNESYPDRLEGNYLGIYQGAVKKNFSPYLRPQETGNR

SKVRWYQLFDEKGGLEFTANGADLNLSALPYSAAQIEAADHAFDLTNNYTWVRALSAQMGVGGDDSWGQKVHPEFCLDAQKAR

QLRLVIQPLLLK

SEQ ID No. 13

MSNKLVKEKRVDQADLAWLTDPEVYEVNTIPPHSDHESFQSQEELEEGKSSLVQSLDGNWLIDYAENGQGPINFYAEDFDDSN

FKSVKVPGNLELQGFGQPQYVNIQYPWDGSEEIFPPQVPSKNPLASYVRYFDLDEALWDKEVSLKFAGAATAIYVWLNGHFVG

YGEDSFTPSEFMVTKFLKKEGNRLAVALYKYSSASWLEDQDFWRLSGLFRSVTLEAKPLLHLEDLKLTASLTDNYQKGKLEVE

ANIAYRLPNASFKLEVRDSEGDLVAEKVGPIRSEKLGFSLADLPVAAWSAEKPNLYQVRLYLYQAGSLLEVSRQEVGFRNFEL

KDGIMYLNGQRIVFKGVNRHEFDSKLGRAITEADMIWDIKTMKQSNINAVRCSHYPNQSLFYRLCDKYGLYVIDEANLESHGT

WEKVGHEDPSFNVPGDDQHWLGASLSRVKNMMARDKNHASILIWSLGNESYAGTVFAQMADYVRKADPTRVQHYEGVTHNRKF

-continued

DDATQIESRMYAPAKEIEEYLTKKPAKPFISVEYAHAMGNSVGDLAAYTALEKYPHYQGGFIWDWIDQGLEKDGHLLYGGDFD
DRPTDYEFCGDGLVFADRTTSPKLANVKALYSNLKLEVKDGQLFIKNDNLFTNSSAYYFLASLLVDGKLTYQSQPLTFGLEPG
ESGTFVLPWPEVEDEKGEIVYQVTAHLKEDLPWADEGFTVAEAEEAVTKLPEFYPAGRPELVDSDFNLGLKGNGFRILFSKAK
GWPVSIKYAGREYLKRLPEFTFWRALTDNDRGAGYGYDLAKWENAGKYARLQDISYEIKENSALVKTTFTLPVALKGDLTITY
EVDSLGKIAVTANFPGAVENGLLPAFGLNFALPKELSDYRYYGLGPNESYADRLEGSYLGIYQGAVEKNFTPYLRPQEAGNRS
KVRYYQLFDEEGGLEFTANGADLNLSALPYSAAQIEAADHAFELTNNYTWVRALAAQMGVGGDDSWGQKVHPEFCLDAQEARQ
LKLVIQPLLLK

SEQ ID No. 14
MSNKLVKEKRVDQADLAWLTDPEVYEVNTIPPHFDHESFQSQEELEEGKSSLVQSLDGDWLIDYAENGQGPVNFYAEDFDDSN
FKSVKVPGNLELQGFGQPQYVNVQYPWDGSEEIFPPQIPSKNPLASYVRYFDLDEAFWDKEVSLKFDGAATAIYVWLNGHFVG
YGEDSFTPSEFMVTKFLKKENNRLAVALYKYSSASWLEDQDFWRMSGLFRSVTLQAKPRLHLEDLKLTASLTDNYQKGKLEVE
ANIAYRLPNASFKLEVRDSEGDLVAEKLGPIRSEQLEFTLADLPVAAWSAEKPNLYQVRLYLYQAGSLLEVSRQEVGFRNFEL
KDGIMYLNGQRIVFKGANRHEFDSKLGRAITEEDMIWDIKTMKRSNINAVRCSHYPNQSLFYRLCDKYGLYVIDEANLESHGT
WEKVGGHEDPSFNVPGDDQHWLGASLSRVKNMMARDKNHASILIWSLGNESYAGTVFAQMADYVRKADPTRVQHYEGVTHNRK
FDDATQIESRMYAPAKVIEEYLTNKPAKPFISVEYAHAMGNSVGDLAAYTALEKYPHYQGGFIWDWIDQGLEKDGHLLYGGDF
DDRPTDYEFCGNGLVFADRTESPKLANVKALYANLKLEVKDGQLFLKNDNLFTNSSYYFLTSLLVDGKLTYQSRPLTFGLEP
GESGTFALPWPEVADEKGEVVYRVTAHLKEDLPWADEGFTVAEAEEVAQKLPEFKPEGRPDLVDSDYNLGLKGNNFQILFSKV
KGWPVSLKYAGREYLKRLPEFTFWRALTDNDRGAGYGYDLARWENAGKYARLKDISCEVKEDSVLVKTAFTLPVALKGDLTVT
YEVDGRGKIAVIADFPGAEEEAGLLPAFGLNLALPKELTDYRYYGLGPNESYPDRLEGNYLGIYQGAVKKNFSPYLRPQETGNR
SKVRWYQLFDEKGGLEFTANGADLNLSALPYSAAQIEAADHAFELTNNYTWVRALSAQMGVGGDDSWGQKVHPEFCLDAQKAR
QLRLVIQPLLLK

SEQ ID No. 15
MSNKLVKEKRVDQADLAWLTDPEVYEVNTIPPHSDHESFQSQEELEEGKSSLVQSLDGDWLIDYAENGQGPVNFYAEDFDDSN
FKSVKVPGNLELQGFGQPQYVNVQYPWDGSEEIFPPQIPSKNPLASYVRYFDLDEAFWDKEVSLKFDGAATAIYVWLNGHFVG
YGEDSFTPSEFMVTKFLKKENNRLAVALYKYSSASWLEDQDFWRMSGLFRSVTLQAKPRLHLEDLKLTASLTDNYQKGKLEVE
ANIAYRLPNASFKLEVRDSEGDLVAEKLGPIRSEQLEFTLADLPVAAWSAEKPNLYQVRLYLYQAGSLLEVSRQEVGFRNFEL
KDGIMYLNGQRIVFKGANRHEFDSKLGRAITEEDMIWDIKTMKRSNINAVRCSHYPNQSLFYRLCDKYGLYVIDEANLESHGT
WEKVGGHEDPSFNVPGDDQHWLGASLSRVKNMMARDKNHASILIWSLGNESYAGTVFAQMADYVRKADPTRVQHYEGVIHNRK
FDDATQIESRMYAPAKVIEEYLTNKPAKPFISVEYAHAMGNSVGDLAAYTALEKYPHYQGGFIWDWIDQGLEKDGHLLYGGDF
DDRPTDYEFCGNGLVFADRTESPKLANVKALYANLKLEVKDGQLFLKNDNLFTNSSYYFLTSLLVDGKLTYQSRPLTFGLEP
GESGTFALPWPEVADEKGEVVYRVTAHLKEDLPWADEGFTVAEAEEVAQKLPEFKPEGRPDLVDSDYNLGLKGNNFQILFSKV
KGWPVSLKYAGREYLKRLPEFTFWRALTDNDRGAGYGYDLARWENAGKYARLKDISCEVKEDSVLVKTAFTLPVALKGDLTVT
YEVDGRGKIAVTADFPGAEEEAGLLPAFGLNLALPKELTDYRYYGLGPNESYPDRLEGNYLGIYQGAVKKNFSPYLRPQETGNR
SKVRWYQLFDEKGGLEFTANGADLNLSALPYSAAQIEAADHAFELTNNYTWVRALSAQMGVGGDDSWGQKVHPEFCLDAQKAR
QLRLVIQPLLLK

SEQ ID No. 16
MSNKLVKEKRVDQADLAWLTDPEVYEVNTIPPHSDHESFQSQEELEEGKSSLVQSLDGDWLIDYAENGQGPVNFYAEDFDDSN
FKSVKVPGNLELQGFGQPQYVNIQYPWDGSEEIFPPQVPSKNPLASYVRYFDLDEAFWDKEVSLKFAGATIAIYVWLNGHFVG
YGEDSFTPSEFMVTKFLKKENNRLAVALYKYSSASWLEDQDFWRLSGLFRSVTLQAKPLLHLEDLKLTASLTDNYQKGKLEVE
ANIAYRLPNASFKLEVRDSEGDLVAEKLGPIRSEQLEFTLADLPVAAWSAEKPNLYQVRLYLYQAGSLLEVSRQEVGFRNFEL
KDGIMYLNGQRIVFKGVNRHEFDSKLGRAITEEDMIWDIKTMKRSNINAVRCSHYPNQSLFYRLCDKYGLYVIDEANLESHGT
WEKVGHEDPSFNVPGDDQHWLGASLSRVKNMMARDKNHASILIWSLGNESYAGTVFAQMADYVRKADPTRVQHYEGVIHNRKF

-continued

DDATQIESRMYAPAKEIEEYLTKKPAKPFISVEYAHAMGNSVGDLAAYTALEKYPHYQGGFIWDWIDQGLEKDGHLLYGGGDF

DDRPTDYEFCGNGLVFADRTTSPKLANVKALYSNLKLEVKDGQLFLKNDNLFTNSSAYYFLTSLLVDGKLTYQSQPLTFGLEP

GESGTFVLPWPEVEDEKGEIVYQVTAHLKEDLPWADEGFTVAEAEEAVTKLPEFYPAGRPELVDSDFNLGLKGNGFRILFSKA

KGWPVSIKYAGREYLKRLPEFTFWRALTDNDRGAGYGYDLAKWENAGKYARLQDISYEIKENSVLVKTAFTLPVALKGDLTIT

YEVDSLGKIAVTANFPGAVENGLLPAFGLNFALPKELSDYRYYGLGPNESYADRLEGSYLGIYQGAVEKNFTPYLRPQEAGNR

SKVRYYQLFDEESGLEFTANGADLNLSALPYSAAQIEAADHAFELSNNYTWVRALAAQMGVGGDDSWGQKVHPEFCLDAQEAR

QLKLVIQPLLLK

SEQ ID No. 17
MSNKLVKEKRVDQADLAWLTDPEVYEVNTIPPHSDHESFQSQEELEEGKSSLVQSLDGDWLIDYAENGQGPVNFYAEDFDDSN

FKSVKVPGNLELQGFGQPQYVNVQYPWDGSEEIFPPQIPSKNPLASYVRYFDLDEAFWDKEVSLKFDGAATAIYVWLNGHFVG

YGEDSFTPSEFMVTKFLKKENNRLAVALYKYSSASWLEDQDFWRMSGLFRSVTLQAKPRLHLEDLKLTASLTDNYQKGKLEVE

ANIAYRLPNASFKLEVRDSEGDLVAEKLGPIRSEQLEFTLADLPVAAWSAEKPNLYQVRLYLYQAGSLLEVSRQEVGFRNFEL

KDGIMYLNGQRIVFKGVNRHEFDSKLGRAITEEDMIWDIKTIKRSNINAVRCSHYPNQSLFYRLCDKYGLYVIDEANLESHGT

WEKVGGHEDPSFNVPGDDQHWLGASLSRVKNMMARDKNHASILIWSLGNESYAGTVFAQMADYVRKADPTRVQHYEGVTHNRK

FDDATQIESRMYAPAKVIEEYLTNKPAKPFISVEYAHAMGNSVGDLAAYTALEKYPHYQGGFIWDWIDQGLEKDGHLLYGGDF

DDRPTDYEFCGNGLVFADRTESPKLANVKALYANLKLEVKDGQLFLKNDNLFTNSSYYFLTSLLVDGKLTYQSRPLTFGLEP

GESGTFALPWPEVADEKGEVVYRVTAHLKEDLPWADEGFTVAEAEEVAQKLPEFKPEGRPDLVDSDYNLGLKGNNFQILFSKV

KGWPVSLKYAGREYLKRLPEFTFWRALTDNDRGAGYGYDLARWENAGKYARLKDISCEVKEDSVLVKTAFTLPVALKGDLTVT

YEVDGRGKIAVTADFPGAEEEAGLLPAFGLNLALPKELTDYRYYGLGPNESYPDRLEGNYLGIYQGAVKKNFSPYLRPQETGNR

SKVRWYQLFDEKGGLEFTANGADLNLSALPYSAAQIEAADHAFDLTNNYTWVRALSAQMGVGGDDSWGQKVHPEFCLDAQKAR

QLRLVIQPLLLK

SEQ ID No. 18
MSNKLVKEKRVDQADLAWLTDPEVYEVNTIPPHSDHESFQSQEELEEGKSSLVQSLDGDWLIDYAENGQGPVNFYAEDFDDSN

FKSVKVPGNLELQGFGQPQYVNVQYPWDGSEEIFPPQIPSKNPLASYVRYFDLDEAFWDKEVSLKFDGAATAIYVWLNGHFVG

YGEDSFTPSEFMVTKFLKKENNRLAVALYKYSSASWLEDQDFWRMSGLFRSVTLQAKPRLHLEDLKLTASLTDNYQKGKLEVE

ANIAYRLPNASFKLEVRDSEGDLVAEKLGPIGSEQLEFTLADLPVAAWSAEKPNLYQVRLYLYQAGSLLEVSRQEVGFRNFEL

KDGIMYLNGQRIVFKGVNRHEFDSKLGRAITEEDMIWDIKTIKRSNINAVRCSHYPNQSLFYRLCDKYGLYVIDEANLESHGT

WEKVGGHEDPSFNVPGDDQHWLGASLSRVKNMMARDKNHASILIWSLGNESYAGTVFAQMADYVRKADPTRVQHYEGVTHNRK

FDDATQIESRMYAPAKVIEEYLTNKPAKPFISVEYAHAMGNSVGDLAAYTALEKYPHYQGGFIWDWIDQGLEKDGHLLYGGDF

DDRPTDYEFCGNGLVFADRTESPKLANVKALYANLKLEVKDGQLFLKNDNLFTNSSYYFLTSLLVDGKLTYQSRPLTFGLEP

GESGTFALPWPEVADEKGEVVYRVTAHLKEDLPWADEGFTVAEAEEVAQKLPEFKPEGRPDLVDSDYNLGLKGNNFQILFSKV

KGWPVSLKYAGREYLKRLPEFTFWRALTDNDRGAGYGYDLARWENAGKYARLKDISCEVKEDSVLVKTAFTLPVALKGDLTVT

YEVDGRGKIAVTADFPGAEEEAGLLPAFGLNLALPKELTDYRYYGLGPNESYPDRLEGNYLGIYQGAVKKNFSPYLRPQETGNR

SKVRWYQLFDEKGGLEFTANGADLNLSALPYSAAQIEAADHAFELTNNYTWVRALSAQMGVGGDDSWGQKVHPEFCLDAQKAR

QLRLVIQPLLLK

SEQ ID No. 19
MSNKLVKEKRVDQADLAWLTDPEVYEVNTIPPHSDHESFQSQEELEEGKSSLVQSLDGNWLIDYAENGQGPINFYAEDFDDSN

FKSVKVPGNLELQGFGQPQYVNIQYPWDGSEEIFPPQVPSKNPLASYVRYFDLDEALWDKEVSLKFAGAATAIYVWLNGHFVG

YGEDSFTPSEFMVTKFLKKEGNRLAVALYKYSSASWLEDQDFWRLSGLFRSVTLEAKPLLHLEDLKLTASLTDNYQKGKLEVE

ANIAYRLPNASFKLEVRDSEGDLVAEKVGPIRSEKLDFSLADLPVAAWSAEKPNLYQVRLYLYQAGSLLEVSRQEVGFRNFEL

KDGIMYLNGQRIVFKGVNRHEFDSKLGRAITEADMIWDIKTMKQSNINAVRCSHYPNQSLFYRLCDKYGLYVIDEANLESHGT

WEKVGHEDPSFNVPGDDQHWLGASLSRVKNMMARDKNHASILIWSLGNESYAGTVFAQMADYVRKADPTRVQHYEGVTHNRKF

```
DDATQIESRMYAPAKEIEEYLTKKPAKPFISVEYAHAMGNSVGDLAAYTALEKYPHYQGGFIWDWIDQGLEKDGHLLYGGDFD

DRPTDYEFCGDGLVFADRTTSPKLANVKALYSNLKLEVKDGQLFIKNDNLFTNSSAYYFLTSLLVDGKLIYQSQPLTFGLEPG

ESGTFALPWPEVEDEKGEIVYQVTAHLKEDLPWADEGFTVAEAEEAVTKLPEFYPAGRPELVDSDFNLGLKGNGFRILFSKAK

GWPVSIKYAGREYLKRLPEFTFWRALTDNDRGAGYGYDLAKWENAGKYARLQDISYEIKENSALVKTAFTLPVALKGDLTITY

EVDSLGKIAVTANFPGAVENGLLPAFGLNFALPKELSDYRYYGLGPNESYADRLEGSYLGIYQGMVEKNFTPYLRPQEAGNRS

KVRYYQLFDEEGGLEFTANGADLNLSALPYSAAQIEAADHAFELTNNYTWVRALAAQMGVGGDDSWGQKVHPEFCLDAQEARQ

LKLVIQPLLLK
```

(G145 Domain a)

SEQ ID No. 20

```
MQANINWLDNPEVFRVNQLPAHSDHPFFRDYREWQKQHSSYQQSLNGKWKFHFSANPMDRPQDFYQRDFDSSNFDSIPVPSEI

ELSNYTQNQYINVLFPWEGKIFRRPAYALDPNDHEEGSFSKGADNTVGSYLKRFDLSSALIGKDVHIKFEGVEQAMYVWLNGH

FVGYAEDSFTPSEFDLTPYIQDKDNLLAVEVFKHSTASWLEDQDMFRFSGIFRSVELLGIPATHLMDMDLKPRVADNYQDGIF

NLKLHFIGKKAGSFHLLVKDIKGHTLLEKNEDIKENVQINNEKFENVHLWNNHDPYLYQLLIEVYDEQQNLLELIPFQFGFRR

IEISPEKVVLLNGKRLIINGVNRHEWDAKRGRSITMSDMTTDINTFKENNINAVRTCHYPNQIPWYYLCDQNGIYVMAENNLE

SHGTWQKMGEIEPSDNVPGSIPQWKEAVIDRARNNYETFKNHTSILFWSLGNESYAGDNIIAMNEFYKSHDDTRLVHYEGVVH

RPELKDKISDVESCMYLPPKKVEEYLQNDPPKPFMECEYMHDMGNSDGGMGSYIKLLDKYPQYFGGFIWDFIDQALLVHDEIS

GHDVLRYGGDFDDRHSDYEFSGDGLMFADRTPKPAMQEVRYYYGLHK
```

(G145 Domain b)

SEQ ID No. 21

```
MDYTNNQLHIIYGDATFGVNGKDFQYIFSYERGGLESLKVHGKEWLYRVPTPTFWRATTDNDRGSGFNLKAAQWLGADMFIKC

TDIHLKVDRHDFAELPIAPFNNKFSNHEYAKSAEISFTYQTLTTPATNAKIIYNIDDVGHIKVTMRYYGKKGLPPLPVIGIRL

IMPTAAIGFDYEGLSGETYPDRMAGAKEGKFHIDGLPVTEYLVPQENGMHMQTKKLTINRETTQNNVDRTNEKFSLSIQQAEK

PFNFSCLPYTAEELENATHIEELPLVRRTVLVIAGAVRGVGGIDSWGTDVESAYHINPELDHEFSFILN
```

SEQ ID No. 22

```
MTDVTHVDRASQAWLTDPTVFEVNRTPAHSSHKWYARDPQSGQWSDLKQSLDGEWRVEVVQAADINLEEEPATAESFDDSSFE

RIQVPGHLQTAGLMNHKYVNVQYPWDGHENPLEPNIPENNHVALYRRKFTVSAPVANAKQAGGSVSIVFHGMATAIYVWVNGA

FVGYGEDGFTPNEFDITELLHDGENVVAVACYEYSSASWLEDQDFWRLHGLFRSVELAARPHVHIENTQIEADWDPEAGTASL

DAALTVLNAADAATVRATLKDADGNTVWQTTGDAEAQTAISSGPLQGIAPWSAESPTLYELDVDVIDQAGDVIECTSQKVGFR

RFRIEDGILTINGKRIVFKGADRHEFDAEQGRAITEQDMIDDVVFCKRHNINSIRTSHYPNQERWYELCDEYGIYLIDEANLE

AHGSWSLPGDVLTEDTIVPGSKREWEGACVDRVNSMMRRDYNHPSVLIWSLGNESYVGDVFRAMYKHVHDIDPNRPVHYEGVT

HNRDYDDVTDIETRMYSHADEIEKYLKDDPKKPYLSCEYMHAMGNSVGNMDEYTALERYPKYQGGFIWDFIDQAIYATQPDGT

RSLRYGGDFGDRPSDYEFSGDGLLFANRKPSPKAQEVKQLYSNVHIDVTKDSVSVKNDNLFTATGDYVFVLSVLADGKPVWQS

TRRFDVPAGETRTFDVAWPVAAYRADARELVLQVSQRLAKATDWAESGYELAFGQTVVPADATATPDTKPADGTITVGRWNAG

VRGAGREVLLSRTQGGMVSYTFAGNEFVLRRPAITTFRPLTDNDRGAGHGFERVQWLGAGRYARCVDNVLEQIDDSTLKGTYT

YELATAQRTKVTVSYTAHTDGRVNLHVEYPGEQGDLPTIPAFGIEWTLPVQYTNLRFFGTGPAETYLDRKHAKLGVWSTNAFA

DHAPYLMPQETGNHEDVRWAEITDDHGHGMRVSRADGAAPFAVSLLPYSSFMLEEAQHQDELPKPKHMFLRVLAAQMGVGGDD

SWMSPVHPQYHIPADKPISLDVDLELI
```

(G224 Domain a)

SEQ ID No. 23

```
MDADIKWLDEPETFRVNQLPAHSDHYYYGNYDEWRHNNSRFAQNLDGQWQFNFAENLRERENDFYKMDYDSSSFGTIEVPSEI

ELNNYAQNNYINTLIPWEGKIYRRPAYTLSPDDAQEGSFSDGDDNTIGEYLKHFDLDPSLRGKQVRIRFDGVERAMYVWLNGH

FIGYAEDSFIPSEFDLTPYIQDEGNVLAVEVFKHSTASWIEDQDMFRFSGIFRSVNLLAQPLVHVEDLNIRPIVTDNYQDGIF

NVELQLHGEKIGNVNVRVIDNDGNTLVNETHPVDSTVKVQDQFLENVHLWDNHDPYLYQLLIEIRDDEGNLVELVPYRFGFRR

IEINKDHVVLLNGQRLIINGVNRHEWDARRGRAITMDDMTSDIHTFKENNINAVRTCHYPDQIPWYYLCDDNGIYMMAENNLE
```

```
SHATWQKMGAIEPSYNVPGSVPQWRDVVVDRARTNYETFKNHPSILFWSLGNESYAGDNIVKMNEFYKKHDDSRLVHYEGVCH

TPEYRDRISDVESWMYLPPKEVEEYLKNNPDKPFMECEYMHDMGNSDGGMGSYISLLDKYPQYFGGFIWDFIDQALLVKDPVS

GQEVMRYGGDFDDRHSDYEFSGDGLMFADRTPKPAMQEVRYYYGLHK (G224 Domain b)
                                                                     SEQ ID No. 24
MAYTNKLRVIYGDATLGLSGDGFHYIFSYERGGLESLKLNGKEWLYREPMPTFWRATTDNDRGSGFNIRSAQWLAADTFHKCV GIDLTVDNQHFAELPIAPITNEFSDPVSAESVKIKYTFATLTVPATQVTVIYEVNGQGEIKVTMHYYGHEDLPGLPVVGMRFI MPTVATGFDYQGLSGETYPDRMAGATEGTFHVDGLPVTKYLVPQENGMHMATHALTITRDSTQNNADHSREPFSLTVKQDAQP

FAFSCLPYTAEELENATHIEELPLARRTVLVVAGAVRGVGGIDSWGADVEEQYHIPADRDVEFSFVLNAK

SEQ ID No. 25
MSNKLVKEKRVDQADLAWLTDPEVYEVNTIPPHSDHESFQSQEELEEGKSSLVQSLDGNWLIDYAENGQGPINFYAEDFDDSN

FKSVKVPGNLELQGFGQPQYVNIQYPWDGSEEIFPPQVPSKIPLASYVRYFDLDEALWDKEVSLKFAGAATAIYVWLNGHFVG

YGEDSFTPSEFMVTKFLKKEGNRLAVALYKYSSASWLEDQDFWRLSGLFRSVTLEAKPLLHLEDLKLTASLTDNYQKGKLEVE

ANIAYRLPNASFKLEVRDSEGDLVAEKVGPIRSEKLDFSLADLPVAAWSAEKPNLYQVRLYLYQAGSLLEVSRQEVGFRNFEL

KDGIMYLNGQRIVFKGVNRHEFDSKLGRAITEADMIWDIKTMKQSNINAVRCSHYPNQSLFYRLCDKYGLYVIDEANLESHGT

WEKVGHEDPSFNVPGDDQHWLGASLSRVKNMMARDKNHASILIWSLGNESYAGTVFAQMADYVRKADPTRVQHYEGVTHNRKF

DDATQIESRMYAPAKEIEEYLTKKPAKPFISVEYAHAMGNSVGDLAAYTALEKYPHYQGGFIWDWIDQGLEKDGHLLYGGDFD

DRPTDYEFCGDGLVFADRTTSPKLANVKALYSNLKLEVKDGQLFIKNDNLFTNSSAYYFLTSLLVDGKLTYQSQPLTFGLEPG

ESGTFALPWPEVEDEKGEIVYQVTAHLKEDLPWADEGFTVAEAEEAVTKLPEFYPAGRPELVDSDFNLGLKGNGFRILFSKAK

GWPVSIKYAGREYLKRLPEFTFWRALTDNDRGAGYGYDLAKWENAGKYARLQDISYEIKENSALVKTTFILPVALKGDLTITY

EVDSLGKIAVTANFPGAVENGLLPAFGLNFALPKELSDYRYYGLGPNESYADRLEGSYLGIYQGMVEKNFTPYLRPQEAGNRS

KVRYYQLFDEEGGLEFTANGADLNLSALPYSAAQIEAADHAFELTNNYTWVRALAAQMGVGGDDSWGQKVHPEFCLDAQEARQ

LKLVIQPLLLK (G282 Domain a)
                                                                     SEQ ID No. 26
MQANINWLDNPEVFRVNQLPAHSDHPFFRDYREWQKQHSSYQQSLNGKWKFHFSANPMDRPQDFYQRDFDSSNFDSIPVPSEI ELSNYTQNQYINVLFPWEGKIFRRPAYALDPNDHEEGSFSKGADNTVGSYLKRFDLSSALIGKDVHIKFEGVEQAMYVWLNGH FVGYAEDSFTPSEFDLTPYIQEKDNLLAVEVFKHSTASWLEDQDMFRFSGIFRSVELLGIPATHLMDMDLKPRVADNYQDGIF NLKLHFIGKKAGSFHLLVKDIKGHTLLEKNEDIKENVQINNEKFENVHLWNNHDPYLYQLLIEVYDEQQNLLELIPFQFGFRR IEISPEKVVLLNGKRLIINGVNRHEWDAKRGRSITMSDMTTDINTFKENNINAVRTCHYPNQIPWYYLCDQNGIYVMAENNLE SHGTWQKMGEIEPSDNVPGSIPQWKEAVIDRARNNYETFKNHTSILFWSLGNESYAGDNIIAMNEFYKSHDDTRLVHYEGVVH RPELKDKISDVESCMYLPPKKVEEYLQNDPPKPFMECEYMHDMGNSNGGMDSYIKLLDKYPQYFGGFIWDFIDQALLVHDEIS

GHDVLRYGGDFDDRHSDYEFSGDGLMFADRKPKPAMQEVRYYYGLHK (G282 Domain b)
                                                                     SEQ ID No. 27
MDYTNNQLHIIYGDATFGVNGKDFQYIFSYERGGLESLKVHGKEWLYRVPTPTFWRATTDNDRGSGFNLKAAQWLGADMFTKC TDIHLKVDRHDFAELPIAPFNNKFSNHEYAKSAEISFTYQTLTTPATNAKIIYNIDDGGHIKVTMRYYGKKGLPPLPVIGIRL IMPTAATGFDYEGLSGETYPDRMAGAKEGKFHIDGLPVTEYLVPQENGMHMQTKKLTINRETTQNNVDRTNEKFSLSIQQAEK

PFNFSCLPYTAEELENATHIEELPLVRRTVLVIAGAVRGVGGIDSWGTDVESAYHINPDLDHEFSFILN (G334 Domain a)
                                                                     SEQ ID No. 28
MKANIKWLDDPEVFRINQLPAHSDHPFYKDYREWQKHSSSFKQSLNGAWQFHFSKDPQSRPIDFYKLSFDSSSFDTIPVPSEI ELNGYAQNQYTNTLYPWESKIYRKPAYTLGRGIKDGDFSQGKDNTVGSYLKHFDLNPALAGHDIHIQFEGVERAMYVYLNGHF IGYAEDSFTPSEFDLTPYIQAKDNILAVEVFKHSTASWLEDQDMFRFSGIFRSVELLALPRTHLMDLDIKPTVVNDYHDGVFN AKLHFMGKTSGNVHVLIEDIDGKTLLNKKLPLKSTVEIENETFANVHLWDNHDPYLYQLIIEVHDQDGKLVELIPYQFGFRKI
```

-continued

EITKDHVVLLNGKRLIINGVNRHEWDAKRGRSITLADMKQDIATFKHNNINAVRTCHYPNQIPWYYLCDQNGIYMMAENNLES

HGTWQKLGQVEATSNVPGSIPEWREVVVDRARSNYETFKNHTAILFWSLGNESYAGSNIAAMNKLYKDHDSSRLTHYEGVFHA

PEFKKEISDLESCMYLPPKEAEEYLQNPKKPLVECEYMHDMGNSDGGIGSYIKLIDKYPQYMGGFIWDFIDQALLVHDPVSGQ

DVLRYGGDFDDRHSDYEFSGDGLMFADRTPKPAMQEVRYYYGLHK (G334 Domain b)

SEQ ID No. 29
MAYTNNLHVVYGEASLGVNGQDFAYLFSYERGVLESLKIKDKEWLYRTPTPTFWRATTDNDRGSGFNQKAAQWLGADMFTKCV

GIHVQVDDHQFDELPIAPINNQFSNQEFAHEVKVAFDYETLTTPATKVKIIYNINDAGHMTITMHYFGKKGLPPLPVIGMRFI

MPTKAKSFDYTGLSGETYPDRMAGAERGTFHIDGLPVTKYLVPQENGMHMQTNELVITRNSTQNNADKDGDFSLKITQTKQPF

NFSLLPYTAEELENATHIEELPLARRSVLVIAGAVRGVGGIDSWGSDVEEQYHIDPEQDHEFSFTLN

SEQ ID No 30
MNMTKIQTYLNDPKIVSVNTVDAHSDHKYFESLEEFSEGEMKLRQSLNGKWKIHYAQNTNQVLKDFYKTEFDETDLNFINVPG

HLELQGFGSPQYVNTQYPWDGKEFLRPPQVPQESNAVASYVKHFTLNDALKDKKVFISFQGVATSIFVWVNGNFVGYSEDSFT

PSEFEISDYLVEGDNKLAVAVYRYSTASWLEDQDFWRLYGIFRDVYLYAIPKVHVQDLFVKGDYDYQTKAGQLDIDLKTVGDY

EDKKIKYVLSDYEGIVTEGDASVNGDGELSVSLENLKIKPWSAESPKLYDLILHVLDDDQVVEVVPVKVGFRRFEIKDKLMLL

NGKRIVFKGVNRHEFNARIGRCITEEDMLWDIKVMKQHNINAVRTSHYPNQTRWYELCDEYGLYVIDEANLETHGTWQKLGLC

EPSWNIPASEPEWLPACLDRANNMFQRDKNHASVIIWSCGNESYAGKDIADMADYFRSVDNTRPVHYEGVAWCREFDYITDIE

SRMYAKPADIEEYLTTGKLVDLSSVSDKHFASGNLTNKPQKPYISCEYMHTMGNSGGGLQLYTDLEKYPEYQGGFIWDFIDQA

IYKTLPNGSEFLSYGGDWHDRPSDYEFCGNGIVFADRTLTPKLQTVKHLYSNIKIAVDEKSVTIKNDNLFEDLSAYTFLARVY

EDGRKVSESEYHFDVKPGEEATFPVNFVVEASNSEQIYEVACVLREATKWAPKGHEIVRGQYVVEKISTETPVKAPLNVVEGD

FNIGIQGQNFSILLSRAQNTLVSAKYNGVEFIEKGPKLSFTRAYTDNDRGAGYPFEMAGWKVAGNYSKVTDTQIQIEDDSVKV

TYVHELPGLSDVEVKVTYQVDYKGRIFVTANYDGKAGLPNFPEFGLEFAIGSQFTNLSYYGYGAEEESYRDKLPGAYLGRYETS

VEKTFAPYLMPQESGNHYGTREFTVSDDNHNGLKFTALNKAFEFSALRNSTEQIENARHQYELQESDATWIKVLAAQMGVGGD

DSWGAPVHDEFLLSSADSYQLSFMIEPLN

SEQ ID No 31
MNNKLAQVKRVDQADLAWLTDPEIYEVNTIPPHSDHESFQSLEELEEGKSSLVQSLDGDWLIDYAENGEGPANFYEENFDDSS

FKSVKVPGNLELQGFGQPQYVNVQYPWDGSDEIFPPMIPSKNPVASYVRYFDLEEAFWDKEVSLKFAGAATAIYVWLNGHFVG

YGEDSFTPSEFMVTKFLKKEGNRLAVALYKYSSASWLEDQDFWRMSGLFRSVTLEAKPLLHLQDLKLTASLTNDYQKGSLQVE

ADIDYRLPNSSFKLELRDSAGELVAEKVGPIRSEKLDFSLADLPVAAWSAEEPNLYQVRLSLYQQGSLLEVSRQEVGFRNFEL

KDGIMYLNGKRIVFKGVNRHEFDSKLGRAITEADMIWDIKTMKQSNINAVRCSHYPNQSIFYHLCDKYGLYVIDEANLESHGT

WEKVGGHEDPSFNVPGDDQRWLGASLSRVKNMMARDKNHASILIWSLGNESYAGKVFAQMADYVRQADPTRVQHYEGVTHNRK

FDDATQIESRMYAPAKEIEEYLTKKPAKPFVSCEYAHAMGNSVGDLAAYTALEKYPHYQGGFIWDWIDQGLEKEGHLLYGGDF

DDRPSDYEFCGDGLVFADRTTSPKLANVKALYSNLKLELKDGQLFLKNDNLFTNSSAYYFLISLLVDGKLTYQSQPLTFALEP

GESGTFALPWPEVEDEKGEIVYQVTAHLKEDLPWADEGFTVAEAEEAVTKLPEFYPAGRPELVDSDYNLGIKGNGFRILFSKA

KGWPVSIKYAGREYLKRLPEFTFWRALTDNDRGAGYGYDLAKWENAGKYARLQDISYEIKENSVLVKTAFTLPVALKGDLTIT

YEVDSLGKIAVTANFPGAVENGLLPAFGLNFALPKELSDYRYYGLGPNESYADRLEGSYLGIYQGAVEKNFTPYLRPQEVGNR

SKVRYYQLFDEEGGLEFTANGANLNLSALPYSAAQIEAADHAFELTNNYTWVRALAAQMGVGGDDSWGQKVHPEFCLDAQEAR

QLKLVIQPLFTE

SEQ ID NO: 32
MADTAELAIVHATTASASWLTDPTVFAANRKPAHSSHRYVIGETSEPKQSLDGEWKVRIEQARNVDVESAPFAAVDFED

GDFGAIEVPGHLQMAGYLKNKYVNIQYPWDGHEDPQAPNIPENNHVAIYRRRFALDAQLARTLENDGTVSLTFHGAATA

IYVWLDGTFVGYGEDGFTPSEFDVTEALRNGNGNAADSPEAEHTLTVACYEYSSASWLEDQDFWRLHGLFRTVELAAQP

HTHVETVQLEADYTAADTAGTADTAELNAALTLRNPADAMTIESTLRDGDGNVVWESTQACNGEIALNSGKMTNIAPWS

-continued

```
AESPTLYTLTVRVVGHDGAIIETVTQKIGFRTFRIENGIMTLNGKRIVFKGADRHEFDAKRGRAITREDMLSDVVFCKR

HNINAIRTSHYPNQEYWYDLCDEYGLYLIDETNMETHGTWVANNVERPEDGIPGSRPEWEDACVDRINSMMRRDYNHPS

VLIWSLGNESSAGEVFRAMYRHAHTIDPNRPVHYEGSVHMREFEDVTDIESRMYAHADEIERYLNDGSPAHTDGPKKPY

ISCEYMHAMGNSCGNMDEYTALERYPMYQGGFIWDFIDQAIETKLPDGTTRMCYGGDFGDRPSDYEFSGDGLLFADRTP

SPKAQEVKQLYANVKIAVSVDEARITNDNLFVSTGDYRFVLRILADGKPVWSTTRRFDVAAGESASFEVDWPVDDYRSN

AEELVLEVSQQLGNACDWAPAGYELAFGQCVVAGAKTTADAVDAAGAPADGTVTLGRWNAGVRGQGREALFSRTQGGMV

SYTFGEREFVLRRPSITTFRPLTDNDRGAGHAFERAAWAVAGKYARCVDCAIANRGENAVEATYTYELAIPQRTKVTVR

YVADTAGLVSLDVEYPGEKNGDLPTIPAFGIEWALPVEYANLRFYGAGPEETYADRRHAKLGVWSTTAGDDCAPYLLPQ

ETGNHEDVRWAEITDDSGHGVRVKRGAGAKPFAMSLLPYSSTMLEEALHQDELPKPRHMFLRLLAAQMGVGGDDSWMSP

VHEQYQLPADQPLSLNVQLKLF
```

SEQ ID NO: 33

```
MANETRIEHASETWLADSTVFEVNRVPAHSDHKCYAHDSQTNEWSDLRQSLDGEWRVEVVQASDIEFNEEPFVRENFDD

SAFERIQVPGHLQMAGLMNNKYVNIQYPWDGHENPAEPNIPENNHVALYRKTFTMANRLADTKNAGGTVSIVFHGMATA

IYVWVNGMFVGYGEDGFTPNEFDITEMLHDGENVVAVACYEYSSASWLEDQDFWRLHGLFRSVELAAQPHVHIENMQIE

SDWDPESGSASLDAALTVRNAADAATISATLKDSDGNVVWETANCADPDTSISTGSLNGIRPWSAEDPVLYEFEVTVID

HAGNIAEVAVQKVGFRRFRIEDGIMTINGKRIVFKGADRHEFDPKRGRAITEQDMIDDVVFCKRHNLNAIRTSHYPNQE

RWYELCDEYGIYLIDETNLETHGSWCLPGDVLTEETAVPGSKAHWEGACVDRVNSMVRRDYNHPSVLIWSLGNESYTGD

VFRAMYKRVHDIDPNRPVHYEGVTHNRDYNDVTDIETRMYAHADAIEEYLKNDPQKPYISCEYMHAMGNSCGNMDEYTA

LERYPKYQGGFIWDFIDQAIYATQPDGTTSLRYGGDFGDRPSDYEFSGNGLVFADRKPTPKAQEVKQLYSNVHIDVAED

SVTIKNDNLFTSTGEYTFVLRVLADGEPVWQSERRFDVPAGSTEKLDVDWPLDLYRDGASELVLEVSQRLAKATNWAVA

GYELAFGQTVVAGSKKASAPVKPVDGIVTVGRWNVGVQGSGREVLLSRTQGGLVSYTFNNREFVLRRPAVTTFRALTDN

DRGAGHGFERAQWLGAGRYARCIGNEIEQIDENTVKASYTYELATPQRTKVTVSYTADTTGRVNLHVEYPGEPGDLPTI

PAFGIEWTLPVQYSNLRFFGAGPEETYQDRKHAKLGVWSTDAFKDHAPYLMPQETGNHEDVRWAEITDEKGHGLRISRA

EGAEPFAMSLQPYSSFMLEEAQHQDELPAPKHMFLRVLAEQMGVGGDDSWMSPVHPQYHIPADQPISLDVDLDLI
```

(Reference enzyme)

SEQ ID NO: 34

```
MVEDATRSDSTTQMSSTPEVVYSSAVDSKQNRTSDFDANWKFMLSDSVQAQDPAFDDSAWQQVDLPHDYSITQKYSQSN

EAESAYLPGGTGWYRKSFTIDRDLAGKRIAINFDGVYMNATVWFNGVKLGTHPYGYSPFSFDLTGNAKFGGENTIVVKV

ENRLPSSRWYSGSGIYRDVTLTVTDGVHVGNNGVAIKTPSLATQNGGNVTMNLTTKVANDTEAAANITLKQTVFPKGGK

TDAAIGTVTTASKSIAAGASADVTSTITAASPKLWSIKNPNLYTVRTEVLNGDTVLDTYDTEYGFRWTGFDATSGFSLN

GEKVKLKGVSMHHDQGSLGAVANRRAIERQVEILQKMGVNSIRTTHNPAAKALIDVCNEKGVLVVEEVFDMWNRSKNGN

TEDYGKWFGQTIAGDNAVLGGDKDETWAKFDLTSTINRDRNAPSVIMWSLGNEMMEGISGSVSDFPATSAKLVAWTKAA

DSTRPMTYGDNKIKANWNESNTMGDNLTANGGVVGTNYSDGANYDKIRTTHPSWAIYGSETASAINSRGIYNRTTGGAQ

SSDKQLTSYDNSAVGWGAVASSAWYDVVQRDFVAGTYVWTGFDYLGEPTPWNGTGSGAVGSWPSPKNSYFGIVDTAGFP

KDTYYFYQSQWNDDVHTLHILPAWNENVVAKGSGNKVPVVVYTDAAKVKLYFTPKGSTEKRLIGEKSFTKKTTAAGYTY

QVYEGTDKDSTAHKNMYLTWNVPWAEGTISAEAYDENNRLIPEGSTEGNASVTTTGKAAKLKADADRKTITADGKDLSY

IEVDVTDANGHIVPDAANRVTFDVKGAGKLVGVDNGSSPDHDSYQADNRKAFSGKVLAIVQSTKEAGEITVTAKADGLQ

SSTVKIATTAVPGTSTEKTVRSFYYSRNYYVKTGNKPILPSDVEVRYSDGTSDRQNVTWDAVSDDQIAKAGSFSVAGTV

AGQKISVRVTMIDEIGALLNYSASTPVGTPAVLPGSRPAVLPDGTVTSANFAVHWTKPADTVYNTAGTVKVPGTATVFG

KEFKVTATIRVQRSQVTIGSSVSGNALRLTQNIPADKQSDTLDAIKDGSTTVDANTGGGANPSAWTNWAYSKAGHNTAE

ITFEYATEQQLGQIVMYFFRDSNAVRFPDAGKTKIQISADGKNWTDLAATETIAAQESSDRVKPYTYDFAPVGATFVKV

TVTNADTTTPSGVVCAGLTEIELKTATSKFVTNTSAALSSLTVNGTKVSDSVLAAGSYNTPAIIADVKAEGEGNASVTV
```

LPAHDNVIRVITESEDHVTRKTFTINLGTEQEFPADSDERD (Reference enzyme)
SEQ ID No: 35
MSCLIPENLRNPKKVHENRLPTRAYYYDQDIFESLNGPWAFALFDAPLDAPDAKNLDWETAKKWSTISVPSHWELQEDW

KYGKPIYTNVQYPIPIDIPNPPTVNPTGVYARTFELDSKSIESFEHRLRFEGVDNCYELYVNGQYVGFNKGSRNGAEFD

IQKYVSEGENLVVVKVFKWSDSTYIEDQDQWWLSGIYRDVSLLKLPKKAHIEDVRVTTTFVDSQYQDAELSVKVDVQGS

SYDHINFTLYEPEDGSKVYDASSLLNEENGNTTFSTKEFISFSTKKNEETAFKINVKAPEHWTAENPTLYKYQLDLIGS

DGSVIQSIKHHVGFRQVELKDGNITVNGKDILFRGVNRHDHHPRFGRAVPLDFVVRDLILMKKFNINAVRNSHYPNHPK

VYDLFDKLGFWVIDEADLETHGVQEPFNRHTNLEAEYPDTKNKLYDVNAHYLSDNPEYEVAYLDRASQLVLRDVNHPSI

IIWSLGNEACYGRNHKAMYKLIKQLDPTRLVHYEGDLNALSADIFSFMYPTFEIMERWRKNHTDENGKFEKPLILCEYG

HAMGNGPGSLKEYQELFYKEKFYQGGFIWEWANHGIEFEDVSTADGKLHKAYAYGGDFKEEVHDGVFIMDGLCNSEHNP

TPGLVEYKKVIEPVHIKIAHGSVTITNKHDFITTDHLLFIDKDTGKTIDVPSLKPEESVTIPSDTTYVVAVLKDDAGVL

KAGHEIAWGQAELPLKVPDFVTETAEKAAKINDGKRYVSVESSGLHFILDKLLGKIESLKVKGKEISSKFEGSSITFWR

PPTNNDEPRDFKNWKKYNIDLMKQNIHGVSVEKGSNGSLAVVTVNSRISPVVFYYGFETVQKYTIFANKINLNTSMKLT

GEYQPPDFPRVGYEFWLGDSYESFEWLGRGPGESYPDKKESQRFGLYDSKDVEEFVYDYPQENGNHTDTHFLNIKFEGA

GKLSIFQKEKPFNFKISDEYGVDEAAHACDVKRYGRHYLRLDHAIHGVSEACGPAVLDQYRLKAQDFNFEFDLAFE

Examples

General Material and Methods
Molecular Cloning and Genetic Techniques

Techniques for restriction enzyme digestions, ligation, transformation and other standard molecular biology manipulations were based on methods described in the literature (Maniatis et al. "Molecular cloning: a laboratory manual, 2nd edition" Cold Spring Harbor Laboratory Press, Cold Spring Harbor, N.Y., 1989; Sambrook and Russell "Molecular Cloning: A Laboratory Manual, 3rd edition" Cold Spring Harbor Laboratory Press, Cold Spring Harbor, N.Y. 2001; Miller "Experiment in molecular genetics" Cold Spring Harbor Laboratory Press, 1972); or as suggested by the manufacturer. The PCR was carried out in a DNA thermal cycler obtained from (Bio-Rad, USA). DNA sequencing was performed by LGC, Berlin, Germany. Proteins were analyzed by polyacrylamide gel electrophoresis (PAGE) under the denaturation conditions using sodium dodecyl sulphate on gels containing 10% SDS (Mini-PROTEAN® TGX Stain-Free™ gel, Biorad, USA). Protein concentrations were determined using BCA method by following the protocol supplied with the kit.

Bacterial Strains, Plasmid and Growth Conditions

Escherichia coli strain TOP10 (Invitrogen) was used for the cloning and isolation of plasmids. The beta-galactosidase deficient E. coli strain BW25113 (Δ(araD-araB)567, ΔlacZ4787(::rrnB-3), λ-, rph-1, Δ(rhaD-rhaB)568, hsdR514) (Datsenko K A, Wanner B L; 2000, Proc Natl Acad Sci U.S.A. 97: 6640-6645) was used in combination with the pBAD/His vector (obtained from Invitrogen™ Life Technologies Corporation Europe BV) for recombinant protein production.

Growth Media for Protein Expression

2×PY medium containing (16 g/L BD BBL™ Phyton™ Peptone, 10 g/L Yeast Extract, 5 g/L NaCl) was used for the recombinant protein production. The growth medium was supplemented with ampicillin (100 µg/ml) to maintain the plasmid. Protein production was initiated by adding 0.05% of arabinose in to the culture medium.

Example 1: Construction of the Expression Vector for the Production of Lactases The genomic DNA of the lactic acid bacteria or bifidobacteria was extracted using commercial genomic extraction kit by following the supplied protocol (DNeasy, Qaigen, Germany). The lactase gene was amplified by PCR using two synthetic primers, using the purified genomic DNA source as biomass, and the PCR reagents were supplied in the Phusion U Hot start DNA polymerase (Thermo Scientific, USA) kit. The lactase gene was cloned into the start codon of the expression vector pBAD/His using the USER cloning method (Nour-Eldin HH, Geu-Flores F, Halkier BA, Plant Secondary Metabolism Engineering, Methods in Molecular Biology, 643; 2010), resulting in the expression construct. With the USER cloning method long, complementary overhangs in both PCR product and destination vector were generated. These overhangs can anneal to each other to form a stable hybridization product which was used to transform into E. coli without ligation. For the generation of overhangs in the PCR product, a single deoxyuradine residue is included in the upstream region of each primer to amplify target DNA. The lactase gene was amplified using the forward primer (5'-ATTAAC-CAUGCGACGCAACTTCGAATGGCC-3' (SEQ ID NO: 36)) and reverse primer (ATCTTCTCUTTACCGCCTTAC-CACGAGCACG (SEQ ID NO: 37)) containing a uridine at 9th position (as shown in bold), followed by with the lactase gene sequence. In parallel, the vector DNA was PCR amplified using the forward (5'-AGAGAAGAUTTTCAGCCT-GATACAGATTAAATC-3' (SEQ ID NO: 38)) and reverse primer (5'-ATGGTTAAUTCCTCCTGTTAGCC-CAAAAAACGG-3' (SEQ ID NO: 39)) pair containing single deoxyuracil residue at 9th positions (as highlighted in bold) followed by vector DNA sequence. The PCR products were purified using the commercial PCR purification kit (Qiagen, Denmark). The purified PCR products (lactase gene and the vector DNA) were mixed in equimolar amount and incubated with a commercial USER enzyme mix (New England Biolabs, USA) by following the supplied protocol.

These enzymes remove the uracil residue and also the short fragment upstream of the uridine, thereby creating complementary overhang in the PCR products. These complementary overhangs anneal with each other resulting in the pBAD-lactase expression vector. Aliquots of the ligation mixture were transformed into chemically competent E. coli TOP 10 cells. Transformants were selected at 37° C. on LB-Amp plates (LB; Luria-Bertani, Amp; 100 µg/ml ampicillin). The following day, colony PCR was carried out using a small biomass from the overnight grown transformant using the vector primers (primer 1; 5'-CGGCGTCACACTTTGCTATGCC-3' (SEQ ID NO: 40) and primer 2; 5'-CCGCGCTACTGCCGCCAGGC-3' (SEQ ID NO: 41)). The positive clones from the colony PCR were cultured in 5 mL LB-Amp medium and plasmid DNA was isolated from the cells. The cloned lactase gene was sequenced to verify that no additional mutations had been introduced during the amplification of the gene. The plasmid DNA was transformed in to the expression host E. coli strain BW25113.

Example 2: Expression of Lactases in E. coli Expression Host

The lactase enzyme was produced in E. coli BW25113 using the pBAD expression system. Freshly transformed E. coli BW25113 cells carrying the plasmid DNA were collected from a Lb-Amp plate using a sterile loop and used to inoculate 5 mL of Lb-Amp medium. The overnight grown culture (200 µL) was used to inoculate 50 mL 2×PY medium (containing 100 µg/mL ampicillin) in a 250 mL flask in a shaker (Innova® 42). The culture was grown at 37° C. at 220 rpm until the OD600 reached between 0.6-0.8. The lactase expression was initiated by adding 0.05% arabinose into the culture medium and the cells were cultured for additional 16-20 hours at 18° C. at 180 rpm. Cells were harvested by centrifugation (5000 rpm, 10 min at 4° C.) and were stored at −20° C. until further use.

Example 3: Protein Purification Using Immobilized Metal Affinity Chromatography Cells from 50 mL culture was thawed on ice and the cells were lysed using 10 mL mixture of lysis buffer (BugBuster® (Novagen) containing 2 mg/mL Lysozyme (Sigma Aldrich), 1 unit Benzonase (Sigma Aldrich), and 1× Complete Protease inhibitor cocktail (EDTA-free, Roche)) by incubating the cells at room temperature for 30 min. After 30 min, the cell debris was removed by centrifugation at 16000 rpm for 20 min at 4° C. The obtained supernatant was filtered through 0.45 µm pore diameter filter. A gravity flow Ni-Sepharose (GE Healthcare) column was prepared with 1 mL slurry by washing out the ethanol and water. The column was then equilibrated with washing buffer (50 mM of $NaH_2PO_4$, pH 8.0 containing 300 mM of NaCl and 20 mM of Imidazole). The cell-free extract was applied to the column and the non-bound proteins were eluted from the column. The column was washed with 20 mL of washing buffer and the retained proteins were eluted with 3.5 mL of elution buffer (50 mM of $NaH_2PO_4$, pH 8.0 containing 300 mM of NaCl and 250 mM of imidazole). The collected fractions were analyzed by SDS-PAGE on gels containing 10% acrylamide and those contained the purified lactase enzymes combined together. The buffer was exchanged against the storage buffer (50 mM $KH_2PO_4$ buffer pH 7.0 containing 10 mM NaCl, 1 mM $MgCl_2$), using a prepacked PD-10 desalting G-25 gel filtration column (GE Healthcare). The purified enzymes were stored at 4° C. until further use.

Example 4: Protein Purification Using Gel Filtration Chromatography

Cells from 50 mL culture was thawed on ice and the cells were lysed using 10 mL mixture of lysis buffer (BugBuster® (Novagen) containing 2 mg/ml lysozyme, 1 unit Benzonase (Sigma Aldrich), and 1× Complete Protease inhibitor cocktail (EDTA-free, Roche)) by incubating the cells at room temperature (25° C.) for 30 min. After 30 min, the cell debris was removed by centrifugation at 16000 rpm for 20 min at 4° C. The obtained supernatant was filtered through 0.45 µm pore diameter filter. The clear cell-free extract was concentrated by filtering through a 30000 Dalton filter (Vivaspin 20, GE Healthcare) by following the supplied protocol. A gravity flow Sephadex G50 superfine (Pharmacia Chemicals, Sweden) column was prepared with 1 g of column material (prepared by boiling in 100 mL water for 1 hour, cooled to room temperature). A column was prepared by applying 20 mL of the cooled slurry on a 30 mL filtration column. The column was washed with MilliQ water and equilibrated with wash buffer B (50 mM of $NaH_2PO_4$ buffer, pH 7.0). 500 µL of the concentrated supernatant was applied on the column and allowed the supernatant to enter in the column bed. The wash buffer (50 mM of $NaH_2PO_4$ buffer, pH 7.0) was applied on top of the column and the eluent fractions were collected individually. The collected fractions were analyzed on SDS-PAGE gel (containing 10% acrylamide). The protein fractions were combined together and buffer was exchanged against the storage buffer (50 mM $KH_2PO_4$ buffer pH 7.0 containing 10 mM NaCl, 1 mM $MgCl_2$) with the desalting column as described in earlier section. The purified enzymes were stored at 4° C. until further use.

Example 5: Protein Concentration Measurement Using BCA Assay

The concentration of purified lactases was determined using Pierce™ BCA protein assay kit (Thermo Fisher Scientific, Germany) by following the protocol supplied with the kit.

Example 6: Activity Determination Using Purified Enzymes on Lactose as Substrate at pH 6.7 at 37° C.

To measure the beta-galactosidase activity, the purified lactases were diluted to 40× in buffer A (50 mM $NaH_2PO_4$ buffer pH 6.7 containing 100 µM of $MgSO_4$). In a separate reaction, the diluted enzyme was incubated with lactose solution prepared in buffer B (140 mM of lactose prepared in 100 mM sodium-citrate buffer of pH 6.7, containing 100 µM of $MgSO_4$). The reaction mixture was prepared by mixing 13 µL of diluted enzyme and 37 µL of lactose solution in a PCR tube. The reaction mixture was incubated in a DNA thermal cycler with the following incubation parameters (reaction time; 10 min at 37° C., enzyme inactivation; 10 min at 95° C., cooling; 4° C.). The reaction mixtures were stored at −20° C. until further use. To determine the amount of glucose formed during the reaction, 10 µL of the reaction mixture was transferred to one well of standard microtiter plate (Thermo Fischer Scientific, Denmark) containing 80 µL of buffer C (100 mM of $NaH_2PO_4$ buffer, pH 7.0, containing glucose oxidase; 0.6 g/L (Sigma Aldrich), 2,2'-azino-bis(3-ethylbenzothiazoline-6-sulfonic acid diammonium salt); ABTS: 1.0 g/L (Sigma Aldrich), horseradish peroxidase; 0.02 g/L (Sigma Adrich)) and incubated at 30° C. for 40 min. After 40 min, the absorbance was determined at 610 nm using FLUOStar Omega UV-plate reader (BMG Labtech, Germany). The absorbance values between 0.1 and 1.5 were used for calculations, if the A610 nm value >1.5, the reaction mixture was diluted up to 10× with buffer A. With each purified enzyme, the reactions were carried out in triplicate and the mean value of the triplicate measurement was used for calculation. The protein purification performed with the E. coli cells transformed with the empty pBAD/His was used for normalization. Using a known concentration of glucose (0-2.5 mM), a standard curve was drawn and the slope of the curve was used to calculate the glucose formed during the reaction. The maximum absorbance value for each lactase was used to determine μM of glucose formed per sec, described as 1 Unit of Activity with Lactose at pH 6.7 at 37° C. (UAL-1). The specific activity at pH 6.7 at 37° C. is defined as μM of glucose formed per second per μM of enzyme (μM of glucose/sec/μM of enzyme) and determined by dividing UAL-1 by the protein concentration in μM, described as SUAL-1. The specific activity of SEQ ID NO:34 and SEQ ID NO:35 were determined under the similar conditions. The high specific activity at pH 6.7 is highly desired for robustness for the enzyme in fresh and fermented milk applications. The detail results of the specific activity of enzymes at pH 6.7 at 37° C. are described in FIG. 1.

Additionally the activity was described as μmole of glucose formed per minute per milligram of enzyme added. The results are shown in FIG. 14.

Example 7: Activity Determination Using Purified Enzymes in the Presence of Galactose at pH 6.7 at 37° C.

The purified lactases were diluted to 40× in buffer A (50 mM NaH$_2$PO$_4$ buffer pH 6.7 containing 100 μM of MgSO$_4$). In separate reactions, the diluted enzymes were incubated with buffer D (140 mM of lactose and 140 mM of galactose prepared in 100 mM sodium-citrate buffer of pH 6.7, containing 100 μM of MgSO$_4$). The reaction mixture consists of 13 μL of the diluted enzyme and 37 μL of buffer D in a PCR tube. The reaction mixture was incubated in thermal cycler with the following incubation parameters (reaction time: 10 min at 37° C., enzyme inactivation: 10 min at 95° C., cooling: 4° C.). The reaction mixtures were stored at −20° C. until further use. To determine the amount of glucose formed during the reaction, 10 μL of the reaction mixture was transferred to one well of standard microtiter plate (Thermo Fischer Scientific, Denmark) containing 80 μL of buffer C (100 mM of NaH$_2$PO$_4$ buffer, pH 7.0, containing glucose oxidase; 0.6 g/L (Sigma Aldrich), 2,2'-azino-bis(3-ethylbenzothiazoline-6-sulfonic acid diammonium salt); ABTS: 1.0 g/L (Sigma Aldrich), horseradish peroxidase; 0.02 g/L (Sigma Adrich)) and incubated at 30° C. for 40 min. After 40 min, the absorbance was determined at 610 nm using FLUOStar Omega UV-plate reader (BMG Labtech, Germany). The absorbance values between 0.1 and 1.5 were used for calculations, if the A610 nm value >1.5, the reaction mixture was diluted up to 10× with buffer A. With each purified enzyme, the reactions were carried out in triplicate and the mean value of the triplicate measurement was used for calculation. The protein purification performed with the E. coli cells transformed with the empty pBAD/His was used for normalization. Using a known concentration of glucose (0-2.5 mM), a standard curve was drawn and the slope of the curve was used to calculate the absorbance corresponding to 1 μM of glucose formed during the reaction. The maximum absorbance value for each lactase was used to determine μM of glucose formed per sec, described as 1 Unit of Activity with Galactose at pH 6.7 at 37° C. (UAG). The specific activity at pH 6.7 at 37° C. in presence of galactose is defined as μM of glucose formed per second per μM of enzyme (μM of glucose/sec/μM of enzyme) and determined by dividing UAG by the protein concentration in μM, described as SUAG.

The percentage inhibition of enzymes with galactose is calculated by using the formula % inhibition=100*(A−B)/A Where A is specific activity in of enzymes with lactose at pH 6.7 at 37° C. (SUAL) as described in the example 6, and B stand for the specific activity of enzymes in presence of galactose at pH 6.7 at 37° C. (SUAG) as described in the example 7. The detail results of the % galactose inhibition are described the FIG. 2 and FIG. 14. The lower galactose inhibition is highly relevant for the applications where very low lactose concentration is desired. Additionally the activity was described as μmole of glucose formed per minute per milligram of enzyme added. The results are shown in FIG. 14.

Note: relatively high standard deviations in galactose inhibition measurement are due to trace amounts of glucose impurities in purchased galactose.

Example 8: Activity Determination Using Purified Enzymes on Lactose as Substrate at pH 6.7 at 4° C.

The purified lactases were diluted up to 40× in buffer A (50 mM NaH$_2$PO$_4$ buffer pH 6.7 containing 100 μM of MgSO$_4$). In a separate reaction, the diluted enzyme was incubated with lactose solution prepared in buffer B (140 mM of lactose prepared in 100 mM sodium-citrate buffer of pH 6.7, containing 100 μM of MgSO$_4$). The reaction mixture was prepared by mixing 13 μL of diluted purified enzyme and 37 μL of lactose solution in a PCR tube. The reaction mixture was incubated in a DNA thermal cycler using the following incubating parameters (reaction time; 60 min at 4° C., enzyme inactivation; 10 min at 95° C., storage; 4° C.). The reaction mixtures were stored at −20° C. freezer until further use. The amount of glucose formed during the reaction was determined by following the protocol described in example 6. The maximum absorbance value for each lactase was used to determine μM of glucose formed per sec, described as 1 Unit of Activity with Lactose at pH 6.7 at 4° C. (UAL-2). The specific activity at pH 6.7 at 4° C. is defined as μM of glucose formed per second per μM of enzyme (μM of glucose/sec/μM of enzyme), and is determined by dividing UAL-2 by the protein concentration in μM, described as SUAL-2. The high specific activity at pH 6.7 at 4° C. is highly desired for the lactose hydrolysis for fresh/pasteurized milk applications. The detail results of the specific activity of enzymes at pH 6.7 at 4° C. are described in the FIG. 3. Additionally the activity was described as μmole of glucose formed per minute per milligram of enzyme added. The results are shown in FIG. 14.

Example 9: Activity Determination Using Purified Enzymes on Lactose as Substrate at pH 6.7 at 43° C.

The purified lactases were diluted to 40× in buffer A (50 mM NaH$_2$PO$_4$ buffer pH 6.7 containing 100 μM of MgSO$_4$).

In a separate reaction, the diluted enzyme was incubated with lactose solution prepared in buffer B (140 mM of lactose prepared in 100 mM sodium-citrate buffer of pH 6.7, containing 100 µM of $MgSO_4$). The reaction mixture was prepared by mixing 13 µL of diluted purified enzyme and 37 µL of lactose solution in a PCR tube. The reaction mixture was incubated in a DNA thermal cycler using the following incubating parameters (reaction time; 10 min at 43° C., enzyme inactivation; 10 min at 95° C., storage; 4° C.). The reaction mixtures were stored at −20° C. freezer until further use. The amount of the glucose formed during the reaction was determined by following the protocol described in example 6. The maximum absorbance value for each lactase was used to determine µM of glucose formed per sec, described as 1 Unit of Activity with Lactose at pH 6.7 at 43° C. (UAL-3). The specific activity at pH 6.7 at 43° C. is defined as µM of glucose formed per second per µM of enzyme (µM of glucose/sec/µM of enzyme), and is determined by dividing UAL-3 by the protein concentration in µM, described as SUAL-3. The high specific activity at pH 6.7 at 43° C. is highly desired for the lactose hydrolysis for the fermented milk applications. The detail results of the specific activity of enzymes at pH 6.7 at 43° C. are described in FIG. 4. Additionally the activity was described as µmole of glucose formed per minute per milligram of enzyme added. The results are shown in FIG. 14.

Example 10: Activity Determination Using Purified Enzymes on Lactose as Substrate at pH 5.5 at 4° C.

The purified lactases were diluted up to 40× in buffer A (50 mM $NaH_2PO_4$ buffer pH 6.7 containing 100 µM of $MgSO_4$). In a separate reaction, the diluted enzyme was incubated with lactose solution prepared in buffer E (140 mM of lactose prepared in 100 mM sodium-citrate buffer of pH 5.5, containing 100 µM of $MgSO_4$). The reaction mixture was prepared by mixing 13 µL of diluted purified enzyme and 37 µL of lactose solution in a PCR tube. The reaction mixture was incubated in a DNA thermal cycler using the following incubating parameters (reaction time; 60 min at 4° C., enzyme inactivation; 10 min at 95° C., storage; 4° C.). The substrate solution was prepared in a buffer of pH 5.5 and enzyme solution had a pH of 6.7. To initiate the reaction, 13 µL of enzyme was added to 37 µL of substrate solution. This mixing of these two buffers eventually increases the reaction pH from 5.5 to 5.7. The reaction mixtures were stored at −20° C. freezer until further use. To determine the amount of glucose formed during the reaction, 10 µL of the reaction mixture was transferred to one well of standard microtiter plate containing 80 µL of buffer C and incubated at 30° C. for 40 min. After 40 min, the absorbance was determined at 610 nm using FLUOStar Omega UV-plate reader (BMG Labtech, Germany). The absorbance value between 0.1 and 1.5 were used for calculations, if the A610 nm value >1.5, the reaction mixture was diluted up to 5× with buffer A. With each purified enzyme, the reactions were carried out in triplicate and the mean value of the triplicate measurement was used for calculations. The maximum absorbance value for each lactase was used to determine µM of glucose formed per sec, described as 1 Unit of Activity with Lactose at pH 5.5 at 4° C. (UAL-4). The specific activity at pH 5.5 at 4° C. is defined as µM of glucose formed per second per µM of enzyme (µM glucose/sec/µM of enzyme), and is determined by dividing UAL-4 by the protein concentration in µM, described as SUAL-4. The high specific activity at pH 5.5 at 4° C. is relevant for the lactose hydrolysis in the fermented milk applications. The detail results of the specific activity of enzymes at pH 5.5 at 4° C. are described in the FIG. 5. Additionally the activity was described as µmole of glucose formed per minute per milligram of enzyme added. The results are shown in FIG. 15.

Example 11: Activity Determination Using Purified Enzymes on Lactose as Substrate at pH 5.5 at 37° C.

The purified lactases were diluted up to 40× in buffer A (50 mM $NaH_2PO_4$ buffer pH 6.7 containing 100 µM of $MgSO_4$). In a separate reaction, the diluted enzyme was incubated with lactose solution prepared in buffer E (140 mM of lactose prepared in 100 mM sodium-citrate buffer of pH 5.5, containing 100 µM of $MgSO_4$). The reaction mixture was prepared by mixing 13 µL of diluted purified enzyme and 37 µL of lactose solution in a PCR tube. The substrate solution was prepared in a buffer of pH 5.5 and enzyme solution had a pH of 6.7. To initiate the reaction, 13 µL of enzyme was added to 37 µL of substrate solution. This mixing of these two buffers eventually increases the reaction pH from 5.5 to 5.7. The reaction mixture was incubated in a DNA thermal cycler using the following incubating parameters (reaction time; 10 min at 37° C., enzyme inactivation; 10 min at 95° C., storage; 4° C.). The reaction mixtures were stored at −20° C. until further use. The amount of glucose formed during the reaction was determined by following the protocol as described in the example 10. The maximum absorbance value for each lactase was used to determine µM of glucose formed per sec, described as 1 Unit of Activity with Lactose at pH 5.5 at 37° C. (UAL-5). The specific activity at pH 5.5 at 37° C. is defined as µM of glucose formed per second per µM of enzyme (µM of glucose/sec/µM of enzyme), and is determined by dividing UAL-5 by the protein concentration in µM, described as SUAL-5. The high specific activity at pH 5.5 at 37° C. is relevant for the lactose hydrolysis in the fermented milk applications and sweet whey lactose hydrolysis. The detail results of the specific activity of enzymes at pH 5.5 at 37° C. are described in the FIG. 6. Additionally the activity was described as µmole of glucose formed per minute per milligram of enzyme added. The results are shown in FIG. 15.

Example 12: Activity Determination Using Purified Enzymes on Lactose as Substrate at pH 5.5 at 43° C.

The purified lactases were diluted up to 40× in buffer A (50 mM $NaH_2PO_4$ buffer pH 6.7 containing 100 µM of $MgSO_4$). In a separate reaction, the diluted enzyme was incubated with lactose solution prepared in buffer E (140 mM of lactose prepared in 100 mM sodium-citrate buffer of pH 5.5, containing 100 µM of $MgSO_4$). The reaction mixture was prepared by mixing 13 µL of diluted purified enzyme and 37 µL of lactose solution in a PCR tube. The substrate solution was prepared in a buffer of pH 5.5 and enzyme solution had a pH of 6.7. To initiate the reaction, 13 µL of enzyme was added to 37 µL of substrate solution. This mixing of these two buffers eventually increases the reaction pH from 5.5 to 5.7.

The reaction mixture was incubated in a DNA thermal cycler using the following incubating parameters (reaction time; 10 min at 43° C., enzyme inactivation; 10 min at 95° C., storage; 4° C.). The reaction mixtures were stored at −20° C. until further use. The amount of glucose formed during the reaction was determined by following the protocol described in the example 10. The maximum absorbance value for each lactase was used to determine μM of glucose formed per sec, described as 1 Unit of Activity with Lactose at pH 5.5 at 43° C. (UAL-6). The specific activity at pH 5.5 at 43° C. is defined as μM of glucose formed per second per μM of enzyme (μM of glucose/sec/μM of enzyme), and is determined by dividing UAL-6 by the protein concentration in μM, described as SUAL-6. The high specific activity at pH 5.5 at 43° C. is relevant for the lactose hydrolysis in the fermented milk applications and sweet whey lactose hydrolysis. The detail results of the specific activity of enzymes at pH 5.5 at 43° C. are described in the FIG. 7. Additionally the activity was described as μmole of glucose formed per minute per milligram of enzyme added. The results are shown in FIG. 15.

Example 13: Activity Determination Using Purified Enzymes on Lactose as Substrate at pH 4.5 at 4° C.

The purified lactases were diluted up to 40× in buffer A (50 mM NaH$_2$PO$_4$ buffer pH 6.7 containing 100 μM of MgSO$_4$). In a separate reaction, the diluted enzyme was incubated with lactose solution prepared in buffer F (140 mM of lactose prepared in 100 mM sodium-citrate buffer of pH 4.5, containing 100 μM of MgSO$_4$). The reaction mixture was prepared by mixing 13 μL of diluted purified enzyme and 37 μL of lactose solution in a PCR tube. The substrate solution was prepared in a buffer of pH 4.5 and enzyme solution had a pH of 6.7. To initiate the reaction, 13 μL of enzyme was added to 37 μL of substrate solution. This mixing of these two buffers eventually increases the reaction pH from 4.5 to 4.7.

The reaction mixture was incubated in a DNA thermal cycler using the following incubating parameters (reaction time; 60 min at 4° C., enzyme inactivation; 10 min at 95° C., storage; 4° C.). To determine the amount of glucose formed during the reaction, 10 μL of the reaction mixture was transferred to one well of standard microtiter plate containing 80 μL of buffer C (as described in example 6) and incubated at 30° C. for 40 min. After 40 min, the absorbance was determined at 610 nm using FLUOStar Omega UV-plate reader. The absorbance value between 0.1 and 1.5 were used for calculations, if the A610 nm value >1.5, the reaction mixture was diluted up to 5× with buffer A. With each purified enzyme, the reactions were carried out in triplicate and the mean value of the triplicate measurement was used for calculation. The maximum absorbance value for each lactase was used to determine μM of glucose formed per sec, described as 1 Unit of Activity with Lactose at pH 4.5 at 4° C. (UAL-7). The specific activity at pH 4.5 at 4° C. is defined as μM of glucose formed per second per μM of enzyme (μM of glucose/sec/μM of enzyme), and is determined by dividing UAL-7 by the protein concentration in μM, described as SUAL-7. The high specific activity at pH 4.5 at 4° C. is relevant for the lactose hydrolysis in the fermented milk applications. The detail results of the specific activity of enzymes at pH 4.5 at 4° C. are described in the FIG. 8. Additionally the activity was described as μmole of glucose formed per minute per milligram of enzyme added. The results are shown in FIG. 16.

Example 14: Activity Determination Using Purified Enzymes on Lactose as Substrate at pH 4.5 at 37° C.

The purified lactases were diluted up to 40× in buffer A (50 mM NaH$_2$PO$_4$ buffer pH 6.7 containing 100 μM of MgSO$_4$). In a separate reaction, the diluted enzyme was incubated with lactose solution prepared in buffer F (140 mM of lactose prepared in 100 mM sodium-citrate buffer of pH 4.5, containing 100 μM of MgSO$_4$). The reaction mixture was prepared by mixing 13 μL of diluted purified enzyme and 37 μL of lactose solution in a PCR tube. The substrate solution was prepared in a buffer of pH 4.5 and enzyme solution had a pH of 6.7. To initiate the reaction, 13 μL of enzyme was added to 37 μL of substrate solution. This mixing of these two buffers eventually increases the reaction pH from 4.5 to 4.7.

The reaction mixture was incubated in a DNA thermal cycler using the following incubating parameters (reaction time; 10 min at 37° C., enzyme inactivation; 10 min at 95° C., storage; 4° C.). The reaction mixtures were stored at −20° C. until further use. The amount of glucose formed during the reaction was determined by following the protocol described in the example 13. The maximum absorbance value for each lactase was used to determine μM of glucose formed per sec, described as 1 Unit of Activity with Lactose at pH 4.5 at 37° C. (UAL-8). The specific activity at pH 4.5 at 37° C. is defined as μM of glucose formed per second per μM of enzyme (μM of glucose/sec/μM of enzyme), and is determined by dividing UAL-8 by the protein concentration in μM, described as SUAL-8. The high specific activity at pH 4.5 at 37° C. is relevant for the lactose hydrolysis in the fermented milk applications and acidic whey lactose hydrolysis. The detail results of the specific activity of enzymes at pH 4.5 at 37° C. are described in the FIG. 9. Additionally the activity was described as μmole of glucose formed per minute per milligram of enzyme added. The results are shown in FIG. 16.

Example 15: Activity Determination Using Purified Enzymes on Lactose as Substrate at pH 4.5 at 43° C.

The purified lactases were diluted up to 40× in buffer A (50 mM NaH$_2$PO$_4$ buffer pH 6.7 containing 100 μM of MgSO$_4$). In a separate reaction, the diluted enzyme was incubated with lactose solution prepared in buffer F (140 mM of lactose prepared in 100 mM sodium-citrate buffer of pH 4.5, containing 100 μM of MgSO$_4$). The reaction mixture was prepared by mixing 13 μL of diluted purified enzyme and 37 μL of lactose solution in a PCR tube. The substrate solution was prepared in a buffer of pH 4.5 and enzyme solution had a pH of 6.7. To initiate the reaction, 13 μL of enzyme was added to 37 μL of substrate solution. This mixing of these two buffers eventually increases the reaction pH from 4.5 to 4.7. The reaction mixture was incubated in a DNA thermal cycler using the following incubating parameters (reaction time; 10 min at 43° C., enzyme inactivation; 10 min at 95° C., storage; 4° C.). The reaction mixtures were stored at −20° C. until further use. The amount of glucose formed during the reaction was determined by following the protocol described in the example 13. The maximum absorbance value for each lactase was used to determine μM of glucose formed per sec, described as 1 Unit of Activity with Lactose at pH 4.5 at 43° C. (UAL-9). The specific activity at pH 4.5 at 43° C. is defined as μM of glucose formed per second per μM of enzyme (μM of glucose/sec/μM of enzyme), and is determined by dividing UAL-9 by the protein concentration in μM, described as SUAL-9. The high specific activity at pH 4.5 at 43° C. is relevant for the lactose hydrolysis in the fermented milk applications and acidic whey lactose hydrolysis. The detail results of the specific activity of enzymes at pH 4.5 at 43° C. are described in the FIG. 10. Additionally the activity was described as µmole of glucose formed per minute per milligram of enzyme added. The results are shown in FIG. 16.

Example 16: Activity Determination in BLU Units

The commercially available NOLA™ Fit enzyme (Chr-Hansen, Denmark) was diluted in a range from 0.5 BLU/mL to 2.5 BLU/mL in buffer G (50 mM $NaH_2PO_4$ buffer pH 7.0 containing 100 µM of $MgSO_4$, 0.045% Brij, Sigma Aldrich). The diluted enzyme was incubated with lactose solution prepared in buffer H (105 mM of lactose prepared in 100 mM sodium-citrate buffer of pH 6.7, containing 100 µM of $MgSO_4$). The reaction mixture was prepared by mixing 13 µL of diluted purified enzyme and 37 µL of lactose solution in a PCR tube. The reaction mixture was incubated in a DNA thermal cycler using the following incubating parameters (reaction time; 10 min at 37° C., enzyme inactivation; 10 min at 95° C., storage; 4° C.). The amount of glucose conversion was determined by transferring 10 µL of the reaction mixture in a single well of standard microtiter plate containing 80 µL of buffer C and incubated at 30° C. for 40 min. After 40 min, the absorbance was determined at 610 nm using FLUOStar Omega UV-plate reader (BMG Labtech, Germany). The measured absorbance values were used to draw a standard curve against BLU/mL. The maximum slope of the curve was used to determine the activity of new enzymes in BLU/mL.

Example 17: Activity Determination of New Lactases in BLU/mL Using Lactose as Substrate The purified lactases were diluted up to 50× in buffer A (50 mM $NaH_2PO_4$ buffer pH 6.7 containing 100 µM of $MgSO_4$). In a separate reaction, the diluted enzyme was incubated with lactose solution prepared in buffer H (105 mM of lactose prepared in 100 mM sodium-citrate buffer of pH 6.7, containing 100 µM of $MgSO_4$). The reaction mixture was prepared by mixing 13 µL of diluted purified enzyme and 37 µL of lactose solution in a PCR tube. The reaction mixture was incubated in a DNA thermal cycler using the following incubating parameters (reaction time; 10 min at 37° C., enzyme inactivation; 10 min at 95° C., storage; 4° C.). After the reaction, 10 µL of the reaction mixture was transferred to one well of standard microtiter plate containing 80 µL of buffer C (as described in example 6) and incubated at 30° C. for 40 min. After 40 min, the absorbance was determined at 610 nm using FLUOStar Omega UV-plate reader. The absorbance value between 0.1 and 1.5 were used for calculations, if the A610 nm value >1.5, the reaction mixture was diluted up to 5× with buffer A. The maximum absorbance values were used to calculate the enzyme activity in BLU/mL, using standard curve described in example 16.

Example 18: Percentage Residual Lactose Measurement in Fresh Milk at Cold Temperature 2 mL of commercial pasteurized milk (1.5% Fat pasteurized milk, Arla Food) was mixed with 10-125 µL of enzyme (equivalent to 10 BLU/mL) as determined in the example 17, in 10 mL glass tube. The samples were incubated under constant conditions for 24 hours at 4° C. After the incubation, the reaction was stopped by heat inactivation at 95° C. for 7 min, followed by storage at −20° C. until further use. The amount of remaining lactose in the milk was analyzed using an HPLC assay. Samples for analysis were treated with 1.8 mL protein precipitation solution (0.083 M PCA and 2 mM Na-EDTA) and 2 mL of MQW prior to centrifugation at 2800 rpm for 30 min at 4° C. An aliquot of the supernatant was diluted a total of 200-fold using a Janus dilution robot (PerkinElmer, Waltham, Mass., USA). The diluted samples were analyzed on a Dionex ICS-5000 system (Thermo Fischer Scientific, Waltham (Mass.), USA) using 4×250 mm CarboPac SA20 analytical column (Thermo Fischer Scientific, Waltham, Mass., USA) and a pulsed amperometric detector. The detector was set to a simple three-step potential waveform, selective for detection of carbohydrates. The eluent was set to 1 mM KOH and was continuously regenerated through a trap column (CR-TC, Thermo Fischer Scientific, Waltham (MA), USA). The flow rate of the eluent was 1.2 mL/min and the analysis time was 10 min per injection. The lactose in each sample was quantified using a three-point external calibration curve prepared by adding known amounts of lactose monohydrate (Sigma-Aldrich, St. Louis, Mo., USA) to MQW. Concentrations were calculated based on the chromatographic peak heights. The measured percentage residual lactose in fresh milk is shown in FIG. 11.

Example 19: Activity Determination in UHT Milk at Room Temperature 2 mL of UHT milk (1.5% Fat UHT milk, Arla Food) was mixed with 2-25 µL of enzyme (equivalent to 2 BLU/mL) as determined in example 17, in 10 mL glass tube. The samples were incubated under constant conditions for 24 hours at 25° C. After the incubation, the reaction was stopped by heat inactivation at 95° C. for 7 min, followed by storage at −20° C. until further use. The amount of residual lactose in UHT milk was analyzed using HPLC by following the protocol as described in example 18. The percentage of residual lactose in fresh milk after hydrolysis is listed in the FIG. 12.

Example 20: Enzyme Performance at High Temperature in Buffer

The purified enzyme was diluted to 5 BLU/mL in buffer A (50 mM $NaH_2PO_4$ buffer pH 6.7 containing 100 µM of $MgSO_4$). In a separate reaction, 13 µL of the diluted enzyme was incubated in a DNA thermal cycler with lactose solution (105 mM lactose prepared in 100 mM sodium-citrate buffer of pH 6.7, containing 100 µM of $MgSO_4$). The reaction mixture was prepared by mixing 13 µL of enzyme and 37 µL of lactose solution in a PCR tube. The reaction mixture was incubated in a DNA thermal cycler using the following incubating parameters (reaction time; 10 min at 37° C., enzyme inactivation; 10 min at 95° C., storage; 4° C.). After the reaction, 10 µL of the reaction mixture was transferred to one well of standard microtiter plate containing 80 µL of buffer C (as described in example 6) and incubated at 30° C. for 40 min. After 40 min, the absorbance was determined at 610 nm using FLUOStar Omega UV-plate reader. The absorbance value between 0.1 and 1.5 were used for calculations, if the A610 nm value >1.5, the reaction mixture was diluted up to 5× with buffer A. The measured absorbance was called Abs37° C., and considered as reference value for calculations.

To measure the impact of heat treatment on enzyme activity, in a separate reaction, 13 µL of the diluted enzyme (5 BLU/mL) was incubated in a DNA thermal cycler using the following incubating parameter (at 72° C. for 15 sec or 74° C. for 15 sec or 76° C. for 6 sec or 78° C. for 6 sec or 80° C. for 4 sec or 85° C. for 5 sec or 90° C. for 5 sec or 95°

C. for 5 sec, followed by storage at 4° C.). The activity of the heat treated enzyme was determined by incubation with the lactose solution (105 mM lactose prepared in 100 mM sodium-citrate buffer of pH 6.7, containing 100 μM of MgSO$_4$), as described above. The measured absorbance at different temperature (for example at 72° C., 74° C., 76° C., 78° C., 80° C., 85° C., 90° C. or 95° C.) was called as Abs72° C., Abs74° C., Abs76° C., Abs78° C., Abs80° C., Abs85° C., Abs90° C., Abs95° C.

The percentage residual activity at high temperature was determined using the formula, % residual activity=(Abs72° C./Abs37° C.)*100

The percentages residual activities of different enzymes at different temperature are described in FIG. 13.

Example 21: Percentage Residual Lactose after the High Heat Treatment

The effect of heat treatment on the enzyme performance in pasteurized milk was determined by incubating a fixed amount of enzyme in the milk followed by a heat treatment. In separate reactions, 50 μL of the pasteurized milk was mixed with 10 BLU/mL of purified enzyme (as determined in example 17), in a PCR tube. The milk sample was incubated at 72° C. for 15 or 76° C. for 10 sec or 85° C. for 5 sec and 90° C. for 5 sec, followed by incubation at 5° C. for 24 h. After 24 h at 5° C., the reaction was stopped by heating the reaction at 95° C. for 7 min, followed by storage at −20° C. The residual lactose was measured by using the LactoSens® assay kit (Chr. Hansen, Denmark), by following the supplied protocol. The measured residual lactose was determined in g/L was determined at different temperature. The detection limit of the LactoSens® kit is between 0.2 g/L to 10 g/L. The results are described in the table 2.

TABLE 2

The percentage residual lactose in the pasteurized milk treated with a fixed amount of the purified enzyme followed by incubation at different temperature (72° C. for 15 sec, 76° C. for 10 sec, 85° C. for 5 sec and 90° C. for 5 sec followed by incubation at 4 C. for 24 h), determined using LactoSens ® assay kit. The LactoSens ® kit detection limits are in range of 0.2 g/L to 10 g/L of lactose. Here ND; not determined.

| G-number | Residual lactose at 4° C. (g/L) | Residual lactose at 72° C. (g/L) | Residual lactose at 76° C. (g/L) | Residual lactose at 85° C. (g/L) | Residual lactose at 90° C. (g/L) |
|---|---|---|---|---|---|
| G4 | <0.2 | >10.0 | ND | ND | ND |
| G11 | <0.2 | >10.0 | ND | ND | ND |
| G16 | <0.2 | >10.0 | ND | ND | ND |
| G33 | <0.2 | 4.7 | ND | ND | ND |
| G35 | <0.2 | >10.0 | >10.0 | ND | ND |
| G40 | <0.2 | <0.2 | <0.2 | >10.0 | ND |
| G44 | 0.9 | >10.0 | ND | ND | ND |
| G57 | <0.2 | >10.0 | ND | ND | ND |
| G62 | 8.4 | >10.0 | >10.0 | >10.0 | ND |
| G66 | 0.35 | >10.0 | ND | ND | ND |
| G83 | 0.3 | 2.1 | 6.0 | >10.0 | ND |
| G84 | 0.25 | 0.65 | 0.5 | 7.6 | >10 |
| G95 | 0.3 | 6.0 | 8.6 | >10 | ND |
| G100 | 0.4 | 2.4 | 2.6 | >10.0 | ND |
| G104 | 0.35 | 0.45 | 0.5 | 0.45 | >10 |
| G108 | 0.35 | 1.3 | 1.55 | ND | ND |
| G109 | 0.35 | 1.45 | 3.4 | >10.0 | ND |
| G118 | 0.45 | 0.95 | 0.8 | >10.0 | >10 |
| G158 | <0.2 | 3.9 | >10.0 | ND | ND |
| G256 | 0.3 | 1.0 | 0.75 | 3.4 | >10 |
| G282 | <0.2 | <0.2 | <0.2 | <0.2 | >10 |
| G335 | <0.2 | 0.35 | 8.0 | >10.0 | ND |
| G600 | <0.2 | >10.0 | >10.0 | >10.0 | ND |
| G500 | <0.2 | >10.0 | ND | ND | ND |

The invention claimed is:

1. A method for producing a dairy product, comprising treating a milk-based substrate comprising lactose with a peptide selected from peptides having the amino acid sequence of any one of SEQ ID NO:1, SEQ ID NO:22, or SEQ ID NO:32, and variants thereof having from 1 to 5 amino acid substitutions, additions or deletions relative thereto, wherein said treating takes place at a pH of 4 to 7 and at a temperature selected from (i) a temperature of not more than 25° C. and (ii) a temperature of between 40° C. and 100° C. wherein the peptide exhibits beta-galactosidase enzyme activity at the temperature and reduces lactose content of the substrate.

2. The method according to claim 1, wherein said treating takes place at a temperature of not more than 25° C.

3. The method according to claim 1, wherein said dairy product is fermented milk product and said treating is performed during or prior to fermentation.

4. The method according to claim 1, which method does not require the addition of further enzyme after fermentation.

5. The method according to claim 1, wherein said dairy product is a fermented milk product and said treating is performed immediately following fermentation.

6. The method according to claim 1, wherein said dairy product is fresh milk and said treating is performed prior to, in conjunction with, or immediately following pasteurization.

7. The method according to claim 1, wherein said dairy product is ultra-heat treated (UHT) milk and said treating is performed prior to, in conjunction with, or immediately following ultra-heat treatment.

8. The method according to claim 1, wherein said treating takes place at a temperature of between 40° C. and 100° C.

9. The method according to claim 1, wherein the method comprises treating said milk-based substrate with said peptide, wherein said peptide has the amino acid sequence of SEQ ID NO:1 or a variant thereof having from 1 to 5 amino acid substitutions relative thereto.

10. The method according to claim 9, wherein said peptide has the amino acid sequence of SEQ ID NO:1.

11. The method according to claim 1, wherein the method comprises treating said milk-based substrate with said peptide, wherein said peptide has the amino acid sequence of SEQ ID NO:22 or a variant thereof having from 1 to 5 amino acid substitutions relative thereto, wherein said peptide exhibits beta-galactosidase enzyme activity at 72° C.

12. The method according to claim 11, wherein said peptide has the amino acid sequence of SEQ ID NO:22.

13. The method according to claim 1, wherein the method comprises treating said milk-based substrate with said peptide, wherein said peptide has the amino acid sequence of SEQ ID NO:32 or a variant thereof having from 1 to 5 amino acid substitutions relative thereto.

14. The method according to claim 9, wherein said peptide has the amino acid sequence of SEQ ID NO:32.

* * * * *

SEQUENCE LISTING

<160> NUMBER OF SEQ ID NOS: 41

<210> SEQ ID NO 1
<211> LENGTH: 1049
<212> TYPE: PRT
<213> ORGANISM: Bifidobacterium adolescentis

<400> SEQUENCE: 1

Met Ala Asp Thr Ala Glu Leu Ala Ile Val His Ala Thr Thr Ala Ser
1               5                   10                  15

Ala Ser Trp Leu Thr Asp Pro Thr Val Phe Ala Ala Asn Arg Lys Pro
                20                  25                  30

Ala His Ser Ser His Arg Tyr Val Ile Gly Glu Thr Ser Glu Pro Lys
            35                  40                  45

Gln Ser Leu Asp Gly Glu Trp Lys Val Arg Ile Glu Gln Ala Arg Asn
        50                  55                  60

Val Asp Val Glu Ser Ala Pro Phe Ala Ala Val Asp Phe Glu Asp Gly
65                  70                  75                  80

Asp Phe Gly Ala Ile Glu Val Pro Gly His Leu Gln Met Ala Gly Tyr
                85                  90                  95

Leu Lys Asn Lys Tyr Val Asn Ile Gln Tyr Pro Trp Asp Gly His Glu
                100                 105                 110

Asp Pro Gln Ala Pro Asn Ile Pro Glu Asn Asn His Val Ala Ile Tyr
            115                 120                 125

Arg Arg Arg Phe Ala Leu Asp Ala Gln Leu Ala Arg Thr Leu Glu Asn

```
                   130                 135                 140
Asp Gly Thr Val Ser Leu Thr Phe His Gly Ala Ala Thr Ala Ile Tyr
145                 150                 155                 160

Val Trp Leu Asp Gly Thr Phe Val Gly Tyr Gly Glu Asp Gly Phe Thr
                165                 170                 175

Pro Ser Glu Phe Asp Val Thr Glu Ala Leu Arg Asn Gly Asn Gly Asn
            180                 185                 190

Ala Ala Asp Ser Pro Glu Ala Glu His Thr Leu Thr Val Ala Cys Tyr
            195                 200                 205

Glu Tyr Ser Ser Ala Ser Trp Leu Glu Asp Gln Asp Phe Trp Arg Leu
        210                 215                 220

His Gly Leu Phe Arg Thr Val Glu Leu Ala Ala Gln Pro His Thr His
225                 230                 235                 240

Val Glu Thr Val Gln Leu Glu Ala Asp Tyr Thr Ala Ala Asp Thr Ala
                245                 250                 255

Gly Thr Ala Asp Thr Ala Glu Leu Asn Ala Ala Leu Thr Leu Arg Asn
            260                 265                 270

Ser Ala Asp Ala Met Thr Ile Glu Ser Thr Leu Arg Asp Gly Asp Gly
            275                 280                 285

Asn Val Val Trp Glu Ser Thr Gln Ala Cys Asn Gly Glu Ile Ala Leu
        290                 295                 300

Asn Ser Gly Lys Met Thr Asn Ile Ala Pro Trp Ser Ala Glu Ser Pro
305                 310                 315                 320

Thr Leu Tyr Thr Leu Thr Val Arg Val Val Gly His Asp Gly Ala Ile
                325                 330                 335

Ile Glu Thr Val Thr Gln Lys Ile Gly Phe Arg Thr Phe Arg Ile Glu
            340                 345                 350

Asn Gly Ile Met Thr Leu Asn Gly Lys Arg Ile Val Phe Lys Gly Ala
        355                 360                 365

Asp Arg His Glu Phe Asp Ala Lys Arg Gly Arg Ala Ile Thr Arg Glu
        370                 375                 380

Asp Met Leu Ser Asp Val Val Phe Cys Lys Arg His Asn Ile Asn Ala
385                 390                 395                 400

Ile Arg Thr Ser His Tyr Pro Asn Gln Glu Tyr Trp Tyr Asp Leu Cys
                405                 410                 415

Asp Glu Tyr Gly Leu Tyr Leu Ile Asp Glu Thr Asn Met Glu Thr His
            420                 425                 430

Gly Thr Trp Val Ala Asn Asn Val Glu Arg Pro Glu Asp Gly Ile Pro
        435                 440                 445

Gly Ser Arg Pro Glu Trp Glu Gly Ala Cys Val Asp Arg Ile Asn Ser
        450                 455                 460

Met Met Arg Arg Asp Tyr Asn His Pro Ser Val Leu Ile Trp Ser Leu
465                 470                 475                 480

Gly Asn Glu Ser Ser Ala Gly Glu Val Phe Arg Ala Met Tyr Arg His
                485                 490                 495

Ala His Thr Ile Asp Pro Asn Arg Pro Val His Tyr Glu Gly Ser Val
            500                 505                 510

His Met Arg Glu Phe Glu Asp Val Thr Asp Ile Glu Ser Arg Met Tyr
        515                 520                 525

Ala His Ala Asp Glu Ile Glu Arg Tyr Leu Asn Asp Gly Ser Pro Ala
        530                 535                 540

His Thr Asp Gly Pro Lys Lys Pro Tyr Ile Ser Cys Glu Tyr Met His
545                 550                 555                 560
```

```
Ala Met Gly Asn Ser Cys Gly Asn Met Asp Glu Tyr Thr Ala Leu Glu
            565                 570                 575

Arg Tyr Pro Met Tyr Gln Gly Gly Phe Ile Trp Asp Phe Ile Asp Gln
            580                 585                 590

Ala Ile Glu Thr Lys Leu Pro Asp Gly Thr Thr Arg Met Cys Tyr Gly
            595                 600                 605

Gly Asp Phe Gly Asp Arg Pro Ser Asp Tyr Glu Phe Ser Gly Asp Gly
            610                 615                 620

Leu Leu Phe Ala Asp Arg Thr Pro Ser Pro Lys Ala Gln Glu Val Lys
625                 630                 635                 640

Gln Leu Tyr Ala Asn Val Lys Ile Val Val Ser Val Asp Glu Ala Arg
            645                 650                 655

Ile Thr Asn Asp Asn Leu Phe Val Ser Thr Gly Asp Tyr Arg Phe Val
            660                 665                 670

Leu Arg Ile Leu Ala Asp Gly Lys Pro Val Trp Ser Thr Thr Arg Arg
            675                 680                 685

Phe Asp Val Ala Ala Gly Glu Ser Ala Ser Phe Glu Val Asp Trp Pro
            690                 695                 700

Val Asp Asp Tyr Arg Ser Asn Ala Glu Glu Leu Val Leu Glu Val Ser
705                 710                 715                 720

Gln Gln Leu Gly Asn Ala Cys Asp Trp Ala Pro Ala Gly Tyr Glu Leu
            725                 730                 735

Ala Phe Gly Gln Cys Val Val Ala Gly Ala Lys Thr Thr Ala Asp Ala
            740                 745                 750

Val Asp Ala Ala Gly Ala Pro Ala Asp Gly Thr Val Thr Leu Gly Arg
            755                 760                 765

Trp Asn Ala Gly Val Arg Gly Gln Gly Arg Glu Ala Leu Phe Ser Arg
            770                 775                 780

Thr Gln Gly Gly Met Val Ser Tyr Thr Phe Gly Glu Arg Glu Phe Val
785                 790                 795                 800

Leu Arg Arg Pro Ser Ile Thr Thr Phe Arg Pro Leu Thr Asp Asn Asp
            805                 810                 815

Arg Gly Ala Gly His Ala Phe Glu Arg Ala Ala Trp Ala Val Ala Gly
            820                 825                 830

Lys Tyr Ala Arg Cys Val Asp Cys Ala Ile Ala Asn Arg Gly Glu Asn
            835                 840                 845

Ala Val Glu Ala Thr Tyr Thr Tyr Glu Leu Ala Ile Pro Gln Arg Thr
            850                 855                 860

Lys Val Thr Val Arg Tyr Val Ala Asp Thr Ala Gly Leu Val Ser Leu
865                 870                 875                 880

Asp Val Glu Tyr Pro Gly Glu Lys Asn Gly Asp Leu Pro Thr Ile Pro
            885                 890                 895

Ala Phe Gly Ile Glu Trp Ala Leu Pro Val Glu Tyr Ala Asn Leu Arg
            900                 905                 910

Phe Tyr Gly Ala Gly Pro Glu Thr Tyr Ala Asp Arg Arg His Ala
            915                 920                 925

Lys Leu Gly Val Trp Ser Thr Thr Ala Gly Asp Cys Ala Pro Tyr
            930                 935                 940

Leu Leu Pro Gln Glu Thr Gly Asn His Glu Asp Val Arg Trp Ala Glu
945                 950                 955                 960

Ile Thr Asp Asp Ser Gly His Gly Val Arg Val Lys Arg Gly Ala Gly
            965                 970                 975
```

```
Ala Lys Pro Phe Ala Met Ser Leu Leu Pro Tyr Ser Thr Met Leu
            980                 985                 990

Glu Glu Ala Leu His Gln Asp Glu Leu Pro Lys Pro Arg His Met Phe
        995                1000                1005

Leu Arg Leu Leu Ala Ala Gln Met Gly Val Gly Gly Asp Asp Ser
    1010                1015                1020

Trp Met Ser Pro Val His Glu Gln Tyr Gln Leu Pro Ala Asp Gln
    1025                1030                1035

Pro Leu Ser Leu Asn Val Gln Leu Lys Leu Phe
    1040                1045

<210> SEQ ID NO 2
<211> LENGTH: 625
<212> TYPE: PRT
<213> ORGANISM: Lactobacillus sakei

<400> SEQUENCE: 2

Met Gln Pro Asn Ile Gln Trp Leu Asp Thr Pro Ala Val Phe Arg Val
  1               5                  10                  15

Gly Gln Leu Pro Ala His Ser Asp His Arg Tyr Tyr Ala Thr Leu Ala
             20                  25                  30

Glu Met Ala Gln Gln Ser Ser Phe Glu Gln Ser Leu Asn Gly Thr
         35                  40                  45

Trp Gln Phe His Tyr Ser Val Asn Ala Ala Ser Arg Pro Lys Ser Phe
 50                  55                  60

Tyr Glu Leu Ala Phe Asp Ala Gln Asp Phe Glu Pro Ile Thr Val Pro
 65                  70                  75                  80

Gln His Ile Glu Leu Ala Gly Tyr Glu Gln Leu His Tyr Ile Asn Thr
                 85                  90                  95

Met Tyr Pro Trp Glu Gly His Tyr Arg Arg Pro Ala Phe Ser Thr
            100                 105                 110

Ser Asp Asp Lys Gln His Leu Gly Met Phe Ser Glu Ala Asp Tyr Asn
            115                 120                 125

Pro Val Gly Ser Tyr Leu His His Phe Asp Leu Thr Pro Ala Leu Arg
        130                 135                 140

Asn Gln Arg Val Ile Ile Arg Phe Glu Gly Val Glu Gln Ala Met Tyr
145                 150                 155                 160

Val Trp Leu Asn Gly Gln Phe Ile Gly Tyr Ala Glu Asp Ser Phe Thr
                165                 170                 175

Pro Ser Glu Phe Asp Leu Thr Pro Tyr Leu Lys Glu Thr Asp Asn Cys
            180                 185                 190

Leu Ala Val Glu Val His Lys Arg Ser Ser Ala Ala Phe Ile Glu Asp
        195                 200                 205

Gln Asp Phe Phe Arg Phe Gly Ile Phe Arg Asp Val Lys Leu Leu
    210                 215                 220

Ala Lys Pro Arg Thr His Leu Glu Asp Leu Trp Val Ile Pro Glu Tyr
225                 230                 235                 240

Asp Val Val Gln Gln Thr Gly Gln Val Lys Leu Arg Leu Gln Phe Ser
                245                 250                 255

Gly Asp Glu Asn Arg Val His Leu Arg Ile Arg Asp Gln His Gln Ile
            260                 265                 270

Ile Leu Thr Ala Asp Leu Thr Ser Ala Ala Gln Val Asn Gly Leu Tyr
        275                 280                 285

Lys Met Pro Glu Leu Val Gln Ala Trp Ser Asn Gln Thr Pro Asn Leu
    290                 295                 300
```

Tyr Thr Leu Glu Leu Glu Val Asp Gln Ala Gly Glu Thr Ile Glu
305                 310                 315                 320

Ile Ser Gln Gln Pro Phe Gly Phe Arg Lys Ile Glu Ile Lys Asp Lys
            325                 330                 335

Val Met Leu Leu Asn Gly Lys Arg Leu Val Ile Asn Gly Val Asn Arg
                340                 345                 350

His Glu Trp His Pro Glu Thr Gly Arg Thr Ile Thr Ala Glu Asp Glu
            355                 360                 365

Ala Trp Asp Ile Ala Cys Met Gln Arg Asn His Ile Asn Ala Val Arg
        370                 375                 380

Thr Ser His Tyr Pro Asp Arg Leu Ser Phe Tyr Asn Gly Cys Asp Gln
385                 390                 395                 400

Ala Gly Ile Tyr Met Met Ala Glu Thr Asn Leu Glu Ser His Gly Ser
                405                 410                 415

Trp Gln Lys Met Gly Ala Val Glu Pro Ser Trp Asn Val Pro Gly Ser
            420                 425                 430

Tyr Asp Glu Trp Glu Ala Ala Thr Leu Asp Arg Ala Arg Thr Asn Phe
        435                 440                 445

Glu Thr Phe Lys Asn His Val Ser Ile Leu Phe Trp Ser Leu Gly Asn
    450                 455                 460

Glu Ser Tyr Ala Gly Ser Val Leu Glu Lys Met Asn Ala Tyr Tyr Lys
465                 470                 475                 480

Gln Gln Asp Pro Thr Arg Leu Val His Tyr Glu Gly Val Phe Arg Ala
                485                 490                 495

Pro Glu Tyr Lys Ala Thr Ile Ser Asp Val Glu Ser Arg Met Tyr Ala
            500                 505                 510

Thr Pro Ala Glu Ile Lys Ala Tyr Leu Asp Asn Ala Pro Gln Lys Pro
        515                 520                 525

Phe Ile Leu Cys Glu Tyr Met His Asp Met Gly Asn Ser Leu Gly Gly
    530                 535                 540

Met Gln Ser Tyr Ile Asp Leu Leu Ser Gln Tyr Asp Met Tyr Gln Gly
545                 550                 555                 560

Gly Phe Ile Trp Asp Phe Ile Asp Gln Ala Leu Leu Val Thr Asp Pro
                565                 570                 575

Val Thr Gly Gln Arg Glu Leu Arg Tyr Gly Gly Asp Phe Asp Asp Arg
            580                 585                 590

Pro Ser Asp Tyr Glu Phe Ser Gly Asp Gly Leu Val Phe Ala Thr Arg
        595                 600                 605

Asp Glu Lys Pro Ala Met Gln Glu Val Arg Tyr Tyr Gly Glu His
    610                 615                 620

Lys
625

<210> SEQ ID NO 3
<211> LENGTH: 330
<212> TYPE: PRT
<213> ORGANISM: Lactobacillus sakei

<400> SEQUENCE: 3

Met Lys Asn Gln Gln Cys Arg Arg Leu Asp Thr Ile Met Ala Asn Thr
1               5                   10                  15

Asn Lys Arg Leu Ala Val Ile Phe Gly Asp Val Thr Leu Gly Leu Lys
            20                  25                  30

Gly Pro Asp Phe His Tyr Leu Phe Ser Tyr Gln Thr Gly Gly Pro Glu

```
                  35                  40                  45
Ser Leu Arg Ile Gln Gly Lys Glu Trp Leu Tyr Arg Ser Pro Lys Pro
 50                  55                  60

Thr Phe Trp Arg Ala Thr Thr Asp Asn Asp Arg Gly Asn Gln Phe Pro
 65                  70                  75                  80

Leu Lys Ser Gly Met Trp Leu Ala Ala Asp Gln Phe Ile Ala Cys Gln
                 85                  90                  95

Ser Ile Thr Val Ala Ile Asp Gly Gln Thr Ile Pro Leu Pro Ile Ala
                100                 105                 110

Pro Glu Asn Asn Arg Tyr Ser Gly Gln Glu Thr Ala Gln Glu Val Thr
                115                 120                 125

Val Thr Tyr Thr Tyr Gln Thr Ile Thr Thr Pro Gln Thr Thr Val Glu
        130                 135                 140

Val Ser Tyr Thr Ile Gln Ala Ser Gly Lys Ile Arg Val Ala Val Thr
145                 150                 155                 160

Tyr His Gly Gln Ala Gly Leu Pro Ser Leu Pro Val Phe Gly Leu Arg
                165                 170                 175

Phe Val Met Pro Thr Pro Ala Thr Arg Phe Ile Tyr Gln Gly Leu Ser
                180                 185                 190

Gly Glu Thr Tyr Pro Asp Arg Met Ala Gly Met Ala Gly Glu Tyr
                195                 200                 205

Glu Val Thr Gly Leu Pro Val Thr Pro Tyr Leu Val Pro Gln Asp Cys
        210                 215                 220

Gly Val His Met Ala Thr Asp Trp Val Thr Ile Tyr Arg Gln Ala Val
225                 230                 235                 240

Leu Asp Asn Arg Leu Arg Glu Pro Val Glu Thr Gly Leu Lys Phe Lys
                245                 250                 255

Met Val Asp Gln Pro Phe Ala Phe Ser Cys Leu Pro Tyr Thr Ala Glu
                260                 265                 270

Glu Leu Glu Asn Ala Thr His His Ser Glu Leu Pro Ala Pro His Arg
                275                 280                 285

Thr Val Leu Ser Leu Leu Gly Ala Val Arg Gly Val Gly Gly Ile Asp
        290                 295                 300

Ser Trp Gly Ser Asp Val Glu Ala Ala Tyr Gln Ile Asp Ala Thr Gln
305                 310                 315                 320

Asp His His Leu Glu Phe Glu Ile Ser Phe
                325                 330

<210> SEQ ID NO 4
<211> LENGTH: 1049
<212> TYPE: PRT
<213> ORGANISM: Bifidobacterium adolescentis

<400> SEQUENCE: 4

Met Ala Asp Thr Ala Glu Leu Ala Ile Val His Ala Thr Thr Ala Ser
1               5                   10                  15

Ala Ser Trp Leu Thr Asp Pro Thr Val Phe Ala Ala Asn Arg Lys Pro
                20                  25                  30

Ala His Ser Ser His Arg Tyr Val Ile Gly Glu Thr Ser Glu Pro Lys
        35                  40                  45

Gln Ser Leu Asp Gly Glu Trp Lys Val Arg Ile Glu Gln Ala Arg Asn
 50                  55                  60

Val Asp Val Glu Ser Ala Pro Phe Ala Ala Val Asp Phe Glu Asp Gly
 65                  70                  75                  80
```

```
Asp Phe Gly Ala Ile Glu Val Pro Gly His Leu Gln Met Ala Gly Tyr
                 85                  90                  95
Leu Lys Asn Lys Tyr Val Asn Ile Gln Tyr Pro Trp Asp Gly His Glu
            100                 105                 110
Asp Pro Gln Ala Pro Asn Ile Pro Glu Asn Asn His Val Ala Ile Tyr
        115                 120                 125
Arg Arg Arg Phe Ala Leu Asp Ala Gln Leu Ala Arg Thr Leu Glu Asn
    130                 135                 140
Asp Gly Thr Val Ser Leu Thr Phe His Gly Ala Ala Thr Ala Ile Tyr
145                 150                 155                 160
Val Trp Leu Asp Gly Thr Phe Val Gly Tyr Gly Glu Asp Gly Phe Thr
                165                 170                 175
Pro Ser Glu Phe Asp Val Thr Glu Ala Leu Arg Asn Gly Asn Gly Asn
            180                 185                 190
Ala Ala Asp Ser Pro Glu Ala Glu His Thr Leu Thr Val Ala Cys Tyr
        195                 200                 205
Glu Tyr Ser Ser Ala Ser Trp Leu Glu Asp Gln Asp Phe Trp Arg Leu
    210                 215                 220
His Gly Leu Phe Arg Thr Val Glu Leu Ala Ala Gln Pro His Thr His
225                 230                 235                 240
Val Glu Thr Val Gln Leu Glu Ala Asp Tyr Thr Ala Ala Asp Thr Ala
                245                 250                 255
Gly Thr Ala Asp Thr Ala Glu Leu Asn Ala Ala Leu Thr Leu Arg Asn
            260                 265                 270
Pro Ala Asp Ala Met Thr Ile Glu Ser Thr Leu Arg Asp Gly Asp Gly
        275                 280                 285
Asn Val Val Trp Glu Ser Thr Gln Ala Cys Asn Gly Glu Ile Ala Leu
    290                 295                 300
Asn Ser Gly Lys Met Thr Asn Ile Ala Pro Trp Ser Ala Glu Ser Pro
305                 310                 315                 320
Thr Leu Tyr Thr Leu Thr Val Arg Val Val Gly His Asp Gly Ala Ile
                325                 330                 335
Ile Glu Thr Val Thr Gln Lys Ile Gly Phe Arg Thr Phe Arg Ile Glu
            340                 345                 350
Asn Gly Ile Met Thr Leu Asn Gly Lys Arg Ile Val Phe Lys Gly Ala
        355                 360                 365
Asp Arg His Glu Phe Asp Ala Lys Arg Gly Arg Ala Ile Thr Arg Glu
    370                 375                 380
Asp Met Leu Ser Asp Val Val Phe Cys Lys Arg His Asn Ile Asn Ala
385                 390                 395                 400
Ile Arg Thr Ser His Tyr Pro Asn Gln Glu Tyr Trp Tyr Asp Leu Cys
                405                 410                 415
Asp Glu Tyr Gly Leu Tyr Leu Ile Asp Glu Thr Asn Met Glu Thr His
            420                 425                 430
Gly Thr Trp Val Ala Asn Asn Val Glu Arg Pro Glu Asp Gly Ile Pro
        435                 440                 445
Gly Ser Arg Pro Glu Trp Glu Gly Ala Cys Val Asp Arg Ile Asn Ser
    450                 455                 460
Met Met Arg Arg Asp Tyr Asn His Pro Ser Val Leu Ile Trp Ser Leu
465                 470                 475                 480
Gly Asn Glu Ser Ser Ala Gly Glu Val Phe Arg Ala Met Tyr Arg His
                485                 490                 495
Ala His Thr Ile Asp Pro Asn Arg Pro Val His Tyr Glu Gly Ser Val
```

```
                500                 505                 510
His Met Arg Glu Phe Glu Asp Val Thr Asp Ile Glu Ser Arg Met Tyr
            515                 520                 525
Ala His Ala Asp Glu Ile Glu Arg Tyr Leu Asn Asp Gly Ser Pro Ala
            530                 535                 540
His Thr Asp Gly Pro Lys Lys Pro Tyr Ile Ser Cys Glu Tyr Met His
545                 550                 555                 560
Ala Met Gly Asn Ser Cys Gly Asn Met Asp Glu Tyr Thr Ala Leu Glu
                565                 570                 575
Arg Tyr Pro Met Tyr Gln Gly Gly Phe Ile Trp Asp Phe Ile Asp Gln
                580                 585                 590
Ala Ile Glu Thr Lys Leu Pro Asp Gly Thr Thr Arg Met Cys Tyr Gly
                595                 600                 605
Gly Asp Phe Gly Asp Arg Pro Ser Asp Tyr Glu Phe Ser Gly Asp Gly
            610                 615                 620
Leu Leu Phe Ala Asp Arg Thr Pro Ser Pro Lys Ala Gln Glu Val Lys
625                 630                 635                 640
Gln Leu Tyr Ala Asn Val Lys Ile Ala Val Ser Val Asp Glu Ala Arg
                645                 650                 655
Ile Thr Asn Asp Asn Leu Phe Val Ser Thr Gly Asp Tyr Arg Phe Val
                660                 665                 670
Leu Arg Ile Leu Ala Asp Gly Lys Pro Val Trp Ser Thr Arg Arg
            675                 680                 685
Phe Asp Val Ala Ala Gly Glu Ser Ala Ser Phe Glu Val Asp Trp Pro
            690                 695                 700
Val Asp Asp Tyr Arg Ser Asn Ala Glu Glu Leu Val Leu Glu Val Ser
705                 710                 715                 720
Gln Gln Leu Gly Asn Ala Cys Asp Trp Ala Pro Ala Gly Tyr Glu Leu
                725                 730                 735
Ala Phe Gly Gln Cys Val Val Ala Gly Ala Lys Thr Thr Ala Asp Ala
                740                 745                 750
Val Asp Ala Ala Gly Ala Pro Ala Asp Gly Thr Val Thr Leu Gly Arg
                755                 760                 765
Trp Asn Ala Gly Val Arg Gly Gln Gly Arg Glu Ala Leu Phe Ser Arg
            770                 775                 780
Thr Gln Gly Gly Met Val Ser Tyr Thr Phe Gly Glu Arg Glu Phe Val
785                 790                 795                 800
Leu Arg Arg Pro Ser Ile Thr Thr Phe Arg Pro Leu Thr Asp Asn Asp
                805                 810                 815
Arg Gly Ala Gly His Ala Phe Glu Arg Ala Ala Trp Ala Val Ala Gly
            820                 825                 830
Lys Tyr Ala Arg Cys Val Asp Cys Ala Ile Ala Asn Arg Gly Glu Asn
            835                 840                 845
Ala Val Glu Ala Thr Tyr Thr Tyr Glu Leu Ala Ile Pro Gln Arg Thr
            850                 855                 860
Lys Val Thr Val Arg Tyr Val Ala Asp Thr Ala Gly Leu Val Ser Leu
865                 870                 875                 880
Asp Val Glu Tyr Pro Gly Glu Lys Asn Gly Asp Leu Pro Thr Ile Pro
                885                 890                 895
Ala Phe Gly Ile Glu Trp Ala Leu Pro Val Glu Tyr Ala Asn Leu Arg
                900                 905                 910
Phe Tyr Gly Ala Gly Pro Glu Glu Thr Tyr Ala Asp Arg Arg His Ala
            915                 920                 925
```

```
Lys Leu Gly Val Trp Ser Thr Thr Ala Gly Asp Asp Cys Ala Pro Tyr
            930                 935                 940

Leu Leu Pro Gln Glu Thr Gly Asn His Glu Asp Val Arg Trp Ala Glu
945                 950                 955                 960

Ile Thr Asp Asp Ser Gly His Gly Val Arg Val Lys Arg Gly Ala Gly
            965                 970                 975

Ala Lys Pro Phe Ala Met Ser Leu Leu Pro Tyr Ser Ser Thr Met Leu
            980                 985                 990

Glu Glu Ala Leu His Gln Asp Glu Leu Pro Lys Pro Arg His Met Phe
            995                1000                1005

Leu Arg Leu Leu Ala Ala Gln Met Gly Val Gly Gly Asp Asp Ser
        1010                1015                1020

Trp Met Ser Pro Val His Glu Gln Tyr Gln Leu Pro Ala Asp Gln
        1025                1030                1035

Pro Leu Ser Leu Asn Val Gln Leu Lys Leu Phe
        1040                1045

<210> SEQ ID NO 5
<211> LENGTH: 626
<212> TYPE: PRT
<213> ORGANISM: Lactobacillus amylovorus

<400> SEQUENCE: 5

Met Lys Ala Asn Ile Lys Trp Leu Asp Asp Pro Glu Val Phe Arg Ile
1               5                  10                  15

Asn Gln Leu Pro Ala His Ser Asp His Pro Phe Tyr Lys Asp Tyr Arg
            20                  25                  30

Glu Trp Gln Asn His Ser Ser Phe Lys Gln Ser Leu Asn Gly Ala
        35                  40                  45

Trp Gln Phe His Phe Ser Lys Asp Pro Gln Ser Arg Pro Ile Asp Phe
    50                  55                  60

Tyr Lys Arg Ser Phe Asp Ser Ser Phe Asp Thr Ile Pro Val Pro
65                  70                  75                  80

Ser Glu Ile Glu Leu Asn Gly Tyr Ala Gln Asn Gln Tyr Thr Asn Ile
            85                  90                  95

Leu Tyr Pro Trp Glu Ser Lys Ile Tyr Arg Lys Pro Ala Tyr Thr Leu
            100                 105                 110

Gly Arg Gly Ile Lys Asp Gly Asp Phe Ser Gln Gly Lys Asp Asn Thr
        115                 120                 125

Val Gly Ser Tyr Leu Lys His Phe Asp Leu Asn Pro Ala Leu Ala Gly
    130                 135                 140

His Asp Ile His Ile Gln Phe Glu Gly Val Glu Arg Ala Met Tyr Val
145                 150                 155                 160

Tyr Leu Asn Gly His Phe Ile Gly Tyr Ala Glu Asp Ser Phe Thr Pro
            165                 170                 175

Ser Glu Phe Asp Leu Thr Pro Tyr Ile Gln Ala Lys Asn Ile Leu
            180                 185                 190

Ala Val Glu Val Phe Lys His Ser Thr Ala Ser Trp Leu Glu Asp Gln
        195                 200                 205

Asp Met Phe Arg Phe Ser Gly Ile Phe Arg Ser Val Glu Leu Leu Ala
    210                 215                 220

Leu Pro Arg Thr His Leu Met Asp Leu Asp Ile Lys Pro Thr Val Val
225                 230                 235                 240

Asn Asp Tyr His Asp Gly Val Phe Asn Ala Lys Leu His Phe Met Gly
```

```
                    245                 250                 255
Lys Thr Ser Gly Asn Val His Val Leu Ile Glu Asp Ile Asp Gly Lys
                260                 265                 270

Thr Leu Leu Asn Lys Lys Leu Pro Leu Lys Ser Thr Val Glu Ile Glu
            275                 280                 285

Asn Glu Thr Phe Ala Asn Val His Leu Trp Asp Asn His Asp Pro Tyr
        290                 295                 300

Leu Tyr Gln Leu Ile Ile Glu Val His Asp Gln Asp Gly Lys Leu Val
305                 310                 315                 320

Glu Leu Ile Pro Tyr Gln Phe Gly Phe Arg Lys Ile Glu Ile Thr Lys
                325                 330                 335

Asp His Val Val Leu Asn Gly Lys Arg Leu Ile Ile Asn Gly Val
                340                 345                 350

Asn Arg His Glu Trp Asp Ala Lys Arg Gly Arg Ser Ile Thr Leu Ala
            355                 360                 365

Asp Met Lys Gln Asp Ile Ala Thr Phe Lys His Asn Asn Ile Asn Ala
        370                 375                 380

Val Arg Thr Cys His Tyr Pro Asn Gln Ile Pro Trp Tyr Tyr Leu Cys
385                 390                 395                 400

Asp Gln Asn Gly Ile Tyr Met Met Ala Glu Asn Leu Glu Ser His
                405                 410                 415

Gly Thr Trp Gln Lys Leu Gly Gln Val Glu Ala Thr Ser Asn Val Pro
            420                 425                 430

Gly Ser Ile Pro Glu Trp Arg Glu Val Val Asp Arg Ala Arg Ser
        435                 440                 445

Asn Tyr Glu Thr Phe Lys Asn His Thr Ala Ile Leu Phe Trp Ser Leu
        450                 455                 460

Gly Asn Glu Ser Tyr Ala Gly Ser Asn Ile Ala Ala Met Asn Lys Leu
465                 470                 475                 480

Tyr Lys Asp His Asp Ser Ser Arg Leu Thr His Tyr Glu Gly Val Phe
                485                 490                 495

His Ala Pro Glu Phe Lys Lys Glu Ile Ser Asp Leu Glu Ser Cys Met
                500                 505                 510

Tyr Leu Pro Pro Lys Glu Ala Glu Glu Tyr Leu Gln Asn Pro Lys Lys
            515                 520                 525

Pro Leu Val Glu Cys Glu Tyr Met His Asp Met Gly Thr Pro Asp Gly
        530                 535                 540

Gly Met Gly Ser Tyr Ile Lys Leu Ile Asp Lys Tyr Pro Gln Tyr Met
545                 550                 555                 560

Gly Gly Phe Ile Trp Asp Phe Ile Asp Gln Ala Leu Leu Val His Asp
                565                 570                 575

Pro Val Ser Gly Gln Asp Val Leu Arg Tyr Gly Asp Phe Asp Asp
                580                 585                 590

Arg His Ser Asp Tyr Glu Phe Ser Gly Asp Gly Leu Met Phe Ala Asp
            595                 600                 605

Arg Thr Pro Lys Pro Ala Met Gln Glu Val Arg Tyr Tyr Tyr Gly Leu
        610                 615                 620

His Lys
625

<210> SEQ ID NO 6
<211> LENGTH: 316
<212> TYPE: PRT
<213> ORGANISM: Lactobacillus amylovorus
```

<400> SEQUENCE: 6

```
Met Ala Tyr Thr Asn Asn Leu His Val Val Tyr Gly Glu Ala Ser Leu
1               5                   10                  15

Gly Val Asn Gly Gln Asp Phe Ala Tyr Leu Phe Ser Tyr Glu Arg Gly
            20                  25                  30

Gly Leu Glu Ser Leu Lys Ile Lys Asp Lys Glu Trp Leu Tyr Arg Thr
        35                  40                  45

Pro Thr Pro Thr Phe Trp Arg Ala Thr Thr Asp Asn Asp Arg Gly Ser
    50                  55                  60

Gly Phe Asn Gln Lys Ala Ala Gln Trp Leu Gly Ala Asp Met Phe Thr
65                  70                  75                  80

Lys Cys Val Gly Ile His Val Gln Val Asp Asp His Arg Phe Asp Glu
                85                  90                  95

Leu Pro Val Ala Pro Ile Asn Asn Gln Phe Ser Asn Gln Glu Phe Ala
            100                 105                 110

His Glu Val Lys Val Ala Phe Asp Tyr Glu Thr Leu Thr Thr Pro Ala
        115                 120                 125

Thr Lys Val Lys Ile Ile Tyr Asn Ile Asn Asp Phe Gly His Met Thr
130                 135                 140

Ile Thr Met His Tyr Phe Gly Lys Lys Gly Leu Pro Pro Leu Pro Val
145                 150                 155                 160

Ile Gly Met Arg Phe Ile Met Pro Thr Lys Ala Lys Ser Phe Asp Tyr
                165                 170                 175

Thr Gly Leu Ser Gly Glu Thr Tyr Pro Asp Arg Met Ala Gly Ala Glu
            180                 185                 190

Arg Gly Thr Phe His Ile Asp Gly Leu Pro Val Thr Lys Tyr Leu Val
        195                 200                 205

Pro Gln Glu Asn Gly Met His Met Gln Thr Asn Glu Leu Val Ile Thr
    210                 215                 220

Arg Asn Ser Thr Gln Asn Asn Ala Asp Lys Asp Gly Asp Phe Ser Leu
225                 230                 235                 240

Lys Ile Thr Gln Thr Lys Gln Pro Phe Asn Phe Ser Leu Leu Pro Tyr
                245                 250                 255

Thr Ala Glu Glu Leu Glu Asn Ala Thr His Ile Glu Glu Leu Pro Leu
            260                 265                 270

Ala Arg Arg Ser Val Leu Val Ile Ala Gly Ala Val Arg Gly Val Gly
        275                 280                 285

Gly Ile Asp Ser Trp Gly Ser Asp Val Glu Gln Tyr His Ile Asp
    290                 295                 300

Pro Glu Gln Asp His Glu Phe Ser Phe Thr Leu Asn
305                 310                 315
```

<210> SEQ ID NO 7
<211> LENGTH: 1052
<212> TYPE: PRT
<213> ORGANISM: Bifidobacterium bifidum

<400> SEQUENCE: 7

```
Met Asn Thr Thr Asp Asp Gln Arg Lys Asn Gly Asp Pro Ile Val Ser
1               5                   10                  15

Pro Ser Ile Pro Thr Thr Ala Trp Leu Ala Asp Pro Arg Val Tyr Ala
            20                  25                  30

Val His Arg Leu Asp Ala His Ser Asp His Ala Cys Trp Ser Arg Ser
        35                  40                  45
```

```
Pro Val Asp Gly Glu Ser Thr Asp Leu Arg Gln Ser Leu Asp Gly Glu
    50                  55                  60

Trp Arg Val Arg Val Glu Thr Ala Pro Thr Gly Arg Phe Pro Asp Gly
65                  70                  75                  80

Thr Ser Asp Gly Pro Asp Trp Ile Ser Asp Val Ser Pro Leu Phe Ala
                85                  90                  95

Ala Pro Gly Phe Asp Asp Ser Ser Phe Ser Arg Val Gln Val Pro Ser
            100                 105                 110

His Leu Glu Thr Ala Gly Leu Leu Ala Pro Gln Tyr Val Asn Val Gln
        115                 120                 125

Tyr Pro Trp Asp Gly His Glu Asp Pro Lys Ala Pro Ala Ile Pro Glu
    130                 135                 140

His Gly His Val Ala Val Tyr Arg Arg Glu Phe Asp Ala Asp Gly Glu
145                 150                 155                 160

Val Ala Gln Ala Val Arg Glu Gly Arg Pro Val Thr Leu Thr Phe Gln
                165                 170                 175

Gly Ala Ala Thr Ala Ile Tyr Val Trp Leu Asn Gly Ser Phe Ile Gly
            180                 185                 190

Tyr Ala Glu Asp Ser Phe Thr Pro Ser Glu Phe Asp Val Thr Asp Ala
        195                 200                 205

Ile Lys Val Asp Gly Asn Val Leu Ala Val Ala Cys Tyr Glu Tyr Ser
    210                 215                 220

Ser Ala Ser Trp Leu Glu Asp Gln Asp Phe Trp Arg Leu His Gly Leu
225                 230                 235                 240

Phe Arg Ser Val Glu Leu Asn Ala Arg Pro Ala Ala His Val Ala Asp
                245                 250                 255

Leu His Ala Asp Ala Asp Trp Asp Leu Ala Thr Ser Arg Gly Ser Leu
            260                 265                 270

Ser Leu Asp Val Leu Ile Asp Gly Ala Ala Asn Ala Ala Thr Ala Asp
        275                 280                 285

Phe Ala Leu Arg Asp Lys Asn Gly Thr Ile Val Trp Arg Thr Ala Thr
    290                 295                 300

Lys Ala Asp Gly Thr Leu His Ala Glu Ala Glu Ile Asp Asp Ala Ala
305                 310                 315                 320

Pro Trp Ser Ala Glu Arg Pro Asp Leu Tyr Glu Leu Ser Val Thr Leu
                325                 330                 335

Leu Asp Ala Asp Gly Lys Val Leu Glu Thr Ala Arg Thr Arg Ile Gly
            340                 345                 350

Phe Arg His Val Ala Ile Glu Asp Gly Ile Leu Lys Leu Asn Gly Lys
        355                 360                 365

Arg Leu Val Phe Arg Gly Val Asn Arg His Glu Phe Asp Cys Arg Arg
    370                 375                 380

Gly Arg Ala Ile Thr Glu Glu Asp Met Leu Trp Asp Ile Arg Phe Met
385                 390                 395                 400

Lys Arg His Asn Ile Asn Ala Val Arg Thr Ser His Tyr Pro Asn Gln
                405                 410                 415

Ser Arg Trp Tyr Glu Leu Cys Asp Glu Tyr Gly Ile Tyr Leu Ile Asp
            420                 425                 430

Glu Thr Asn Leu Glu Thr His Gly Ser Trp Asn Ser Pro Gly Asp Ile
        435                 440                 445

Pro Val Gly Thr Ser Val Pro Gly Asp Asp Glu Ala Trp Leu Gly Ala
    450                 455                 460
```

-continued

```
Cys Ile Asp Arg Leu Asp Ser Met Ile Leu Arg Asp Arg Asn His Pro
465                 470                 475                 480

Ser Val Leu Val Trp Ser Leu Gly Asn Glu Ser Tyr Ala Gly Glu Val
                485                 490                 495

Leu Lys Ala Met Ser Ala His Ala His Gln Leu Asp Pro Gly Arg Pro
            500                 505                 510

Val His Tyr Glu Gly Val Asn Trp Asn His Ala Tyr Asp Gly Ile Ser
        515                 520                 525

Asp Phe Glu Ser Arg Met Tyr Ala Lys Pro Ala Glu Ile Gln Asp Trp
    530                 535                 540

Leu Glu His Gly Asp Glu Arg Gly Glu Ala Ser Lys Pro Phe Val Ser
545                 550                 555                 560

Cys Glu Tyr Met His Ala Met Gly Asn Ser Cys Gly Gly Leu Ser Glu
                565                 570                 575

Phe Ile Asp Leu Glu Arg Tyr Glu Arg Tyr Ser Gly Gly Phe Ile Trp
            580                 585                 590

Asp Tyr Ile Asp Gln Gly Leu Val Gln Arg Leu Pro Asp Gly Ser Glu
        595                 600                 605

Arg Leu Ser Val Gly Gly Glu Trp Gly Asp Arg Pro Thr Asp Tyr Glu
    610                 615                 620

Phe Val Gly Asn Gly Ile Val Phe Ala Asp Arg Thr Pro Ser Pro Lys
625                 630                 635                 640

Ala Gln Glu Val Lys Gln Leu Tyr Ser Pro Val Lys Leu Ala Pro Asp
                645                 650                 655

Gly His Gly Val Thr Ile Glu Asn Arg Asn Leu Phe Ala Gly Thr Asp
            660                 665                 670

Gly Tyr Val Phe Ala Ala Arg Leu Leu Glu Asp Gly His Glu Ile Trp
        675                 680                 685

His Ala Asp Tyr Arg Phe Asp Val Ala Ala Gly Asp Thr Gln His His
    690                 695                 700

Asp Ile Ala Phe Pro Asp Ile Asp Ala Asp Gly Asp Thr Arg Glu Val
705                 710                 715                 720

Thr Tyr Glu Val Asp Leu Leu Leu Ala Glu Ala Thr Ala Trp Ala Pro
                725                 730                 735

Ala Gly Tyr Glu Leu Ala Phe Gly Gln Leu Thr Gly Thr Leu Asn Pro
            740                 745                 750

Glu Gln Asp Ile Thr Glu Thr Ser His Asp Asp Gly Arg Ala Thr
        755                 760                 765

Arg Thr Leu Ser Arg Trp Asn Ala Gly Ile Arg Arg Asp Asp Glu Glu
    770                 775                 780

Ile Leu Leu Ser Arg Thr Gln Gly Gly Ile Val Ser Trp Lys Arg Asp
785                 790                 795                 800

Asp Arg Glu Met Val Ile Arg Pro Glu Leu Val Thr Phe Arg Pro
                805                 810                 815

Leu Thr Asp Asn Asp Arg Gly Asn His Ser Gly Phe Arg Ala Ala
            820                 825                 830

Trp Phe Ala Ala Gly Arg Tyr Ala Ile Val Thr Glu Thr Lys Ile His
        835                 840                 845

Glu Ser Asp Asp Gly Leu Val Ala Glu Tyr Gln Tyr Glu Leu Ala Asp
    850                 855                 860

Pro Asn His Thr Pro Val Ser Val Thr Tyr His Val Asn Ser Asp Met
865                 870                 875                 880

Arg Met Gln Leu Thr Val Glu Tyr Pro Gly Asn Ala Thr Asp Met Ala
```

```
            885                 890                 895
Ser Leu Pro Ala Phe Gly Ile Glu Trp Glu Leu Pro Gly Glu Tyr Asp
            900                 905                 910

Arg Leu Arg Tyr Tyr Gly Pro Gly Glu Glu Thr Tyr Arg Asp Arg
            915                 920                 925

Lys Gln Gly Gly Lys Leu Gly Ile Trp Asp Ala Thr Ala Lys Ala Ser
        930                 935                 940

Met Ala Pro Tyr Leu Met Val Gln Glu Thr Gly Ser His Glu Asp Val
945                 950                 955                 960

Arg Trp Leu Glu Ala Thr Asp Ile Gln Gly His Gly Leu Arg Val Thr
                965                 970                 975

Gln Arg Gly Asp Arg His Phe Thr Ala Ser Leu Leu Pro Trp Asn Thr
                    980                 985                 990

Tyr Thr Ile Glu Ala Ala Arg Arg His Glu Asp Leu Pro Lys Pro Arg
                995                 1000                1005

His Asn Tyr Leu Arg Leu Leu Ala Ala Gln Met Gly Val Gly Gly
        1010                1015                1020

Asp Asp Ser Trp Gly Ala Pro Val His Thr Ala Tyr Gln Leu Pro
        1025                1030                1035

Ala Gly Arg Pro Leu Thr Leu Asp Val Asn Leu Glu Leu Ile
        1040                1045                1050

<210> SEQ ID NO 8
<211> LENGTH: 1052
<212> TYPE: PRT
<213> ORGANISM: Bifidobacterium bifidum

<400> SEQUENCE: 8

Met Asn Thr Thr Asp Asp Gln Arg Lys Asn Gly Asp Pro Ile Val Ser
1               5                   10                  15

Pro Ser Ile Pro Thr Thr Ala Trp Leu Ala Asp Pro Arg Val Tyr Ala
            20                  25                  30

Val His Arg Leu Asp Ala His Ser Asp His Ala Cys Trp Ser Arg Ser
        35                  40                  45

Pro Val Asp Gly Glu Ser Thr Asp Leu Arg Gln Ser Leu Asp Gly Glu
    50                  55                  60

Trp Arg Val Arg Val Glu Thr Ala Pro Thr Gly Arg Phe Pro Asp Gly
65                  70                  75                  80

Thr Ser Asp Gly Pro Asp Trp Ile Ser Asp Val Ser Pro Leu Phe Ala
                85                  90                  95

Ala Pro Gly Phe Asp Asp Ser Ser Phe Ser Arg Val Gln Val Pro Ser
            100                 105                 110

His Leu Glu Thr Ala Gly Leu Leu Ala Pro Gln Tyr Val Asn Val Gln
        115                 120                 125

Tyr Pro Trp Asp Gly His Glu Asp Pro Lys Ala Pro Ala Ile Pro Glu
    130                 135                 140

His Gly His Val Ala Val Tyr Arg Arg Glu Phe Asp Ala Asp Gly Glu
145                 150                 155                 160

Val Ala Gln Ala Val Arg Glu Gly Arg Pro Val Thr Leu Thr Phe Gln
                165                 170                 175

Gly Ala Ala Thr Ala Ile Tyr Val Trp Leu Asn Gly Ser Phe Ile Gly
            180                 185                 190

Tyr Ala Glu Asp Ser Phe Thr Pro Ser Glu Phe Asp Val Thr Asp Ala
        195                 200                 205
```

```
Ile Lys Val Asp Gly Asn Val Leu Ala Val Ala Cys Tyr Glu Tyr Ser
210                 215                 220

Ser Ala Ser Trp Leu Glu Asp Gln Asp Phe Trp Arg Leu His Gly Leu
225                 230                 235                 240

Phe Arg Ser Val Glu Leu Asn Ala Arg Pro Ala Ala His Val Ala Asp
                245                 250                 255

Leu His Ala Asp Ala Asp Trp Asp Leu Ala Thr Ser Arg Gly Ser Leu
            260                 265                 270

Ser Leu Asp Val Leu Ile Asp Gly Ala Ala Asn Ala Thr Ala Asp
        275                 280                 285

Phe Ala Leu Trp Asp Lys Asn Gly Thr Ile Val Trp His Ile Val Thr
290                 295                 300

Lys Ala Asp Gly Thr Leu His Ala Glu Ala Glu Ile Asp Asp Ala Ala
305                 310                 315                 320

Pro Trp Ser Ala Glu Arg Pro Asp Leu Tyr Glu Leu Ser Val Thr Leu
                325                 330                 335

Leu Asp Ala Asp Gly Lys Val Leu Glu Thr Ala Arg Thr Arg Ile Gly
            340                 345                 350

Phe Arg His Val Ala Ile Glu Asp Gly Ile Leu Lys Leu Asn Gly Lys
        355                 360                 365

Arg Leu Val Phe Arg Gly Val Asn Arg His Glu Phe Asp Cys Arg Arg
370                 375                 380

Gly Arg Ala Ile Thr Glu Glu Asp Met Leu Trp Asp Ile Arg Phe Met
385                 390                 395                 400

Lys Arg His Asn Ile Asn Ala Val Arg Thr Ser His Tyr Pro Asn Gln
                405                 410                 415

Ser Arg Trp Tyr Glu Leu Cys Asp Glu Tyr Gly Ile Tyr Leu Ile Asp
            420                 425                 430

Glu Thr Asn Leu Glu Thr His Gly Ser Trp Asn Ser Pro Gly Asp Ile
        435                 440                 445

Pro Val Gly Thr Ser Val Pro Gly Asp Asp Glu Ala Trp Leu Gly Ala
450                 455                 460

Cys Ile Asp Arg Leu Asp Ser Met Ile Leu Arg Asp Arg Asn His Pro
465                 470                 475                 480

Ser Val Leu Val Trp Ser Leu Gly Asn Glu Ser Tyr Ala Gly Glu Val
                485                 490                 495

Leu Lys Ala Met Ser Ala His Ala His Arg Leu Asp Pro Gly Arg Pro
            500                 505                 510

Val His Tyr Glu Gly Val Asn Trp Asn His Ala Tyr Asp Gly Ile Ser
        515                 520                 525

Asp Phe Glu Ser Arg Met Tyr Ala Lys Pro Ala Glu Ile Gln Asp Trp
530                 535                 540

Leu Glu His Gly Asp Glu Arg Gly Glu Ala Ser Lys Pro Phe Val Ser
545                 550                 555                 560

Cys Glu Tyr Met His Ala Met Gly Asn Ser Cys Gly Gly Leu Ser Glu
                565                 570                 575

Phe Ile Asp Leu Glu Arg Tyr Glu Arg Tyr Ser Gly Gly Phe Ile Trp
            580                 585                 590

Asp Tyr Ile Asp Gln Gly Leu Val Gln Arg Leu Pro Asp Gly Ser Glu
        595                 600                 605

Arg Leu Ser Val Gly Gly Glu Trp Gly Asp Arg Pro Thr Asp Tyr Glu
610                 615                 620

Phe Val Gly Asn Gly Ile Val Phe Ala Asp Arg Thr Pro Ser Pro Lys
```

```
                625               630              635              640
        Ala Gln Glu Val Lys Gln Leu Tyr Ser Pro Val Lys Leu Ala Pro Asp
                            645              650              655

Gly His Gly Val Thr Ile Glu Asn Arg Asn Leu Phe Ala Gly Thr Asp
                        660              665              670

Gly Tyr Val Phe Ala Ala Arg Leu Leu Glu Asp Gly His Glu Ile Trp
                    675              680              685

His Ala Asp Tyr Arg Phe Asp Val Ala Ala Gly Asp Thr Gln His His
                690              695              700

Asp Ile Ala Phe Pro Asp Ile Asp Ala Asp Gly Asp Thr Arg Glu Val
        705              710              715              720

Thr Tyr Glu Val Asp Leu Leu Ala Glu Ala Thr Ala Trp Ala Pro
                            725              730              735

Ala Gly Tyr Glu Leu Ala Phe Gly Gln Leu Thr Gly Thr Leu Asn Pro
                        740              745              750

Glu Gln Asp Ile Thr Glu Thr Ser His Asp Asp Asp Gly Arg Ala Thr
                        755              760              765

Arg Thr Leu Ser Arg Trp Asn Ala Gly Ile Arg Arg Asp Asp Lys Glu
        770              775              780

Ile Leu Leu Ser Arg Thr Gln Gly Gly Ile Val Ser Trp Lys Arg Asp
        785              790              795              800

Asp Arg Glu Met Val Ile Arg Arg Pro Glu Leu Val Thr Phe Arg Pro
                            805              810              815

Leu Thr Asp Asn Asp Arg Gly Asn His Ser Gly Phe Asp Arg Ala Ala
                        820              825              830

Trp Phe Ala Ala Gly Arg Tyr Ala Ile Val Thr Glu Thr Lys Ile His
                    835              840              845

Glu Ser Asp Asp Gly Leu Val Ala Glu Tyr Gln Tyr Glu Leu Ala Asp
                850              855              860

Pro Asn His Thr Pro Val Ser Val Thr Tyr His Val Asn Ser Asp Met
        865              870              875              880

Arg Met Gln Leu Thr Val Glu Tyr Pro Gly Asn Ala Thr Asp Met Ala
                            885              890              895

Ser Leu Pro Ala Phe Gly Ile Glu Trp Glu Leu Pro Gly Glu Tyr Asp
                        900              905              910

Arg Leu Arg Tyr Gly Pro Gly Pro Glu Glu Thr Tyr Arg Asp Arg
                    915              920              925

Lys Gln Gly Gly Lys Leu Gly Ile Trp Asp Ala Thr Ala Lys Ala Ser
                930              935              940

Met Ala Pro Tyr Leu Met Val Gln Glu Thr Gly Ser His Glu Asp Val
        945              950              955              960

Arg Trp Leu Glu Ala Thr Asp Ile Gln Gly His Gly Leu Arg Val Thr
                            965              970              975

Gln Arg Gly Asp Arg His Phe Thr Ala Ser Leu Leu Pro Trp Asn Thr
                        980              985              990

Tyr Met Ile Glu Ala Ala Arg Arg  His Glu Asp Leu Pro  Glu Pro Arg
                    995              1000              1005

His Asn  Tyr Leu Arg Leu Leu  Ala Ala Gln Met  Gly Val Gly Gly
                1010              1015              1020

Asp Asp  Ser Trp Gly Ala Pro  Val His Thr Ala Tyr  Gln Leu Pro
                1025              1030              1035

Ala Gly  Arg Pro Leu Thr Leu  Asp Val Asn Leu Glu  Leu Ile
                1040              1045              1050
```

<210> SEQ ID NO 9
<211> LENGTH: 1055
<212> TYPE: PRT
<213> ORGANISM: Bifidobacterium breve

<400> SEQUENCE: 9

```
Met Thr Asn Ser Met Gln Gly Lys Ala Lys Thr Ile Met Thr Asn Leu
1               5                   10                  15

Gln Ser Ala Gln Gln Phe Ser Gln Ala Trp Leu Thr Asp Pro Arg Val
            20                  25                  30

Phe Ala Val Asn Arg Leu Ala Ala His Ser Ser His Lys Phe Tyr Asp
        35                  40                  45

His Ser Pro Gln Cys Gly Glu Ala Met Asp Leu Lys Gln Ser Leu Asp
    50                  55                  60

Gly Gln Trp Arg Val Gln Met Leu Asp Leu Ala Asp Leu Ala Asp Asn
65                  70                  75                  80

Glu Leu Ala Glu Ala Ala Phe Ala Gln Pro Gly Tyr Asp Ala Ala Gly
                85                  90                  95

Phe Ser Pro Ile Glu Val Pro Ser Ala Leu Glu Thr Lys Gly Phe Leu
            100                 105                 110

Asn His Gln Tyr Val Asn Gln Gln Tyr Pro Trp Ser Gly His Glu Ser
        115                 120                 125

Pro Val Ala Pro Asp Val Pro Lys His Asn His Val Ala Leu Tyr Arg
    130                 135                 140

His Glu Phe Ser Leu Glu Pro Lys Ala Ala Val Leu Glu Ala Asn
145                 150                 155                 160

Lys Thr Ala Ala Asp Asp Ala Ala Lys Arg Arg Val Thr Leu Thr Phe
                165                 170                 175

Gln Gly Ala Ala Thr Ala Ile Val Val Trp Leu Asn Gly Ala Phe Ile
            180                 185                 190

Gly Tyr Ala Glu Asp Ser Phe Thr Pro Ser Glu Phe Asp Val Thr Asp
        195                 200                 205

Val Leu Arg Asp Gly Val Asn Thr Leu Ala Val Ala Cys Phe Glu Phe
    210                 215                 220

Ser Ser Ala Ser Trp Leu Glu Asp Gln Asp Phe Trp Arg Leu His Gly
225                 230                 235                 240

Ile Phe Arg Ser Val Glu Leu Glu Ala Gln Pro Leu Val His Val Asn
                245                 250                 255

Asp Leu Arg Val Leu Ala Asp Tyr Asp His Thr Thr Gly Glu Gly Ser
            260                 265                 270

Leu Asp Val Val Ala Leu Leu Arg Asn Ala Gly Thr Ala Ala Ala Val
        275                 280                 285

Ala Ala Thr Val Leu Asp Ala Ala Gly Asn Thr Val Trp His Ser Lys
    290                 295                 300

Leu Thr Ala Gly Ala Asp Ala Glu Thr Leu Thr Val Lys Ala Asn Val
305                 310                 315                 320

Gly Lys Val Asn Pro Trp Ser Ala Glu Pro Thr Leu Tyr Thr Leu
                325                 330                 335

Gln Val Val Ala Thr Asp Ala Ala Gly Gln Val Ile Glu Ala Ala Leu
            340                 345                 350

Gln Arg Ile Gly Phe Arg His Phe Ala Ile Glu Asp Gly Leu Met Lys
        355                 360                 365

Leu Asn Gly Lys Arg Ile Val Phe Lys Gly Val Asp Arg His Glu Phe
```

```
                370             375             380
Asp Ala Arg Thr Gly Arg Thr Ile Ala Glu Ala Asp Met Ile Glu Asp
385                 390                 395                 400

Ile His Ser Phe Lys Arg Leu Asn Ile Asn Ala Val Arg Thr Ser His
                405                 410                 415

Tyr Pro Asn Glu Thr Arg Trp Tyr Glu Leu Cys Asp Glu Tyr Gly Ile
            420                 425                 430

Tyr Val Leu Asp Glu Thr Asn Leu Glu Thr His Gly Ser Trp Thr Asp
        435                 440                 445

Pro Gly Asp Val Phe Gln Pro Ala Arg Ala Ile Pro Gly Ser Lys Asp
    450                 455                 460

Glu Trp Arg Ala Ala Cys Val Asp Arg Thr Ala Ser Met Val Arg Arg
465                 470                 475                 480

Asp Tyr Asn His Pro Ser Val Val Ile Trp Ser Leu Gly Asn Glu Ala
                485                 490                 495

Phe Gly Gly Asp Val Phe Tyr Ser Met Arg Asp Phe Val His Glu Asn
            500                 505                 510

Asp Pro Phe Arg Pro Val His Tyr Glu Gly Thr Phe Asn Asp Pro Glu
        515                 520                 525

Phe Ser Ala Ala Thr Asp Ile Met Ser Arg Met Tyr Ala Lys Pro Asp
    530                 535                 540

Glu Ile Val Lys Leu Tyr Leu Gly Glu Asp Gly Lys Lys Pro Tyr Ile
545                 550                 555                 560

Ser Cys Glu Tyr Ser His Ser Met Gly Asn Ser Thr Gly Gly Leu His
                565                 570                 575

Leu Tyr Thr Glu Leu Glu Arg Tyr Pro Leu Tyr Gln Gly Gly Phe Ile
            580                 585                 590

Trp Asp Tyr Val Asp Gln Ala Leu Trp Gln Asp Cys Gly Asn Gly Thr
        595                 600                 605

Glu Arg Leu Ala Tyr Gly Gly Asp Phe Glu Asp Arg Pro Asn Asp Tyr
    610                 615                 620

Glu Phe Ser Gly Asp Gly Val Met Phe Ala Asp Arg Thr Pro Ser Pro
625                 630                 635                 640

Lys Ala Gln Glu Val Lys Gln Leu Tyr Ala Asn Val Lys Leu Val Pro
                645                 650                 655

Asp Glu Ser Gly Val Thr Ile Thr Asn Asp Asn Leu Phe Ile Ser Thr
            660                 665                 670

Ala Ser Ser Leu Phe Thr Ala Arg Val Leu Val Asp Gly Ala Glu Arg
        675                 680                 685

Trp His Ala Asn Tyr Arg Phe Asp Val Pro Ala Gly Glu Thr Val Arg
    690                 695                 700

Glu Pro Ile Ala Phe Pro Lys Val Thr Asp Leu Val Ala Leu Ser Gly
705                 710                 715                 720

Ser Ala Glu Val Thr Tyr Glu Val Asp Gln Arg Leu Ala Glu Ala Thr
                725                 730                 735

Asp Trp Ala Pro Ala Gly Tyr Glu Leu Thr Phe Gly Gln Tyr Val Ala
            740                 745                 750

Ala Val Ser Phe Asp Asp Gly Ala Ala Asp Ala Val Ala Gly Asp
        755                 760                 765

Ala Glu Val Ala Ala Asp Gly Phe Asn Ala Gly Ile His Thr Asp Phe
    770                 775                 780

Gly Glu Val Leu Leu Ser Lys Thr Gln Gly Gly Met Val Ser Phe Lys
785                 790                 795                 800
```

```
Arg Asp Gly Arg Glu Met Val Ile Arg Arg Pro Asn Leu Thr Thr Phe
                805                 810                 815

Arg Ala Leu Thr Asp Asn Asp Arg Gly Asn Gly Ser Gly Phe Glu Arg
            820                 825                 830

Ala Gln Trp Met Ala Ala Gly Arg Tyr Ala Arg Val Thr Gly Thr Ser
        835                 840                 845

Val Glu Glu Thr Ala Asp Gly Lys Gly Leu Lys Ala Thr Tyr Ser Tyr
    850                 855                 860

Glu Leu Ala Asp Ala Lys His Thr Pro Val Thr Val His Tyr Glu Val
865                 870                 875                 880

Asp Ala Ala Leu Arg Val His Leu Thr Val Glu Tyr Pro Gly Glu Ala
                885                 890                 895

Asp Ala Ala Thr Leu Pro Ala Phe Gly Leu Glu Trp Ile Leu Pro Lys
            900                 905                 910

Gln Tyr Asp Arg Leu Arg Phe Tyr Gly Leu Gly Pro Glu Glu Thr Tyr
        915                 920                 925

Ala Asp Arg Leu His Gly Ala Lys Leu Gly Val Phe Ser Arg Thr Ala
    930                 935                 940

Ala Glu Asp Cys Ala Pro Tyr Leu Leu Pro Gln Glu Thr Gly Asn His
945                 950                 955                 960

Glu Gln Val Arg Trp Ala Glu Ile Thr Asp Gly Tyr Gly His Gly Met
                965                 970                 975

Arg Val Thr Ala Ala Gly Gly Thr Arg Phe Ala Thr Ser Leu Leu Pro
            980                 985                 990

Tyr Ser Ser Leu Met Phe Glu Asp Ala Leu His Gln Asn Glu Leu Pro
        995                 1000                1005

Lys Pro Arg His Thr Phe Leu Arg Leu Leu Ala Ala Gln Met Gly
    1010                1015                1020

Val Gly Gly Asp Asp Thr Trp Gly Ala Pro Val His Asp Glu Phe
    1025                1030                1035

Gln Val Pro Ala Asp Gln Pro Leu Lys Leu Asp Val Thr Leu Glu
    1040                1045                1050

Leu Ile
    1055

<210> SEQ ID NO 10
<211> LENGTH: 689
<212> TYPE: PRT
<213> ORGANISM: Bifidobacterium catenulatum

<400> SEQUENCE: 10

Met Thr Gln Arg Arg Ser Tyr Arg Trp Pro Gln Pro Leu Ala Gly Gln
1               5                   10                  15

Gln Ala Arg Ile Trp Tyr Gly Gly Asp Tyr Asn Pro Asp Gln Trp Pro
            20                  25                  30

Glu Glu Val Trp Asp Asp Val Arg Leu Met Lys Lys Ala Gly Val
        35                  40                  45

Asn Leu Val Ser Val Gly Ile Phe Ser Trp Ala Lys Ile Glu Thr Ser
    50                  55                  60

Glu Gly Val Tyr Asp Phe Asp Trp Leu Asp Arg Ile Ile Asp Lys Leu
65                  70                  75                  80

Gly Glu Ala Gly Ile Ala Val Asp Leu Ala Ser Ala Thr Ala Ser Pro
                85                  90                  95

Pro Met Trp Leu Thr Gln Ala His Pro Glu Val Leu Trp Lys Asp Tyr
```

```
                100                 105                 110
Arg Gly Asp Val Cys Gln Pro Gly Ala Arg Gln His Trp Arg Pro Thr
            115                 120                 125

Ser Pro Val Phe Arg Glu Tyr Ala Leu Lys Leu Cys Arg Ala Met Ala
        130                 135                 140

Glu His Tyr Lys Gly Asn Pro Tyr Val Val Ala Trp His Val Ser Asn
145                 150                 155                 160

Glu Tyr Gly Cys His Asn Arg Phe Asp Tyr Ser Glu Asp Ala Glu Arg
                165                 170                 175

Ala Phe Arg Lys Trp Cys Glu Glu Arg Tyr Gly Thr Ile Asp Ala Val
            180                 185                 190

Asn Asp Ala Trp Gly Thr Ala Phe Trp Ala Gln Arg Met Asn Asp Phe
        195                 200                 205

Thr Glu Ile Val Pro Pro Arg Phe Ile Gly Asp Gly Asn Phe Met Asn
    210                 215                 220

Pro Gly Lys Leu Leu Asp Phe Lys Arg Phe Ser Ser Asp Ala Leu Lys
225                 230                 235                 240

Ala Phe Tyr Val Ala Glu Arg Asp Ala Leu Ala Glu Ile Thr Pro Asp
                245                 250                 255

Leu Pro Leu Thr Thr Asn Phe Met Val Ser Ala Ala Gly Ser Val Leu
            260                 265                 270

Asp Tyr Asp Asp Trp Gly Arg Glu Val Asp Phe Val Ser Asn Asp His
        275                 280                 285

Tyr Phe Ile Pro Gly Glu Ala His Leu Asp Glu Leu Ala Phe Ser Ala
    290                 295                 300

Ser Leu Val Asp Gly Ile Ala Arg Lys Asp Pro Trp Phe Leu Met Glu
305                 310                 315                 320

His Ser Thr Ser Ala Val Asn Trp Arg Pro Val Asn Tyr Arg Lys Glu
                325                 330                 335

Pro Gly Gln Leu Val Arg Asp Ser Leu Ala His Val Ala Met Gly Ala
            340                 345                 350

Asp Ala Val Cys Tyr Phe Gln Trp Arg Gln Ser Lys Ala Gly Ala Glu
        355                 360                 365

Lys Phe His Ser Ala Met Val Pro His Thr Gly Glu Asp Ser Ala Val
    370                 375                 380

Phe Arg Asp Val Cys Glu Leu Gly Ala Asp Leu Asn Thr Leu Ala Asp
385                 390                 395                 400

Asn Gly Leu Leu Gly Thr Lys Leu Ala Lys Ser Lys Val Ala Val Val
                405                 410                 415

Phe Asp Tyr Glu Ser Glu Trp Ala Thr Glu His Thr Ala Thr Pro Thr
            420                 425                 430

Gln Lys Val His His Val Asp Glu Pro Leu Gln Trp Phe Arg Ala Leu
        435                 440                 445

Ala Asp His Gly Val Thr Ala Asp Val Val Pro Val Ser Ser Asn Trp
    450                 455                 460

Asp Glu Tyr Glu Val Val Leu Pro Ser Val Tyr Ile Leu Ser Glu
465                 470                 475                 480

Glu Thr Thr Arg Arg Val Arg Asp Tyr Val Val Asn Gly Gly Arg Leu
                485                 490                 495

Ile Val Thr Tyr Tyr Thr Gly Leu Ser Asp Glu Lys Asp His Val Trp
            500                 505                 510

Leu Gly Gly Tyr Pro Gly Ser Ile Arg Asp Val Val Gly Val Arg Val
        515                 520                 525
```

Glu Glu Phe Met Pro Met Gly Asp Asp Phe Pro Gly Val Pro Asp Cys
            530                 535                 540

Leu Gly Leu Ser Asn Gly Ala Val Ala His Asp Ile Ala Asp Val Ile
545                 550                 555                 560

Gly Ser Val Asp Gly Thr Ala Thr Val Leu Glu Thr Phe Arg Asp Asp
                565                 570                 575

Pro Trp Thr Gly Met Asp Gly Ala Pro Ala Ile Val Ala Asn Thr Phe
            580                 585                 590

Gly Glu Gly Arg Ser Val Tyr Val Gly Ala Arg Leu Gly Arg Asp Gly
        595                 600                 605

Ile Ala Lys Ser Leu Pro Glu Ile Phe Glu Ser Leu Gly Met Ala Glu
    610                 615                 620

Thr Gly Glu Asn Asp Ser Arg Val Leu Arg Val Glu Arg Glu Gly Ser
625                 630                 635                 640

Asp Gly Ser Arg Phe Val Phe Ser Phe Asn Arg Thr His Glu Ala Val
                645                 650                 655

Gln Ile Pro Phe Glu Gly Lys Ile Val Val Ser Ser Phe Ala Glu Val
            660                 665                 670

Ser Gly Glu Asn Val Ser Ile Lys Pro Asn Gly Val Ile Val Thr Lys
        675                 680                 685

Gln

<210> SEQ ID NO 11
<211> LENGTH: 1023
<212> TYPE: PRT
<213> ORGANISM: Bifidobacterium catenulatum

<400> SEQUENCE: 11

Met Ala Asn Ser Asn Arg Val Glu His Ala Ser Glu Thr Trp Leu Thr
1               5                   10                  15

Asp Ala Thr Val Phe Glu Val Asn Arg Thr Pro Ala His Ser Asn His
            20                  25                  30

Lys Cys Phe Thr His Asp Pro Gln Ser Gly Glu His Ser Asp Leu Thr
        35                  40                  45

Gln Ser Leu Asp Gly Glu Trp Arg Val Glu Ile Val Gln Ala Ser Asp
    50                  55                  60

Ile Asp Phe Asn Glu Glu Pro Phe Val Ala Glu Asn Phe Asp Asp Ser
65                  70                  75                  80

Ser Phe Cys Arg Ala Gln Val Pro Gly His Leu Gln Met Ala Gly Leu
                85                  90                  95

Leu Lys Asn Lys Tyr Val Asn Ile Gln Tyr Pro Trp Asp Gly His Glu
            100                 105                 110

Asn Pro Leu Glu Pro Asn Val Pro Glu Asn Asn His Val Ala Leu Tyr
        115                 120                 125

Arg Arg Lys Phe Val Val Ser Lys Arg Leu Ala Asp Thr Lys Glu Ser
    130                 135                 140

Glu Gly Ser Val Ser Ile Val Phe His Gly Met Ala Thr Ala Ile Tyr
145                 150                 155                 160

Val Trp Val Asn Gly Leu Phe Ala Gly Tyr Gly Glu Asp Gly Phe Thr
                165                 170                 175

Pro Asn Glu Phe Asp Ile Thr Asp Leu Leu His Asp Gly Glu Asn Val
            180                 185                 190

Val Ala Val Ala Cys Tyr Glu Tyr Ser Ser Ala Ser Trp Leu Glu Asp
        195                 200                 205

```
Gln Asp Phe Trp Arg Leu His Gly Leu Phe Arg Ser Val Glu Leu Thr
    210                 215                 220

Ala Gln Pro His Val His Val Glu Asn Met Gln Leu Glu Ala Asp Trp
225                 230                 235                 240

Asp Ala Glu Ser Gly Thr Ala Ser Leu Asp Ala Leu Ser Val Arg
                245                 250                 255

Asn Ala Ser Asp Ala Ala Thr Ile Ser Ala Thr Leu Lys Asp Ser Glu
            260                 265                 270

Gly Asn Val Val Trp Glu Ala Ser Thr Asn Ala Asp Ala Asn Thr Thr
        275                 280                 285

Phe Ala Ser Gly Ser Leu Gln Gly Leu Glu Pro Trp Ser Ala Glu Ser
290                 295                 300

Pro Ser Leu Tyr Glu Leu Glu Val Asn Val Ile Asp Gln Ala Gly Asn
305                 310                 315                 320

Ile Val Glu Ala Ala Val Gln Lys Val Gly Phe Arg Arg Phe Arg Ile
                325                 330                 335

Glu Asn Gly Ile Met Thr Leu Asn Gly Lys Arg Ile Val Phe Lys Gly
            340                 345                 350

Ala Asp Arg His Glu Phe Asp Ala Lys Arg Gly Arg Ser Ile Thr Glu
        355                 360                 365

Gln Asp Met Ile Asp Asp Val Ile Phe Cys Lys Arg His Asn Ile Asn
370                 375                 380

Ala Ile Arg Thr Ser His Tyr Pro Asn Gln Glu Arg Trp Tyr Asp Leu
385                 390                 395                 400

Cys Asp Glu Tyr Gly Ile Tyr Leu Ile Asp Glu Thr Asn Leu Glu Thr
                405                 410                 415

His Gly Ser Trp Cys Leu Pro Gly Asp Val Val Thr Ala Glu Thr Ala
            420                 425                 430

Val Pro Gly Ser Lys Ala His Trp Glu Gly Ala Cys Val Asp Arg Val
        435                 440                 445

Asn Ser Met Val Arg Arg Asp Tyr Asn His Pro Ser Val Val Ile Trp
450                 455                 460

Ser Leu Gly Asn Glu Ser Tyr Thr Gly Asp Val Phe Arg Ala Met Tyr
465                 470                 475                 480

Lys His Val His Asp Ile Asp Pro Asn Arg Pro Val His Tyr Glu Gly
                485                 490                 495

Val Thr Lys Asn Arg Asp Tyr Asp Asp Val Thr Asp Ile Glu Thr Arg
            500                 505                 510

Met Tyr Glu His Ala Asp Val Val Glu Glu Tyr Leu Lys Asn Asp Pro
        515                 520                 525

Gln Lys Pro Tyr Ile Ser Cys Glu Tyr Met His Ala Met Gly Asn Ser
530                 535                 540

Val Gly Asn Leu Asp Glu Tyr Thr Ala Leu Glu Arg Tyr Pro His Tyr
545                 550                 555                 560

Gln Gly Gly Phe Ile Trp Asp Phe Ile Asp Gln Ala Ile Tyr Ala Thr
                565                 570                 575

Gln Pro Asp Gly Ser Thr Arg Leu Cys Tyr Gly Gly Asp Phe Gly Asp
            580                 585                 590

Arg Pro Ser Asp Tyr Glu Phe Ser Gly Asn Gly Leu Val Phe Ala Asp
        595                 600                 605

Arg Thr Pro Thr Pro Lys Ala Gln Glu Val Lys Gln Leu Tyr Ser Asn
610                 615                 620
```

-continued

Val His Ile Asp Val Thr Asp Arg Ser Val Ser Ile Lys Asn Asp Asn
625                 630                 635                 640

Leu Phe Ile Ser Thr Gly Gly Tyr Gln Phe Val Leu Arg Ile Leu Ala
            645                 650                 655

Asp Gly Glu Pro Val Trp Gln Ser Glu Arg Arg Phe Asp Val Pro Ala
            660                 665                 670

Asp Ser Ala Cys Thr Phe Asp Val Glu Trp Pro Val Asp Leu Tyr Arg
        675                 680                 685

Ala Asn Ala Asp Glu Leu Val Leu Glu Val Ser Gln Arg Leu Ala Glu
    690                 695                 700

Ala Thr Asp Trp Ala Pro Ala Gly Tyr Glu Leu Ala Phe Gly Gln Thr
705                 710                 715                 720

Ile Val Ala Gly Thr Lys Ala Ala Glu Asp Ala Ala Leu Pro Ala Asp
                725                 730                 735

Gly Ile Val Thr Val Gly Arg Trp Asn Ala Gly Val Gln Gly Ser Gly
            740                 745                 750

Arg Glu Ile Leu Leu Ser Arg Thr Gln Gly Gly Leu Val Ser Tyr Thr
        755                 760                 765

Phe Asp Gly His Glu Phe Val Leu Arg Arg Pro Ala Ile Thr Thr Phe
770                 775                 780

Arg Ala Leu Thr Asp Asn Asp Arg Gly Ala Gly His Gly Phe Glu Arg
785                 790                 795                 800

Ala Gln Trp Met Val Ala Gly Arg Tyr Ala Arg Cys Val Asp Asn Val
                805                 810                 815

Ile Glu Gln Val Asp Glu Asp Thr Leu Lys Ala Val Tyr Thr Tyr Glu
            820                 825                 830

Leu Ala Thr Pro Gln Cys Thr Lys Val Thr Val Gly Tyr Thr Ala Asp
        835                 840                 845

Thr Thr Gly Arg Leu Asn Leu His Val Glu Tyr Pro Gly Glu Ser Gly
850                 855                 860

Glu Leu Pro Thr Ile Pro Ala Phe Gly Ile Glu Trp Thr Leu Pro Val
865                 870                 875                 880

Gln Tyr Ser Asn Leu Arg Phe Phe Gly Ala Gly Pro Glu Glu Thr Tyr
                885                 890                 895

Gln Asp Arg Lys His Ala Lys Leu Gly Val Trp Ser Thr Asp Ala Phe
            900                 905                 910

Lys Asp His Ala Pro Tyr Leu Met Pro Gln Glu Thr Gly Asn His Glu
        915                 920                 925

Glu Val Arg Trp Ala Glu Ile Thr Asp Glu Asn Gly His Gly Leu Arg
930                 935                 940

Val Ser Arg Ala Asn Gly Ala Ala Pro Phe Ala Val Ser Leu Gln Pro
945                 950                 955                 960

Tyr Ser Ser Phe Met Ile Glu Glu Ala Gln His Gln Asp Glu Leu Pro
                965                 970                 975

Ala Pro Lys His Met Phe Leu Arg Val Leu Ala Ala Gln Met Gly Val
            980                 985                 990

Gly Gly Asp Asp Ser Trp Met Ser Pro Val His Ser Gln Tyr His Ile
        995                 1000                1005

Thr Ala Asp Gln Pro Ile Ser Leu Asp Val Asn Leu Glu Leu Ile
    1010                1015                1020

<210> SEQ ID NO 12
<211> LENGTH: 1008
<212> TYPE: PRT

<213> ORGANISM: Lactobacillus delbrueckii

<400> SEQUENCE: 12

| | | | | | | | | | | | | | | |
|---|---|---|---|---|---|---|---|---|---|---|---|---|---|---|
| Met | Ser | Asn | Lys | Leu | Val | Lys | Glu | Lys | Arg | Val | Asp | Gln | Ala | Asp | Leu |
| 1 | | | | 5 | | | | | 10 | | | | | 15 | |
| Ala | Trp | Leu | Thr | Asp | Pro | Glu | Val | Tyr | Glu | Val | Asn | Thr | Ile | Pro | Pro |
| | | | 20 | | | | | 25 | | | | | 30 | | |
| His | Ser | Asp | His | Glu | Ser | Phe | Gln | Ser | Gln | Glu | Glu | Leu | Glu | Glu | Gly |
| | | 35 | | | | | 40 | | | | | 45 | | | |
| Lys | Ser | Ser | Leu | Val | Gln | Ser | Leu | Asp | Gly | Asp | Trp | Leu | Ile | Asp | Tyr |
| | 50 | | | | | 55 | | | | | 60 | | | | |
| Ala | Glu | Asn | Gly | Gln | Gly | Pro | Val | Asn | Phe | Tyr | Ala | Glu | Asp | Phe | Asp |
| 65 | | | | | 70 | | | | | 75 | | | | | 80 |
| Asp | Ser | Asn | Phe | Lys | Ser | Val | Lys | Val | Pro | Gly | Asn | Leu | Glu | Leu | Gln |
| | | | | 85 | | | | | 90 | | | | | 95 | |
| Gly | Phe | Gly | Gln | Pro | Gln | Tyr | Val | Asn | Val | Gln | Tyr | Pro | Trp | Asp | Gly |
| | | | 100 | | | | | 105 | | | | | 110 | | |
| Ser | Glu | Glu | Ile | Phe | Pro | Pro | Gln | Ile | Pro | Ser | Lys | Asn | Pro | Leu | Ala |
| | | 115 | | | | | 120 | | | | | 125 | | | |
| Ser | Tyr | Val | Arg | Tyr | Phe | Asp | Leu | Asp | Glu | Ala | Phe | Trp | Asp | Lys | Glu |
| | 130 | | | | | 135 | | | | | 140 | | | | |
| Val | Ser | Leu | Lys | Phe | Asp | Gly | Ala | Ala | Thr | Ala | Ile | Tyr | Val | Trp | Leu |
| 145 | | | | | 150 | | | | | 155 | | | | | 160 |
| Asn | Gly | His | Phe | Val | Gly | Tyr | Gly | Glu | Asp | Ser | Phe | Thr | Pro | Ser | Glu |
| | | | | 165 | | | | | 170 | | | | | 175 | |
| Phe | Met | Val | Thr | Lys | Phe | Leu | Lys | Lys | Glu | Asn | Asn | Arg | Leu | Ala | Val |
| | | | 180 | | | | | 185 | | | | | 190 | | |
| Ala | Leu | Tyr | Lys | Tyr | Ser | Ser | Ala | Ser | Trp | Leu | Glu | Asp | Gln | Asp | Phe |
| | | 195 | | | | | 200 | | | | | 205 | | | |
| Trp | Arg | Met | Ser | Gly | Leu | Phe | Arg | Ser | Val | Thr | Leu | Gln | Ala | Lys | Pro |
| | 210 | | | | | 215 | | | | | 220 | | | | |
| Arg | Leu | His | Leu | Glu | Asp | Leu | Lys | Leu | Thr | Ala | Ser | Leu | Thr | Asp | Asn |
| 225 | | | | | 230 | | | | | 235 | | | | | 240 |
| Tyr | Gln | Lys | Gly | Lys | Leu | Glu | Val | Glu | Ala | Asn | Ile | Ala | Tyr | Arg | Leu |
| | | | | 245 | | | | | 250 | | | | | 255 | |
| Pro | Asn | Ala | Ser | Phe | Lys | Leu | Glu | Val | Arg | Asp | Ser | Glu | Gly | Asp | Leu |
| | | | 260 | | | | | 265 | | | | | 270 | | |
| Val | Ala | Glu | Lys | Leu | Gly | Pro | Ile | Arg | Ser | Glu | Gln | Leu | Glu | Phe | Thr |
| | | 275 | | | | | 280 | | | | | 285 | | | |
| Leu | Ala | Asp | Leu | Pro | Val | Ala | Ala | Trp | Ser | Ala | Glu | Lys | Pro | Asn | Leu |
| | 290 | | | | | 295 | | | | | 300 | | | | |
| Tyr | Gln | Val | Arg | Leu | Tyr | Leu | Tyr | Gln | Ala | Gly | Ser | Leu | Leu | Glu | Val |
| 305 | | | | | 310 | | | | | 315 | | | | | 320 |
| Ser | Arg | Gln | Glu | Val | Gly | Phe | Arg | Asn | Phe | Glu | Leu | Lys | Asp | Gly | Ile |
| | | | | 325 | | | | | 330 | | | | | 335 | |
| Met | Tyr | Leu | Asn | Gly | Gln | Arg | Ile | Val | Phe | Lys | Gly | Ala | Asn | Arg | His |
| | | | 340 | | | | | 345 | | | | | 350 | | |
| Glu | Phe | Asp | Ser | Lys | Leu | Gly | Arg | Ala | Ile | Thr | Glu | Glu | Asp | Met | Ile |
| | | 355 | | | | | 360 | | | | | 365 | | | |
| Trp | Asp | Ile | Lys | Thr | Met | Lys | Arg | Ser | Asn | Ile | Asn | Ala | Val | Arg | Cys |
| | 370 | | | | | 375 | | | | | 380 | | | | |
| Ser | His | Tyr | Pro | Asn | Gln | Ser | Leu | Phe | Tyr | Arg | Leu | Cys | Asp | Lys | Tyr |
| 385 | | | | | 390 | | | | | 395 | | | | | 400 |

-continued

Gly Leu Tyr Val Ile Asp Glu Ala Asn Leu Glu Ser His Gly Thr Trp
                405                 410                 415
Glu Lys Val Gly Gly His Glu Asp Pro Ser Phe Asn Val Pro Gly Asp
            420                 425                 430
Asp Gln His Trp Leu Gly Ala Ser Leu Ser Arg Val Lys Asn Met Met
        435                 440                 445
Ala Arg Asp Lys Asn His Ala Ser Ile Leu Ile Trp Ser Leu Gly Asn
450                 455                 460
Glu Ser Tyr Ala Gly Thr Val Phe Ala Gln Met Ala Asp Tyr Val Arg
465                 470                 475                 480
Lys Ala Asp Pro Thr Arg Val Gln His Tyr Glu Gly Val Thr His Asn
                485                 490                 495
Arg Lys Phe Asp Asp Ala Thr Gln Ile Glu Ser Arg Met Tyr Ala Pro
            500                 505                 510
Ala Lys Val Ile Glu Glu Tyr Leu Thr Asn Lys Pro Ala Lys Pro Phe
        515                 520                 525
Ile Ser Val Glu Tyr Ala His Ala Met Gly Asn Ser Val Gly Asp Leu
530                 535                 540
Ala Ala Tyr Thr Ala Leu Glu Lys Tyr Pro His Tyr Gln Gly Gly Phe
545                 550                 555                 560
Ile Trp Asp Trp Ile Asp Gln Gly Leu Glu Lys Asp Gly His Leu Leu
                565                 570                 575
Tyr Gly Gly Asp Phe Asp Asp Arg Pro Thr Asp Tyr Glu Phe Cys Gly
            580                 585                 590
Asn Gly Leu Val Phe Ala Asp Arg Thr Glu Ser Pro Lys Leu Ala Asn
        595                 600                 605
Val Lys Ala Leu Tyr Ala Asn Leu Lys Leu Glu Val Lys Asp Gly Gln
    610                 615                 620
Leu Phe Leu Lys Asn Asp Asn Leu Phe Thr Asn Ser Ser Tyr Tyr
625                 630                 635                 640
Phe Leu Thr Ser Leu Leu Val Asp Gly Lys Leu Thr Tyr Gln Ser Arg
                645                 650                 655
Pro Leu Thr Phe Gly Leu Glu Pro Gly Glu Ser Gly Thr Phe Ala Leu
            660                 665                 670
Pro Trp Pro Glu Val Ala Asp Glu Lys Gly Glu Val Val Tyr Arg Val
        675                 680                 685
Thr Ala His Leu Lys Glu Asp Leu Pro Trp Ala Asp Glu Gly Phe Thr
    690                 695                 700
Val Ala Glu Ala Glu Val Ala Gln Lys Leu Pro Glu Phe Lys Pro
705                 710                 715                 720
Glu Gly Arg Pro Asp Leu Val Asp Ser Asp Tyr Asn Leu Gly Leu Lys
                725                 730                 735
Gly Asn Asn Phe Gln Ile Leu Phe Ser Lys Val Lys Gly Trp Pro Val
            740                 745                 750
Ser Leu Lys Tyr Ala Gly Arg Glu Tyr Leu Lys Arg Leu Pro Glu Phe
        755                 760                 765
Thr Phe Trp Arg Ala Leu Thr Asp Asn Asp Arg Gly Ala Gly Tyr Gly
    770                 775                 780
Tyr Asp Leu Ala Arg Trp Glu Asn Ala Gly Lys Tyr Ala Arg Leu Lys
785                 790                 795                 800
Asp Ile Ser Cys Glu Val Lys Glu Asp Ser Val Leu Val Lys Thr Ala
                805                 810                 815
Phe Thr Leu Pro Val Ala Leu Lys Gly Asp Leu Thr Val Thr Tyr Glu

```
            820                 825                830
Val Asp Gly Arg Gly Lys Ile Ala Val Thr Ala Asp Phe Pro Gly Ala
        835                 840                 845

Glu Glu Ala Gly Leu Leu Pro Ala Phe Gly Leu Asn Leu Ala Leu Pro
    850                 855                 860

Lys Glu Leu Thr Asp Tyr Arg Tyr Gly Leu Gly Pro Asn Glu Ser
865                 870                 875                 880

Tyr Pro Asp Arg Leu Glu Gly Asn Tyr Leu Gly Ile Tyr Gln Gly Ala
                885                 890                 895

Val Lys Lys Asn Phe Ser Pro Tyr Leu Arg Pro Gln Glu Thr Gly Asn
            900                 905                 910

Arg Ser Lys Val Arg Trp Tyr Gln Leu Phe Asp Glu Lys Gly Gly Leu
        915                 920                 925

Glu Phe Thr Ala Asn Gly Ala Asp Leu Asn Leu Ser Ala Leu Pro Tyr
    930                 935                 940

Ser Ala Ala Gln Ile Glu Ala Ala Asp His Ala Phe Asp Leu Thr Asn
945                 950                 955                 960

Asn Tyr Thr Trp Val Arg Ala Leu Ser Ala Gln Met Gly Val Gly Gly
                965                 970                 975

Asp Asp Ser Trp Gly Gln Lys Val His Pro Glu Phe Cys Leu Asp Ala
            980                 985                 990

Gln Lys Ala Arg Gln Leu Arg Leu Val Ile Gln Pro Leu Leu Leu Lys
        995                 1000                1005

<210> SEQ ID NO 13
<211> LENGTH: 1007
<212> TYPE: PRT
<213> ORGANISM: Lactobacillus delbrueckii

<400> SEQUENCE: 13

Met Ser Asn Lys Leu Val Lys Glu Lys Arg Val Asp Gln Ala Asp Leu
1               5                   10                  15

Ala Trp Leu Thr Asp Pro Glu Val Tyr Glu Val Asn Thr Ile Pro Pro
            20                  25                  30

His Ser Asp His Glu Ser Phe Gln Ser Gln Glu Leu Glu Glu Gly
        35                  40                  45

Lys Ser Ser Leu Val Gln Ser Leu Asp Gly Asn Trp Leu Ile Asp Tyr
50                  55                  60

Ala Glu Asn Gly Gln Gly Pro Ile Asn Phe Tyr Ala Glu Asp Phe Asp
65                  70                  75                  80

Asp Ser Asn Phe Lys Ser Val Lys Val Pro Gly Asn Leu Glu Leu Gln
                85                  90                  95

Gly Phe Gly Gln Pro Gln Tyr Val Asn Ile Gln Tyr Pro Trp Asp Gly
            100                 105                 110

Ser Glu Glu Ile Phe Pro Pro Gln Val Pro Ser Lys Asn Pro Leu Ala
        115                 120                 125

Ser Tyr Val Arg Tyr Phe Asp Leu Asp Glu Ala Leu Trp Asp Lys Glu
    130                 135                 140

Val Ser Leu Lys Phe Ala Gly Ala Ala Thr Ala Ile Tyr Val Trp Leu
145                 150                 155                 160

Asn Gly His Phe Val Gly Tyr Gly Glu Asp Ser Phe Thr Pro Ser Glu
                165                 170                 175

Phe Met Val Thr Lys Phe Leu Lys Lys Glu Gly Asn Arg Leu Ala Val
            180                 185                 190
```

```
Ala Leu Tyr Lys Tyr Ser Ser Ala Ser Trp Leu Glu Asp Gln Asp Phe
            195                 200                 205

Trp Arg Leu Ser Gly Leu Phe Arg Ser Val Thr Leu Glu Ala Lys Pro
210                 215                 220

Leu Leu His Leu Glu Asp Leu Lys Leu Thr Ala Ser Leu Thr Asp Asn
225                 230                 235                 240

Tyr Gln Lys Gly Lys Leu Glu Val Glu Ala Asn Ile Ala Tyr Arg Leu
                245                 250                 255

Pro Asn Ala Ser Phe Lys Leu Glu Val Arg Asp Ser Glu Gly Asp Leu
            260                 265                 270

Val Ala Glu Lys Val Gly Pro Ile Arg Ser Glu Lys Leu Gly Phe Ser
        275                 280                 285

Leu Ala Asp Leu Pro Val Ala Ala Trp Ser Ala Glu Lys Pro Asn Leu
290                 295                 300

Tyr Gln Val Arg Leu Tyr Leu Tyr Gln Ala Gly Ser Leu Leu Glu Val
305                 310                 315                 320

Ser Arg Gln Glu Val Gly Phe Arg Asn Phe Glu Leu Lys Asp Gly Ile
                325                 330                 335

Met Tyr Leu Asn Gly Gln Arg Ile Val Phe Lys Gly Val Asn Arg His
            340                 345                 350

Glu Phe Asp Ser Lys Leu Gly Arg Ala Ile Thr Glu Ala Asp Met Ile
        355                 360                 365

Trp Asp Ile Lys Thr Met Lys Gln Ser Asn Ile Asn Ala Val Arg Cys
370                 375                 380

Ser His Tyr Pro Asn Gln Ser Leu Phe Tyr Arg Leu Cys Asp Lys Tyr
385                 390                 395                 400

Gly Leu Tyr Val Ile Asp Glu Ala Asn Leu Glu Ser His Gly Thr Trp
                405                 410                 415

Glu Lys Val Gly His Glu Asp Pro Ser Phe Asn Val Pro Gly Asp Asp
            420                 425                 430

Gln His Trp Leu Gly Ala Ser Leu Ser Arg Val Lys Asn Met Met Ala
        435                 440                 445

Arg Asp Lys Asn His Ala Ser Ile Leu Ile Trp Ser Leu Gly Asn Glu
450                 455                 460

Ser Tyr Ala Gly Thr Val Phe Ala Gln Met Ala Asp Tyr Val Arg Lys
465                 470                 475                 480

Ala Asp Pro Thr Arg Val Gln His Tyr Glu Gly Val Thr His Asn Arg
                485                 490                 495

Lys Phe Asp Asp Ala Thr Gln Ile Glu Ser Arg Met Tyr Ala Pro Ala
            500                 505                 510

Lys Glu Ile Glu Glu Tyr Leu Thr Lys Lys Pro Ala Lys Pro Phe Ile
        515                 520                 525

Ser Val Glu Tyr Ala His Ala Met Gly Asn Ser Val Gly Asp Leu Ala
530                 535                 540

Ala Tyr Thr Ala Leu Glu Lys Tyr Pro His Tyr Gln Gly Gly Phe Ile
545                 550                 555                 560

Trp Asp Trp Ile Asp Gln Gly Leu Glu Lys Asp Gly His Leu Leu Tyr
                565                 570                 575

Gly Gly Asp Phe Asp Asp Arg Pro Thr Asp Tyr Glu Phe Cys Gly Asp
            580                 585                 590

Gly Leu Val Phe Ala Asp Arg Thr Thr Ser Pro Lys Leu Ala Asn Val
        595                 600                 605

Lys Ala Leu Tyr Ser Asn Leu Lys Leu Glu Val Lys Asp Gly Gln Leu
```

```
                610             615             620
Phe Ile Lys Asn Asp Asn Leu Phe Thr Asn Ser Ser Ala Tyr Tyr Phe
625                 630             635                 640

Leu Ala Ser Leu Leu Val Asp Gly Lys Leu Thr Tyr Gln Ser Gln Pro
            645             650                 655

Leu Thr Phe Gly Leu Glu Pro Gly Glu Ser Gly Thr Phe Val Leu Pro
            660             665             670

Trp Pro Glu Val Glu Asp Glu Lys Gly Glu Ile Val Tyr Gln Val Thr
        675             680             685

Ala His Leu Lys Glu Asp Leu Pro Trp Ala Asp Glu Gly Phe Thr Val
    690             695             700

Ala Glu Ala Glu Ala Val Thr Lys Leu Pro Glu Phe Tyr Pro Ala
705             710             715             720

Gly Arg Pro Glu Leu Val Asp Ser Asp Phe Asn Leu Gly Leu Lys Gly
                725             730             735

Asn Gly Phe Arg Ile Leu Phe Ser Lys Ala Lys Gly Trp Pro Val Ser
            740             745             750

Ile Lys Tyr Ala Gly Arg Glu Tyr Leu Lys Arg Leu Pro Glu Phe Thr
        755             760             765

Phe Trp Arg Ala Leu Thr Asp Asn Asp Arg Gly Ala Gly Tyr Gly Tyr
770             775             780

Asp Leu Ala Lys Trp Glu Asn Ala Gly Lys Tyr Ala Arg Leu Gln Asp
785             790             795             800

Ile Ser Tyr Glu Ile Lys Glu Asn Ser Ala Leu Val Lys Thr Thr Phe
                805             810             815

Thr Leu Pro Val Ala Leu Lys Gly Asp Leu Thr Ile Thr Tyr Glu Val
            820             825             830

Asp Ser Leu Gly Lys Ile Ala Val Thr Ala Asn Phe Pro Gly Ala Val
        835             840             845

Glu Asn Gly Leu Leu Pro Ala Phe Gly Leu Asn Phe Ala Leu Pro Lys
    850             855             860

Glu Leu Ser Asp Tyr Arg Tyr Tyr Gly Leu Gly Pro Asn Glu Ser Tyr
865             870             875             880

Ala Asp Arg Leu Glu Gly Ser Tyr Leu Gly Ile Tyr Gln Gly Ala Val
                885             890             895

Glu Lys Asn Phe Thr Pro Tyr Leu Arg Pro Gln Glu Ala Gly Asn Arg
            900             905             910

Ser Lys Val Arg Tyr Tyr Gln Leu Phe Asp Glu Glu Gly Gly Leu Glu
        915             920             925

Phe Thr Ala Asn Gly Ala Asp Leu Asn Leu Ser Ala Leu Pro Tyr Ser
930             935             940

Ala Ala Gln Ile Glu Ala Asp His Ala Phe Glu Leu Thr Asn Asn
945             950             955             960

Tyr Thr Trp Val Arg Ala Leu Ala Ala Gln Met Gly Val Gly Gly Asp
                965             970             975

Asp Ser Trp Gly Gln Lys Val His Pro Glu Phe Cys Leu Asp Ala Gln
            980             985             990

Glu Ala Arg Gln Leu Lys Leu Val Ile Gln Pro Leu Leu Leu Lys
        995             1000            1005

<210> SEQ ID NO 14
<211> LENGTH: 1008
<212> TYPE: PRT
<213> ORGANISM: Lactobacillus delbrueckii
```

<400> SEQUENCE: 14

```
Met Ser Asn Lys Leu Val Lys Glu Lys Arg Val Asp Gln Ala Asp Leu
1               5                   10                  15

Ala Trp Leu Thr Asp Pro Glu Val Tyr Glu Val Asn Thr Ile Pro Pro
            20                  25                  30

His Phe Asp His Glu Ser Phe Gln Ser Gln Glu Glu Leu Glu Glu Gly
        35                  40                  45

Lys Ser Ser Leu Val Gln Ser Leu Asp Gly Asp Trp Leu Ile Asp Tyr
    50                  55                  60

Ala Glu Asn Gly Gln Gly Pro Val Asn Phe Tyr Ala Glu Asp Phe Asp
65                  70                  75                  80

Asp Ser Asn Phe Lys Ser Val Lys Val Pro Gly Asn Leu Glu Leu Gln
                85                  90                  95

Gly Phe Gly Gln Pro Gln Tyr Val Asn Val Gln Tyr Pro Trp Asp Gly
            100                 105                 110

Ser Glu Glu Ile Phe Pro Pro Gln Ile Pro Ser Lys Asn Pro Leu Ala
        115                 120                 125

Ser Tyr Val Arg Tyr Phe Asp Leu Asp Glu Ala Phe Trp Asp Lys Glu
    130                 135                 140

Val Ser Leu Lys Phe Asp Gly Ala Ala Thr Ala Ile Tyr Val Trp Leu
145                 150                 155                 160

Asn Gly His Phe Val Gly Tyr Gly Glu Asp Ser Phe Thr Pro Ser Glu
                165                 170                 175

Phe Met Val Thr Lys Phe Leu Lys Lys Glu Asn Asn Arg Leu Ala Val
            180                 185                 190

Ala Leu Tyr Lys Tyr Ser Ser Ala Ser Trp Leu Glu Asp Gln Asp Phe
        195                 200                 205

Trp Arg Met Ser Gly Leu Phe Arg Ser Val Thr Leu Gln Ala Lys Pro
    210                 215                 220

Arg Leu His Leu Glu Asp Leu Lys Leu Thr Ala Ser Leu Thr Asp Asn
225                 230                 235                 240

Tyr Gln Lys Gly Lys Leu Glu Val Glu Ala Asn Ile Ala Tyr Arg Leu
                245                 250                 255

Pro Asn Ala Ser Phe Lys Leu Glu Val Arg Asp Ser Glu Gly Asp Leu
            260                 265                 270

Val Ala Glu Lys Leu Gly Pro Ile Arg Ser Glu Gln Leu Glu Phe Thr
        275                 280                 285

Leu Ala Asp Leu Pro Val Ala Ala Trp Ser Ala Glu Lys Pro Asn Leu
    290                 295                 300

Tyr Gln Val Arg Leu Tyr Leu Tyr Gln Ala Gly Ser Leu Leu Glu Val
305                 310                 315                 320

Ser Arg Gln Glu Val Gly Phe Arg Asn Phe Glu Leu Lys Asp Gly Ile
                325                 330                 335

Met Tyr Leu Asn Gly Gln Arg Ile Val Phe Lys Gly Ala Asn Arg His
            340                 345                 350

Glu Phe Asp Ser Lys Leu Gly Arg Ala Ile Thr Glu Glu Asp Met Ile
        355                 360                 365

Trp Asp Ile Lys Thr Met Lys Arg Ser Asn Ile Asn Ala Val Arg Cys
    370                 375                 380

Ser His Tyr Pro Asn Gln Ser Leu Phe Tyr Arg Leu Cys Asp Lys Tyr
385                 390                 395                 400

Gly Leu Tyr Val Ile Asp Glu Ala Asn Leu Glu Ser His Gly Thr Trp
```

-continued

```
                        405                 410                 415
    Glu Lys Val Gly Gly His Glu Asp Pro Ser Phe Asn Val Pro Gly Asp
                    420                 425                 430

Asp Gln His Trp Leu Gly Ala Ser Leu Ser Arg Val Lys Asn Met Met
                435                 440                 445

Ala Arg Asp Lys Asn His Ala Ser Ile Leu Ile Trp Ser Leu Gly Asn
    450                 455                 460

Glu Ser Tyr Ala Gly Thr Val Phe Ala Gln Met Ala Asp Tyr Val Arg
    465                 470                 475                 480

Lys Ala Asp Pro Thr Arg Val Gln His Tyr Glu Gly Val Thr His Asn
                    485                 490                 495

Arg Lys Phe Asp Asp Ala Thr Gln Ile Glu Ser Arg Met Tyr Ala Pro
                500                 505                 510

Ala Lys Val Ile Glu Glu Tyr Leu Thr Asn Lys Pro Ala Lys Pro Phe
                515                 520                 525

Ile Ser Val Glu Tyr Ala His Ala Met Gly Asn Ser Val Gly Asp Leu
                530                 535                 540

Ala Ala Tyr Thr Ala Leu Glu Lys Tyr Pro His Tyr Gln Gly Gly Phe
    545                 550                 555                 560

Ile Trp Asp Trp Ile Asp Gln Gly Leu Glu Lys Asp Gly His Leu Leu
                    565                 570                 575

Tyr Gly Gly Asp Phe Asp Asp Arg Pro Thr Asp Tyr Glu Phe Cys Gly
                580                 585                 590

Asn Gly Leu Val Phe Ala Asp Arg Thr Glu Ser Pro Lys Leu Ala Asn
                595                 600                 605

Val Lys Ala Leu Tyr Ala Asn Leu Lys Leu Glu Val Lys Asp Gly Gln
                610                 615                 620

Leu Phe Leu Lys Asn Asp Asn Leu Phe Thr Asn Ser Ser Ser Tyr Tyr
    625                 630                 635                 640

Phe Leu Thr Ser Leu Leu Val Asp Gly Lys Leu Thr Tyr Gln Ser Arg
                    645                 650                 655

Pro Leu Thr Phe Gly Leu Glu Pro Gly Glu Ser Gly Thr Phe Ala Leu
                660                 665                 670

Pro Trp Pro Glu Val Ala Asp Glu Lys Gly Glu Val Val Tyr Arg Val
                675                 680                 685

Thr Ala His Leu Lys Glu Asp Leu Pro Trp Ala Asp Glu Gly Phe Thr
                690                 695                 700

Val Ala Glu Ala Glu Glu Val Ala Gln Lys Leu Pro Glu Phe Lys Pro
    705                 710                 715                 720

Glu Gly Arg Pro Asp Leu Val Asp Ser Asp Tyr Asn Leu Gly Leu Lys
                    725                 730                 735

Gly Asn Asn Phe Gln Ile Leu Phe Ser Lys Val Lys Gly Trp Pro Val
                740                 745                 750

Ser Leu Lys Tyr Ala Gly Arg Glu Tyr Leu Lys Arg Leu Pro Glu Phe
                755                 760                 765

Thr Phe Trp Arg Ala Leu Thr Asp Asn Asp Arg Gly Ala Gly Tyr Gly
                770                 775                 780

Tyr Asp Leu Ala Arg Trp Glu Asn Ala Gly Lys Tyr Ala Arg Leu Lys
    785                 790                 795                 800

Asp Ile Ser Cys Glu Val Lys Glu Asp Ser Val Leu Val Lys Thr Ala
                    805                 810                 815

Phe Thr Leu Pro Val Ala Leu Lys Gly Asp Leu Thr Val Thr Tyr Glu
                820                 825                 830
```

```
Val Asp Gly Arg Gly Lys Ile Ala Val Thr Ala Asp Phe Pro Gly Ala
        835                 840                 845

Glu Glu Ala Gly Leu Leu Pro Ala Phe Gly Leu Asn Leu Ala Leu Pro
850                 855                 860

Lys Glu Leu Thr Asp Tyr Arg Tyr Tyr Gly Leu Gly Pro Asn Glu Ser
865                 870                 875                 880

Tyr Pro Asp Arg Leu Glu Gly Asn Tyr Leu Gly Ile Tyr Gln Gly Ala
            885                 890                 895

Val Lys Lys Asn Phe Ser Pro Tyr Leu Arg Pro Gln Glu Thr Gly Asn
        900                 905                 910

Arg Ser Lys Val Arg Trp Tyr Gln Leu Phe Asp Glu Lys Gly Gly Leu
        915                 920                 925

Glu Phe Thr Ala Asn Gly Ala Asp Leu Asn Leu Ser Ala Leu Pro Tyr
930                 935                 940

Ser Ala Ala Gln Ile Glu Ala Ala Asp His Ala Phe Glu Leu Thr Asn
945                 950                 955                 960

Asn Tyr Thr Trp Val Arg Ala Leu Ser Ala Gln Met Gly Val Gly Gly
            965                 970                 975

Asp Asp Ser Trp Gly Gln Lys Val His Pro Glu Phe Cys Leu Asp Ala
        980                 985                 990

Gln Lys Ala Arg Gln Leu Arg Leu  Val Ile Gln Pro Leu  Leu Leu Lys
        995                 1000                1005

<210> SEQ ID NO 15
<211> LENGTH: 1008
<212> TYPE: PRT
<213> ORGANISM: Lactobacillus delbrueckii

<400> SEQUENCE: 15

Met Ser Asn Lys Leu Val Lys Glu Lys Arg Val Asp Gln Ala Asp Leu
1               5                   10                  15

Ala Trp Leu Thr Asp Pro Glu Val Tyr Glu Val Asn Thr Ile Pro Pro
            20                  25                  30

His Ser Asp His Glu Ser Phe Gln Ser Gln Glu Glu Leu Glu Glu Gly
        35                  40                  45

Lys Ser Ser Leu Val Gln Ser Leu Asp Gly Asp Trp Leu Ile Asp Tyr
    50                  55                  60

Ala Glu Asn Gly Gln Gly Pro Val Asn Phe Tyr Ala Glu Asp Phe Asp
65                  70                  75                  80

Asp Ser Asn Phe Lys Ser Val Lys Val Pro Gly Asn Leu Glu Leu Gln
                85                  90                  95

Gly Phe Gly Gln Pro Gln Tyr Val Asn Val Gln Tyr Pro Trp Asp Gly
            100                 105                 110

Ser Glu Glu Ile Phe Pro Pro Gln Ile Pro Ser Lys Asn Pro Leu Ala
        115                 120                 125

Ser Tyr Val Arg Tyr Phe Asp Leu Asp Glu Ala Phe Trp Asp Lys Glu
    130                 135                 140

Val Ser Leu Lys Phe Asp Gly Ala Ala Thr Ala Ile Tyr Val Trp Leu
145                 150                 155                 160

Asn Gly His Phe Val Gly Tyr Gly Glu Asp Ser Phe Thr Pro Ser Glu
                165                 170                 175

Phe Met Val Thr Lys Phe Leu Lys Lys Glu Asn Asn Arg Leu Ala Val
            180                 185                 190

Ala Leu Tyr Lys Tyr Ser Ser Ala Ser Trp Leu Glu Asp Gln Asp Phe
```

-continued

```
            195                 200                 205
Trp Arg Met Ser Gly Leu Phe Arg Ser Val Thr Leu Gln Ala Lys Pro
210                 215                 220

Arg Leu His Leu Glu Asp Leu Lys Leu Thr Ala Ser Leu Thr Asp Asn
225                 230                 235                 240

Tyr Gln Lys Gly Lys Leu Glu Val Glu Ala Asn Ile Ala Tyr Arg Leu
                245                 250                 255

Pro Asn Ala Ser Phe Lys Leu Glu Val Arg Asp Ser Glu Gly Asp Leu
                260                 265                 270

Val Ala Glu Lys Leu Gly Pro Ile Arg Ser Glu Gln Leu Glu Phe Thr
            275                 280                 285

Leu Ala Asp Leu Pro Val Ala Ala Trp Ser Ala Glu Lys Pro Asn Leu
290                 295                 300

Tyr Gln Val Arg Leu Tyr Leu Tyr Gln Ala Gly Ser Leu Leu Glu Val
305                 310                 315                 320

Ser Arg Gln Glu Val Gly Phe Arg Asn Phe Glu Leu Lys Asp Gly Ile
                325                 330                 335

Met Tyr Leu Asn Gly Gln Arg Ile Val Phe Lys Gly Ala Asn Arg His
                340                 345                 350

Glu Phe Asp Ser Lys Leu Gly Arg Ala Ile Thr Glu Asp Met Ile
                355                 360                 365

Trp Asp Ile Lys Thr Met Lys Arg Ser Asn Ile Asn Ala Val Arg Cys
370                 375                 380

Ser His Tyr Pro Asn Gln Ser Leu Phe Tyr Arg Leu Cys Asp Lys Tyr
385                 390                 395                 400

Gly Leu Tyr Val Ile Asp Glu Ala Asn Leu Glu Ser His Gly Thr Trp
                405                 410                 415

Glu Lys Val Gly Gly His Glu Asp Pro Ser Phe Asn Val Pro Gly Asp
                420                 425                 430

Asp Gln His Trp Leu Gly Ala Ser Leu Ser Arg Val Lys Asn Met Met
                435                 440                 445

Ala Arg Asp Lys Asn His Ala Ser Ile Leu Ile Trp Ser Leu Gly Asn
450                 455                 460

Glu Ser Tyr Ala Gly Thr Val Phe Ala Gln Met Ala Asp Tyr Val Arg
465                 470                 475                 480

Lys Ala Asp Pro Thr Arg Val Gln His Tyr Glu Gly Val Thr His Asn
                485                 490                 495

Arg Lys Phe Asp Asp Ala Thr Gln Ile Glu Ser Arg Met Tyr Ala Pro
                500                 505                 510

Ala Lys Val Ile Glu Glu Tyr Leu Thr Asn Lys Pro Ala Lys Pro Phe
            515                 520                 525

Ile Ser Val Glu Tyr Ala His Ala Met Gly Asn Ser Val Gly Asp Leu
            530                 535                 540

Ala Ala Tyr Thr Ala Leu Glu Lys Tyr Pro His Tyr Gln Gly Gly Phe
545                 550                 555                 560

Ile Trp Asp Trp Ile Asp Gln Gly Leu Glu Lys Asp Gly His Leu Leu
                565                 570                 575

Tyr Gly Gly Asp Phe Asp Asp Arg Pro Thr Asp Tyr Glu Phe Cys Gly
                580                 585                 590

Asn Gly Leu Val Phe Ala Asp Arg Thr Glu Ser Pro Lys Leu Ala Asn
            595                 600                 605

Val Lys Ala Leu Tyr Ala Asn Leu Lys Leu Glu Val Lys Asp Gly Gln
            610                 615                 620
```

```
Leu Phe Leu Lys Asn Asp Asn Leu Phe Thr Asn Ser Ser Tyr Tyr
625                 630                 635                 640

Phe Leu Thr Ser Leu Leu Val Asp Gly Lys Leu Thr Tyr Gln Ser Arg
                645                 650                 655

Pro Leu Thr Phe Gly Leu Glu Pro Gly Glu Ser Gly Thr Phe Ala Leu
            660                 665                 670

Pro Trp Pro Glu Val Ala Asp Glu Lys Gly Glu Val Val Tyr Arg Val
            675                 680                 685

Thr Ala His Leu Lys Glu Asp Leu Pro Trp Ala Asp Glu Gly Phe Thr
        690                 695                 700

Val Ala Glu Ala Glu Val Ala Gln Lys Leu Pro Glu Phe Lys Pro
705                 710                 715                 720

Glu Gly Arg Pro Asp Leu Val Asp Ser Asp Tyr Asn Leu Gly Leu Lys
                725                 730                 735

Gly Asn Asn Phe Gln Ile Leu Phe Ser Lys Val Lys Gly Trp Pro Val
            740                 745                 750

Ser Leu Lys Tyr Ala Gly Arg Glu Tyr Leu Lys Arg Leu Pro Glu Phe
        755                 760                 765

Thr Phe Trp Arg Ala Leu Thr Asp Asn Asp Arg Gly Ala Gly Tyr Gly
770                 775                 780

Tyr Asp Leu Ala Arg Trp Glu Asn Ala Gly Lys Tyr Ala Arg Leu Lys
785                 790                 795                 800

Asp Ile Ser Cys Glu Val Lys Glu Asp Ser Val Leu Val Lys Thr Ala
                805                 810                 815

Phe Thr Leu Pro Val Ala Leu Lys Gly Asp Leu Thr Val Thr Tyr Glu
            820                 825                 830

Val Asp Gly Arg Gly Lys Ile Ala Val Thr Ala Asp Phe Pro Gly Ala
            835                 840                 845

Glu Glu Ala Gly Leu Leu Pro Ala Phe Gly Leu Asn Leu Ala Leu Pro
850                 855                 860

Lys Glu Leu Thr Asp Tyr Arg Tyr Tyr Gly Leu Gly Pro Asn Glu Ser
865                 870                 875                 880

Tyr Pro Asp Arg Leu Glu Gly Asn Tyr Leu Gly Ile Tyr Gln Gly Ala
            885                 890                 895

Val Lys Lys Asn Phe Ser Pro Tyr Leu Arg Pro Gln Glu Thr Gly Asn
            900                 905                 910

Arg Ser Lys Val Arg Trp Tyr Gln Leu Phe Asp Glu Lys Gly Gly Leu
        915                 920                 925

Glu Phe Thr Ala Asn Gly Ala Asp Leu Asn Leu Ser Ala Leu Pro Tyr
        930                 935                 940

Ser Ala Ala Gln Ile Glu Ala Asp His Ala Phe Glu Leu Thr Asn
945                 950                 955                 960

Asn Tyr Thr Trp Val Arg Ala Leu Ser Ala Gln Met Gly Val Gly Gly
            965                 970                 975

Asp Asp Ser Trp Gly Gln Lys Val His Pro Glu Phe Cys Leu Asp Ala
            980                 985                 990

Gln Lys Ala Arg Gln Leu Arg Leu  Val Ile Gln Pro Leu  Leu Leu Lys
        995                 1000                1005

<210> SEQ ID NO 16
<211> LENGTH: 1008
<212> TYPE: PRT
<213> ORGANISM: Lactobacillus delbrueckii
```

```
<400> SEQUENCE: 16

Met Ser Asn Lys Leu Val Lys Glu Lys Arg Val Asp Gln Ala Asp Leu
1               5                   10                  15

Ala Trp Leu Thr Asp Pro Glu Val Tyr Glu Val Asn Thr Ile Pro Pro
            20                  25                  30

His Ser Asp His Glu Ser Phe Gln Ser Gln Glu Glu Leu Glu Glu Gly
        35                  40                  45

Lys Ser Ser Leu Val Gln Ser Leu Asp Gly Asp Trp Leu Ile Asp Tyr
    50                  55                  60

Ala Glu Asn Gly Gln Gly Pro Val Asn Phe Tyr Ala Glu Asp Phe Asp
65                  70                  75                  80

Asp Ser Asn Phe Lys Ser Val Lys Val Pro Gly Asn Leu Glu Leu Gln
                85                  90                  95

Gly Phe Gly Gln Pro Gln Tyr Val Asn Ile Gln Tyr Pro Trp Asp Gly
            100                 105                 110

Ser Glu Glu Ile Phe Pro Pro Gln Val Pro Ser Lys Asn Pro Leu Ala
        115                 120                 125

Ser Tyr Val Arg Tyr Phe Asp Leu Asp Glu Ala Phe Trp Asp Lys Glu
    130                 135                 140

Val Ser Leu Lys Phe Ala Gly Ala Ala Thr Ala Ile Tyr Val Trp Leu
145                 150                 155                 160

Asn Gly His Phe Val Gly Tyr Gly Glu Asp Ser Phe Thr Pro Ser Glu
                165                 170                 175

Phe Met Val Thr Lys Phe Leu Lys Lys Glu Asn Asn Arg Leu Ala Val
            180                 185                 190

Ala Leu Tyr Lys Tyr Ser Ser Ala Ser Trp Leu Glu Asp Gln Asp Phe
        195                 200                 205

Trp Arg Leu Ser Gly Leu Phe Arg Ser Val Thr Leu Gln Ala Lys Pro
    210                 215                 220

Leu Leu His Leu Glu Asp Leu Lys Leu Thr Ala Ser Leu Thr Asp Asn
225                 230                 235                 240

Tyr Gln Lys Gly Lys Leu Glu Val Glu Ala Asn Ile Ala Tyr Arg Leu
                245                 250                 255

Pro Asn Ala Ser Phe Lys Leu Glu Val Arg Asp Ser Glu Gly Asp Leu
            260                 265                 270

Val Ala Glu Lys Leu Gly Pro Ile Arg Ser Glu Gln Leu Glu Phe Thr
        275                 280                 285

Leu Ala Asp Leu Pro Val Ala Ala Trp Ser Ala Glu Lys Pro Asn Leu
    290                 295                 300

Tyr Gln Val Arg Leu Tyr Leu Tyr Gln Ala Gly Ser Leu Leu Glu Val
305                 310                 315                 320

Ser Arg Gln Glu Val Gly Phe Arg Asn Phe Glu Leu Lys Asp Gly Ile
                325                 330                 335

Met Tyr Leu Asn Gly Gln Arg Ile Val Phe Lys Gly Val Asn Arg His
            340                 345                 350

Glu Phe Asp Ser Lys Leu Gly Arg Ala Ile Thr Glu Glu Asp Met Ile
        355                 360                 365

Trp Asp Ile Lys Thr Met Lys Arg Ser Asn Ile Asn Ala Val Arg Cys
    370                 375                 380

Ser His Tyr Pro Asn Gln Ser Leu Phe Tyr Arg Leu Cys Asp Lys Tyr
385                 390                 395                 400

Gly Leu Tyr Val Ile Asp Glu Ala Asn Leu Glu Ser His Gly Thr Trp
                405                 410                 415
```

```
Glu Lys Val Gly His Glu Asp Pro Ser Phe Asn Val Pro Gly Asp Asp
            420                 425                 430

Gln His Trp Leu Gly Ala Ser Leu Ser Arg Val Lys Asn Met Met Ala
            435                 440                 445

Arg Asp Lys Asn His Ala Ser Ile Leu Ile Trp Ser Leu Gly Asn Glu
            450                 455                 460

Ser Tyr Ala Gly Thr Val Phe Ala Gln Met Ala Asp Tyr Val Arg Lys
465                 470                 475                 480

Ala Asp Pro Thr Arg Val Gln His Tyr Glu Gly Val Thr His Asn Arg
                485                 490                 495

Lys Phe Asp Asp Ala Thr Gln Ile Glu Ser Arg Met Tyr Ala Pro Ala
                500                 505                 510

Lys Glu Ile Glu Glu Tyr Leu Thr Lys Lys Pro Ala Lys Pro Phe Ile
            515                 520                 525

Ser Val Glu Tyr Ala His Ala Met Gly Asn Ser Val Gly Asp Leu Ala
            530                 535                 540

Ala Tyr Thr Ala Leu Glu Lys Tyr Pro His Tyr Gln Gly Gly Phe Ile
545                 550                 555                 560

Trp Asp Trp Ile Asp Gln Gly Leu Glu Lys Asp Gly His Leu Leu Tyr
                565                 570                 575

Gly Gly Gly Asp Phe Asp Asp Arg Pro Thr Asp Tyr Glu Phe Cys Gly
                580                 585                 590

Asn Gly Leu Val Phe Ala Asp Arg Thr Thr Ser Pro Lys Leu Ala Asn
            595                 600                 605

Val Lys Ala Leu Tyr Ser Asn Leu Lys Leu Glu Val Lys Asp Gly Gln
            610                 615                 620

Leu Phe Leu Lys Asn Asp Asn Leu Phe Thr Asn Ser Ser Ala Tyr Tyr
625                 630                 635                 640

Phe Leu Thr Ser Leu Leu Val Asp Gly Lys Leu Thr Tyr Gln Ser Gln
                645                 650                 655

Pro Leu Thr Phe Gly Leu Glu Pro Gly Glu Ser Gly Thr Phe Val Leu
            660                 665                 670

Pro Trp Pro Glu Val Glu Asp Glu Lys Gly Glu Ile Val Tyr Gln Val
            675                 680                 685

Thr Ala His Leu Lys Glu Asp Leu Pro Trp Ala Asp Glu Gly Phe Thr
            690                 695                 700

Val Ala Glu Ala Glu Glu Ala Val Thr Lys Leu Pro Glu Phe Tyr Pro
705                 710                 715                 720

Ala Gly Arg Pro Glu Leu Val Asp Ser Asp Phe Asn Leu Gly Leu Lys
                725                 730                 735

Gly Asn Gly Phe Arg Ile Leu Phe Ser Lys Ala Lys Gly Trp Pro Val
            740                 745                 750

Ser Ile Lys Tyr Ala Gly Arg Glu Tyr Leu Lys Arg Leu Pro Glu Phe
            755                 760                 765

Thr Phe Trp Arg Ala Leu Thr Asp Asn Asp Arg Gly Ala Gly Tyr Gly
            770                 775                 780

Tyr Asp Leu Ala Lys Trp Glu Asn Ala Gly Lys Tyr Ala Arg Leu Gln
785                 790                 795                 800

Asp Ile Ser Tyr Glu Ile Lys Glu Asn Ser Val Leu Val Lys Thr Ala
                805                 810                 815

Phe Thr Leu Pro Val Ala Leu Lys Gly Asp Leu Thr Ile Thr Tyr Glu
            820                 825                 830
```

-continued

```
Val Asp Ser Leu Gly Lys Ile Ala Val Thr Ala Asn Phe Pro Gly Ala
            835                 840                 845

Val Glu Asn Gly Leu Leu Pro Ala Phe Gly Leu Asn Phe Ala Leu Pro
850                 855                 860

Lys Glu Leu Ser Asp Tyr Arg Tyr Tyr Gly Leu Gly Pro Asn Glu Ser
865                 870                 875                 880

Tyr Ala Asp Arg Leu Glu Gly Ser Tyr Leu Gly Ile Tyr Gln Gly Ala
                885                 890                 895

Val Glu Lys Asn Phe Thr Pro Tyr Leu Arg Pro Gln Glu Ala Gly Asn
            900                 905                 910

Arg Ser Lys Val Arg Tyr Tyr Gln Leu Phe Asp Glu Glu Ser Gly Leu
        915                 920                 925

Glu Phe Thr Ala Asn Gly Ala Asp Leu Asn Leu Ser Ala Leu Pro Tyr
    930                 935                 940

Ser Ala Ala Gln Ile Glu Ala Ala Asp His Ala Phe Glu Leu Ser Asn
945                 950                 955                 960

Asn Tyr Thr Trp Val Arg Ala Leu Ala Ala Gln Met Gly Val Gly Gly
                965                 970                 975

Asp Asp Ser Trp Gly Gln Lys Val His Pro Glu Phe Cys Leu Asp Ala
            980                 985                 990

Gln Glu Ala Arg Gln Leu Lys Leu  Val Ile Gln Pro Leu  Leu Leu Lys
        995                1000                1005
```

<210> SEQ ID NO 17
<211> LENGTH: 1008
<212> TYPE: PRT
<213> ORGANISM: Lactobacillus delbrueckii

<400> SEQUENCE: 17

```
Met Ser Asn Lys Leu Val Lys Glu Lys Arg Val Asp Gln Ala Asp Leu
1               5                   10                  15

Ala Trp Leu Thr Asp Pro Glu Val Tyr Glu Val Asn Thr Ile Pro Pro
            20                  25                  30

His Ser Asp His Glu Ser Phe Gln Ser Gln Glu Glu Leu Glu Glu Gly
        35                  40                  45

Lys Ser Ser Leu Val Gln Ser Leu Asp Gly Asp Trp Leu Ile Asp Tyr
    50                  55                  60

Ala Glu Asn Gly Gln Gly Pro Val Asn Phe Tyr Ala Glu Asp Phe Asp
65                  70                  75                  80

Asp Ser Asn Phe Lys Ser Val Lys Val Pro Gly Asn Leu Glu Leu Gln
                85                  90                  95

Gly Phe Gly Gln Pro Gln Tyr Val Asn Val Gln Tyr Pro Trp Asp Gly
            100                 105                 110

Ser Glu Glu Ile Phe Pro Pro Gln Ile Pro Ser Lys Asn Pro Leu Ala
        115                 120                 125

Ser Tyr Val Arg Tyr Phe Asp Leu Asp Glu Ala Phe Trp Asp Lys Glu
    130                 135                 140

Val Ser Leu Lys Phe Asp Gly Ala Ala Thr Ala Ile Tyr Val Trp Leu
145                 150                 155                 160

Asn Gly His Phe Val Gly Tyr Gly Glu Asp Ser Phe Thr Pro Ser Glu
                165                 170                 175

Phe Met Val Thr Lys Phe Leu Lys Lys Glu Asn Asn Arg Leu Ala Val
            180                 185                 190

Ala Leu Tyr Lys Tyr Ser Ser Ala Ser Trp Leu Glu Asp Gln Asp Phe
        195                 200                 205
```

```
Trp Arg Met Ser Gly Leu Phe Arg Ser Val Thr Leu Gln Ala Lys Pro
    210                 215                 220

Arg Leu His Leu Glu Asp Leu Lys Leu Thr Ala Ser Leu Thr Asp Asn
225                 230                 235                 240

Tyr Gln Lys Gly Lys Leu Glu Val Glu Ala Asn Ile Ala Tyr Arg Leu
                245                 250                 255

Pro Asn Ala Ser Phe Lys Leu Glu Val Arg Asp Ser Glu Gly Asp Leu
                260                 265                 270

Val Ala Glu Lys Leu Gly Pro Ile Arg Ser Glu Gln Leu Glu Phe Thr
            275                 280                 285

Leu Ala Asp Leu Pro Val Ala Ala Trp Ser Ala Glu Lys Pro Asn Leu
        290                 295                 300

Tyr Gln Val Arg Leu Tyr Leu Gln Ala Gly Ser Leu Leu Glu Val
305                 310                 315                 320

Ser Arg Gln Glu Val Gly Phe Arg Asn Phe Glu Leu Lys Asp Gly Ile
                325                 330                 335

Met Tyr Leu Asn Gly Gln Arg Ile Val Phe Lys Gly Val Asn Arg His
                340                 345                 350

Glu Phe Asp Ser Lys Leu Gly Arg Ala Ile Thr Glu Glu Asp Met Ile
        355                 360                 365

Trp Asp Ile Lys Thr Ile Lys Arg Ser Asn Ile Asn Ala Val Arg Cys
    370                 375                 380

Ser His Tyr Pro Asn Gln Ser Leu Phe Tyr Arg Leu Cys Asp Lys Tyr
385                 390                 395                 400

Gly Leu Tyr Val Ile Asp Glu Ala Asn Leu Glu Ser His Gly Thr Trp
                405                 410                 415

Glu Lys Val Gly Gly His Glu Asp Pro Ser Phe Asn Val Pro Gly Asp
                420                 425                 430

Asp Gln His Trp Leu Gly Ala Ser Leu Ser Arg Val Lys Asn Met Met
        435                 440                 445

Ala Arg Asp Lys Asn His Ala Ser Ile Leu Ile Trp Ser Leu Gly Asn
    450                 455                 460

Glu Ser Tyr Ala Gly Thr Val Phe Ala Gln Met Ala Asp Tyr Val Arg
465                 470                 475                 480

Lys Ala Asp Pro Thr Arg Val Gln His Tyr Glu Gly Val Thr His Asn
                485                 490                 495

Arg Lys Phe Asp Asp Ala Thr Gln Ile Glu Ser Arg Met Tyr Ala Pro
                500                 505                 510

Ala Lys Val Ile Glu Glu Tyr Leu Thr Asn Lys Pro Ala Lys Pro Phe
            515                 520                 525

Ile Ser Val Glu Tyr Ala His Ala Met Gly Asn Ser Val Gly Asp Leu
        530                 535                 540

Ala Ala Tyr Thr Ala Leu Glu Lys Tyr Pro His Tyr Gln Gly Gly Phe
545                 550                 555                 560

Ile Trp Asp Trp Ile Asp Gln Gly Leu Glu Lys Asp Gly His Leu Leu
                565                 570                 575

Tyr Gly Gly Asp Phe Asp Asp Arg Pro Thr Asp Tyr Glu Phe Cys Gly
                580                 585                 590

Asn Gly Leu Val Phe Ala Asp Arg Thr Glu Ser Pro Lys Leu Ala Asn
            595                 600                 605

Val Lys Ala Leu Tyr Ala Asn Leu Lys Leu Glu Val Lys Asp Gly Gln
610                 615                 620
```

```
Leu Phe Leu Lys Asn Asp Asn Leu Phe Thr Asn Ser Ser Ser Tyr Tyr
625                 630                 635                 640

Phe Leu Thr Ser Leu Leu Val Asp Gly Lys Leu Thr Tyr Gln Ser Arg
            645                 650                 655

Pro Leu Thr Phe Gly Leu Glu Pro Gly Glu Ser Gly Thr Phe Ala Leu
            660                 665                 670

Pro Trp Pro Glu Val Ala Asp Glu Lys Gly Glu Val Val Tyr Arg Val
        675                 680                 685

Thr Ala His Leu Lys Glu Asp Leu Pro Trp Ala Asp Glu Gly Phe Thr
        690                 695                 700

Val Ala Glu Ala Glu Glu Val Ala Gln Lys Leu Pro Glu Phe Lys Pro
705                 710                 715                 720

Glu Gly Arg Pro Asp Leu Val Asp Ser Asp Tyr Asn Leu Gly Leu Lys
                725                 730                 735

Gly Asn Asn Phe Gln Ile Leu Phe Ser Lys Val Lys Gly Trp Pro Val
            740                 745                 750

Ser Leu Lys Tyr Ala Gly Arg Glu Tyr Leu Lys Arg Leu Pro Glu Phe
            755                 760                 765

Thr Phe Trp Arg Ala Leu Thr Asp Asn Asp Arg Gly Ala Gly Tyr Gly
770                 775                 780

Tyr Asp Leu Ala Arg Trp Glu Asn Ala Gly Lys Tyr Ala Arg Leu Lys
785                 790                 795                 800

Asp Ile Ser Cys Glu Val Lys Glu Asp Ser Val Leu Val Lys Thr Ala
                805                 810                 815

Phe Thr Leu Pro Val Ala Leu Lys Gly Asp Leu Thr Val Thr Tyr Glu
            820                 825                 830

Val Asp Gly Arg Gly Lys Ile Ala Val Thr Ala Asp Phe Pro Gly Ala
        835                 840                 845

Glu Glu Ala Gly Leu Leu Pro Ala Phe Gly Leu Asn Leu Ala Leu Pro
850                 855                 860

Lys Glu Leu Thr Asp Tyr Arg Tyr Tyr Gly Leu Gly Pro Asn Glu Ser
865                 870                 875                 880

Tyr Pro Asp Arg Leu Glu Gly Asn Tyr Leu Gly Ile Tyr Gln Gly Ala
                885                 890                 895

Val Lys Lys Asn Phe Ser Pro Tyr Leu Arg Pro Gln Glu Thr Gly Asn
            900                 905                 910

Arg Ser Lys Val Arg Trp Tyr Gln Leu Phe Asp Glu Lys Gly Gly Leu
            915                 920                 925

Glu Phe Thr Ala Asn Gly Ala Asp Leu Asn Leu Ser Ala Leu Pro Tyr
930                 935                 940

Ser Ala Ala Gln Ile Glu Ala Ala Asp His Ala Phe Asp Leu Thr Asn
945                 950                 955                 960

Asn Tyr Thr Trp Val Arg Ala Leu Ser Ala Gln Met Gly Val Gly Gly
                965                 970                 975

Asp Asp Ser Trp Gly Lys Val His Pro Glu Phe Cys Leu Asp Ala
            980                 985                 990

Gln Lys Ala Arg Gln Leu Arg Leu Val Ile Gln Pro Leu Leu Leu Lys
        995                 1000                1005

<210> SEQ ID NO 18
<211> LENGTH: 1008
<212> TYPE: PRT
<213> ORGANISM: Lactobacillus delbrueckii

<400> SEQUENCE: 18
```

-continued

```
Met Ser Asn Lys Leu Val Lys Glu Lys Arg Val Asp Gln Ala Asp Leu
1               5                   10                  15

Ala Trp Leu Thr Asp Pro Glu Val Tyr Glu Val Asn Thr Ile Pro Pro
            20                  25                  30

His Ser Asp His Glu Ser Phe Gln Ser Gln Glu Glu Leu Glu Glu Gly
            35                  40                  45

Lys Ser Ser Leu Val Gln Ser Leu Asp Gly Asp Trp Leu Ile Asp Tyr
50                      55                  60

Ala Glu Asn Gly Gln Gly Pro Val Asn Phe Tyr Ala Glu Asp Phe Asp
65                      70                  75                  80

Asp Ser Asn Phe Lys Ser Val Lys Val Pro Gly Asn Leu Glu Leu Gln
                85                  90                  95

Gly Phe Gly Gln Pro Gln Tyr Val Asn Val Gln Tyr Pro Trp Asp Gly
                100                 105                 110

Ser Glu Glu Ile Phe Pro Pro Gln Ile Pro Ser Lys Asn Pro Leu Ala
                115                 120                 125

Ser Tyr Val Arg Tyr Phe Asp Leu Asp Glu Ala Phe Trp Asp Lys Glu
130                     135                 140

Val Ser Leu Lys Phe Asp Gly Ala Ala Thr Ala Ile Tyr Val Trp Leu
145                     150                 155                 160

Asn Gly His Phe Val Gly Tyr Gly Glu Asp Ser Phe Thr Pro Ser Glu
                165                 170                 175

Phe Met Val Thr Lys Phe Leu Lys Lys Glu Asn Asn Arg Leu Ala Val
                180                 185                 190

Ala Leu Tyr Lys Tyr Ser Ser Ala Ser Trp Leu Glu Asp Gln Asp Phe
                195                 200                 205

Trp Arg Met Ser Gly Leu Phe Arg Ser Val Thr Leu Gln Ala Lys Pro
210                     215                 220

Arg Leu His Leu Glu Asp Leu Lys Leu Thr Ala Ser Leu Thr Asp Asn
225                     230                 235                 240

Tyr Gln Lys Gly Lys Leu Glu Val Glu Ala Asn Ile Ala Tyr Arg Leu
                245                 250                 255

Pro Asn Ala Ser Phe Lys Leu Glu Val Arg Asp Ser Glu Gly Asp Leu
                260                 265                 270

Val Ala Glu Lys Leu Gly Pro Ile Gly Ser Glu Gln Leu Glu Phe Thr
275                     280                 285

Leu Ala Asp Leu Pro Val Ala Ala Trp Ser Ala Glu Lys Pro Asn Leu
290                     295                 300

Tyr Gln Val Arg Leu Tyr Leu Tyr Gln Ala Gly Ser Leu Leu Glu Val
305                     310                 315                 320

Ser Arg Gln Glu Val Gly Phe Arg Asn Phe Glu Leu Lys Asp Gly Ile
                325                 330                 335

Met Tyr Leu Asn Gly Gln Arg Ile Val Phe Lys Gly Val Asn Arg His
                340                 345                 350

Glu Phe Asp Ser Lys Leu Gly Arg Ala Ile Thr Glu Glu Asp Met Ile
                355                 360                 365

Trp Asp Ile Lys Thr Ile Lys Arg Ser Asn Ile Asn Ala Val Arg Cys
                370                 375                 380

Ser His Tyr Pro Asn Gln Ser Leu Phe Tyr Arg Leu Cys Asp Lys Tyr
385                     390                 395                 400

Gly Leu Tyr Val Ile Asp Glu Ala Asn Leu Glu Ser His Gly Thr Trp
                405                 410                 415
```

-continued

Glu Lys Val Gly Gly His Glu Asp Pro Ser Phe Asn Val Pro Gly Asp
            420                 425                 430

Asp Gln His Trp Leu Gly Ala Ser Leu Ser Arg Val Lys Asn Met Met
        435                 440                 445

Ala Arg Asp Lys Asn His Ala Ser Ile Leu Ile Trp Ser Leu Gly Asn
450                 455                 460

Glu Ser Tyr Ala Gly Thr Val Phe Ala Gln Met Ala Asp Tyr Val Arg
465                 470                 475                 480

Lys Ala Asp Pro Thr Arg Val Gln His Tyr Glu Gly Val Thr His Asn
                485                 490                 495

Arg Lys Phe Asp Asp Ala Thr Gln Ile Glu Ser Arg Met Tyr Ala Pro
            500                 505                 510

Ala Lys Val Ile Glu Glu Tyr Leu Thr Asn Lys Pro Ala Lys Pro Phe
        515                 520                 525

Ile Ser Val Glu Tyr Ala His Ala Met Gly Asn Ser Val Gly Asp Leu
    530                 535                 540

Ala Ala Tyr Thr Ala Leu Glu Lys Tyr Pro His Tyr Gln Gly Gly Phe
545                 550                 555                 560

Ile Trp Asp Trp Ile Asp Gln Gly Leu Glu Lys Asp Gly His Leu Leu
                565                 570                 575

Tyr Gly Gly Asp Phe Asp Asp Arg Pro Thr Asp Tyr Glu Phe Cys Gly
            580                 585                 590

Asn Gly Leu Val Phe Ala Asp Arg Thr Glu Ser Pro Lys Leu Ala Asn
        595                 600                 605

Val Lys Ala Leu Tyr Ala Asn Leu Lys Leu Glu Val Lys Asp Gly Gln
    610                 615                 620

Leu Phe Leu Lys Asn Asp Asn Leu Phe Thr Asn Ser Ser Ser Tyr Tyr
625                 630                 635                 640

Phe Leu Thr Ser Leu Leu Val Asp Gly Lys Leu Thr Tyr Gln Ser Arg
                645                 650                 655

Pro Leu Thr Phe Gly Leu Glu Pro Gly Glu Ser Gly Thr Phe Ala Leu
            660                 665                 670

Pro Trp Pro Glu Val Ala Asp Glu Lys Gly Glu Val Val Tyr Arg Val
        675                 680                 685

Thr Ala His Leu Lys Glu Asp Leu Pro Trp Ala Asp Glu Gly Phe Thr
    690                 695                 700

Val Ala Glu Ala Glu Glu Val Ala Gln Lys Leu Pro Glu Phe Lys Pro
705                 710                 715                 720

Glu Gly Arg Pro Asp Leu Val Asp Ser Asp Tyr Asn Leu Gly Leu Lys
                725                 730                 735

Gly Asn Asn Phe Gln Ile Leu Phe Ser Lys Val Lys Gly Trp Pro Val
            740                 745                 750

Ser Leu Lys Tyr Ala Gly Arg Glu Tyr Leu Lys Arg Leu Pro Glu Phe
        755                 760                 765

Thr Phe Trp Arg Ala Leu Thr Asp Asn Asp Arg Gly Ala Gly Tyr Gly
    770                 775                 780

Tyr Asp Leu Ala Arg Trp Glu Asn Ala Gly Lys Tyr Ala Arg Leu Lys
785                 790                 795                 800

Asp Ile Ser Cys Glu Val Lys Glu Asp Ser Val Leu Val Lys Thr Ala
                805                 810                 815

Phe Thr Leu Pro Val Ala Leu Lys Gly Asp Leu Thr Val Thr Tyr Glu
            820                 825                 830

Val Asp Gly Arg Gly Lys Ile Ala Val Thr Ala Asp Phe Pro Gly Ala

```
                   835                840                845
Glu Glu Ala Gly Leu Leu Pro Ala Phe Gly Leu Asn Leu Ala Leu Pro
    850                855                860

Lys Glu Leu Thr Asp Tyr Arg Tyr Tyr Gly Leu Gly Pro Asn Glu Ser
865                870                875                880

Tyr Pro Asp Arg Leu Glu Gly Asn Tyr Leu Gly Ile Tyr Gln Gly Ala
                885                890                895

Val Lys Lys Asn Phe Ser Pro Tyr Leu Arg Pro Gln Glu Thr Gly Asn
            900                905                910

Arg Ser Lys Val Arg Trp Tyr Gln Leu Phe Asp Glu Lys Gly Gly Leu
        915                920                925

Glu Phe Thr Ala Asn Gly Ala Asp Leu Asn Leu Ser Ala Leu Pro Tyr
    930                935                940

Ser Ala Ala Gln Ile Glu Ala Ala Asp His Ala Phe Glu Leu Thr Asn
945                950                955                960

Asn Tyr Thr Trp Val Arg Ala Leu Ser Ala Gln Met Gly Val Gly Gly
                965                970                975

Asp Asp Ser Trp Gly Gln Lys Val His Pro Glu Phe Cys Leu Asp Ala
            980                985                990

Gln Lys Ala Arg Gln Leu Arg Leu  Val Ile Gln Pro Leu  Leu Leu Lys
        995                1000                1005
```

<210> SEQ ID NO 19
<211> LENGTH: 1007
<212> TYPE: PRT
<213> ORGANISM: Lactobacillus delbrueckii

<400> SEQUENCE: 19

```
Met Ser Asn Lys Leu Val Lys Glu Lys Arg Val Asp Gln Ala Asp Leu
1               5                   10                  15

Ala Trp Leu Thr Asp Pro Glu Val Tyr Glu Val Asn Thr Ile Pro Pro
            20                  25                  30

His Ser Asp His Glu Ser Phe Gln Ser Gln Glu Glu Leu Glu Glu Gly
        35                  40                  45

Lys Ser Ser Leu Val Gln Ser Leu Asp Gly Asn Trp Leu Ile Asp Tyr
    50                  55                  60

Ala Glu Asn Gly Gln Gly Pro Ile Asn Phe Tyr Ala Glu Asp Phe Asp
65                  70                  75                  80

Asp Ser Asn Phe Lys Ser Val Lys Val Pro Gly Asn Leu Glu Leu Gln
                85                  90                  95

Gly Phe Gly Gln Pro Gln Tyr Val Asn Ile Gln Tyr Pro Trp Asp Gly
            100                 105                 110

Ser Glu Glu Ile Phe Pro Pro Gln Val Pro Ser Lys Asn Pro Leu Ala
        115                 120                 125

Ser Tyr Val Arg Tyr Phe Asp Leu Asp Glu Ala Leu Trp Asp Lys Glu
    130                 135                 140

Val Ser Leu Lys Phe Ala Gly Ala Ala Thr Ala Ile Tyr Val Trp Leu
145                 150                 155                 160

Asn Gly His Phe Val Gly Tyr Gly Glu Asp Ser Phe Thr Pro Ser Glu
                165                 170                 175

Phe Met Val Thr Lys Phe Leu Lys Glu Gly Asn Arg Leu Ala Val
            180                 185                 190

Ala Leu Tyr Lys Tyr Ser Ser Ala Ser Trp Leu Glu Asp Gln Asp Phe
    195                 200                 205
```

```
Trp Arg Leu Ser Gly Leu Phe Arg Ser Val Thr Leu Glu Ala Lys Pro
    210                 215                 220

Leu Leu His Leu Glu Asp Leu Lys Leu Thr Ala Ser Leu Thr Asp Asn
225                 230                 235                 240

Tyr Gln Lys Gly Lys Leu Glu Val Glu Ala Asn Ile Ala Tyr Arg Leu
                245                 250                 255

Pro Asn Ala Ser Phe Lys Leu Glu Val Arg Asp Ser Glu Gly Asp Leu
                260                 265                 270

Val Ala Glu Lys Val Gly Pro Ile Arg Ser Glu Lys Leu Asp Phe Ser
            275                 280                 285

Leu Ala Asp Leu Pro Val Ala Ala Trp Ser Ala Glu Lys Pro Asn Leu
    290                 295                 300

Tyr Gln Val Arg Leu Tyr Leu Tyr Gln Ala Gly Ser Leu Leu Glu Val
305                 310                 315                 320

Ser Arg Gln Glu Val Gly Phe Arg Asn Phe Glu Leu Lys Asp Gly Ile
                325                 330                 335

Met Tyr Leu Asn Gly Gln Arg Ile Val Phe Lys Gly Val Asn Arg His
                340                 345                 350

Glu Phe Asp Ser Lys Leu Gly Arg Ala Ile Thr Glu Ala Asp Met Ile
    355                 360                 365

Trp Asp Ile Lys Thr Met Lys Gln Ser Asn Ile Asn Ala Val Arg Cys
    370                 375                 380

Ser His Tyr Pro Asn Gln Ser Leu Phe Tyr Arg Leu Cys Asp Lys Tyr
385                 390                 395                 400

Gly Leu Tyr Val Ile Asp Glu Ala Asn Leu Glu Ser His Gly Thr Trp
                405                 410                 415

Glu Lys Val Gly His Glu Asp Pro Ser Phe Asn Val Pro Gly Asp Asp
                420                 425                 430

Gln His Trp Leu Gly Ala Ser Leu Ser Arg Val Lys Asn Met Met Ala
    435                 440                 445

Arg Asp Lys Asn His Ala Ser Ile Leu Ile Trp Ser Leu Gly Asn Glu
    450                 455                 460

Ser Tyr Ala Gly Thr Val Phe Ala Gln Met Ala Asp Tyr Val Arg Lys
465                 470                 475                 480

Ala Asp Pro Thr Arg Val Gln His Tyr Glu Gly Val Thr His Asn Arg
                485                 490                 495

Lys Phe Asp Asp Ala Thr Gln Ile Glu Ser Arg Met Tyr Ala Pro Ala
                500                 505                 510

Lys Glu Ile Glu Glu Tyr Leu Thr Lys Lys Pro Ala Lys Pro Phe Ile
            515                 520                 525

Ser Val Glu Tyr Ala His Ala Met Gly Asn Ser Val Gly Asp Leu Ala
    530                 535                 540

Ala Tyr Thr Ala Leu Glu Lys Tyr Pro His Tyr Gln Gly Gly Phe Ile
545                 550                 555                 560

Trp Asp Trp Ile Asp Gln Gly Leu Glu Lys Asp Gly His Leu Leu Tyr
                565                 570                 575

Gly Gly Asp Phe Asp Asp Arg Pro Thr Asp Tyr Glu Phe Cys Gly Asp
                580                 585                 590

Gly Leu Val Phe Ala Asp Arg Thr Thr Ser Pro Lys Leu Ala Asn Val
            595                 600                 605

Lys Ala Leu Tyr Ser Asn Leu Lys Leu Glu Val Lys Asp Gly Gln Leu
    610                 615                 620

Phe Ile Lys Asn Asp Asn Leu Phe Thr Asn Ser Ser Ala Tyr Tyr Phe
```

|   | 625 |   |   |   | 630 |   |   |   | 635 |   |   |   | 640 |   |
|---|---|---|---|---|---|---|---|---|---|---|---|---|---|---|

Leu Thr Ser Leu Leu Val Asp Gly Lys Leu Thr Tyr Gln Ser Gln Pro
              645              650              655

Leu Thr Phe Gly Leu Glu Pro Gly Glu Ser Gly Thr Phe Ala Leu Pro
         660                 665            670

Trp Pro Glu Val Glu Asp Glu Lys Gly Glu Ile Val Tyr Gln Val Thr
        675                 680            685

Ala His Leu Lys Glu Asp Leu Pro Trp Ala Asp Glu Gly Phe Thr Val
690                695              700

Ala Glu Ala Glu Ala Val Thr Lys Leu Pro Glu Phe Tyr Pro Ala
705              710              715           720

Gly Arg Pro Glu Leu Val Asp Ser Asp Phe Asn Leu Gly Leu Lys Gly
        725                 730            735

Asn Gly Phe Arg Ile Leu Phe Ser Lys Ala Lys Gly Trp Pro Val Ser
        740                 745            750

Ile Lys Tyr Ala Gly Arg Glu Tyr Leu Lys Arg Leu Pro Glu Phe Thr
        755                 760            765

Phe Trp Arg Ala Leu Thr Asp Asn Asp Arg Gly Ala Gly Tyr Gly Tyr
    770              775              780

Asp Leu Ala Lys Trp Glu Asn Ala Gly Lys Tyr Ala Arg Leu Gln Asp
785                790              795           800

Ile Ser Tyr Glu Ile Lys Glu Asn Ser Ala Leu Val Lys Thr Ala Phe
        805                 810            815

Thr Leu Pro Val Ala Leu Lys Gly Asp Leu Thr Ile Thr Tyr Glu Val
        820                 825            830

Asp Ser Leu Gly Lys Ile Ala Val Thr Ala Asn Phe Pro Gly Ala Val
835                840              845

Glu Asn Gly Leu Leu Pro Ala Phe Gly Leu Asn Phe Ala Leu Pro Lys
    850              855              860

Glu Leu Ser Asp Tyr Arg Tyr Tyr Gly Leu Gly Pro Asn Glu Ser Tyr
865                870              875           880

Ala Asp Arg Leu Glu Gly Ser Tyr Leu Gly Ile Tyr Gln Gly Met Val
        885                 890            895

Glu Lys Asn Phe Thr Pro Tyr Leu Arg Pro Gln Glu Ala Gly Asn Arg
        900                 905            910

Ser Lys Val Arg Tyr Tyr Gln Leu Phe Asp Glu Glu Gly Gly Leu Glu
        915                 920            925

Phe Thr Ala Asn Gly Ala Asp Leu Asn Leu Ser Ala Leu Pro Tyr Ser
    930              935              940

Ala Ala Gln Ile Glu Ala Asp His Ala Phe Glu Leu Thr Asn Asn
945                950              955           960

Tyr Thr Trp Val Arg Ala Leu Ala Ala Gln Met Gly Val Gly Gly Asp
        965                 970            975

Asp Ser Trp Gly Gln Lys Val His Pro Glu Phe Cys Leu Asp Ala Gln
        980                 985            990

Glu Ala Arg Gln Leu Lys Leu Val Ile Gln Pro Leu Leu Leu Lys
        995             1000          1005

<210> SEQ ID NO 20
<211> LENGTH: 628
<212> TYPE: PRT
<213> ORGANISM: Lactobacillus helveticus

<400> SEQUENCE: 20

```
Met Gln Ala Asn Ile Asn Trp Leu Asp Asn Pro Glu Val Phe Arg Val
1               5                   10                  15

Asn Gln Leu Pro Ala His Ser Asp His Pro Phe Phe Arg Asp Tyr Arg
            20                  25                  30

Glu Trp Gln Lys Gln His Ser Ser Tyr Gln Gln Ser Leu Asn Gly Lys
            35                  40                  45

Trp Lys Phe His Phe Ser Ala Asn Pro Met Asp Arg Pro Gln Asp Phe
    50                  55                  60

Tyr Gln Arg Asp Phe Asp Ser Ser Asn Phe Asp Ser Ile Pro Val Pro
65                  70                  75                  80

Ser Glu Ile Glu Leu Ser Asn Tyr Thr Gln Asn Gln Tyr Ile Asn Val
                85                  90                  95

Leu Phe Pro Trp Glu Gly Lys Ile Phe Arg Arg Pro Ala Tyr Ala Leu
                100                 105                 110

Asp Pro Asn Asp His Glu Gly Ser Phe Ser Lys Gly Ala Asp Asn
            115                 120                 125

Thr Val Gly Ser Tyr Leu Lys Arg Phe Asp Leu Ser Ser Ala Leu Ile
    130                 135                 140

Gly Lys Asp Val His Ile Lys Phe Glu Gly Val Glu Gln Ala Met Tyr
145                 150                 155                 160

Val Trp Leu Asn Gly His Phe Val Gly Tyr Ala Glu Asp Ser Phe Thr
                165                 170                 175

Pro Ser Glu Phe Asp Leu Thr Pro Tyr Ile Gln Asp Lys Asp Asn Leu
            180                 185                 190

Leu Ala Val Glu Val Phe Lys His Ser Thr Ala Ser Trp Leu Glu Asp
    195                 200                 205

Gln Asp Met Phe Arg Phe Ser Gly Ile Phe Arg Ser Val Glu Leu Leu
    210                 215                 220

Gly Ile Pro Ala Thr His Leu Met Asp Met Asp Leu Lys Pro Arg Val
225                 230                 235                 240

Ala Asp Asn Tyr Gln Asp Gly Ile Phe Asn Leu Lys Leu His Phe Ile
            245                 250                 255

Gly Lys Lys Ala Gly Ser Phe His Leu Leu Val Lys Asp Ile Lys Gly
            260                 265                 270

His Thr Leu Leu Glu Lys Asn Glu Asp Ile Lys Glu Asn Val Gln Ile
    275                 280                 285

Asn Asn Glu Lys Phe Glu Asn Val His Leu Trp Asn Asn His Asp Pro
    290                 295                 300

Tyr Leu Tyr Gln Leu Leu Ile Glu Val Tyr Asp Glu Gln Gln Asn Leu
305                 310                 315                 320

Leu Glu Leu Ile Pro Phe Gln Phe Gly Phe Arg Arg Ile Glu Ile Ser
            325                 330                 335

Pro Glu Lys Val Val Leu Leu Asn Gly Lys Arg Leu Ile Ile Asn Gly
            340                 345                 350

Val Asn Arg His Glu Trp Asp Ala Lys Arg Gly Arg Ser Ile Thr Met
            355                 360                 365

Ser Asp Met Thr Thr Asp Ile Asn Thr Phe Lys Glu Asn Asn Ile Asn
    370                 375                 380

Ala Val Arg Thr Cys His Tyr Pro Asn Gln Ile Pro Trp Tyr Tyr Leu
385                 390                 395                 400

Cys Asp Gln Asn Gly Ile Tyr Val Met Ala Glu Asn Asn Leu Glu Ser
            405                 410                 415

His Gly Thr Trp Gln Lys Met Gly Glu Ile Glu Pro Ser Asp Asn Val
```

```
            420                 425                 430
Pro Gly Ser Ile Pro Gln Trp Lys Glu Ala Val Ile Asp Arg Ala Arg
            435                 440                 445

Asn Asn Tyr Glu Thr Phe Lys Asn His Thr Ser Ile Leu Phe Trp Ser
        450                 455                 460

Leu Gly Asn Glu Ser Tyr Ala Gly Asp Asn Ile Ile Ala Met Asn Glu
465                 470                 475                 480

Phe Tyr Lys Ser His Asp Asp Thr Arg Leu Val His Tyr Glu Gly Val
                485                 490                 495

Val His Arg Pro Glu Leu Lys Asp Lys Ile Ser Asp Val Glu Ser Cys
            500                 505                 510

Met Tyr Leu Pro Pro Lys Lys Val Glu Glu Tyr Leu Gln Asn Asp Pro
        515                 520                 525

Pro Lys Pro Phe Met Glu Cys Glu Tyr Met His Asp Met Gly Asn Ser
        530                 535                 540

Asp Gly Gly Met Gly Ser Tyr Ile Lys Leu Leu Asp Lys Tyr Pro Gln
545                 550                 555                 560

Tyr Phe Gly Gly Phe Ile Trp Asp Phe Ile Asp Gln Ala Leu Leu Val
                565                 570                 575

His Asp Glu Ile Ser Gly His Asp Val Leu Arg Tyr Gly Gly Asp Phe
            580                 585                 590

Asp Asp Arg His Ser Asp Tyr Glu Phe Ser Gly Asp Gly Leu Met Phe
        595                 600                 605

Ala Asp Arg Thr Pro Lys Pro Ala Met Gln Glu Val Arg Tyr Tyr Tyr
        610                 615                 620

Gly Leu His Lys
625

<210> SEQ ID NO 21
<211> LENGTH: 318
<212> TYPE: PRT
<213> ORGANISM: Lactobacillus helveticus

<400> SEQUENCE: 21

Met Asp Tyr Thr Asn Asn Gln Leu His Ile Ile Tyr Gly Asp Ala Thr
1               5                   10                  15

Phe Gly Val Asn Gly Lys Asp Phe Gln Tyr Ile Phe Ser Tyr Glu Arg
            20                  25                  30

Gly Gly Leu Glu Ser Leu Lys Val His Gly Lys Glu Trp Leu Tyr Arg
        35                  40                  45

Val Pro Thr Pro Thr Phe Trp Arg Ala Thr Thr Asp Asn Asp Arg Gly
    50                  55                  60

Ser Gly Phe Asn Leu Lys Ala Ala Gln Trp Leu Gly Ala Asp Met Phe
65                  70                  75                  80

Thr Lys Cys Thr Asp Ile His Leu Lys Val Asp Arg His Asp Phe Ala
                85                  90                  95

Glu Leu Pro Ile Ala Pro Phe Asn Asn Lys Phe Ser Asn His Glu Tyr
            100                 105                 110

Ala Lys Ser Ala Glu Ile Ser Phe Thr Tyr Gln Thr Leu Thr Thr Pro
        115                 120                 125

Ala Thr Asn Ala Lys Ile Ile Tyr Asn Ile Asp Asp Val Gly His Ile
    130                 135                 140

Lys Val Thr Met Arg Tyr Tyr Gly Lys Lys Gly Leu Pro Pro Leu Pro
145                 150                 155                 160
```

```
Val Ile Gly Ile Arg Leu Ile Met Pro Thr Ala Ala Thr Gly Phe Asp
                165                 170                 175

Tyr Glu Gly Leu Ser Gly Glu Thr Tyr Pro Asp Arg Met Ala Gly Ala
            180                 185                 190

Lys Glu Gly Lys Phe His Ile Asp Gly Leu Pro Val Thr Glu Tyr Leu
            195                 200                 205

Val Pro Gln Glu Asn Gly Met His Met Gln Thr Lys Lys Leu Thr Ile
210                 215                 220

Asn Arg Glu Thr Thr Gln Asn Asn Val Asp Arg Thr Asn Glu Lys Phe
225                 230                 235                 240

Ser Leu Ser Ile Gln Gln Ala Glu Lys Pro Phe Asn Phe Ser Cys Leu
                245                 250                 255

Pro Tyr Thr Ala Glu Glu Leu Glu Asn Ala Thr His Ile Glu Glu Leu
            260                 265                 270

Pro Leu Val Arg Arg Thr Val Leu Val Ile Ala Gly Ala Val Arg Gly
            275                 280                 285

Val Gly Gly Ile Asp Ser Trp Gly Thr Asp Val Glu Ser Ala Tyr His
            290                 295                 300

Ile Asn Pro Glu Leu Asp His Glu Phe Ser Phe Ile Leu Asn
305                 310                 315

<210> SEQ ID NO 22
<211> LENGTH: 1023
<212> TYPE: PRT
<213> ORGANISM: Bifidobacterium longum

<400> SEQUENCE: 22

Met Thr Asp Val Thr His Val Asp Arg Ala Ser Gln Ala Trp Leu Thr
1               5                   10                  15

Asp Pro Thr Val Phe Glu Val Asn Arg Thr Pro Ala His Ser Ser His
            20                  25                  30

Lys Trp Tyr Ala Arg Asp Pro Gln Ser Gly Gln Trp Ser Asp Leu Lys
        35                  40                  45

Gln Ser Leu Asp Gly Glu Trp Arg Val Glu Val Gln Ala Ala Asp
    50                  55                  60

Ile Asn Leu Glu Glu Glu Pro Ala Thr Ala Glu Ser Phe Asp Asp Ser
65                  70                  75                  80

Ser Phe Glu Arg Ile Gln Val Pro Gly His Leu Gln Thr Ala Gly Leu
                85                  90                  95

Met Asn His Lys Tyr Val Asn Val Gln Tyr Pro Trp Asp Gly His Glu
            100                 105                 110

Asn Pro Leu Glu Pro Asn Ile Pro Glu Asn Asn His Val Ala Leu Tyr
        115                 120                 125

Arg Arg Lys Phe Thr Val Ser Ala Pro Val Ala Asn Ala Lys Gln Ala
    130                 135                 140

Gly Gly Ser Val Ser Ile Val Phe His Gly Met Ala Thr Ala Ile Tyr
145                 150                 155                 160

Val Trp Val Asn Gly Ala Phe Val Gly Tyr Gly Glu Asp Gly Phe Thr
                165                 170                 175

Pro Asn Glu Phe Asp Ile Thr Glu Leu Leu His Asp Gly Glu Asn Val
            180                 185                 190

Val Ala Val Ala Cys Tyr Glu Tyr Ser Ser Ala Ser Trp Leu Glu Asp
        195                 200                 205

Gln Asp Phe Trp Arg Leu His Gly Leu Phe Arg Ser Val Glu Leu Ala
    210                 215                 220
```

```
Ala Arg Pro His Val His Ile Glu Asn Thr Gln Ile Glu Ala Asp Trp
225                 230                 235                 240

Asp Pro Glu Ala Gly Thr Ala Ser Leu Asp Ala Ala Leu Thr Val Leu
            245                 250                 255

Asn Ala Ala Asp Ala Ala Thr Val Arg Ala Thr Leu Lys Asp Ala Asp
        260                 265                 270

Gly Asn Thr Val Trp Gln Thr Gly Asp Ala Glu Ala Gln Thr Ala
    275                 280                 285

Ile Ser Ser Gly Pro Leu Gln Gly Ile Ala Pro Trp Ser Ala Glu Ser
290                 295                 300

Pro Thr Leu Tyr Glu Leu Asp Val Asp Val Ile Asp Gln Ala Gly Asp
305                 310                 315                 320

Val Ile Glu Cys Thr Ser Gln Lys Val Gly Phe Arg Arg Phe Arg Ile
                325                 330                 335

Glu Asp Gly Ile Leu Thr Ile Asn Gly Lys Arg Ile Val Phe Lys Gly
            340                 345                 350

Ala Asp Arg His Glu Phe Asp Ala Glu Gln Gly Arg Ala Ile Thr Glu
        355                 360                 365

Gln Asp Met Ile Asp Asp Val Val Phe Cys Lys Arg His Asn Ile Asn
370                 375                 380

Ser Ile Arg Thr Ser His Tyr Pro Asn Gln Glu Arg Trp Tyr Glu Leu
385                 390                 395                 400

Cys Asp Glu Tyr Gly Ile Tyr Leu Ile Asp Glu Ala Asn Leu Glu Ala
                405                 410                 415

His Gly Ser Trp Ser Leu Pro Gly Asp Val Leu Thr Glu Asp Thr Ile
            420                 425                 430

Val Pro Gly Ser Lys Arg Glu Trp Glu Gly Ala Cys Val Asp Arg Val
        435                 440                 445

Asn Ser Met Met Arg Arg Asp Tyr Asn His Pro Ser Val Leu Ile Trp
450                 455                 460

Ser Leu Gly Asn Glu Ser Tyr Val Gly Asp Val Phe Arg Ala Met Tyr
465                 470                 475                 480

Lys His Val His Asp Ile Asp Pro Asn Arg Pro Val His Tyr Glu Gly
                485                 490                 495

Val Thr His Asn Arg Asp Tyr Asp Asp Val Thr Asp Ile Glu Thr Arg
            500                 505                 510

Met Tyr Ser His Ala Asp Glu Ile Glu Lys Tyr Leu Lys Asp Asp Pro
        515                 520                 525

Lys Lys Pro Tyr Leu Ser Cys Glu Tyr Met His Ala Met Gly Asn Ser
530                 535                 540

Val Gly Asn Met Asp Glu Tyr Thr Ala Leu Glu Arg Tyr Pro Lys Tyr
545                 550                 555                 560

Gln Gly Gly Phe Ile Trp Asp Phe Ile Asp Gln Ala Ile Tyr Ala Thr
                565                 570                 575

Gln Pro Asp Gly Thr Arg Ser Leu Arg Tyr Gly Gly Asp Phe Gly Asp
            580                 585                 590

Arg Pro Ser Asp Tyr Glu Phe Ser Gly Asp Gly Leu Leu Phe Ala Asn
        595                 600                 605

Arg Lys Pro Ser Pro Lys Ala Gln Glu Val Lys Gln Leu Tyr Ser Asn
610                 615                 620

Val His Ile Asp Val Thr Lys Asp Ser Val Ser Val Lys Asn Asp Asn
625                 630                 635                 640
```

```
Leu Phe Thr Ala Thr Gly Asp Tyr Val Phe Val Leu Ser Val Leu Ala
                645                 650                 655

Asp Gly Lys Pro Val Trp Gln Ser Thr Arg Arg Phe Asp Val Pro Ala
            660                 665                 670

Gly Glu Thr Arg Thr Phe Asp Val Ala Trp Pro Val Ala Ala Tyr Arg
        675                 680                 685

Ala Asp Ala Arg Glu Leu Val Leu Gln Val Ser Gln Arg Leu Ala Lys
    690                 695                 700

Ala Thr Asp Trp Ala Glu Ser Gly Tyr Glu Leu Ala Phe Gly Gln Thr
705                 710                 715                 720

Val Val Pro Ala Asp Ala Thr Ala Thr Pro Asp Thr Lys Pro Ala Asp
                725                 730                 735

Gly Thr Ile Thr Val Gly Arg Trp Asn Ala Gly Val Arg Gly Ala Gly
            740                 745                 750

Arg Glu Val Leu Leu Ser Arg Thr Gln Gly Gly Met Val Ser Tyr Thr
        755                 760                 765

Phe Ala Gly Asn Glu Phe Val Leu Arg Arg Pro Ala Ile Thr Thr Phe
    770                 775                 780

Arg Pro Leu Thr Asp Asn Asp Arg Gly Ala Gly His Gly Phe Glu Arg
785                 790                 795                 800

Val Gln Trp Leu Gly Ala Gly Arg Tyr Ala Arg Cys Val Asp Asn Val
                805                 810                 815

Leu Glu Gln Ile Asp Asp Ser Thr Leu Lys Gly Thr Tyr Thr Tyr Glu
            820                 825                 830

Leu Ala Thr Ala Gln Arg Thr Lys Val Thr Val Ser Tyr Thr Ala His
        835                 840                 845

Thr Asp Gly Arg Val Asn Leu His Val Glu Tyr Pro Gly Glu Gln Gly
    850                 855                 860

Asp Leu Pro Thr Ile Pro Ala Phe Gly Ile Glu Trp Thr Leu Pro Val
865                 870                 875                 880

Gln Tyr Thr Asn Leu Arg Phe Phe Gly Thr Gly Pro Ala Glu Thr Tyr
                885                 890                 895

Leu Asp Arg Lys His Ala Lys Leu Gly Val Trp Ser Thr Asn Ala Phe
            900                 905                 910

Ala Asp His Ala Pro Tyr Leu Met Pro Gln Glu Thr Gly Asn His Glu
        915                 920                 925

Asp Val Arg Trp Ala Glu Ile Thr Asp Asp His Gly His Gly Met Arg
    930                 935                 940

Val Ser Arg Ala Asp Gly Ala Ala Pro Phe Ala Val Ser Leu Leu Pro
945                 950                 955                 960

Tyr Ser Ser Phe Met Leu Glu Glu Ala Gln His Gln Asp Glu Leu Pro
                965                 970                 975

Lys Pro Lys His Met Phe Leu Arg Val Leu Ala Gln Met Gly Val
            980                 985                 990

Gly Gly Asp Asp Ser Trp Met Ser Pro Val His Pro Gln Tyr His Ile
        995                 1000                1005

Pro Ala Asp Lys Pro Ile Ser Leu Asp Val Asp Leu Glu Leu Ile
    1010                1015                1020

<210> SEQ ID NO 23
<211> LENGTH: 628
<212> TYPE: PRT
<213> ORGANISM: Lactobacillus reuteri

<400> SEQUENCE: 23
```

```
Met Asp Ala Asp Ile Lys Trp Leu Asp Glu Pro Thr Phe Arg Val
1               5                   10                  15

Asn Gln Leu Pro Ala His Ser Asp His Tyr Tyr Gly Asn Tyr Asp
                20              25              30

Glu Trp Arg His Asn Asn Ser Arg Phe Ala Gln Asn Leu Asp Gly Gln
        35              40                  45

Trp Gln Phe Asn Phe Ala Glu Asn Leu Arg Glu Arg Glu Asn Asp Phe
    50              55                  60

Tyr Lys Met Asp Tyr Asp Ser Ser Phe Gly Thr Ile Glu Val Pro
65              70                  75                  80

Ser Glu Ile Glu Leu Asn Asn Tyr Ala Gln Asn Asn Tyr Ile Asn Thr
                85                  90                  95

Leu Ile Pro Trp Glu Gly Lys Ile Tyr Arg Arg Pro Ala Tyr Thr Leu
            100                 105             110

Ser Pro Asp Asp Ala Gln Glu Gly Ser Phe Ser Asp Gly Asp Asp Asn
        115                 120             125

Thr Ile Gly Glu Tyr Leu Lys His Phe Asp Leu Asp Pro Ser Leu Arg
    130                 135             140

Gly Lys Gln Val Arg Ile Arg Phe Asp Gly Val Glu Arg Ala Met Tyr
145                 150                 155                 160

Val Trp Leu Asn Gly His Phe Ile Gly Tyr Ala Glu Asp Ser Phe Thr
                165                 170             175

Pro Ser Glu Phe Asp Leu Thr Pro Tyr Ile Gln Asp Glu Gly Asn Val
            180                 185             190

Leu Ala Val Glu Val Phe Lys His Ser Thr Ala Ser Trp Ile Glu Asp
        195                 200             205

Gln Asp Met Phe Arg Phe Ser Gly Ile Phe Arg Ser Val Asn Leu Leu
        210                 215             220

Ala Gln Pro Leu Val His Val Glu Asp Leu Asn Ile Arg Pro Ile Val
225                 230             235             240

Thr Asp Asn Tyr Gln Asp Gly Ile Phe Asn Val Glu Leu Gln Leu His
            245                 250             255

Gly Glu Lys Thr Gly Asn Val Asn Val Arg Val Ile Asp Asn Asp Gly
            260                 265             270

Asn Thr Leu Val Asn Glu Thr His Pro Val Asp Ser Thr Val Lys Val
    275                 280             285

Gln Asp Gln Phe Leu Glu Asn Val His Leu Trp Asp Asn His Asp Pro
290                 295             300

Tyr Leu Tyr Gln Leu Leu Ile Glu Ile Arg Asp Asp Glu Gly Asn Leu
305                 310             315                 320

Val Glu Leu Val Pro Tyr Arg Phe Gly Phe Arg Arg Ile Glu Ile Asn
                325             330             335

Lys Asp His Val Val Leu Leu Asn Gly Gln Arg Leu Ile Ile Asn Gly
        340                 345             350

Val Asn Arg His Glu Trp Asp Ala Arg Arg Gly Arg Ala Ile Thr Met
        355                 360             365

Asp Asp Met Thr Ser Asp Ile His Thr Phe Lys Glu Asn Asn Ile Asn
        370                 375             380

Ala Val Arg Thr Cys His Tyr Pro Asp Gln Ile Pro Trp Tyr Tyr Leu
385                 390             395                 400

Cys Asp Asp Asn Gly Ile Tyr Met Met Ala Glu Asn Asn Leu Glu Ser
                405                 410             415
```

His Ala Thr Trp Gln Lys Met Gly Ala Ile Glu Pro Ser Tyr Asn Val
            420                 425                 430

Pro Gly Ser Val Pro Gln Trp Arg Asp Val Val Asp Arg Ala Arg
            435                 440                 445

Thr Asn Tyr Glu Thr Phe Lys Asn His Pro Ser Ile Leu Phe Trp Ser
450                 455                 460

Leu Gly Asn Glu Ser Tyr Ala Gly Asp Asn Ile Val Lys Met Asn Glu
465                 470                 475                 480

Phe Tyr Lys Lys His Asp Asp Ser Arg Leu Val His Tyr Glu Gly Val
                485                 490                 495

Cys His Thr Pro Glu Tyr Arg Asp Arg Ile Ser Asp Val Glu Ser Trp
            500                 505                 510

Met Tyr Leu Pro Pro Lys Glu Val Glu Glu Tyr Leu Lys Asn Asn Pro
            515                 520                 525

Asp Lys Pro Phe Met Glu Cys Glu Tyr Met His Asp Met Gly Asn Ser
            530                 535                 540

Asp Gly Gly Met Gly Ser Tyr Ile Ser Leu Leu Asp Lys Tyr Pro Gln
545                 550                 555                 560

Tyr Phe Gly Gly Phe Ile Trp Asp Phe Ile Asp Gln Ala Leu Leu Val
                565                 570                 575

Lys Asp Pro Val Ser Gly Gln Glu Val Met Arg Tyr Gly Gly Asp Phe
            580                 585                 590

Asp Asp Arg His Ser Asp Tyr Glu Phe Ser Gly Asp Gly Leu Met Phe
            595                 600                 605

Ala Asp Arg Thr Pro Lys Pro Ala Met Gln Glu Val Arg Tyr Tyr Tyr
610                 615                 620

Gly Leu His Lys
625

<210> SEQ ID NO 24
<211> LENGTH: 319
<212> TYPE: PRT
<213> ORGANISM: Lactobacillus reuteri

<400> SEQUENCE: 24

Met Ala Tyr Thr Asn Lys Leu Arg Val Ile Tyr Gly Asp Ala Thr Leu
1               5                   10                  15

Gly Leu Ser Gly Asp Gly Phe His Tyr Ile Phe Ser Tyr Glu Arg Gly
            20                  25                  30

Gly Leu Glu Ser Leu Lys Leu Asn Gly Lys Glu Trp Leu Tyr Arg Glu
        35                  40                  45

Pro Met Pro Thr Phe Trp Arg Ala Thr Thr Asp Asn Asp Arg Gly Ser
50                  55                  60

Gly Phe Asn Ile Arg Ser Ala Gln Trp Leu Ala Ala Asp Thr Phe His
65                  70                  75                  80

Lys Cys Val Gly Ile Asp Leu Thr Val Asp Asn Gln His Phe Ala Glu
                85                  90                  95

Leu Pro Ile Ala Pro Ile Thr Asn Glu Phe Ser Asp Pro Val Ser Ala
            100                 105                 110

Glu Ser Val Lys Ile Lys Tyr Thr Phe Ala Thr Leu Thr Val Pro Ala
        115                 120                 125

Thr Gln Val Thr Val Ile Tyr Glu Val Asn Gly Gln Gly Glu Ile Lys
130                 135                 140

Val Thr Met His Tyr Tyr Gly His Glu Asp Leu Pro Gly Leu Pro Val
145                 150                 155                 160

```
Val Gly Met Arg Phe Ile Met Pro Thr Val Ala Thr Gly Phe Asp Tyr
            165                 170                 175

Gln Gly Leu Ser Gly Glu Thr Tyr Pro Asp Arg Met Ala Gly Ala Thr
            180                 185                 190

Glu Gly Thr Phe His Val Asp Gly Leu Pro Val Thr Lys Tyr Leu Val
            195                 200                 205

Pro Gln Glu Asn Gly Met His Met Ala Thr His Ala Leu Thr Ile Thr
210                 215                 220

Arg Asp Ser Thr Gln Asn Asn Ala Asp His Ser Arg Glu Pro Phe Ser
225                 230                 235                 240

Leu Thr Val Lys Gln Asp Ala Gln Pro Phe Ala Phe Ser Cys Leu Pro
            245                 250                 255

Tyr Thr Ala Glu Glu Leu Glu Asn Ala Thr His Ile Glu Glu Leu Pro
            260                 265                 270

Leu Ala Arg Arg Thr Val Leu Val Ala Gly Ala Val Arg Gly Val
            275                 280                 285

Gly Gly Ile Asp Ser Trp Gly Ala Asp Val Glu Glu Gln Tyr His Ile
            290                 295                 300

Pro Ala Asp Arg Asp Val Glu Phe Ser Phe Val Leu Asn Ala Lys
305                 310                 315
```

<210> SEQ ID NO 25
<211> LENGTH: 1007
<212> TYPE: PRT
<213> ORGANISM: Lactobacillus delbrueckii

<400> SEQUENCE: 25

```
Met Ser Asn Lys Leu Val Lys Glu Lys Arg Val Asp Gln Ala Asp Leu
1               5                   10                  15

Ala Trp Leu Thr Asp Pro Glu Val Tyr Glu Val Asn Thr Ile Pro Pro
            20                  25                  30

His Ser Asp His Glu Ser Phe Gln Ser Gln Glu Leu Glu Glu Gly
            35                  40                  45

Lys Ser Ser Leu Val Gln Ser Leu Asp Gly Asn Trp Leu Ile Asp Tyr
50                  55                  60

Ala Glu Asn Gly Gln Gly Pro Ile Asn Phe Tyr Ala Glu Asp Phe Asp
65                  70                  75                  80

Asp Ser Asn Phe Lys Ser Val Lys Val Pro Gly Asn Leu Glu Leu Gln
            85                  90                  95

Gly Phe Gly Gln Pro Gln Tyr Val Asn Ile Gln Tyr Pro Trp Asp Gly
            100                 105                 110

Ser Glu Glu Ile Phe Pro Pro Gln Val Pro Ser Lys Ile Pro Leu Ala
            115                 120                 125

Ser Tyr Val Arg Tyr Phe Asp Leu Asp Glu Ala Leu Trp Asp Lys Glu
            130                 135                 140

Val Ser Leu Lys Phe Ala Gly Ala Ala Thr Ala Ile Tyr Val Trp Leu
145                 150                 155                 160

Asn Gly His Phe Val Gly Tyr Gly Glu Asp Ser Phe Thr Pro Ser Glu
            165                 170                 175

Phe Met Val Thr Lys Phe Leu Lys Lys Glu Gly Asn Arg Leu Ala Val
            180                 185                 190

Ala Leu Tyr Lys Tyr Ser Ser Ala Ser Trp Leu Glu Asp Gln Asp Phe
            195                 200                 205

Trp Arg Leu Ser Gly Leu Phe Arg Ser Val Thr Leu Glu Ala Lys Pro
```

-continued

```
            210                 215                 220
Leu Leu His Leu Glu Asp Leu Lys Leu Thr Ala Ser Leu Thr Asp Asn
225                 230                 235                 240

Tyr Gln Lys Gly Lys Leu Glu Val Glu Ala Asn Ile Ala Tyr Arg Leu
                245                 250                 255

Pro Asn Ala Ser Phe Lys Leu Glu Val Arg Asp Ser Glu Gly Asp Leu
            260                 265                 270

Val Ala Glu Lys Val Gly Pro Ile Arg Ser Glu Lys Leu Asp Phe Ser
                275                 280                 285

Leu Ala Asp Leu Pro Val Ala Ala Trp Ser Ala Glu Lys Pro Asn Leu
            290                 295                 300

Tyr Gln Val Arg Leu Tyr Leu Tyr Gln Ala Gly Ser Leu Leu Glu Val
305                 310                 315                 320

Ser Arg Gln Glu Val Gly Phe Arg Asn Phe Glu Leu Lys Asp Gly Ile
                325                 330                 335

Met Tyr Leu Asn Gly Gln Arg Ile Val Phe Lys Gly Val Asn Arg His
            340                 345                 350

Glu Phe Asp Ser Lys Leu Gly Arg Ala Ile Thr Glu Ala Asp Met Ile
                355                 360                 365

Trp Asp Ile Lys Thr Met Lys Gln Ser Asn Ile Asn Ala Val Arg Cys
            370                 375                 380

Ser His Tyr Pro Asn Gln Ser Leu Phe Tyr Arg Leu Cys Asp Lys Tyr
385                 390                 395                 400

Gly Leu Tyr Val Ile Asp Glu Ala Asn Leu Glu Ser His Gly Thr Trp
                405                 410                 415

Glu Lys Val Gly His Glu Asp Pro Ser Phe Asn Val Pro Gly Asp Asp
            420                 425                 430

Gln His Trp Leu Gly Ala Ser Leu Ser Arg Val Lys Asn Met Met Ala
                435                 440                 445

Arg Asp Lys Asn His Ala Ser Ile Leu Ile Trp Ser Leu Gly Asn Glu
            450                 455                 460

Ser Tyr Ala Gly Thr Val Phe Ala Gln Met Ala Asp Tyr Val Arg Lys
465                 470                 475                 480

Ala Asp Pro Thr Arg Val Gln His Tyr Glu Gly Val Thr His Asn Arg
                485                 490                 495

Lys Phe Asp Asp Ala Thr Gln Ile Glu Ser Arg Met Tyr Ala Pro Ala
            500                 505                 510

Lys Glu Ile Glu Glu Tyr Leu Thr Lys Lys Pro Ala Lys Pro Phe Ile
                515                 520                 525

Ser Val Glu Tyr Ala His Ala Met Gly Asn Ser Val Gly Asp Leu Ala
            530                 535                 540

Ala Tyr Thr Ala Leu Glu Lys Tyr Pro His Tyr Gln Gly Gly Phe Ile
545                 550                 555                 560

Trp Asp Trp Ile Asp Gln Gly Leu Glu Lys Asp Gly His Leu Leu Tyr
                565                 570                 575

Gly Gly Asp Phe Asp Asp Arg Pro Thr Asp Tyr Glu Phe Cys Gly Asp
            580                 585                 590

Gly Leu Val Phe Ala Asp Arg Thr Thr Ser Pro Lys Leu Ala Asn Val
                595                 600                 605

Lys Ala Leu Tyr Ser Asn Leu Lys Leu Glu Val Lys Asp Gly Gln Leu
            610                 615                 620

Phe Ile Lys Asn Asp Asn Leu Phe Thr Asn Ser Ser Ala Tyr Tyr Phe
625                 630                 635                 640
```

```
Leu Thr Ser Leu Leu Val Asp Gly Lys Leu Thr Tyr Gln Ser Gln Pro
                645                 650                 655

Leu Thr Phe Gly Leu Glu Pro Gly Glu Ser Gly Thr Phe Ala Leu Pro
            660                 665                 670

Trp Pro Glu Val Glu Asp Glu Lys Gly Glu Ile Val Tyr Gln Val Thr
        675                 680                 685

Ala His Leu Lys Glu Asp Leu Pro Trp Ala Asp Glu Gly Phe Thr Val
    690                 695                 700

Ala Glu Ala Glu Ala Val Thr Lys Leu Pro Glu Phe Tyr Pro Ala
705                 710                 715                 720

Gly Arg Pro Glu Leu Val Asp Ser Asp Phe Asn Leu Gly Leu Lys Gly
                725                 730                 735

Asn Gly Phe Arg Ile Leu Phe Ser Lys Ala Lys Gly Trp Pro Val Ser
            740                 745                 750

Ile Lys Tyr Ala Gly Arg Glu Tyr Leu Lys Arg Leu Pro Glu Phe Thr
        755                 760                 765

Phe Trp Arg Ala Leu Thr Asp Asn Asp Arg Gly Ala Gly Tyr Gly Tyr
    770                 775                 780

Asp Leu Ala Lys Trp Glu Asn Ala Gly Lys Tyr Ala Arg Leu Gln Asp
785                 790                 795                 800

Ile Ser Tyr Glu Ile Lys Glu Asn Ser Ala Leu Val Lys Thr Thr Phe
                805                 810                 815

Thr Leu Pro Val Ala Leu Lys Gly Asp Leu Thr Ile Thr Tyr Glu Val
            820                 825                 830

Asp Ser Leu Gly Lys Ile Ala Val Thr Ala Asn Phe Pro Gly Ala Val
        835                 840                 845

Glu Asn Gly Leu Leu Pro Ala Phe Gly Leu Asn Phe Ala Leu Pro Lys
    850                 855                 860

Glu Leu Ser Asp Tyr Arg Tyr Tyr Gly Leu Gly Pro Asn Glu Ser Tyr
865                 870                 875                 880

Ala Asp Arg Leu Glu Gly Ser Tyr Leu Gly Ile Tyr Gln Gly Met Val
                885                 890                 895

Glu Lys Asn Phe Thr Pro Tyr Leu Arg Pro Gln Glu Ala Gly Asn Arg
            900                 905                 910

Ser Lys Val Arg Tyr Tyr Gln Leu Phe Asp Glu Glu Gly Gly Leu Glu
        915                 920                 925

Phe Thr Ala Asn Gly Ala Asp Leu Asn Leu Ser Ala Leu Pro Tyr Ser
    930                 935                 940

Ala Ala Gln Ile Glu Ala Ala Asp His Ala Phe Glu Leu Thr Asn Asn
945                 950                 955                 960

Tyr Thr Trp Val Arg Ala Leu Ala Ala Gln Met Gly Val Gly Gly Asp
                965                 970                 975

Asp Ser Trp Gly Gln Lys Val His Pro Glu Phe Cys Leu Asp Ala Gln
            980                 985                 990

Glu Ala Arg Gln Leu Lys Leu Val  Ile Gln Pro Leu Leu  Leu Lys
        995                 1000                1005

<210> SEQ ID NO 26
<211> LENGTH: 628
<212> TYPE: PRT
<213> ORGANISM: Lactobacillus helveticus

<400> SEQUENCE: 26

Met Gln Ala Asn Ile Asn Trp Leu Asp Asn Pro Glu Val Phe Arg Val
```

-continued

```
1               5                   10                  15
Asn Gln Leu Pro Ala His Ser Asp His Pro Phe Phe Arg Asp Tyr Arg
                20                  25                  30
Glu Trp Gln Lys Gln His Ser Ser Tyr Gln Gln Ser Leu Asn Gly Lys
                35                  40                  45
Trp Lys Phe His Phe Ser Ala Asn Pro Met Asp Arg Pro Gln Asp Phe
                50                  55                  60
Tyr Gln Arg Asp Phe Asp Ser Ser Asn Phe Asp Ser Ile Pro Val Pro
65              70                  75                  80
Ser Glu Ile Glu Leu Ser Asn Tyr Thr Gln Asn Gln Tyr Ile Asn Val
                85                  90                  95
Leu Phe Pro Trp Glu Gly Lys Ile Phe Arg Arg Pro Ala Tyr Ala Leu
                100                 105                 110
Asp Pro Asn Asp His Glu Glu Gly Ser Phe Ser Lys Gly Ala Asp Asn
                115                 120                 125
Thr Val Gly Ser Tyr Leu Lys Arg Phe Asp Leu Ser Ser Ala Leu Ile
                130                 135                 140
Gly Lys Asp Val His Ile Lys Phe Glu Gly Val Gln Ala Met Tyr
145                 150                 155                 160
Val Trp Leu Asn Gly His Phe Val Gly Tyr Ala Glu Asp Ser Phe Thr
                165                 170                 175
Pro Ser Glu Phe Asp Leu Thr Pro Tyr Ile Gln Glu Lys Asp Asn Leu
                180                 185                 190
Leu Ala Val Glu Val Phe Lys His Ser Thr Ala Ser Trp Leu Glu Asp
                195                 200                 205
Gln Asp Met Phe Arg Phe Ser Gly Ile Phe Arg Ser Val Glu Leu Leu
                210                 215                 220
Gly Ile Pro Ala Thr His Leu Met Asp Met Asp Leu Lys Pro Arg Val
225                 230                 235                 240
Ala Asp Asn Tyr Gln Asp Gly Ile Phe Asn Leu Lys Leu His Phe Ile
                245                 250                 255
Gly Lys Lys Ala Gly Ser Phe His Leu Leu Val Lys Asp Ile Lys Gly
                260                 265                 270
His Thr Leu Leu Glu Lys Asn Glu Asp Ile Lys Glu Asn Val Gln Ile
                275                 280                 285
Asn Asn Glu Lys Phe Glu Asn Val His Leu Trp Asn Asn His Asp Pro
                290                 295                 300
Tyr Leu Tyr Gln Leu Leu Ile Glu Val Tyr Asp Glu Gln Gln Asn Leu
305                 310                 315                 320
Leu Glu Leu Ile Pro Phe Gln Phe Gly Phe Arg Arg Ile Glu Ile Ser
                325                 330                 335
Pro Glu Lys Val Val Leu Leu Asn Gly Lys Arg Leu Ile Ile Asn Gly
                340                 345                 350
Val Asn Arg His Glu Trp Asp Ala Lys Arg Gly Arg Ser Ile Thr Met
                355                 360                 365
Ser Asp Met Thr Thr Asp Ile Asn Thr Phe Lys Glu Asn Asn Ile Asn
                370                 375                 380
Ala Val Arg Thr Cys His Tyr Pro Asn Gln Ile Pro Trp Tyr Tyr Leu
385                 390                 395                 400
Cys Asp Gln Asn Gly Ile Tyr Val Met Ala Glu Asn Asn Leu Glu Ser
                405                 410                 415
His Gly Thr Trp Gln Lys Met Gly Glu Ile Glu Pro Ser Asp Asn Val
                420                 425                 430
```

-continued

```
Pro Gly Ser Ile Pro Gln Trp Lys Glu Ala Val Ile Asp Arg Ala Arg
            435                 440                 445

Asn Asn Tyr Glu Thr Phe Lys Asn His Thr Ser Ile Leu Phe Trp Ser
450                 455                 460

Leu Gly Asn Glu Ser Tyr Ala Gly Asp Asn Ile Ile Ala Met Asn Glu
465                 470                 475                 480

Phe Tyr Lys Ser His Asp Asp Thr Arg Leu Val His Tyr Glu Gly Val
                485                 490                 495

Val His Arg Pro Glu Leu Lys Asp Lys Ile Ser Asp Val Glu Ser Cys
            500                 505                 510

Met Tyr Leu Pro Pro Lys Lys Val Glu Glu Tyr Leu Gln Asn Asp Pro
            515                 520                 525

Pro Lys Pro Phe Met Glu Cys Glu Tyr Met His Asp Met Gly Asn Ser
            530                 535                 540

Asn Gly Gly Met Asp Ser Tyr Ile Lys Leu Leu Asp Lys Tyr Pro Gln
545                 550                 555                 560

Tyr Phe Gly Gly Phe Ile Trp Asp Phe Ile Asp Gln Ala Leu Leu Val
                565                 570                 575

His Asp Glu Ile Ser Gly His Asp Val Leu Arg Tyr Gly Gly Asp Phe
            580                 585                 590

Asp Asp Arg His Ser Asp Tyr Glu Phe Ser Gly Asp Gly Leu Met Phe
            595                 600                 605

Ala Asp Arg Lys Pro Lys Pro Ala Met Gln Glu Val Arg Tyr Tyr Tyr
            610                 615                 620

Gly Leu His Lys
625

<210> SEQ ID NO 27
<211> LENGTH: 318
<212> TYPE: PRT
<213> ORGANISM: Lactobacillus helveticus

<400> SEQUENCE: 27

Met Asp Tyr Thr Asn Asn Gln Leu His Ile Ile Tyr Gly Asp Ala Thr
1               5                   10                  15

Phe Gly Val Asn Gly Lys Asp Phe Gln Tyr Ile Phe Ser Tyr Glu Arg
                20                  25                  30

Gly Gly Leu Glu Ser Leu Lys Val His Gly Lys Glu Trp Leu Tyr Arg
            35                  40                  45

Val Pro Thr Pro Thr Phe Trp Arg Ala Thr Thr Asp Asn Asp Arg Gly
        50                  55                  60

Ser Gly Phe Asn Leu Lys Ala Ala Gln Trp Leu Gly Ala Asp Met Phe
65                  70                  75                  80

Thr Lys Cys Thr Asp Ile His Leu Lys Val Asp Arg His Asp Phe Ala
                85                  90                  95

Glu Leu Pro Ile Ala Pro Phe Asn Asn Lys Phe Ser Asn His Glu Tyr
                100                 105                 110

Ala Lys Ser Ala Glu Ile Ser Phe Thr Tyr Gln Thr Leu Thr Thr Pro
            115                 120                 125

Ala Thr Asn Ala Lys Ile Ile Tyr Asn Ile Asp Asp Gly Gly His Ile
        130                 135                 140

Lys Val Thr Met Arg Tyr Tyr Gly Lys Lys Gly Leu Pro Pro Leu Pro
145                 150                 155                 160

Val Ile Gly Ile Arg Leu Ile Met Pro Thr Ala Ala Thr Gly Phe Asp
```

```
                165                 170                 175
Tyr Glu Gly Leu Ser Gly Glu Thr Tyr Pro Asp Arg Met Ala Gly Ala
            180                 185                 190

Lys Glu Gly Lys Phe His Ile Asp Gly Leu Pro Val Thr Glu Tyr Leu
        195                 200                 205

Val Pro Gln Glu Asn Gly Met His Met Gln Thr Lys Lys Leu Thr Ile
    210                 215                 220

Asn Arg Glu Thr Thr Gln Asn Asn Val Asp Arg Thr Asn Glu Lys Phe
225                 230                 235                 240

Ser Leu Ser Ile Gln Gln Ala Glu Lys Pro Phe Asn Phe Ser Cys Leu
                245                 250                 255

Pro Tyr Thr Ala Glu Glu Leu Glu Asn Ala Thr His Ile Glu Glu Leu
            260                 265                 270

Pro Leu Val Arg Arg Thr Val Leu Val Ile Ala Gly Ala Val Arg Gly
        275                 280                 285

Val Gly Gly Ile Asp Ser Trp Gly Thr Asp Val Glu Ser Ala Tyr His
    290                 295                 300

Ile Asn Pro Asp Leu Asp His Glu Phe Ser Phe Ile Leu Asn
305                 310                 315

<210> SEQ ID NO 28
<211> LENGTH: 626
<212> TYPE: PRT
<213> ORGANISM: Lactobacillus crispatus

<400> SEQUENCE: 28

Met Lys Ala Asn Ile Lys Trp Leu Asp Asp Pro Glu Val Phe Arg Ile
1               5                   10                  15

Asn Gln Leu Pro Ala His Ser Asp His Pro Phe Tyr Lys Asp Tyr Arg
            20                  25                  30

Glu Trp Gln Lys His Ser Ser Phe Lys Gln Ser Leu Asn Gly Ala
        35                  40                  45

Trp Gln Phe His Phe Ser Lys Asp Pro Gln Ser Arg Pro Ile Asp Phe
    50                  55                  60

Tyr Lys Leu Ser Phe Asp Ser Ser Phe Asp Thr Ile Pro Val Pro
65                  70                  75                  80

Ser Glu Ile Glu Leu Asn Gly Tyr Ala Gln Asn Gln Tyr Thr Asn Ile
                85                  90                  95

Leu Tyr Pro Trp Glu Ser Lys Ile Tyr Arg Lys Pro Ala Tyr Thr Leu
            100                 105                 110

Gly Arg Gly Ile Lys Asp Gly Asp Phe Ser Gln Gly Lys Asp Asn Thr
        115                 120                 125

Val Gly Ser Tyr Leu Lys His Phe Asp Leu Asn Pro Ala Leu Ala Gly
    130                 135                 140

His Asp Ile His Ile Gln Phe Glu Gly Val Glu Arg Ala Met Tyr Val
145                 150                 155                 160

Tyr Leu Asn Gly His Phe Ile Gly Tyr Ala Glu Asp Ser Phe Thr Pro
                165                 170                 175

Ser Glu Phe Asp Leu Thr Pro Tyr Ile Gln Ala Lys Asp Asn Ile Leu
            180                 185                 190

Ala Val Glu Val Phe Lys His Ser Thr Ala Ser Trp Leu Glu Asp Gln
        195                 200                 205

Asp Met Phe Arg Phe Ser Gly Ile Phe Arg Ser Val Glu Leu Leu Ala
    210                 215                 220
```

```
Leu Pro Arg Thr His Leu Met Asp Leu Asp Ile Lys Pro Thr Val Val
225                 230                 235                 240

Asn Asp Tyr His Asp Gly Val Phe Asn Ala Lys Leu His Phe Met Gly
            245                 250                 255

Lys Thr Ser Gly Asn Val His Val Leu Ile Glu Asp Ile Asp Gly Lys
        260                 265                 270

Thr Leu Leu Asn Lys Lys Leu Pro Leu Lys Ser Thr Val Glu Ile Glu
    275                 280                 285

Asn Glu Thr Phe Ala Asn Val His Leu Trp Asp Asn His Asp Pro Tyr
290                 295                 300

Leu Tyr Gln Leu Ile Ile Glu Val His Asp Gln Asp Gly Lys Leu Val
305                 310                 315                 320

Glu Leu Ile Pro Tyr Gln Phe Gly Phe Arg Lys Ile Glu Ile Thr Lys
                325                 330                 335

Asp His Val Val Leu Leu Asn Gly Lys Arg Leu Ile Ile Asn Gly Val
            340                 345                 350

Asn Arg His Glu Trp Asp Ala Lys Arg Gly Arg Ser Ile Thr Leu Ala
        355                 360                 365

Asp Met Lys Gln Asp Ile Ala Thr Phe Lys His Asn Asn Ile Asn Ala
    370                 375                 380

Val Arg Thr Cys His Tyr Pro Asn Gln Ile Pro Trp Tyr Tyr Leu Cys
385                 390                 395                 400

Asp Gln Asn Gly Ile Tyr Met Met Ala Glu Asn Asn Leu Glu Ser His
                405                 410                 415

Gly Thr Trp Gln Lys Leu Gly Gln Val Glu Ala Thr Ser Asn Val Pro
            420                 425                 430

Gly Ser Ile Pro Glu Trp Arg Glu Val Val Asp Arg Ala Arg Ser
        435                 440                 445

Asn Tyr Glu Thr Phe Lys Asn His Thr Ala Ile Leu Phe Trp Ser Leu
    450                 455                 460

Gly Asn Glu Ser Tyr Ala Gly Ser Asn Ile Ala Ala Met Asn Lys Leu
465                 470                 475                 480

Tyr Lys Asp His Asp Ser Ser Arg Leu Thr His Tyr Glu Gly Val Phe
                485                 490                 495

His Ala Pro Glu Phe Lys Lys Glu Ile Ser Asp Leu Glu Ser Cys Met
            500                 505                 510

Tyr Leu Pro Pro Lys Glu Ala Glu Glu Tyr Leu Gln Asn Pro Lys Lys
        515                 520                 525

Pro Leu Val Glu Cys Glu Tyr Met His Asp Met Gly Asn Ser Asp Gly
    530                 535                 540

Gly Ile Gly Ser Tyr Ile Lys Leu Ile Asp Lys Tyr Pro Gln Tyr Met
545                 550                 555                 560

Gly Gly Phe Ile Trp Asp Phe Ile Asp Gln Ala Leu Leu Val His Asp
                565                 570                 575

Pro Val Ser Gly Gln Asp Val Leu Arg Tyr Gly Gly Asp Phe Asp Asp
            580                 585                 590

Arg His Ser Asp Tyr Glu Phe Ser Gly Asp Gly Leu Met Phe Ala Asp
        595                 600                 605

Arg Thr Pro Lys Pro Ala Met Gln Glu Val Arg Tyr Tyr Tyr Gly Leu
    610                 615                 620

His Lys
625
```

```
<210> SEQ ID NO 29
<211> LENGTH: 316
<212> TYPE: PRT
<213> ORGANISM: Lactobacillus crispatus

<400> SEQUENCE: 29
```

| | | | | | | | | | | | | | | | |
|---|---|---|---|---|---|---|---|---|---|---|---|---|---|---|---|
| Met | Ala | Tyr | Thr | Asn | Asn | Leu | His | Val | Val | Tyr | Gly | Glu | Ala | Ser | Leu |
| 1 | | | | 5 | | | | | 10 | | | | | 15 | |
| Gly | Val | Asn | Gly | Gln | Asp | Phe | Ala | Tyr | Leu | Phe | Ser | Tyr | Glu | Arg | Gly |
| | | | 20 | | | | | 25 | | | | | 30 | | |
| Val | Leu | Glu | Ser | Leu | Lys | Ile | Lys | Asp | Lys | Glu | Trp | Leu | Tyr | Arg | Thr |
| | | | | 35 | | | | 40 | | | | | 45 | | |
| Pro | Thr | Pro | Thr | Phe | Trp | Arg | Ala | Thr | Asp | Asn | Asp | Arg | Gly | Ser | |
| | 50 | | | | | 55 | | | | | 60 | | | | |
| Gly | Phe | Asn | Gln | Lys | Ala | Ala | Gln | Trp | Leu | Gly | Ala | Asp | Met | Phe | Thr |
| 65 | | | | | 70 | | | | | 75 | | | | | 80 |
| Lys | Cys | Val | Gly | Ile | His | Val | Gln | Val | Asp | Asp | His | Gln | Phe | Asp | Glu |
| | | | | 85 | | | | | 90 | | | | | 95 | |
| Leu | Pro | Ile | Ala | Pro | Ile | Asn | Asn | Gln | Phe | Ser | Asn | Gln | Glu | Phe | Ala |
| | | | | 100 | | | | | 105 | | | | | 110 | |
| His | Glu | Val | Lys | Val | Ala | Phe | Asp | Tyr | Glu | Thr | Leu | Thr | Thr | Pro | Ala |
| | | | 115 | | | | | 120 | | | | | 125 | | |
| Thr | Lys | Val | Lys | Ile | Ile | Tyr | Asn | Ile | Asn | Asp | Ala | Gly | His | Met | Thr |
| | 130 | | | | | 135 | | | | | 140 | | | | |
| Ile | Thr | Met | His | Tyr | Phe | Gly | Lys | Lys | Gly | Leu | Pro | Pro | Leu | Pro | Val |
| 145 | | | | | 150 | | | | | 155 | | | | | 160 |
| Ile | Gly | Met | Arg | Phe | Ile | Met | Pro | Thr | Lys | Ala | Lys | Ser | Phe | Asp | Tyr |
| | | | | 165 | | | | | 170 | | | | | 175 | |
| Thr | Gly | Leu | Ser | Gly | Glu | Thr | Tyr | Pro | Asp | Arg | Met | Ala | Gly | Ala | Glu |
| | | | 180 | | | | | 185 | | | | | 190 | | |
| Arg | Gly | Thr | Phe | His | Ile | Asp | Gly | Leu | Pro | Val | Thr | Lys | Tyr | Leu | Val |
| | | | 195 | | | | | 200 | | | | | 205 | | |
| Pro | Gln | Glu | Asn | Gly | Met | His | Met | Gln | Thr | Asn | Glu | Leu | Val | Ile | Thr |
| | 210 | | | | | 215 | | | | | 220 | | | | |
| Arg | Asn | Ser | Thr | Gln | Asn | Asn | Ala | Asp | Lys | Asp | Gly | Asp | Phe | Ser | Leu |
| 225 | | | | | 230 | | | | | 235 | | | | | 240 |
| Lys | Ile | Thr | Gln | Thr | Lys | Gln | Pro | Phe | Asn | Phe | Ser | Leu | Leu | Pro | Tyr |
| | | | | 245 | | | | | 250 | | | | | 255 | |
| Thr | Ala | Glu | Glu | Leu | Glu | Asn | Ala | Thr | His | Ile | Glu | Glu | Leu | Pro | Leu |
| | | | 260 | | | | | 265 | | | | | 270 | | |
| Ala | Arg | Arg | Ser | Val | Leu | Val | Ile | Ala | Gly | Ala | Val | Arg | Gly | Val | Gly |
| | | 275 | | | | | 280 | | | | | 285 | | | |
| Gly | Ile | Asp | Ser | Trp | Gly | Ser | Asp | Val | Glu | Glu | Gln | Tyr | His | Ile | Asp |
| | 290 | | | | | 295 | | | | | 300 | | | | |
| Pro | Glu | Gln | Asp | His | Glu | Phe | Ser | Phe | Thr | Leu | Asn | | | | |
| 305 | | | | | 310 | | | | | 315 | | | | | |

```
<210> SEQ ID NO 30
<211> LENGTH: 1025
<212> TYPE: PRT
<213> ORGANISM: Streptococcus thermophilus

<400> SEQUENCE: 30
```

| | | | | | | | | | | | | | | | |
|---|---|---|---|---|---|---|---|---|---|---|---|---|---|---|---|
| Met | Asn | Met | Thr | Lys | Ile | Gln | Thr | Tyr | Leu | Asn | Asp | Pro | Lys | Ile | Val |
| 1 | | | | 5 | | | | | 10 | | | | | 15 | |
| Ser | Val | Asn | Thr | Val | Asp | Ala | His | Ser | Asp | His | Lys | Tyr | Phe | Glu | Ser |

```
                20              25              30
Leu Glu Glu Phe Ser Glu Gly Glu Met Lys Leu Arg Gln Ser Leu Asn
                35              40              45
Gly Lys Trp Lys Ile His Tyr Ala Gln Asn Thr Asn Gln Val Leu Lys
    50              55              60
Asp Phe Tyr Lys Thr Glu Phe Asp Glu Thr Asp Leu Asn Phe Ile Asn
 65              70              75              80
Val Pro Gly His Leu Glu Leu Gln Gly Phe Gly Ser Pro Gln Tyr Val
                85              90              95
Asn Thr Gln Tyr Pro Trp Asp Gly Lys Glu Phe Leu Arg Pro Pro Gln
                100             105             110
Val Pro Gln Glu Ser Asn Ala Val Ala Ser Tyr Val Lys His Phe Thr
            115             120             125
Leu Asn Asp Ala Leu Lys Asp Lys Lys Val Phe Ile Ser Phe Gln Gly
        130             135             140
Val Ala Thr Ser Ile Phe Val Trp Val Asn Gly Asn Phe Val Gly Tyr
145             150             155             160
Ser Glu Asp Ser Phe Thr Pro Ser Glu Phe Glu Ile Ser Asp Tyr Leu
                165             170             175
Val Glu Gly Asp Asn Lys Leu Ala Val Ala Val Tyr Arg Tyr Ser Thr
            180             185             190
Ala Ser Trp Leu Glu Asp Gln Asp Phe Trp Arg Leu Tyr Gly Ile Phe
            195             200             205
Arg Asp Val Tyr Leu Tyr Ala Ile Pro Lys Val His Val Gln Asp Leu
        210             215             220
Phe Val Lys Gly Asp Tyr Asp Tyr Gln Thr Lys Ala Gly Gln Leu Asp
225             230             235             240
Ile Asp Leu Lys Thr Val Gly Asp Tyr Glu Asp Lys Lys Ile Lys Tyr
                245             250             255
Val Leu Ser Asp Tyr Glu Gly Ile Val Thr Glu Gly Asp Ala Ser Val
            260             265             270
Asn Gly Asp Gly Glu Leu Ser Val Ser Leu Glu Asn Leu Lys Ile Lys
        275             280             285
Pro Trp Ser Ala Glu Ser Pro Lys Leu Tyr Asp Leu Ile Leu His Val
        290             295             300
Leu Asp Asp Asp Gln Val Val Glu Val Val Pro Val Lys Val Gly Phe
305             310             315             320
Arg Arg Phe Glu Ile Lys Asp Lys Leu Met Leu Leu Asn Gly Lys Arg
                325             330             335
Ile Val Phe Lys Gly Val Asn Arg His Glu Phe Asn Ala Arg Thr Gly
            340             345             350
Arg Cys Ile Thr Glu Glu Asp Met Leu Trp Asp Ile Lys Val Met Lys
            355             360             365
Gln His Asn Ile Asn Ala Val Arg Thr Ser His Tyr Pro Asn Gln Thr
        370             375             380
Arg Trp Tyr Glu Leu Cys Asp Glu Tyr Gly Leu Tyr Val Ile Asp Glu
385             390             395             400
Ala Asn Leu Glu Thr His Gly Thr Trp Gln Lys Leu Gly Leu Cys Glu
            405             410             415
Pro Ser Trp Asn Ile Pro Ala Ser Glu Pro Glu Trp Leu Pro Ala Cys
            420             425             430
Leu Asp Arg Ala Asn Asn Met Phe Gln Arg Asp Lys Asn His Ala Ser
        435             440             445
```

```
Val Ile Ile Trp Ser Cys Gly Asn Glu Ser Tyr Ala Gly Lys Asp Ile
    450                 455                 460

Ala Asp Met Ala Asp Tyr Phe Arg Ser Val Asp Asn Thr Arg Pro Val
465                 470                 475                 480

His Tyr Glu Gly Val Ala Trp Cys Arg Glu Phe Asp Tyr Ile Thr Asp
                485                 490                 495

Ile Glu Ser Arg Met Tyr Ala Lys Pro Ala Asp Ile Glu Glu Tyr Leu
                500                 505                 510

Thr Thr Gly Lys Leu Val Asp Leu Ser Ser Val Ser Asp Lys His Phe
        515                 520                 525

Ala Ser Gly Asn Leu Thr Asn Lys Pro Gln Lys Pro Tyr Ile Ser Cys
530                 535                 540

Glu Tyr Met His Thr Met Gly Asn Ser Gly Gly Leu Gln Leu Tyr
545                 550                 555                 560

Thr Asp Leu Glu Lys Tyr Pro Glu Tyr Gln Gly Gly Phe Ile Trp Asp
                565                 570                 575

Phe Ile Asp Gln Ala Ile Tyr Lys Thr Leu Pro Asn Gly Ser Glu Phe
                580                 585                 590

Leu Ser Tyr Gly Gly Asp Trp His Asp Arg Pro Ser Asp Tyr Glu Phe
            595                 600                 605

Cys Gly Asn Gly Ile Val Phe Ala Asp Arg Thr Leu Thr Pro Lys Leu
            610                 615                 620

Gln Thr Val Lys His Leu Tyr Ser Asn Ile Lys Ile Ala Val Asp Glu
625                 630                 635                 640

Lys Ser Val Thr Ile Lys Asn Asp Asn Leu Phe Glu Asp Leu Ser Ala
                645                 650                 655

Tyr Thr Phe Leu Ala Arg Val Tyr Glu Asp Gly Arg Lys Val Ser Glu
                660                 665                 670

Ser Glu Tyr His Phe Asp Val Lys Pro Gly Glu Glu Ala Thr Phe Pro
            675                 680                 685

Val Asn Phe Val Val Glu Ala Ser Asn Ser Glu Gln Ile Tyr Glu Val
690                 695                 700

Ala Cys Val Leu Arg Glu Ala Thr Lys Trp Ala Pro Lys Gly His Glu
705                 710                 715                 720

Ile Val Arg Gly Gln Tyr Val Val Glu Lys Ile Ser Thr Glu Thr Pro
                725                 730                 735

Val Lys Ala Pro Leu Asn Val Val Glu Gly Asp Phe Asn Ile Gly Ile
                740                 745                 750

Gln Gly Gln Asn Phe Ser Ile Leu Leu Ser Arg Ala Gln Asn Thr Leu
            755                 760                 765

Val Ser Ala Lys Tyr Asn Gly Val Glu Phe Ile Glu Lys Gly Pro Lys
770                 775                 780

Leu Ser Phe Thr Arg Ala Tyr Thr Asp Asn Asp Arg Gly Ala Gly Tyr
785                 790                 795                 800

Pro Phe Glu Met Ala Gly Trp Lys Val Ala Gly Asn Tyr Ser Lys Val
                805                 810                 815

Thr Asp Thr Gln Ile Gln Ile Glu Asp Asp Ser Val Lys Val Thr Tyr
                820                 825                 830

Val His Glu Leu Pro Gly Leu Ser Asp Val Glu Val Lys Val Thr Tyr
            835                 840                 845

Gln Val Asp Tyr Lys Gly Arg Ile Phe Val Thr Ala Asn Tyr Asp Gly
850                 855                 860
```

-continued

```
Lys Ala Gly Leu Pro Asn Phe Pro Glu Phe Gly Leu Glu Phe Ala Ile
865                 870                 875                 880

Gly Ser Gln Phe Thr Asn Leu Ser Tyr Tyr Gly Tyr Gly Ala Glu Glu
                885                 890                 895

Ser Tyr Arg Asp Lys Leu Pro Gly Ala Tyr Leu Gly Arg Tyr Glu Thr
            900                 905                 910

Ser Val Glu Lys Thr Phe Ala Pro Tyr Leu Met Pro Gln Glu Ser Gly
        915                 920                 925

Asn His Tyr Gly Thr Arg Glu Phe Thr Val Ser Asp Asp Asn His Asn
    930                 935                 940

Gly Leu Lys Phe Thr Ala Leu Asn Lys Ala Phe Glu Phe Ser Ala Leu
945                 950                 955                 960

Arg Asn Ser Thr Glu Gln Ile Glu Asn Ala Arg His Gln Tyr Glu Leu
                965                 970                 975

Gln Glu Ser Asp Ala Thr Trp Ile Lys Val Leu Ala Ala Gln Met Gly
            980                 985                 990

Val Gly Gly Asp Asp Ser Trp Gly Ala Pro Val His Asp Glu Phe Leu
        995                 1000                1005

Leu Ser Ser Ala Asp Ser Tyr Gln Leu Ser Phe Met Ile Glu Pro
    1010                1015                1020

Leu Asn
    1025

<210> SEQ ID NO 31
<211> LENGTH: 1008
<212> TYPE: PRT
<213> ORGANISM: Lactobacillus delbrueckii

<400> SEQUENCE: 31

Met Asn Asn Lys Leu Ala Gln Val Lys Arg Val Asp Gln Ala Asp Leu
1               5                   10                  15

Ala Trp Leu Thr Asp Pro Glu Ile Tyr Glu Val Asn Thr Ile Pro Pro
            20                  25                  30

His Ser Asp His Glu Ser Phe Gln Ser Leu Glu Glu Leu Glu Glu Gly
        35                  40                  45

Lys Ser Ser Leu Val Gln Ser Leu Asp Gly Asp Trp Leu Ile Asp Tyr
    50                  55                  60

Ala Glu Asn Gly Glu Gly Pro Ala Asn Phe Tyr Glu Glu Asn Phe Asp
65                  70                  75                  80

Asp Ser Ser Phe Lys Ser Val Lys Val Pro Gly Asn Leu Glu Leu Gln
                85                  90                  95

Gly Phe Gly Gln Pro Gln Tyr Val Asn Val Gln Tyr Pro Trp Asp Gly
            100                 105                 110

Ser Asp Glu Ile Phe Pro Pro Met Ile Pro Ser Lys Asn Pro Val Ala
        115                 120                 125

Ser Tyr Val Arg Tyr Phe Asp Leu Glu Glu Ala Phe Trp Asp Lys Glu
    130                 135                 140

Val Ser Leu Lys Phe Ala Gly Ala Ala Thr Ala Ile Tyr Val Trp Leu
145                 150                 155                 160

Asn Gly His Phe Val Gly Tyr Gly Glu Asp Ser Phe Thr Pro Ser Glu
                165                 170                 175

Phe Met Val Thr Lys Leu Lys Lys Glu Gly Asn Arg Leu Ala Val
            180                 185                 190

Ala Leu Tyr Lys Tyr Ser Ser Ala Ser Trp Leu Glu Asp Gln Asp Phe
    195                 200                 205
```

-continued

Trp Arg Met Ser Gly Leu Phe Arg Ser Val Thr Leu Glu Ala Lys Pro
210                     215                 220

Leu Leu His Leu Gln Asp Leu Lys Leu Thr Ala Ser Leu Thr Asn Asp
225                 230                 235                 240

Tyr Gln Lys Gly Ser Leu Gln Val Glu Ala Asp Ile Asp Tyr Arg Leu
                245                 250                 255

Pro Asn Ser Ser Phe Lys Leu Glu Leu Arg Asp Ser Ala Gly Glu Leu
            260                 265                 270

Val Ala Glu Lys Val Gly Pro Ile Arg Ser Glu Lys Leu Asp Phe Ser
        275                 280                 285

Leu Ala Asp Leu Pro Val Ala Ala Trp Ser Ala Glu Pro Asn Leu
290                 295                 300

Tyr Gln Val Arg Leu Ser Leu Tyr Gln Gln Gly Ser Leu Leu Glu Val
305                 310                 315                 320

Ser Arg Gln Glu Val Gly Phe Arg Asn Phe Glu Leu Lys Asp Gly Ile
                325                 330                 335

Met Tyr Leu Asn Gly Lys Arg Ile Val Phe Lys Gly Val Asn Arg His
            340                 345                 350

Glu Phe Asp Ser Lys Leu Gly Arg Ala Ile Thr Glu Ala Asp Met Ile
        355                 360                 365

Trp Asp Ile Lys Thr Met Lys Gln Ser Asn Ile Asn Ala Val Arg Cys
370                 375                 380

Ser His Tyr Pro Asn Gln Ser Ile Phe Tyr His Leu Cys Asp Lys Tyr
385                 390                 395                 400

Gly Leu Tyr Val Ile Asp Glu Ala Asn Leu Glu Ser His Gly Thr Trp
                405                 410                 415

Glu Lys Val Gly Gly His Glu Asp Pro Ser Phe Asn Val Pro Gly Asp
            420                 425                 430

Asp Gln Arg Trp Leu Gly Ala Ser Leu Ser Arg Val Lys Asn Met Met
        435                 440                 445

Ala Arg Asp Lys Asn His Ala Ser Ile Leu Ile Trp Ser Leu Gly Asn
450                 455                 460

Glu Ser Tyr Ala Gly Lys Val Phe Ala Gln Met Ala Asp Tyr Val Arg
465                 470                 475                 480

Gln Ala Asp Pro Thr Arg Val Gln His Tyr Glu Gly Val Thr His Asn
                485                 490                 495

Arg Lys Phe Asp Asp Ala Thr Gln Ile Glu Ser Arg Met Tyr Ala Pro
            500                 505                 510

Ala Lys Glu Ile Glu Glu Tyr Leu Thr Lys Lys Pro Ala Lys Pro Phe
        515                 520                 525

Val Ser Cys Glu Tyr Ala His Ala Met Gly Asn Ser Val Gly Asp Leu
530                 535                 540

Ala Ala Tyr Thr Ala Leu Glu Lys Tyr Pro His Tyr Gln Gly Gly Phe
545                 550                 555                 560

Ile Trp Asp Trp Ile Asp Gln Gly Leu Glu Lys Glu Gly His Leu Leu
                565                 570                 575

Tyr Gly Gly Asp Phe Asp Asp Arg Pro Ser Asp Tyr Glu Phe Cys Gly
            580                 585                 590

Asp Gly Leu Val Phe Ala Asp Arg Thr Thr Ser Pro Lys Leu Ala Asn
        595                 600                 605

Val Lys Ala Leu Tyr Ser Asn Leu Lys Leu Glu Leu Lys Asp Gly Gln
610                 615                 620

```
Leu Phe Leu Lys Asn Asp Asn Leu Phe Thr Asn Ser Ser Ala Tyr Tyr
625                 630                 635                 640

Phe Leu Thr Ser Leu Leu Val Asp Gly Lys Leu Thr Tyr Gln Ser Gln
            645                 650                 655

Pro Leu Thr Phe Ala Leu Glu Pro Gly Glu Ser Gly Thr Phe Ala Leu
        660                 665                 670

Pro Trp Pro Glu Val Glu Asp Lys Gly Glu Ile Val Tyr Gln Val
    675                 680                 685

Thr Ala His Leu Lys Glu Asp Leu Pro Trp Ala Asp Glu Gly Phe Thr
        690                 695                 700

Val Ala Glu Ala Glu Glu Ala Val Thr Lys Leu Pro Glu Phe Tyr Pro
705                 710                 715                 720

Ala Gly Arg Pro Glu Leu Val Asp Ser Asp Tyr Asn Leu Gly Ile Lys
                725                 730                 735

Gly Asn Gly Phe Arg Ile Leu Phe Ser Lys Ala Lys Gly Trp Pro Val
            740                 745                 750

Ser Ile Lys Tyr Ala Gly Arg Glu Tyr Leu Lys Arg Leu Pro Glu Phe
        755                 760                 765

Thr Phe Trp Arg Ala Leu Thr Asp Asn Asp Arg Gly Ala Gly Tyr Gly
770                 775                 780

Tyr Asp Leu Ala Lys Trp Glu Asn Ala Gly Lys Tyr Ala Arg Leu Gln
785                 790                 795                 800

Asp Ile Ser Tyr Glu Ile Lys Glu Asn Ser Val Leu Val Lys Thr Ala
                805                 810                 815

Phe Thr Leu Pro Val Ala Leu Lys Gly Asp Leu Thr Ile Thr Tyr Glu
            820                 825                 830

Val Asp Ser Leu Gly Lys Ile Ala Val Thr Ala Asn Phe Pro Gly Ala
        835                 840                 845

Val Glu Asn Gly Leu Leu Pro Ala Phe Gly Leu Asn Phe Ala Leu Pro
850                 855                 860

Lys Glu Leu Ser Asp Tyr Arg Tyr Tyr Gly Leu Gly Pro Asn Glu Ser
865                 870                 875                 880

Tyr Ala Asp Arg Leu Glu Gly Ser Tyr Leu Gly Ile Tyr Gln Gly Ala
                885                 890                 895

Val Glu Lys Asn Phe Thr Pro Tyr Leu Arg Pro Gln Glu Val Gly Asn
            900                 905                 910

Arg Ser Lys Val Arg Tyr Tyr Gln Leu Phe Asp Glu Glu Gly Gly Leu
        915                 920                 925

Glu Phe Thr Ala Asn Gly Ala Asn Leu Asn Leu Ser Ala Leu Pro Tyr
930                 935                 940

Ser Ala Ala Gln Ile Glu Ala Ala Asp His Ala Phe Glu Leu Thr Asn
945                 950                 955                 960

Asn Tyr Thr Trp Val Arg Ala Leu Ala Ala Gln Met Gly Val Gly Gly
                965                 970                 975

Asp Asp Ser Trp Gly Gln Lys Val His Pro Gly Phe Cys Leu Asp Ala
            980                 985                 990

Gln Glu Ala Arg Gln Leu Lys Leu  Val Ile Gln Pro Leu  Phe Thr Glu
        995                 1000                1005
```

<210> SEQ ID NO 32
<211> LENGTH: 1049
<212> TYPE: PRT
<213> ORGANISM: Bifidobacterium adolescentis

<400> SEQUENCE: 32

```
Met Ala Asp Thr Ala Glu Leu Ala Ile Val His Ala Thr Ala Ser
1               5                   10                  15

Ala Ser Trp Leu Thr Asp Pro Thr Val Phe Ala Ala Asn Arg Lys Pro
            20                  25                  30

Ala His Ser Ser His Arg Tyr Val Ile Gly Glu Thr Ser Glu Pro Lys
            35                  40                  45

Gln Ser Leu Asp Gly Glu Trp Lys Val Arg Ile Glu Gln Ala Arg Asn
    50                  55                  60

Val Asp Val Glu Ser Ala Pro Phe Ala Ala Val Asp Phe Glu Asp Gly
65                  70                  75                  80

Asp Phe Gly Ala Ile Glu Val Pro Gly His Leu Gln Met Ala Gly Tyr
                85                  90                  95

Leu Lys Asn Lys Tyr Val Asn Ile Gln Tyr Pro Trp Asp Gly His Glu
            100                 105                 110

Asp Pro Gln Ala Pro Asn Ile Pro Glu Asn Asn His Val Ala Ile Tyr
            115                 120                 125

Arg Arg Arg Phe Ala Leu Asp Ala Gln Leu Ala Arg Thr Leu Glu Asn
    130                 135                 140

Asp Gly Thr Val Ser Leu Thr Phe His Gly Ala Ala Thr Ala Ile Tyr
145                 150                 155                 160

Val Trp Leu Asp Gly Thr Phe Val Gly Tyr Gly Glu Asp Gly Phe Thr
                165                 170                 175

Pro Ser Glu Phe Asp Val Thr Glu Ala Leu Arg Asn Gly Asn Gly Asn
            180                 185                 190

Ala Ala Asp Ser Pro Glu Ala Glu His Thr Leu Thr Val Ala Cys Tyr
            195                 200                 205

Glu Tyr Ser Ser Ala Ser Trp Leu Glu Asp Gln Asp Phe Trp Arg Leu
    210                 215                 220

His Gly Leu Phe Arg Thr Val Glu Leu Ala Ala Gln Pro His Thr His
225                 230                 235                 240

Val Glu Thr Val Gln Leu Glu Ala Asp Tyr Thr Ala Ala Asp Thr Ala
                245                 250                 255

Gly Thr Ala Asp Thr Ala Glu Leu Asn Ala Ala Leu Thr Leu Arg Asn
            260                 265                 270

Pro Ala Asp Ala Met Thr Ile Glu Ser Thr Leu Arg Asp Gly Asp Gly
            275                 280                 285

Asn Val Val Trp Glu Ser Thr Gln Ala Cys Asn Gly Glu Ile Ala Leu
    290                 295                 300

Asn Ser Gly Lys Met Thr Asn Ile Ala Pro Trp Ser Ala Glu Ser Pro
305                 310                 315                 320

Thr Leu Tyr Thr Leu Thr Val Arg Val Val Gly His Asp Gly Ala Ile
                325                 330                 335

Ile Glu Thr Val Thr Gln Lys Ile Gly Phe Arg Thr Phe Arg Ile Glu
            340                 345                 350

Asn Gly Ile Met Thr Leu Asn Gly Lys Arg Ile Val Phe Lys Gly Ala
            355                 360                 365

Asp Arg His Glu Phe Asp Ala Lys Arg Gly Arg Ala Ile Thr Arg Glu
    370                 375                 380

Asp Met Leu Ser Asp Val Val Phe Cys Lys Arg His Asn Ile Asn Ala
385                 390                 395                 400

Ile Arg Thr Ser His Tyr Pro Asn Gln Glu Tyr Trp Tyr Asp Leu Cys
                405                 410                 415
```

```
Asp Glu Tyr Gly Leu Tyr Leu Ile Asp Glu Thr Asn Met Glu Thr His
            420                 425                 430

Gly Thr Trp Val Ala Asn Asn Val Glu Arg Pro Glu Asp Gly Ile Pro
        435                 440                 445

Gly Ser Arg Pro Glu Trp Glu Asp Ala Cys Val Asp Arg Ile Asn Ser
    450                 455                 460

Met Met Arg Arg Asp Tyr Asn His Pro Ser Val Leu Ile Trp Ser Leu
465                 470                 475                 480

Gly Asn Glu Ser Ser Ala Gly Glu Val Phe Arg Ala Met Tyr Arg His
                485                 490                 495

Ala His Thr Ile Asp Pro Asn Arg Pro Val His Tyr Glu Gly Ser Val
            500                 505                 510

His Met Arg Glu Phe Glu Asp Val Thr Asp Ile Glu Ser Arg Met Tyr
        515                 520                 525

Ala His Ala Asp Glu Ile Glu Arg Tyr Leu Asn Asp Gly Ser Pro Ala
    530                 535                 540

His Thr Asp Gly Pro Lys Lys Pro Tyr Ile Ser Cys Glu Tyr Met His
545                 550                 555                 560

Ala Met Gly Asn Ser Cys Gly Asn Met Asp Glu Tyr Thr Ala Leu Glu
                565                 570                 575

Arg Tyr Pro Met Tyr Gln Gly Gly Phe Ile Trp Asp Phe Ile Asp Gln
            580                 585                 590

Ala Ile Glu Thr Lys Leu Pro Asp Gly Thr Thr Arg Met Cys Tyr Gly
        595                 600                 605

Gly Asp Phe Gly Asp Arg Pro Ser Asp Tyr Glu Phe Ser Gly Asp Gly
    610                 615                 620

Leu Leu Phe Ala Asp Arg Thr Pro Ser Pro Lys Ala Gln Glu Val Lys
625                 630                 635                 640

Gln Leu Tyr Ala Asn Val Lys Ile Ala Val Ser Val Asp Glu Ala Arg
                645                 650                 655

Ile Thr Asn Asp Asn Leu Phe Val Ser Thr Gly Asp Tyr Arg Phe Val
            660                 665                 670

Leu Arg Ile Leu Ala Asp Gly Lys Pro Val Trp Ser Thr Thr Arg Arg
        675                 680                 685

Phe Asp Val Ala Ala Gly Glu Ser Ala Ser Phe Glu Val Asp Trp Pro
    690                 695                 700

Val Asp Asp Tyr Arg Ser Asn Ala Glu Glu Leu Val Leu Glu Val Ser
705                 710                 715                 720

Gln Gln Leu Gly Asn Ala Cys Asp Trp Ala Pro Ala Gly Tyr Glu Leu
                725                 730                 735

Ala Phe Gly Gln Cys Val Val Ala Gly Ala Lys Thr Thr Ala Asp Ala
            740                 745                 750

Val Asp Ala Ala Gly Ala Pro Ala Asp Gly Thr Val Thr Leu Gly Arg
        755                 760                 765

Trp Asn Ala Gly Val Arg Gly Gln Gly Arg Glu Ala Leu Phe Ser Arg
    770                 775                 780

Thr Gln Gly Gly Met Val Ser Tyr Thr Phe Gly Glu Arg Glu Phe Val
785                 790                 795                 800

Leu Arg Arg Pro Ser Ile Thr Thr Phe Arg Pro Leu Thr Asp Asn Asp
                805                 810                 815

Arg Gly Ala Gly His Ala Phe Glu Arg Ala Ala Trp Ala Val Ala Gly
            820                 825                 830

Lys Tyr Ala Arg Cys Val Asp Cys Ala Ile Ala Asn Arg Gly Glu Asn
```

```
                    835                 840                 845
Ala Val Glu Ala Thr Tyr Thr Tyr Glu Leu Ala Ile Pro Gln Arg Thr
850                 855                 860

Lys Val Thr Val Arg Tyr Val Ala Asp Thr Ala Gly Leu Val Ser Leu
865                 870                 875                 880

Asp Val Glu Tyr Pro Gly Glu Lys Asn Gly Asp Leu Pro Thr Ile Pro
                    885                 890                 895

Ala Phe Gly Ile Glu Trp Ala Leu Pro Val Glu Tyr Ala Asn Leu Arg
                900                 905                 910

Phe Tyr Gly Ala Gly Pro Glu Glu Thr Tyr Ala Asp Arg Arg His Ala
                915                 920                 925

Lys Leu Gly Val Trp Ser Thr Thr Ala Gly Asp Asp Cys Ala Pro Tyr
            930                 935                 940

Leu Leu Pro Gln Glu Thr Gly Asn His Glu Asp Val Arg Trp Ala Glu
945                 950                 955                 960

Ile Thr Asp Asp Ser Gly His Gly Val Arg Val Lys Arg Gly Ala Gly
                    965                 970                 975

Ala Lys Pro Phe Ala Met Ser Leu Leu Pro Tyr Ser Ser Thr Met Leu
                980                 985                 990

Glu Glu Ala Leu His Gln Asp Glu  Leu Pro Lys Pro Arg  His Met Phe
                995                  1000                 1005

Leu Arg Leu Leu Ala Ala Gln  Met Gly Val Gly Gly  Asp Asp Ser
     1010                 1015                 1020

Trp Met Ser Pro Val His Glu  Gln Tyr Gln Leu Pro  Ala Asp Gln
     1025                 1030                 1035

Pro Leu Ser Leu Asn Val Gln  Leu Lys Leu Phe
     1040                 1045
```

<210> SEQ ID NO 33
<211> LENGTH: 1023
<212> TYPE: PRT
<213> ORGANISM: Bifidobacterium adolescentis

<400> SEQUENCE: 33

```
Met Ala Asn Glu Thr Arg Ile Glu His Ala Ser Glu Thr Trp Leu Ala
1               5                   10                  15

Asp Ser Thr Val Phe Glu Val Asn Arg Val Pro Ala His Ser Asp His
                20                  25                  30

Lys Cys Tyr Ala His Asp Ser Gln Thr Asn Glu Trp Ser Asp Leu Arg
            35                  40                  45

Gln Ser Leu Asp Gly Glu Trp Arg Val Glu Val Gln Ala Ser Asp
50                  55                  60

Ile Glu Phe Asn Glu Glu Pro Phe Val Arg Glu Asn Phe Asp Asp Ser
65                  70                  75                  80

Ala Phe Glu Arg Ile Gln Val Pro Gly His Leu Gln Met Ala Gly Leu
                85                  90                  95

Met Asn Asn Lys Tyr Val Asn Ile Gln Tyr Pro Trp Asp Gly His Glu
                100                 105                 110

Asn Pro Ala Glu Pro Asn Ile Pro Glu Asn Asn His Val Ala Leu Tyr
            115                 120                 125

Arg Lys Thr Phe Thr Met Ala Asn Arg Leu Ala Asp Thr Lys Asn Ala
        130                 135                 140

Gly Gly Thr Val Ser Ile Val Phe His Gly Met Ala Thr Ala Ile Tyr
145                 150                 155                 160
```

```
Val Trp Val Asn Gly Met Phe Val Gly Tyr Gly Glu Asp Gly Phe Thr
            165                 170                 175
Pro Asn Glu Phe Asp Ile Thr Glu Met Leu His Asp Gly Glu Asn Val
            180                 185                 190
Val Ala Val Ala Cys Tyr Glu Tyr Ser Ser Ala Ser Trp Leu Glu Asp
            195                 200                 205
Gln Asp Phe Trp Arg Leu His Gly Leu Phe Arg Ser Val Glu Leu Ala
            210                 215                 220
Ala Gln Pro His Val His Ile Glu Asn Met Gln Ile Glu Ser Asp Trp
225                 230                 235                 240
Asp Pro Glu Ser Gly Ser Ala Ser Leu Asp Ala Ala Leu Thr Val Arg
            245                 250                 255
Asn Ala Ala Asp Ala Ala Thr Ile Ser Ala Thr Leu Lys Asp Ser Asp
            260                 265                 270
Gly Asn Val Val Trp Glu Thr Ala Asn Cys Ala Asp Pro Asp Thr Ser
            275                 280                 285
Ile Ser Thr Gly Ser Leu Asn Gly Ile Arg Pro Trp Ser Ala Glu Asp
            290                 295                 300
Pro Val Leu Tyr Glu Phe Glu Val Thr Val Ile Asp His Ala Gly Asn
305                 310                 315                 320
Ile Ala Glu Val Ala Val Gln Lys Val Gly Phe Arg Arg Phe Arg Ile
            325                 330                 335
Glu Asp Gly Ile Met Thr Ile Asn Gly Lys Arg Ile Val Phe Lys Gly
            340                 345                 350
Ala Asp Arg His Glu Phe Asp Pro Lys Arg Gly Arg Ala Ile Thr Glu
            355                 360                 365
Gln Asp Met Ile Asp Asp Val Val Phe Cys Lys Arg His Asn Leu Asn
            370                 375                 380
Ala Ile Arg Thr Ser His Tyr Pro Asn Gln Glu Arg Trp Tyr Glu Leu
385                 390                 395                 400
Cys Asp Glu Tyr Gly Ile Tyr Leu Ile Asp Glu Thr Asn Leu Glu Thr
            405                 410                 415
His Gly Ser Trp Cys Leu Pro Gly Asp Val Leu Thr Glu Thr Ala
            420                 425                 430
Val Pro Gly Ser Lys Ala His Trp Glu Gly Ala Cys Val Asp Arg Val
            435                 440                 445
Asn Ser Met Val Arg Arg Asp Tyr Asn His Pro Ser Val Leu Ile Trp
            450                 455                 460
Ser Leu Gly Asn Glu Ser Tyr Thr Gly Asp Val Phe Arg Ala Met Tyr
465                 470                 475                 480
Lys Arg Val His Asp Ile Asp Pro Asn Arg Pro Val His Tyr Glu Gly
            485                 490                 495
Val Thr His Asn Arg Asp Tyr Asn Asp Val Thr Asp Ile Glu Thr Arg
            500                 505                 510
Met Tyr Ala His Ala Asp Ala Ile Glu Glu Tyr Leu Lys Asn Asp Pro
            515                 520                 525
Gln Lys Pro Tyr Ile Ser Cys Glu Tyr Met His Ala Met Gly Asn Ser
            530                 535                 540
Cys Gly Asn Met Asp Glu Tyr Thr Ala Leu Glu Arg Tyr Pro Lys Tyr
545                 550                 555                 560
Gln Gly Gly Phe Ile Trp Asp Phe Ile Asp Gln Ala Ile Tyr Ala Thr
            565                 570                 575
Gln Pro Asp Gly Thr Thr Ser Leu Arg Tyr Gly Gly Asp Phe Gly Asp
```

-continued

```
              580                 585                 590
Arg Pro Ser Asp Tyr Glu Phe Ser Gly Asn Gly Leu Val Phe Ala Asp
              595                 600                 605
Arg Lys Pro Thr Pro Lys Ala Gln Glu Val Lys Gln Leu Tyr Ser Asn
              610                 615                 620
Val His Ile Asp Val Ala Glu Asp Ser Val Thr Ile Lys Asn Asp Asn
625                 630                 635                 640
Leu Phe Thr Ser Thr Gly Glu Tyr Thr Phe Val Leu Arg Val Leu Ala
              645                 650                 655
Asp Gly Glu Pro Val Trp Gln Ser Glu Arg Arg Phe Asp Val Pro Ala
              660                 665                 670
Gly Ser Thr Glu Lys Leu Asp Val Asp Trp Pro Leu Asp Leu Tyr Arg
              675                 680                 685
Asp Gly Ala Ser Glu Leu Val Leu Glu Val Ser Gln Arg Leu Ala Lys
              690                 695                 700
Ala Thr Asn Trp Ala Val Ala Gly Tyr Glu Leu Ala Phe Gly Gln Thr
705                 710                 715                 720
Val Val Ala Gly Ser Lys Lys Ala Ser Ala Pro Val Lys Pro Val Asp
              725                 730                 735
Gly Ile Val Thr Val Gly Arg Trp Asn Val Gly Val Gln Gly Ser Gly
              740                 745                 750
Arg Glu Val Leu Leu Ser Arg Thr Gln Gly Gly Leu Val Ser Tyr Thr
              755                 760                 765
Phe Asn Asn Arg Glu Phe Val Leu Arg Arg Pro Ala Val Thr Thr Phe
              770                 775                 780
Arg Ala Leu Thr Asp Asn Asp Arg Gly Ala Gly His Gly Phe Glu Arg
785                 790                 795                 800
Ala Gln Trp Leu Gly Ala Gly Arg Tyr Ala Arg Cys Ile Gly Asn Glu
              805                 810                 815
Ile Glu Gln Ile Asp Glu Asn Thr Val Lys Ala Ser Tyr Thr Tyr Glu
              820                 825                 830
Leu Ala Thr Pro Gln Arg Thr Lys Val Thr Val Ser Tyr Thr Ala Asp
              835                 840                 845
Thr Thr Gly Arg Val Asn Leu His Val Glu Tyr Pro Gly Glu Pro Gly
850                 855                 860
Asp Leu Pro Thr Ile Pro Ala Phe Gly Ile Glu Trp Thr Leu Pro Val
865                 870                 875                 880
Gln Tyr Ser Asn Leu Arg Phe Phe Gly Ala Gly Pro Glu Glu Thr Tyr
              885                 890                 895
Gln Asp Arg Lys His Ala Lys Leu Gly Val Trp Ser Thr Asp Ala Phe
              900                 905                 910
Lys Asp His Ala Pro Tyr Leu Met Pro Gln Glu Thr Gly Asn His Glu
              915                 920                 925
Asp Val Arg Trp Ala Glu Ile Thr Asp Glu Lys Gly His Gly Leu Arg
              930                 935                 940
Ile Ser Arg Ala Glu Gly Ala Glu Pro Phe Ala Met Ser Leu Gln Pro
945                 950                 955                 960
Tyr Ser Ser Phe Met Leu Glu Glu Ala Gln His Gln Asp Glu Leu Pro
              965                 970                 975
Ala Pro Lys His Met Phe Leu Arg Val Leu Ala Glu Gln Met Gly Val
              980                 985                 990
Gly Gly Asp Asp Ser Trp Met Ser Pro Val His Pro Gln Tyr His Ile
              995                1000                1005
```

Pro Ala Asp Gln Pro Ile Ser Leu Asp Val Asp Leu Asp Leu Ile
        1010                1015                1020

<210> SEQ ID NO 34
<211> LENGTH: 1305
<212> TYPE: PRT
<213> ORGANISM: Bifidobacterium bifidum

<400> SEQUENCE: 34

Met Val Glu Asp Ala Thr Arg Ser Asp Ser Thr Gln Met Ser Ser
1               5                   10                  15

Thr Pro Glu Val Val Tyr Ser Ser Ala Val Asp Ser Lys Gln Asn Arg
            20                  25                  30

Thr Ser Asp Phe Asp Ala Asn Trp Lys Phe Met Leu Ser Asp Ser Val
        35                  40                  45

Gln Ala Gln Asp Pro Ala Phe Asp Ser Ala Trp Gln Gln Val Asp
    50                  55                  60

Leu Pro His Asp Tyr Ser Ile Thr Gln Lys Tyr Ser Gln Ser Asn Glu
65                  70                  75                  80

Ala Glu Ser Ala Tyr Leu Pro Gly Gly Thr Gly Trp Tyr Arg Lys Ser
                85                  90                  95

Phe Thr Ile Asp Arg Asp Leu Ala Gly Lys Arg Ile Ala Ile Asn Phe
            100                 105                 110

Asp Gly Val Tyr Met Asn Ala Thr Val Trp Phe Asn Gly Val Lys Leu
        115                 120                 125

Gly Thr His Pro Tyr Gly Tyr Ser Pro Phe Ser Phe Asp Leu Thr Gly
130                 135                 140

Asn Ala Lys Phe Gly Gly Glu Asn Thr Ile Val Val Lys Val Glu Asn
145                 150                 155                 160

Arg Leu Pro Ser Ser Arg Trp Tyr Ser Gly Ser Gly Ile Tyr Arg Asp
                165                 170                 175

Val Thr Leu Thr Val Thr Asp Gly Val His Val Gly Asn Asn Gly Val
            180                 185                 190

Ala Ile Lys Thr Pro Ser Leu Ala Thr Gln Asn Gly Gly Asn Val Thr
        195                 200                 205

Met Asn Leu Thr Thr Lys Val Ala Asn Asp Thr Glu Ala Ala Ala Asn
210                 215                 220

Ile Thr Leu Lys Gln Thr Val Phe Pro Lys Gly Gly Lys Thr Asp Ala
225                 230                 235                 240

Ala Ile Gly Thr Val Thr Thr Ala Ser Lys Ser Ile Ala Ala Gly Ala
                245                 250                 255

Ser Ala Asp Val Thr Ser Thr Ile Thr Ala Ala Ser Pro Lys Leu Trp
            260                 265                 270

Ser Ile Lys Asn Pro Asn Leu Tyr Thr Val Arg Thr Glu Val Leu Asn
        275                 280                 285

Gly Asp Thr Val Leu Asp Thr Tyr Asp Thr Glu Tyr Gly Phe Arg Trp
    290                 295                 300

Thr Gly Phe Asp Ala Thr Ser Gly Phe Ser Leu Asn Gly Glu Lys Val
305                 310                 315                 320

Lys Leu Lys Gly Val Ser Met His His Asp Gln Gly Ser Leu Gly Ala
                325                 330                 335

Val Ala Asn Arg Arg Ala Ile Glu Arg Gln Val Glu Ile Leu Gln Lys
            340                 345                 350

Met Gly Val Asn Ser Ile Arg Thr Thr His Asn Pro Ala Ala Lys Ala

-continued

```
                355                 360                 365
Leu Ile Asp Val Cys Asn Glu Lys Gly Val Leu Val Glu Glu Val
370                 375                 380
Phe Asp Met Trp Asn Arg Ser Lys Asn Gly Asn Thr Glu Asp Tyr Gly
385                 390                 395                 400
Lys Trp Phe Gly Gln Thr Ile Ala Gly Asp Asn Ala Val Leu Gly Gly
                    405                 410                 415
Asp Lys Asp Glu Thr Trp Ala Lys Phe Asp Leu Thr Ser Thr Ile Asn
                420                 425                 430
Arg Asp Arg Asn Ala Pro Ser Val Ile Met Trp Ser Leu Gly Asn Glu
                435                 440                 445
Met Met Glu Gly Ile Ser Gly Ser Val Ser Asp Phe Pro Ala Thr Ser
            450                 455                 460
Ala Lys Leu Val Ala Trp Thr Lys Ala Ala Asp Ser Thr Arg Pro Met
465                 470                 475                 480
Thr Tyr Gly Asp Asn Lys Ile Lys Ala Asn Trp Asn Glu Ser Asn Thr
                    485                 490                 495
Met Gly Asp Asn Leu Thr Ala Asn Gly Gly Val Val Gly Thr Asn Tyr
                500                 505                 510
Ser Asp Gly Ala Asn Tyr Asp Lys Ile Arg Thr Thr His Pro Ser Trp
                515                 520                 525
Ala Ile Tyr Gly Ser Glu Thr Ala Ser Ala Ile Asn Ser Arg Gly Ile
530                 535                 540
Tyr Asn Arg Thr Thr Gly Gly Ala Gln Ser Ser Asp Lys Gln Leu Thr
545                 550                 555                 560
Ser Tyr Asp Asn Ser Ala Val Gly Trp Gly Ala Val Ala Ser Ser Ala
                    565                 570                 575
Trp Tyr Asp Val Val Gln Arg Asp Phe Val Ala Gly Thr Tyr Val Trp
                580                 585                 590
Thr Gly Phe Asp Tyr Leu Gly Glu Pro Thr Pro Trp Asn Gly Thr Gly
                595                 600                 605
Ser Gly Ala Val Gly Ser Trp Pro Ser Pro Lys Asn Ser Tyr Phe Gly
                610                 615                 620
Ile Val Asp Thr Ala Gly Phe Pro Lys Asp Thr Tyr Tyr Phe Tyr Gln
625                 630                 635                 640
Ser Gln Trp Asn Asp Asp Val His Thr Leu His Ile Leu Pro Ala Trp
                    645                 650                 655
Asn Glu Asn Val Val Ala Lys Gly Ser Gly Asn Lys Val Pro Val Val
                660                 665                 670
Val Tyr Thr Asp Ala Ala Lys Val Lys Leu Tyr Phe Thr Pro Lys Gly
                675                 680                 685
Ser Thr Glu Lys Arg Leu Ile Gly Glu Lys Ser Phe Thr Lys Lys Thr
                690                 695                 700
Thr Ala Ala Gly Tyr Thr Tyr Gln Val Tyr Glu Gly Thr Asp Lys Asp
705                 710                 715                 720
Ser Thr Ala His Lys Asn Met Tyr Leu Thr Trp Asn Val Pro Trp Ala
                    725                 730                 735
Glu Gly Thr Ile Ser Ala Glu Ala Tyr Asp Glu Asn Asn Arg Leu Ile
                740                 745                 750
Pro Glu Gly Ser Thr Glu Gly Asn Ala Ser Val Thr Thr Gly Lys
                755                 760                 765
Ala Ala Lys Leu Lys Ala Asp Ala Asp Arg Lys Thr Ile Thr Ala Asp
                770                 775                 780
```

```
Gly Lys Asp Leu Ser Tyr Ile Glu Val Asp Val Thr Asp Ala Asn Gly
785                 790                 795                 800

His Ile Val Pro Asp Ala Ala Asn Arg Val Thr Phe Asp Val Lys Gly
            805                 810                 815

Ala Gly Lys Leu Val Gly Val Asp Asn Gly Ser Ser Pro Asp His Asp
        820                 825                 830

Ser Tyr Gln Ala Asp Asn Arg Lys Ala Phe Ser Gly Lys Val Leu Ala
    835                 840                 845

Ile Val Gln Ser Thr Lys Glu Ala Gly Glu Ile Thr Val Thr Ala Lys
850                 855                 860

Ala Asp Gly Leu Gln Ser Ser Thr Val Lys Ile Ala Thr Thr Ala Val
865                 870                 875                 880

Pro Gly Thr Ser Thr Glu Lys Thr Val Arg Ser Phe Tyr Tyr Ser Arg
            885                 890                 895

Asn Tyr Tyr Val Lys Thr Gly Asn Lys Pro Ile Leu Pro Ser Asp Val
        900                 905                 910

Glu Val Arg Tyr Ser Asp Gly Thr Ser Asp Arg Gln Asn Val Thr Trp
    915                 920                 925

Asp Ala Val Ser Asp Asp Gln Ile Ala Lys Ala Gly Ser Phe Ser Val
930                 935                 940

Ala Gly Thr Val Ala Gly Gln Lys Ile Ser Val Arg Val Thr Met Ile
945                 950                 955                 960

Asp Glu Ile Gly Ala Leu Leu Asn Tyr Ser Ala Ser Thr Pro Val Gly
            965                 970                 975

Thr Pro Ala Val Leu Pro Gly Ser Arg Pro Ala Val Leu Pro Asp Gly
        980                 985                 990

Thr Val Thr Ser Ala Asn Phe Ala Val His Trp Thr Lys Pro Ala Asp
    995                 1000                1005

Thr Val Tyr Asn Thr Ala Gly Thr Val Lys Val Pro Gly Thr Ala
    1010                1015                1020

Thr Val Phe Gly Lys Glu Phe Lys Val Thr Ala Thr Ile Arg Val
    1025                1030                1035

Gln Arg Ser Gln Val Thr Ile Gly Ser Ser Val Ser Gly Asn Ala
    1040                1045                1050

Leu Arg Leu Thr Gln Asn Ile Pro Ala Asp Lys Gln Ser Asp Thr
    1055                1060                1065

Leu Asp Ala Ile Lys Asp Gly Ser Thr Thr Val Asp Ala Asn Thr
    1070                1075                1080

Gly Gly Gly Ala Asn Pro Ser Ala Trp Thr Asn Trp Ala Tyr Ser
    1085                1090                1095

Lys Ala Gly His Asn Thr Ala Glu Ile Thr Phe Glu Tyr Ala Thr
    1100                1105                1110

Glu Gln Gln Leu Gly Gln Ile Val Met Tyr Phe Phe Arg Asp Ser
    1115                1120                1125

Asn Ala Val Arg Phe Pro Asp Ala Gly Lys Thr Lys Ile Gln Ile
    1130                1135                1140

Ser Ala Asp Gly Lys Asn Trp Thr Asp Leu Ala Ala Thr Glu Thr
    1145                1150                1155

Ile Ala Ala Gln Glu Ser Ser Asp Arg Val Lys Pro Tyr Thr Tyr
    1160                1165                1170

Asp Phe Ala Pro Val Gly Ala Thr Phe Val Lys Val Thr Val Thr
    1175                1180                1185
```

```
Asn Ala Asp Thr Thr Thr Pro Ser Gly Val Val Cys Ala Gly Leu
    1190                1195                1200

Thr Glu Ile Glu Leu Lys Thr Ala Thr Ser Lys Phe Val Thr Asn
1205                1210                1215

Thr Ser Ala Ala Leu Ser Ser Leu Thr Val Asn Gly Thr Lys Val
    1220                1225                1230

Ser Asp Ser Val Leu Ala Ala Gly Ser Tyr Asn Thr Pro Ala Ile
    1235                1240                1245

Ile Ala Asp Val Lys Ala Glu Gly Glu Gly Asn Ala Ser Val Thr
    1250                1255                1260

Val Leu Pro Ala His Asp Asn Val Ile Arg Val Ile Thr Glu Ser
    1265                1270                1275

Glu Asp His Val Thr Arg Lys Thr Phe Thr Ile Asn Leu Gly Thr
    1280                1285                1290

Glu Gln Glu Phe Pro Ala Asp Ser Asp Glu Arg Asp
    1295                1300                1305

<210> SEQ ID NO 35
<211> LENGTH: 1025
<212> TYPE: PRT
<213> ORGANISM: Kluyveromyces lactis

<400> SEQUENCE: 35

Met Ser Cys Leu Ile Pro Glu Asn Leu Arg Asn Pro Lys Lys Val His
1               5                   10                  15

Glu Asn Arg Leu Pro Thr Arg Ala Tyr Tyr Tyr Asp Gln Asp Ile Phe
            20                  25                  30

Glu Ser Leu Asn Gly Pro Trp Ala Phe Ala Leu Phe Asp Ala Pro Leu
        35                  40                  45

Asp Ala Pro Asp Ala Lys Asn Leu Asp Trp Glu Thr Ala Lys Lys Trp
    50                  55                  60

Ser Thr Ile Ser Val Pro Ser His Trp Glu Leu Gln Glu Asp Trp Lys
65                  70                  75                  80

Tyr Gly Lys Pro Ile Tyr Thr Asn Val Gln Tyr Pro Ile Pro Ile Asp
                85                  90                  95

Ile Pro Asn Pro Pro Thr Val Asn Pro Thr Gly Val Tyr Ala Arg Thr
            100                 105                 110

Phe Glu Leu Asp Ser Lys Ser Ile Glu Ser Phe Glu His Arg Leu Arg
        115                 120                 125

Phe Glu Gly Val Asp Asn Cys Tyr Glu Leu Tyr Val Asn Gly Gln Tyr
    130                 135                 140

Val Gly Phe Asn Lys Gly Ser Arg Asn Gly Ala Glu Phe Asp Ile Gln
145                 150                 155                 160

Lys Tyr Val Ser Glu Gly Glu Asn Leu Val Val Lys Val Phe Lys
                165                 170                 175

Trp Ser Asp Ser Thr Tyr Ile Glu Asp Gln Asp Gln Trp Trp Leu Ser
            180                 185                 190

Gly Ile Tyr Arg Asp Val Ser Leu Leu Lys Leu Pro Lys Lys Ala His
        195                 200                 205

Ile Glu Asp Val Arg Val Thr Thr Thr Phe Val Asp Ser Gln Tyr Gln
    210                 215                 220

Asp Ala Glu Leu Ser Val Lys Val Asp Val Gln Gly Ser Ser Tyr Asp
225                 230                 235                 240

His Ile Asn Phe Thr Leu Tyr Glu Pro Glu Asp Gly Ser Lys Val Tyr
                245                 250                 255
```

```
Asp Ala Ser Ser Leu Leu Asn Glu Glu Asn Gly Asn Thr Thr Phe Ser
            260                 265                 270

Thr Lys Glu Phe Ile Ser Phe Ser Thr Lys Lys Asn Glu Glu Thr Ala
        275                 280                 285

Phe Lys Ile Asn Val Lys Ala Pro Glu His Trp Thr Ala Glu Asn Pro
    290                 295                 300

Thr Leu Tyr Lys Tyr Gln Leu Asp Leu Ile Gly Ser Asp Gly Ser Val
305                 310                 315                 320

Ile Gln Ser Ile Lys His His Val Gly Phe Arg Gln Val Glu Leu Lys
                325                 330                 335

Asp Gly Asn Ile Thr Val Asn Gly Lys Asp Ile Leu Phe Arg Gly Val
            340                 345                 350

Asn Arg His Asp His His Pro Arg Phe Gly Arg Ala Val Pro Leu Asp
        355                 360                 365

Phe Val Val Arg Asp Leu Ile Leu Met Lys Lys Phe Asn Ile Asn Ala
    370                 375                 380

Val Arg Asn Ser His Tyr Pro Asn His Pro Lys Val Tyr Asp Leu Phe
385                 390                 395                 400

Asp Lys Leu Gly Phe Trp Val Ile Asp Glu Ala Asp Leu Glu Thr His
                405                 410                 415

Gly Val Gln Glu Pro Phe Asn Arg His Thr Asn Leu Glu Ala Glu Tyr
            420                 425                 430

Pro Asp Thr Lys Asn Lys Leu Tyr Asp Val Asn Ala His Tyr Leu Ser
        435                 440                 445

Asp Asn Pro Glu Tyr Glu Val Ala Tyr Leu Asp Arg Ala Ser Gln Leu
    450                 455                 460

Val Leu Arg Asp Val Asn His Pro Ser Ile Ile Ile Trp Ser Leu Gly
465                 470                 475                 480

Asn Glu Ala Cys Tyr Gly Arg Asn His Lys Ala Met Tyr Lys Leu Ile
                485                 490                 495

Lys Gln Leu Asp Pro Thr Arg Leu Val His Tyr Glu Gly Asp Leu Asn
            500                 505                 510

Ala Leu Ser Ala Asp Ile Phe Ser Phe Met Tyr Pro Thr Phe Glu Ile
        515                 520                 525

Met Glu Arg Trp Arg Lys Asn His Thr Asp Glu Asn Gly Lys Phe Glu
    530                 535                 540

Lys Pro Leu Ile Leu Cys Glu Tyr Gly His Ala Met Gly Asn Gly Pro
545                 550                 555                 560

Gly Ser Leu Lys Glu Tyr Gln Glu Leu Phe Tyr Lys Glu Lys Phe Tyr
                565                 570                 575

Gln Gly Gly Phe Ile Trp Glu Trp Ala Asn His Gly Ile Glu Phe Glu
            580                 585                 590

Asp Val Ser Thr Ala Asp Gly Lys Leu His Lys Ala Tyr Ala Tyr Gly
        595                 600                 605

Gly Asp Phe Lys Glu Glu Val His Asp Gly Val Phe Ile Met Asp Gly
    610                 615                 620

Leu Cys Asn Ser Glu His Asn Pro Thr Pro Gly Leu Val Glu Tyr Lys
625                 630                 635                 640

Lys Val Ile Glu Pro Val His Ile Lys Ile Ala His Gly Ser Val Thr
                645                 650                 655

Ile Thr Asn Lys His Asp Phe Ile Thr Thr Asp His Leu Leu Phe Ile
            660                 665                 670
```

Asp Lys Asp Thr Gly Lys Thr Ile Asp Val Pro Ser Leu Lys Pro Glu
        675                 680                 685

Glu Ser Val Thr Ile Pro Ser Asp Thr Thr Tyr Val Ala Val Leu
    690                 695                 700

Lys Asp Ala Gly Val Leu Lys Ala Gly His Glu Ile Ala Trp Gly
705                 710                 715                 720

Gln Ala Glu Leu Pro Leu Lys Val Pro Asp Phe Val Thr Glu Thr Ala
            725                 730                 735

Glu Lys Ala Ala Lys Ile Asn Asp Gly Lys Arg Tyr Val Ser Val Glu
            740                 745                 750

Ser Ser Gly Leu His Phe Ile Leu Asp Lys Leu Leu Gly Lys Ile Glu
        755                 760                 765

Ser Leu Lys Val Lys Gly Lys Glu Ile Ser Ser Lys Phe Glu Gly Ser
    770                 775                 780

Ser Ile Thr Phe Trp Arg Pro Pro Thr Asn Asn Asp Glu Pro Arg Asp
785                 790                 795                 800

Phe Lys Asn Trp Lys Lys Tyr Asn Ile Asp Leu Met Lys Gln Asn Ile
                805                 810                 815

His Gly Val Ser Val Glu Lys Gly Ser Asn Gly Ser Leu Ala Val Val
            820                 825                 830

Thr Val Asn Ser Arg Ile Ser Pro Val Val Phe Tyr Gly Phe Glu
        835                 840                 845

Thr Val Gln Lys Tyr Thr Ile Phe Ala Asn Lys Ile Asn Leu Asn Thr
            850                 855                 860

Ser Met Lys Leu Thr Gly Glu Tyr Gln Pro Pro Asp Phe Pro Arg Val
865                 870                 875                 880

Gly Tyr Glu Phe Trp Leu Gly Asp Ser Tyr Glu Ser Phe Glu Trp Leu
                885                 890                 895

Gly Arg Gly Pro Gly Glu Ser Tyr Pro Asp Lys Lys Glu Ser Gln Arg
            900                 905                 910

Phe Gly Leu Tyr Asp Ser Lys Asp Val Glu Glu Phe Val Tyr Asp Tyr
        915                 920                 925

Pro Gln Glu Asn Gly Asn His Thr Asp Thr His Phe Leu Asn Ile Lys
    930                 935                 940

Phe Glu Gly Ala Gly Lys Leu Ser Ile Phe Gln Lys Glu Lys Pro Phe
945                 950                 955                 960

Asn Phe Lys Ile Ser Asp Glu Tyr Gly Val Asp Glu Ala Ala His Ala
                965                 970                 975

Cys Asp Val Lys Arg Tyr Gly Arg His Tyr Leu Arg Leu Asp His Ala
            980                 985                 990

Ile His Gly Val Gly Ser Glu Ala  Cys Gly Pro Ala Val  Leu Asp Gln
        995                 1000                1005

Tyr Arg  Leu Lys Ala Gln Asp  Phe Asn Phe Glu Phe  Asp Leu Ala
    1010                1015                1020

Phe Glu
    1025

<210> SEQ ID NO 36
<211> LENGTH: 30
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:

Synthetic primer
<220> FEATURE:
<221> NAME/KEY: modified_base
<222> LOCATION: (9)..(9)
<223> OTHER INFORMATION: deoxyuracil

<400> SEQUENCE: 36
attaaccaug cgacgcaact tcgaatggcc                                        30

<210> SEQ ID NO 37
<211> LENGTH: 31
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer
<220> FEATURE:
<221> NAME/KEY: modified_base
<222> LOCATION: (9)..(9)
<223> OTHER INFORMATION: deoxyuracil

<400> SEQUENCE: 37
atcttctcut taccgcctta ccacgagcac g                                      31

<210> SEQ ID NO 38
<211> LENGTH: 33
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer
<220> FEATURE:
<221> NAME/KEY: modified_base
<222> LOCATION: (9)..(9)
<223> OTHER INFORMATION: deoxyuracil

<400> SEQUENCE: 38
agagaagaut ttcagcctga tacagattaa atc                                    33

<210> SEQ ID NO 39
<211> LENGTH: 33
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer
<220> FEATURE:
<221> NAME/KEY: modified_base
<222> LOCATION: (9)..(9)
<223> OTHER INFORMATION: deoxyuracil

<400> SEQUENCE: 39
atggttaaut cctcctgtta gcccaaaaaa cgg                                    33

<210> SEQ ID NO 40
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 40
cggcgtcaca ctttgctatg cc                                                  22

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
ccgcgctact gccgccaggc                                                     20
```